US012679844B2

(12) United States Patent
Zhang et al.

(10) Patent No.: US 12,679,844 B2
(45) Date of Patent: Jul. 14, 2026

(54) IMIDAZOTRIAZINE AND PYRROLOPYRIMIDINE DERIVATIVES AS KRAS G12C INHIBITORS

(71) Applicant: BeiGene, Ltd., Grand Cayman (KY)

(72) Inventors: Guoliang Zhang, Beiging (CN); Jianzhuang Miao, Beijing (CN); Ce Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 506 days.

(21) Appl. No.: 18/040,667

(22) PCT Filed: Aug. 4, 2021

(86) PCT No.: PCT/CN2021/110640

§ 371 (c)(1),
(2) Date: Feb. 6, 2023

(87) PCT Pub. No.: WO2022/028492

PCT Pub. Date: Feb. 10, 2022

(65) Prior Publication Data

US 2023/0322788 A1 Oct. 12, 2023

(51) Int. Cl.
*C07D 487/04* (2006.01)

(52) U.S. Cl.
CPC .................................. *C07D 487/04* (2013.01)

(58) Field of Classification Search
CPC ....................................................... A61P 35/00
See application file for complete search history.

(56) References Cited

U.S. PATENT DOCUMENTS 9,969,748 B2 * 5/2018 Ford ....................... A61P 43/00
2021/0147418 A1 5/2021 Cai

FOREIGN PATENT DOCUMENTS

| | | | |
|---|---|---|---|
| CN | 102971323 | A | 3/2017 |
| CN | 106507674 | A | 3/2017 |
| CN | 112047948 | A | 12/2020 |
| CN | 114057744 | A | 2/2022 |
| WO | 2004065389 | A1 | 8/2004 |
| WO | 2011089400 | A1 | 7/2011 |
| WO | 2011141713 | A1 | 11/2011 |
| WO | 2014152588 | A1 | 9/2014 |
| WO | 2015054572 | A1 | 4/2015 |
| WO | 2016049524 | A1 | 3/2016 |
| WO | 2016164675 | A1 | 10/2016 |
| WO | 2016168540 | A1 | 10/2016 |
| WO | 2017015562 | A1 | 1/2017 |
| WO | 2017058728 | A1 | 4/2017 |
| WO | 2017058792 | A1 | 4/2017 |
| WO | 2017058805 | A1 | 4/2017 |
| WO | 2017058915 | A1 | 4/2017 |
| WO | 2017087528 | A1 | 5/2017 |
| WO | 2017205193 | A1 | 11/2017 |
| WO | 2018064510 | A1 | 4/2018 |
| WO | 2018068017 | A1 | 4/2018 |
| WO | 2018119183 | A2 | 6/2018 |
| WO | 2018206539 | A1 | 11/2018 |
| WO | 2018218069 | A1 | 11/2018 |
| WO | 2019051291 | A1 | 3/2019 |
| WO | 2019055540 | A1 | 3/2019 |
| WO | 2019137985 | A1 | 7/2019 |
| WO | 2019141250 | A1 | 7/2019 |
| WO | 2019150305 | A1 | 8/2019 |
| WO | 2019155399 | A1 | 8/2019 |
| WO | 2019213516 | A1 | 11/2019 |
| WO | 2019213526 | A1 | 11/2019 |
| WO | 2019215203 | A1 | 11/2019 |
| WO | 2019217307 | A1 | 11/2019 |
| WO | 2019217691 | A1 | 11/2019 |
| WO | 2019232419 | A1 | 12/2019 |
| WO | 2020027083 | A1 | 2/2020 |
| WO | 2020027084 | A1 | 2/2020 |
| WO | 2020028706 | A1 | 2/2020 |
| WO | 2020035031 | A1 | 2/2020 |
| WO | 2020047192 | A1 | 3/2020 |
| WO | 2022028492 | A1 | 2/2022 |

OTHER PUBLICATIONS

Fell, Jay B., et al. "Discovery of tetrahydropyridopyrimidines as irreversible covalent inhibitors of KRAS-G12C with in vivo activity." ACS medicinal chemistry letters 9.12 (2018): 1230-1234.
Li Huili et al., "Research Advances on KRAS and Its Inhibitors", 13 pages, 2020.
Patricelli, Matthew P., et al. "Selective inhibition of oncogenic KRAS output with small molecules targeting the inactive state." Cancer discovery 6.3 (2016): 316-329.
International Search Report issued Sep. 28, 2021 in PCT/CN2021/110640.
Written Opinion issued Sep. 28, 2021 in PCT/CN2021/110640.
Martinez Gonzales, Sonia, et al., "Identification of novel PI3K inhibitors through a scaffold hopping strategy," Biororganic & Medicinal Chemistry Letters, vol. 27, pp. 4794-4799, Sep. 30, 2017.
Kessler, D et al., "Drugging an undruggable pocket on KRAS," Proceedings of the National Academy of Sciences, 116 (32): 15823-15829, 2019.
Cox, A. D., et al. "Drugging the undruggable RAS: Mission possible?," Nature reviews Drug discovery 13(11):828-851, 2 2014.
Papke, B. et al., "Drugging RAS: Know the enemy," Science 355(6330):1158-1163, 2017.

* cited by examiner

*Primary Examiner* — Joseph K Mckane
*Assistant Examiner* — Anna Grace Kuckla
(74) *Attorney, Agent, or Firm* — Foley & Lardner LLP

(57) ABSTRACT

Disclosed herein are imidazotriazine and pyrrolopyrimidine derivatives or a stereoisomer thereof, or a pharmaceutically acceptable salt thereof useful as a G12C inhibitors, and a pharmaceutical composition comprising the same. Also disclosed herein is a method of treating cancer using the imidazotriazine and pyrrolopyrimidine derivatives or a stereoisomer thereof, or a pharmaceutically acceptable salt thereof as G12C inhibitors.

18 Claims, No Drawings

IMIDAZOTRIAZINE AND PYRROLOPYRIMIDINE DERIVATIVES AS KRAS G12C INHIBITORS

CROSS-REFERENCE TO RELATED APPLICATION

This application is a Section 371 of International Application No. PCT/CN2021/110640 filed Aug. 4, 2021, which was published in the English language Feb. 10, 2022, under International Publication No. WO 2022/028492 A1, which claims priority to International Application No. PCT/CN2020/107110 filed Aug. 5, 2020, the disclosures of which are incorporated herein by reference in their entireties.

FIELD OF THE INVENTION

Disclosed herein are imidazotriazine and pyrrolopyrimidine derivatives or a stereoisomer thereof, or a pharmaceutically acceptable salt thereof useful as G12C inhibitors, and a pharmaceutical composition comprising the same. Also disclosed herein is a method of treating cancer using the imidazotriazine and pyrrolopyrimidine derivatives or a stereoisomer thereof, or a pharmaceutically acceptable salt thereof as G12C inhibitors.

BACKGROUND OF THE INVENTION

RAS is one of the most well-known oncogenes. In human beings, three RAS genes (HRAS, KRAS and NRAS) encode four highly homologous RAS proteins (HRAS, KRAS-4A, KRAS-4B and NRAS). RAS proteins are small GTPases, they function as binary molecular switches that involved in transduction of extracellular growth and differentiation signaling.

RAS generally cycles between a GDP-bound "off" state and a GTP-bound "on" state. This cycle is regulated by several factors. Guanine nucleotide exchange factors (GEFs), including SOS1 and SOS2 facilitate the exchange and formation of GTP-bound RAS. While, GTPase-activating proteins (GAPs), for example, NF-1 promote the hydrolysis of GTP and therefore turn RAS back to GDP-bound inactivate state (Kessler et al, PNAS, 2019, 116 (32): 15823-15829). Once bound to GTP, RAS initiates conformational changes in two specific regions Switch 1 and Switch 2, which allows engagement and activation of downstream effector proteins to initiate a cascade of intracellular signaling pathways. These effectors include RAF-MEK-ERK and PI3K-AKT-mTOR pathways, both of which have crucial roles in regulating cell proliferation, differentiation, and survival (Cox et al., Nature Reviews Drug Discovery, 2014, 13:828-851).

RAS mutations have been identified in around 30% of human tumors. These mutations occur frequently as single-base missense mutations in codons 12, 13 or 61, resulting in stabilization of the activated GTP-bound RAS form and constitutive activation of RAS downstream signaling pathways. KRAS is the most frequently mutated RAS in cancer, account for 85% of all RAS-driven cancers, followed by NRAS (12%) and HRAS (3%). KRAS mutation has been detected in around 95% of pancreatic ductal adenocarcinoma, 50% of colorectal adenocarcinoma and 30% of lung adenocarcinoma. The majority of KRAS mutations occur at residue 12, and the mutation type varied in different cancers. In colon cancer and pancreatic cancer, the predominant KRAS mutation is G12D (glycine to lysine), while in non-small cell lung cancer (NSCLC), nearly half of KRAS mutations are G12C (glycine to cysteine) (Cox et al., Nature Reviews Drug Discovery, 2014, 13:828-851).

Based on the critical role of RAS in cell proliferation and its high mutation rate in human cancers, RAS has long been considered as a therapeutic target for many cancers. However, despite several decades of research effort, no anti-RAS small molecular has been clinically approved. The main reason is that druggable pockets on the surface of RAS are lacking (Papke et al., Science, 2017, 355: 1158-1163). Recently, more and more studies suggested that RAS might be able to be drugged with small molecules. Several inhibitors that directly target KRAS G12C are under the investigation (Patricelli et al, Cancer Discovery, 2016, 6(3); 316-29) (Fell et al, ACS Med. Chem. Lett. 2018, 9, 12, 1230-1234).

Small molecule selectively inhibitors of KRAS are being developed to prevent or treat diseases, for example, WO2015/054572A1 provides compounds having activity as inhibitors of G12C mutant RAS protein. WO2016/164675A1 and WO2017/015562A1 disclose substituted quinazoline compounds as KRAS G12C inhibitors. Compounds with KRAS G12C inhibitory activity are further reported by WO2014/152588A1, WO2016/049524A1, WO2016/168540A1, WO2017/058728A1, WO2017/058792A1, WO2017/058805A1, WO2017/058915A1, WO2017/087528A1, WO2018/064510A1, WO2018/068017A1, WO2018/119183A2, WO2018/206539A1, WO2018/218069A1, WO2019/051291A1, WO2019/055540A1, WO2019/137985A1, WO2019/141250A1, WO2019/150305A1, WO2019/155399A1, WO2019/213516 A1, WO2019/213526A1, WO2019/215203A1, WO20192/17307A1, WO2019/217691A1, WO2019/232419A1, WO2020/028706A1, WO2020/027084A1, WO2020/027083A1, WO2020/035031A1, WO2020/047192A1.

Thus, new inhibitors that selectively target mutant KRAS with high efficacy and safety are still highly desirable. Continued efforts on developing KRAS G12C inhibitors will arise a new therapeutic way for KRAS G12C driven cancers.

SUMMARY OF THE INVENTION

One objective of the present invention is to provide compounds exhibiting potent KRAS G12C inhibitory activity. Disclosed herein are compounds, or pharmaceutically acceptable salts, stereoisomers thereof.

Aspect 1: A compound of Formula (I) or (II):

(I)

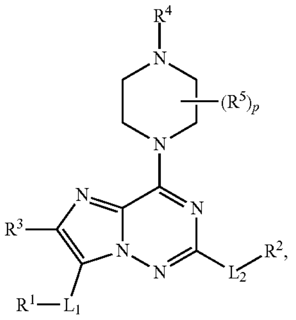

-continued (II)

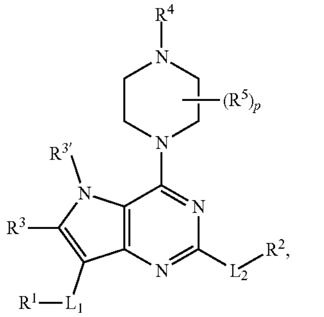

or a pharmaceutically acceptable salt thereof, or a stereoisomer thereof, wherein $L_1$ and $L_2$ are each selected from a single bond, —CO—NH—, —NH—CO—, —O—, —$NR^a$—, —$NR^a(CH_2)_m$—, —S—, —$(CH_2)_m$—, —O—$(CH_2)_m$—, —O—$CH(R^a)$—, —$CH(R^a)$—, —$CH(R^a)(CH_2)_m$—, —$(CH_2)_mO$—, —CO—, —$SO_2$—, cycloalkylene, oxetandiyl, tetrahydrofurandiyl, tetrahydropyrandiyl, azetidindiyl, pyrrilidindiyl, piperidindiyl, or piperizindiyl;

$R^1$ is selected from —$C_{1-8}$alkyl, —$C_{2-8}$alkenyl, —$C_{2-8}$alkynyl, —$NR^bR^c$, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^6$ (such as —$(R^6)_{q1}$, wherein each $R^6$ are the same or different in case q1 is more than 1);

$R^2$ is selected from —$NR^bR^c$, cycloalkyl, heterocyclyl, aryl, or heteroaryl, each of said cycloalkyl, heterocyclyl, aryl, or heteroaryl is optionally substituted with at least one $R^6$ (such as —$(R^6)_{q2}$, wherein each $R^6$ are the same or different in case q2 is more than 1), each $R^6$ is selected from —$C_{1-8}$alkyl, halogen, hydroxy, oxo, —$C_{1-8}$alkoxy, —$NR^bR^c$, cycloalkyl, heterocyclyl, aryl, or heteroaryl, wherein said —$C_{1-8}$alkyl, —$C_{1-8}$alkoxy, cycloalkyl, heterocyclyl, aryl, or heteroaryl is optionally substituted with at least one halogen, hydroxy, amino, CN, cycloalkyl, heterocyclyl, aryl or heteroaryl, or two $R^6$, when on two adjacent carbon atoms of a phenyl ring, together with the two intervening carbon atoms to which they are attached, form a 5- to 8-membered ring comprising 0, 1 or 2 heteroatoms independently selected from nitrogen, oxygen or optionally oxidized sulfur as ring member (s);

$R^3$ is selected from hydrogen, halogen, oxo, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^{3'}$ is selected from hydrogen, oxo, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^4$ is selected from

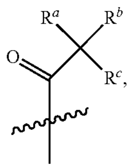 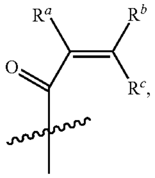 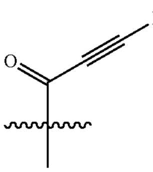 ,

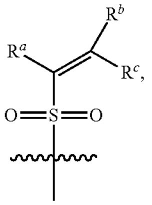 or 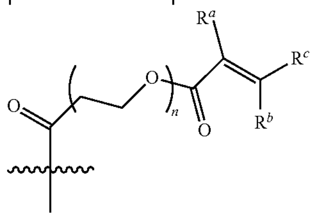 ;

$R^5$ is selected from hydrogen, halogen, —$C_{1-8}$alkyl, —$C_{2-8}$alkenyl, —$C_{2-8}$alkynyl, oxo, —$NR^bR^c$, —$(CH_2)_m$—C(O)—$NR^dR^e$, cycloalkyl, heterocyclyl, aryl, heteroaryl or —$(CH_2)_m$—CN;

each $R^a$, $R^b$ and $R^c$ are independently hydrogen, deuterium (D), cyano (CN), halogen, hydroxy, —$C_{1-8}$alkoxy, —$C_{1-8}$alkyl, —$C_{2-8}$alkenyl, —$C_{2-8}$alkynyl, cycloalkyl, heterocyclyl, aryl, heteroaryl, —$NR^dR^e$, or —CO—$NR^dR^e$, each of said —$C_{1-8}$alkyl, —$C_{2-8}$alkenyl, —$C_{2-8}$alkynyl, cycloalkyl, heterocyclyl, aryl, or heteroaryl is optionally substituted with $R^f$; or ($R^a$ and $R^b$), ($R^a$ and $R^c$) or ($R^b$ and $R^c$) together with the atom(s) to which they are attached, form a 4- to 6-membered ring, said ring is optionally substituted with at least one $R^g$;

each $R^f$ is selected from halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, or heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$ and $R^f$ are each independently hydrogen, deuterium (D), halogen, oxo, or —$C_{1-8}$alkyl; each said —$C_{1-8}$alkyl is optionally substituted with at least one halogen, oxo, —$CF_3$ or —$COCH_3$;

p is independently selected from 0, 1, 2, 3 or 4;

q1 and q2 are independently selected from 0, 1, 2, 3, 4, 5, 6, 7 or 8;

each m and n are independently 0, 1, 2, 3, 4, 5 or 6.

Aspect 2: The compound according to Aspect 1, wherein $R^1$ is selected from —$C_{2-4}$alkenyl; carbocyclic ring selected from 5- to 6-membered monocyclic carbocyclic ring (e.g., phenyl), 7- to 12-membered bicyclic carbocyclic ring (e.g., naphthalenyl, indenyl, or indanyl) and 10- to 15-membered tricyclic carbocyclic ring (e.g., fluorenyl); heteroaryl ring selected from 5- to 8-membered monocyclic heteroaryl, 7- to 12-membered bicyclic heteroaryl and 11- to 14-membered tricyclic heteroaryl; heterocyclyl ring selected from 4- to 9-membered monocyclic heterocyclyl, 7- to 12-membered bicyclic heterocyclyl and 11- to 14-membered tricyclic heterocyclyl; each of said —$C_{2-4}$alkenyl, carbocyclic ring, heteroaryl ring and heterocyclyl ring is optionally substituted with at least one $R^6$ (such as —$(R^6)_{q1}$, wherein each $R^6$ are the same or different in case q1 is more than 1), wherein $R^6$ is selected from halogen, hydroxy, oxo, —$NR^bR^c$, —$C_{1-8}$ alkyl, —$C_{1-8}$alkoxy, -halo$C_{1-8}$ alkyl, cycloalkyl, heterocyclyl, aryl, or heteroaryl; wherein $R^b$ and $R^c$ are independently hydrogen, deuterium (D), or —$C_{1-8}$alkyl.

Aspect 3: The compound according to any one of Aspects 1 or 2, wherein $R^1$ is selected from phenyl, naphthalenyl, indanyl, fluorenyl, indazolyl, dihydroacenaphthylenyl, quinolinyl, isoquinolinyl, indolyl, 2,3-dihydrobenzofuranyl, or dihydroindenyl, wherein each of said phenyl, naphthalenyl, indanyl, fluorenyl, indazolyl, dihydroacenaphthylenyl, quinolinyl, isoquinolinyl, indolyl, 2,3-dihydrobenzofuranyl or dihydroindenyl is optionally substituted with at least one $R^6$ selected from $-C_{1-8}$alkyl, $-C_{1-8}$alkoxy, -halo$C_{1-8}$ alkyl, oxo, halogen, hydroxy, $-NH_2$, or $C_{3-6}$ cycloalkyl.

Aspect 4: The compound according to any one of Aspects 1-2, wherein $R^1$ is selected from,

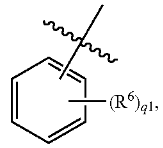

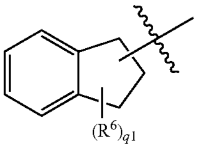

,

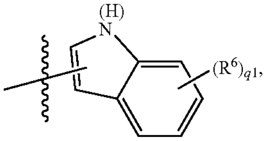

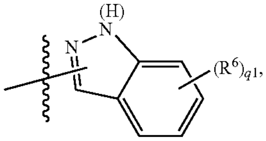

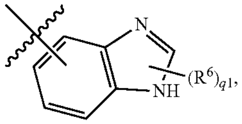

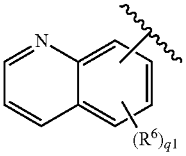

,

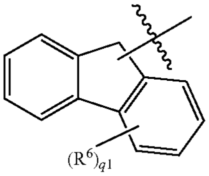

,

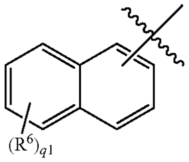

,

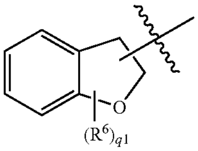

,

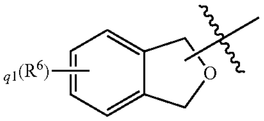

,

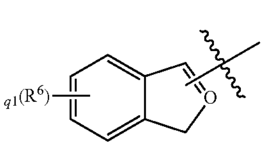

,

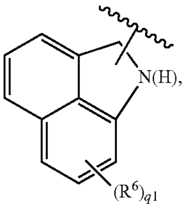

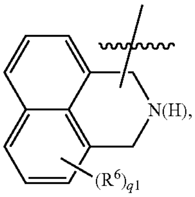

or

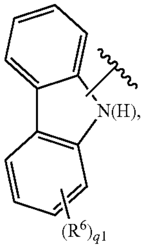

wherein $R^6$ is selected from F, Br, Cl, OH, $-OCH_3$, oxo, CN, $-CH_2CN$, $-NH_2$, $-CF_3$, $-CF_2H$,

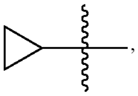 [SMILES: *C1CC1]

, $CH_2CH_3$, or $CH_3$; and wherein q1=0, 1 or 2.

Aspect 5: The compound according to any one of Aspects 1-4, wherein $R^1$ is selected from

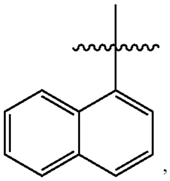

,

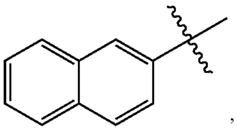

,

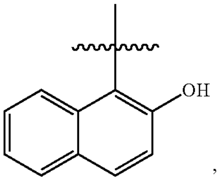

,

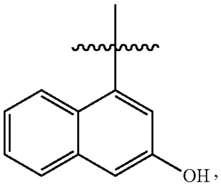

,

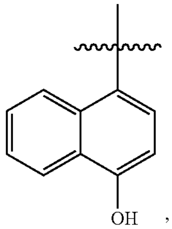

,

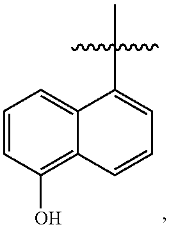

,

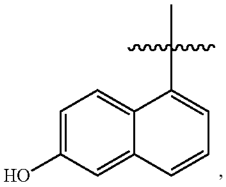

,

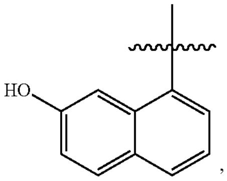

,

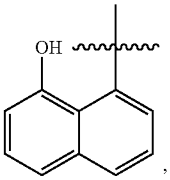

,

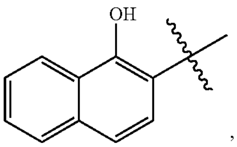

,

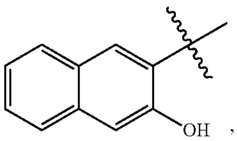

,

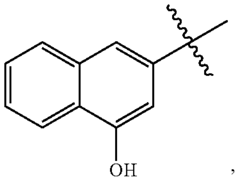

,

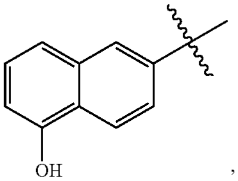

,

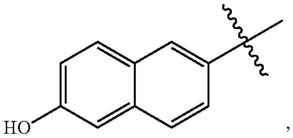

,

-continued
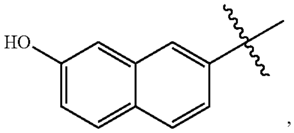, 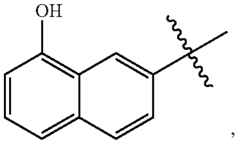,
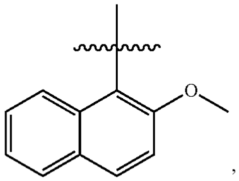, 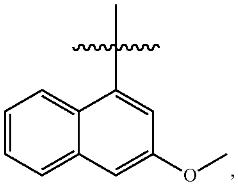,
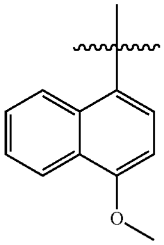, 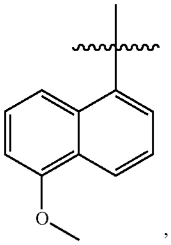,
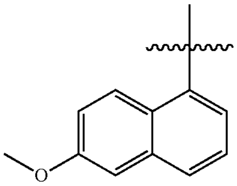, 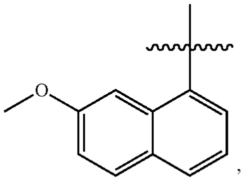,
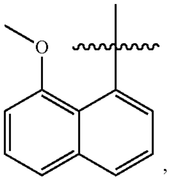, 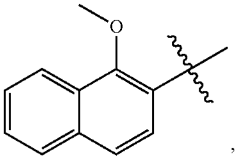,
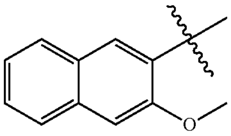, 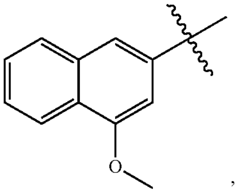,
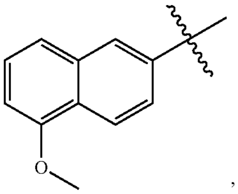, 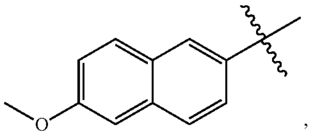,
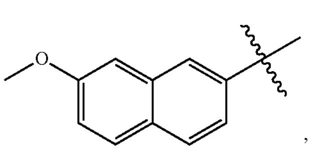, 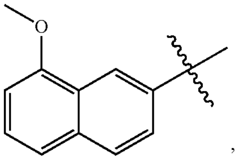,
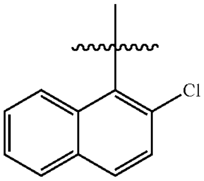, 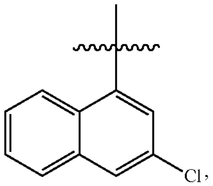,
-continued
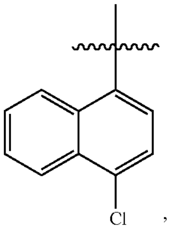, 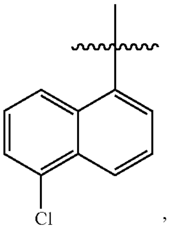,
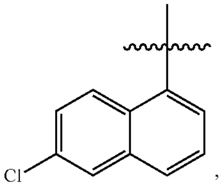, 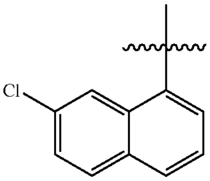,
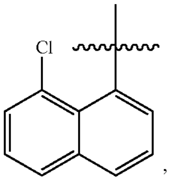, 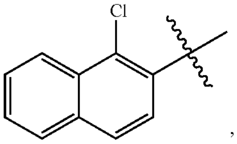,
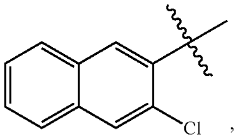, 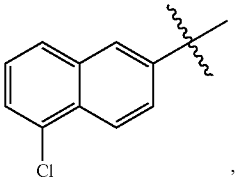,
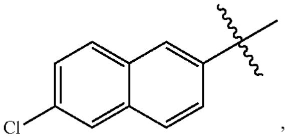,
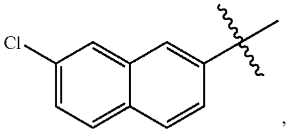, 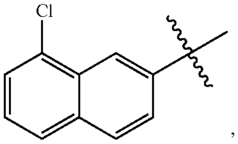,
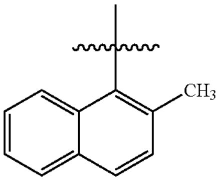, 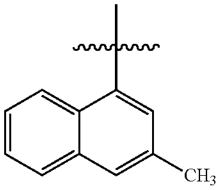,
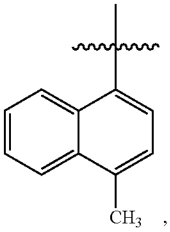, 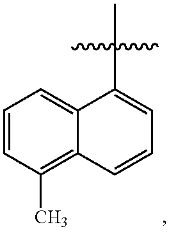,
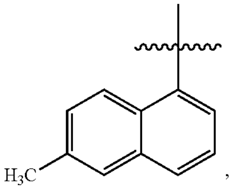, 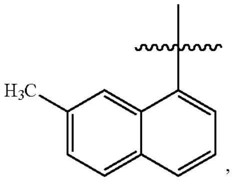, -continued
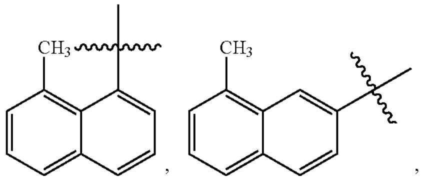
, ,
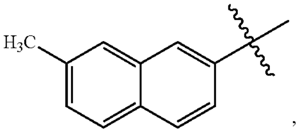
,
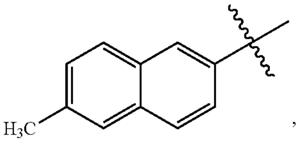
,
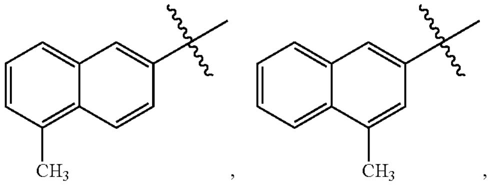
, ,
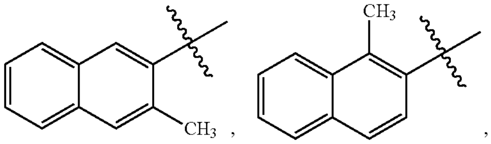
, ,
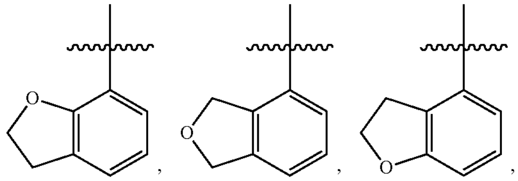
, , ,
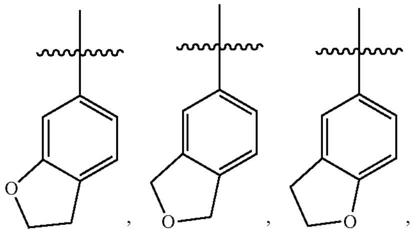
, , ,
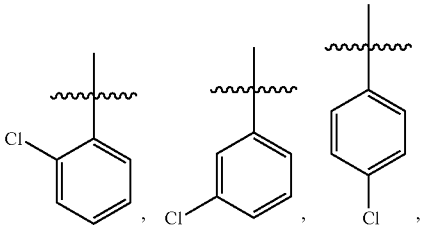
, , ,
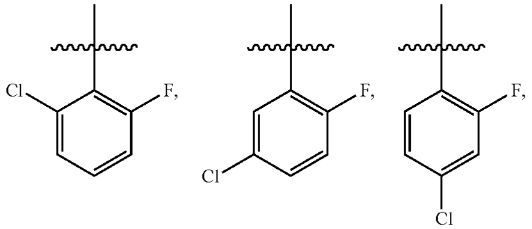
-continued
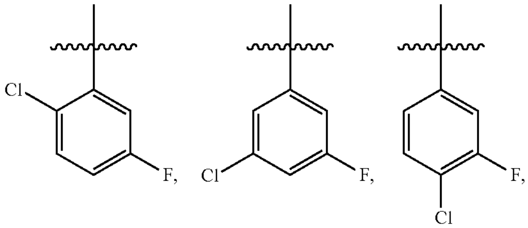
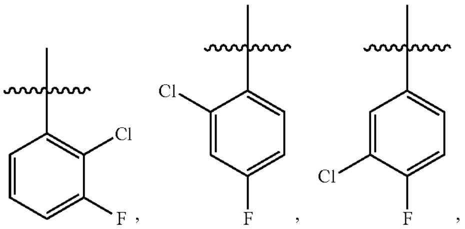
, , ,
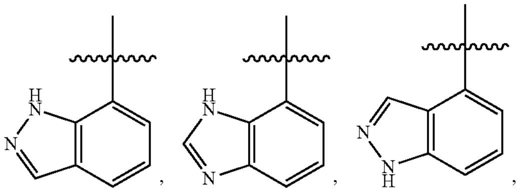
, , ,
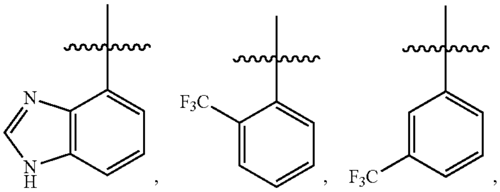
, , ,
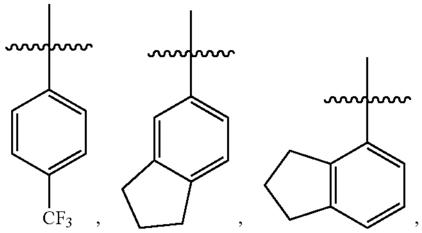
, , ,
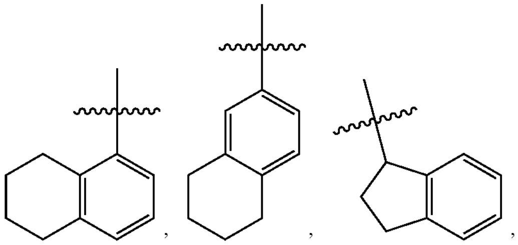
, , ,
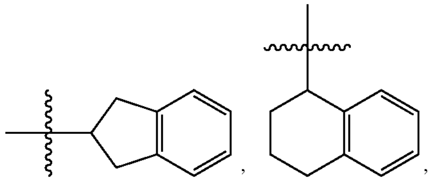
, ,
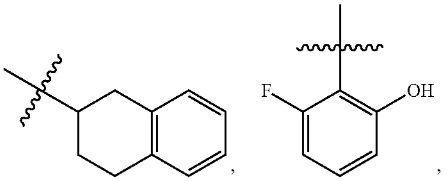
, , -continued
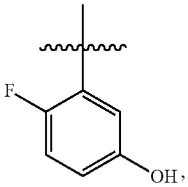,
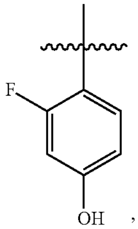,
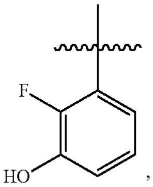,
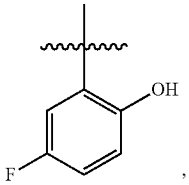,
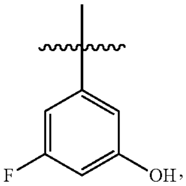,
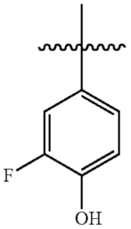,
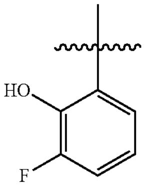,
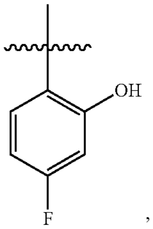,
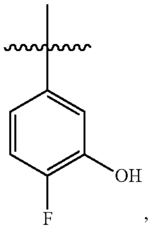,
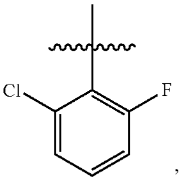,
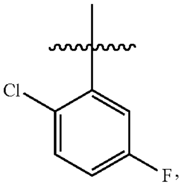,
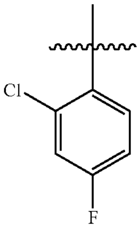,
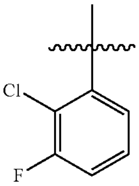,
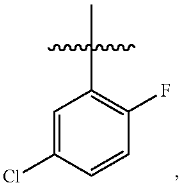,
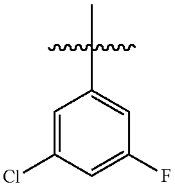,
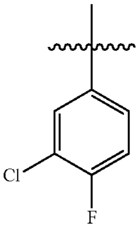,
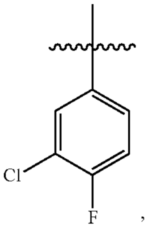,
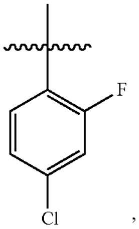,
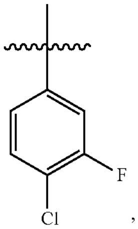,
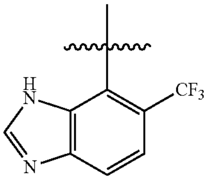,
-continued
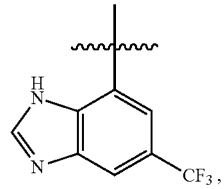,
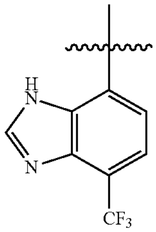,
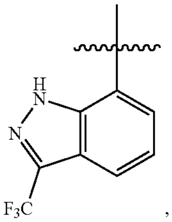,
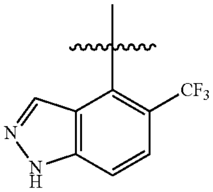,
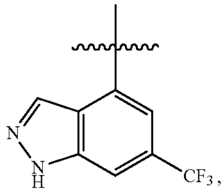,
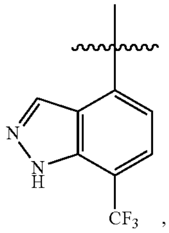,
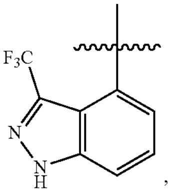,
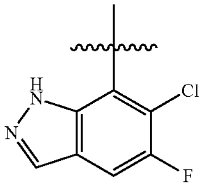,
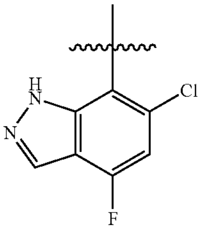,
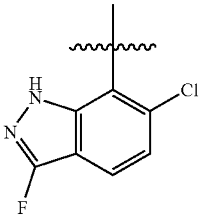,
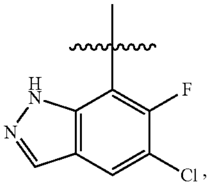,
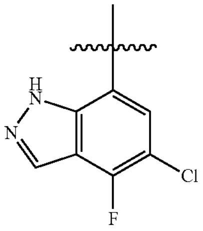,
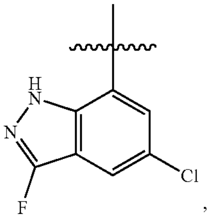,
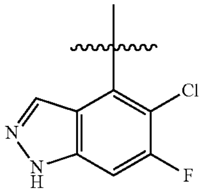, -continued

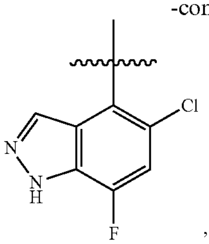,
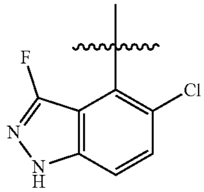,
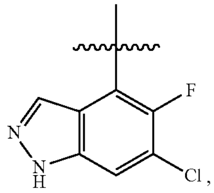,
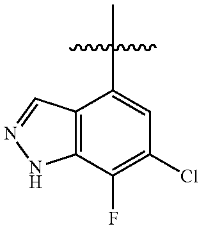,
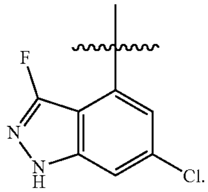.

Aspect 6: The compound according to any one of Aspects 1-5, wherein $L_1$ is selected from a single bond, —CO—NH—, —$CH_2$—, —$CH_2CH_2$—, —$CH_2CH_2CH_2$—, —C(O)—, or —$CH(CH_3)$—.

Aspect 7: The compound according to any one of Aspects 1-6, wherein $L_2$ is selected from a single bond, —O—, —O—$(CH_2)_m$—, —O—$CH(R^a)$—, —O—$CH(R^a)$—$(CH_2)_m$—, cyclopropylene, azetidindiyl, and —$NR^a(CH_2)_m$—, wherein m=1 or 2; and $R^a$ is selected from hydrogen, methyl, or deuterium (D).

Aspect 8: The compound according to any one of Aspects 1-7, wherein $L_2$ is selected from a single bond —O—$CH_2$—, —O—$CH_2CH_2$—, —O—$CH_2CH_2CH_2$—, —O—, —O—$CH(CH_3)$—, —NH—$CH_2$—, —NH—$CH_2CH_2$—, —O—$CH(CH_3)CH_2$—,

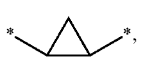, 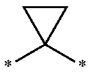, 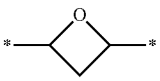, 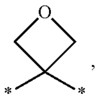, 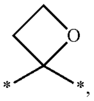, 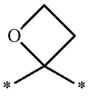 or 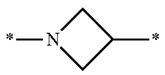, wherein the asterisks * refer to the linking positions.

Aspect 9: The compound according to any one of Aspects 1-5, wherein $R^2$ is selected from

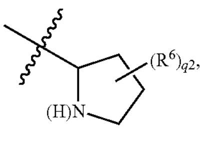 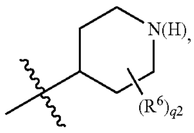

-continued

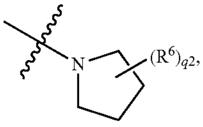

—$NR^bR^c$,

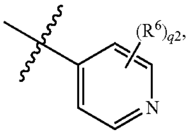 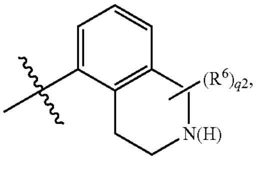 or

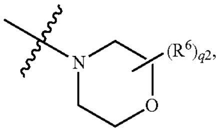

wherein each $R^6$ is selected from halogen, hydroxy, —$C_{1-8}$alkyl, —$C_{1-8}$alkoxy and heterocyclyl, wherein —$C_{1-8}$alkyl is optionally substituted with hydroxy or halogen; each q2 is 0, 1, 2 or 3; $R^b$ and $R^c$ are independently hydrogen, deuterium (D), halogen, or —$C_{1-8}$alkyl.

Aspect 10: The compound according to Aspect 9, wherein $R^6$ is selected from $CH_3$, OH, $CH_2OH$, F, —$CHF_2$, —$OCH_3$, Cl, or Br, or

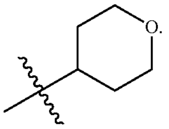

Aspect 11: The compound according to any one of Aspects 1-10, wherein $R^2$ is selected from

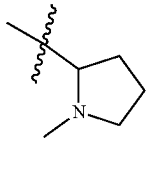, 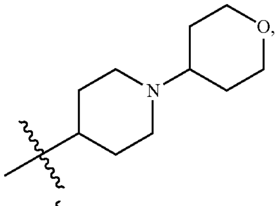

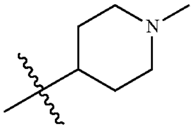, 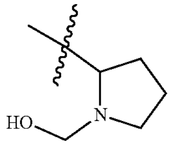, 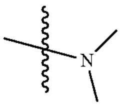,

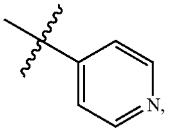 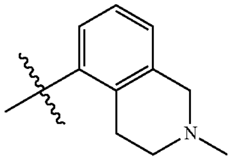,

-continued

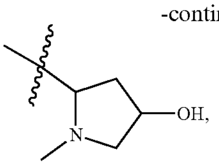

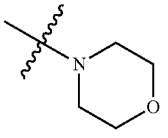

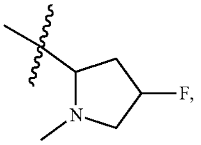

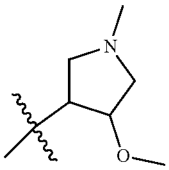

(such as

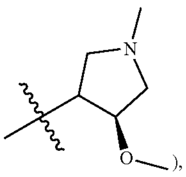

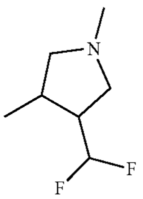

(such as

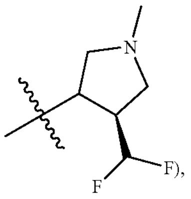

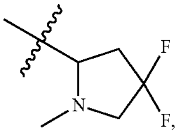

or

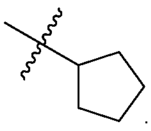

Aspect 12: The compound according to any one of Aspects 1-11, wherein $R^3$ is selected from hydrogen, halogen, oxo, or —$C_{1-8}$alkyl.

Aspect 13: The compound according to any one of Aspects 1-12, wherein $R^4$ is

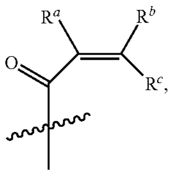

wherein $R^a$ is selected from hydrogen, deuterium (D), halogen (F, Cl, Br or I), —$C_{1-8}$alkyl or —$C_{1-8}$alkoxy, said —$C_{1-8}$alkyl or —$C_{1-8}$alkoxy is optionally substituted with at least one halogen (such as F, Cl), hydroxy, —$C_{1-8}$alkoxy, or —$NR^dCOR^e$;

$R^b$ is selected from hydrogen and —$C_{1-8}$alkyl;

$R^c$ is selected from hydrogen, halogen (such as F, Cl, Br or I), —$C_{1-8}$alkyl, —CN, —$NR^dR^e$, —CO—$NR^dR^e$, or heteroaryl (such as pyridinyl, pyrazole or imidazole), wherein said —$C_{1-8}$alkyl is optionally substituted with at least one $R^f$;

each $R^f$ is selected from halogen (e.g., F, Br or Cl), hydroxy, —$NR^dR^e$, —$C_{1-8}$alkoxy, 4- to 7-membered heterocyclyl (such as azetidinyl, pyrrolidinyl, piperidinyl, or morpholinyl), wherein each said —$C_{1-8}$alkoxy or 4- to 7-membered heterocyclyl is optionally substituted with halogen, hydroxy or —$C_{1-4}$alkyl; and $R^d$ and $R^e$ are each independently hydrogen, deuterium (D), halogen or —$C_{1-8}$alkyl, wherein said —$C_{1-8}$alkyl is optionally substituted with at least one halogen or —$COCH_3$.

Aspect 14: The compound according to any one of Aspects 1-12, wherein $R^4$ is selected from

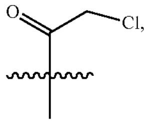

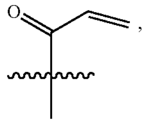

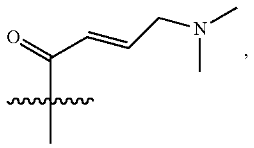

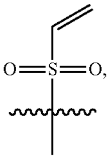

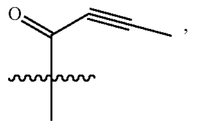

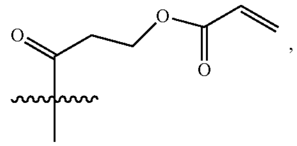

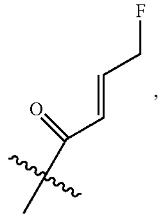

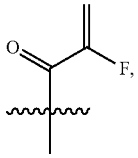

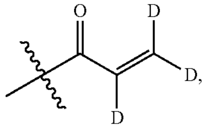

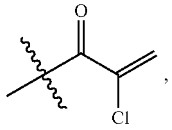

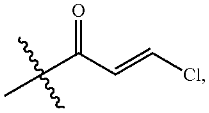

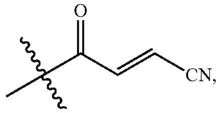

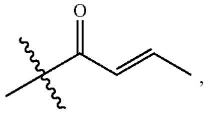

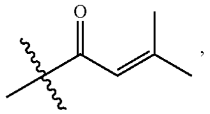

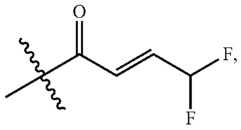

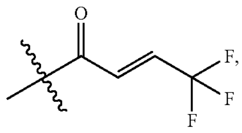

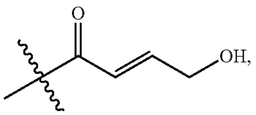

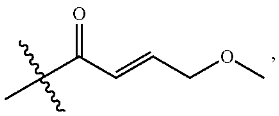

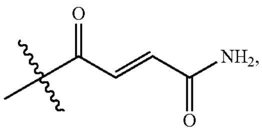

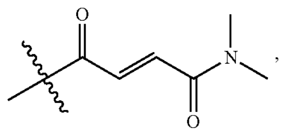

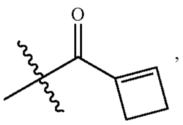

-continued

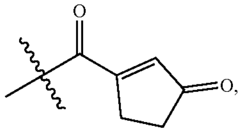O,

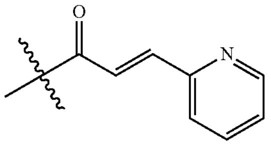,

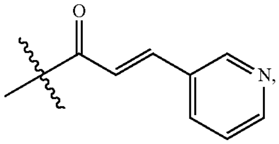N,

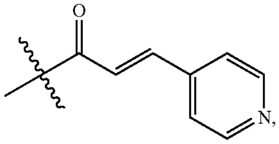N,

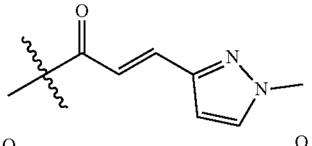,

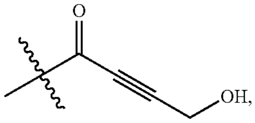OH,

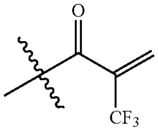,

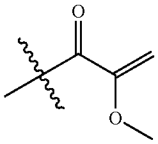,

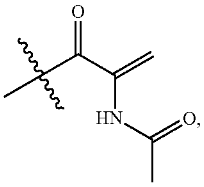O,

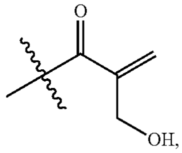OH,

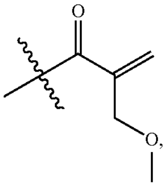O,

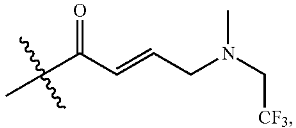CF3,

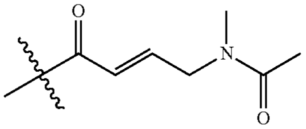,

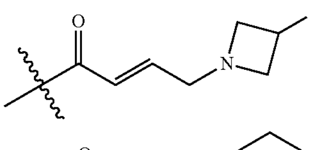F,

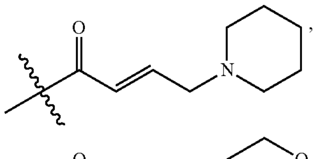,

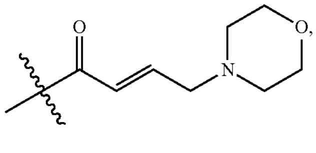O,

-continued

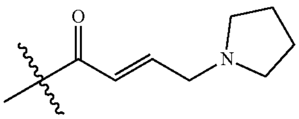,

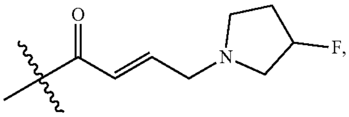F,

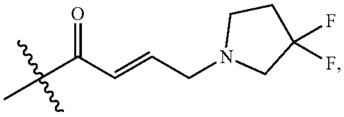F, or

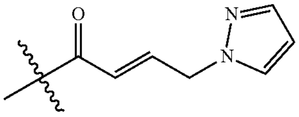.

Aspect 15: The compound according to any one of Aspects 1-14, wherein $R^5$ is selected from hydrogen, halogen, —$C_{1-8}$alkyl, —$NR^bR^c$, —$(CH_2)_m$—C(O)—$NR^dR^e$, or —$(CH_2)_m$~CN, each $R^b$ and $R^c$ are independently hydrogen, —$C_{1-8}$alkyl, —$C_{2-8}$alkenyl, —$C_{2-8}$alkynyl, cycloalkyl, heterocyclyl, aryl, or heteroaryl; or ($R^b$ and $R^c$) together with the atom(s) to which they are attached, form a 4- to 6-membered ring, said ring is optionally substituted with at least one $R^g$;

$R^d$, $R^e$ and $R^g$ are each independently hydrogen, deuterium (D), halogen, oxo, —$C_{1-8}$alkyl; and each m is independently 0, 1, 2, or 3.

Aspect 16: The compound according to any one of Aspects 1-15, wherein $R^5$ is selected from —$CH_3$, —$C_2H_5$, —$C_3H_7$, —$C_4H_9$, —$C_5H_{11}$, —$(CH_2)_m$—C(O)—$NR^dR^e$, —$(CH_2)_m$~CN, or hydrogen, wherein each m=0 or 1; and p=1.

Aspect 17: The compound according to Aspect 1 selected from

A1

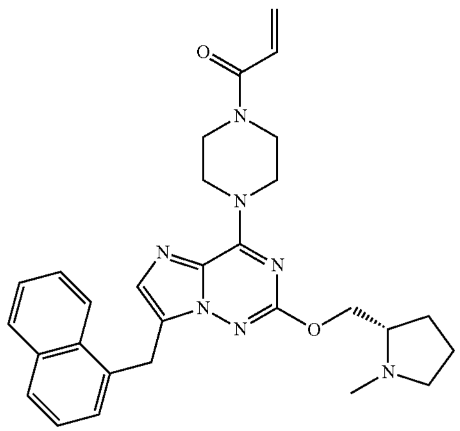

-continued
A2
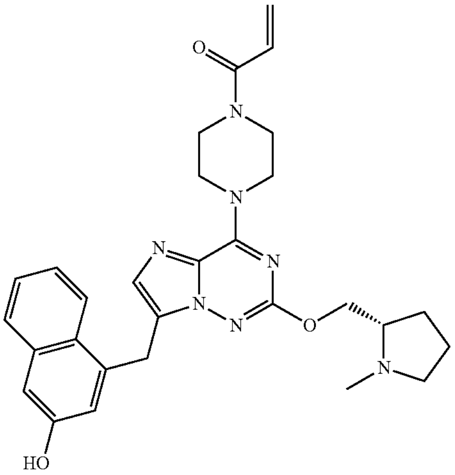
A3
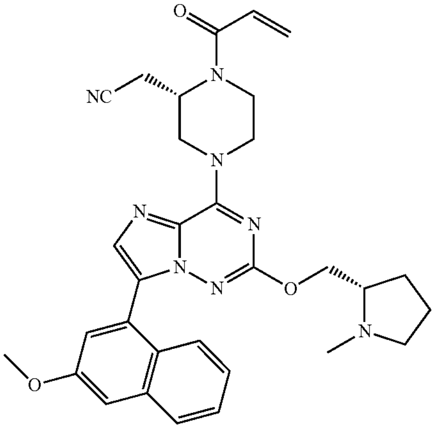
A4
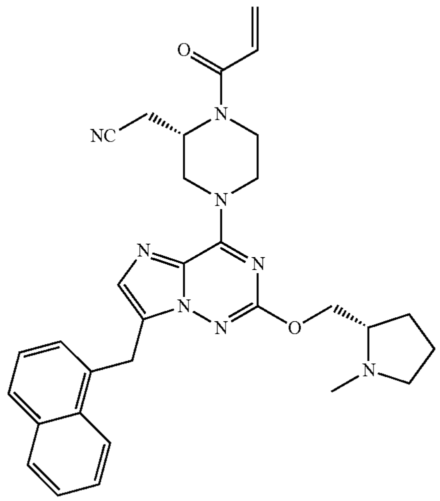
-continued
A5
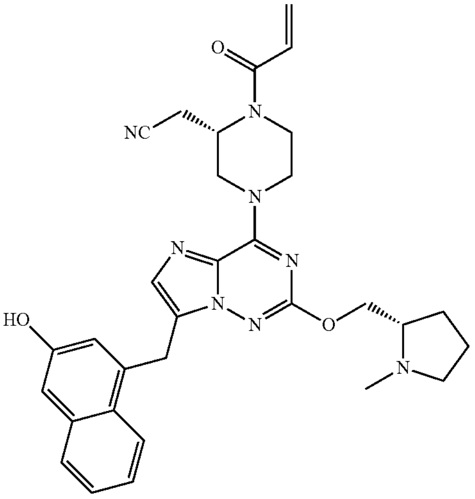
A6
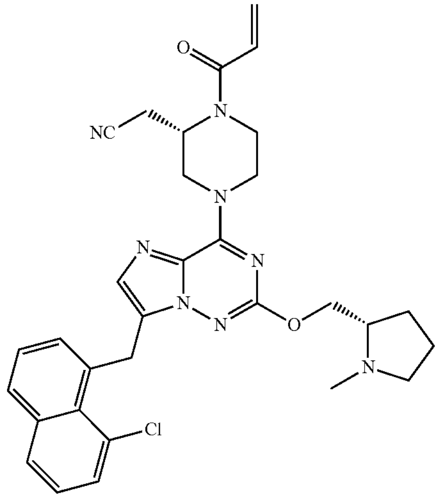
A7
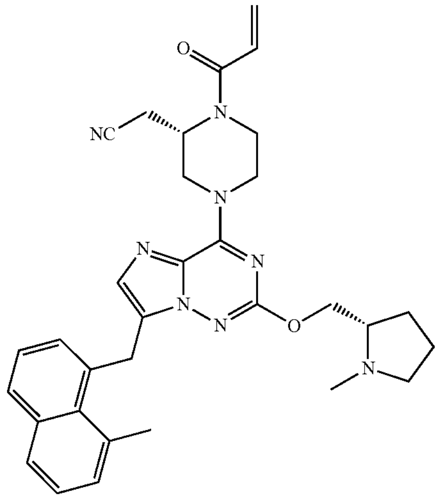

-continued
A8
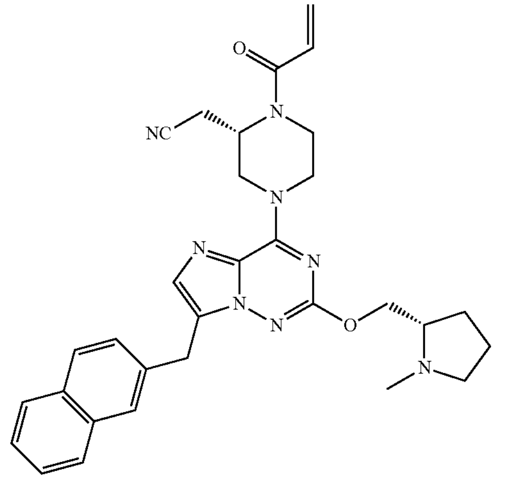
A9
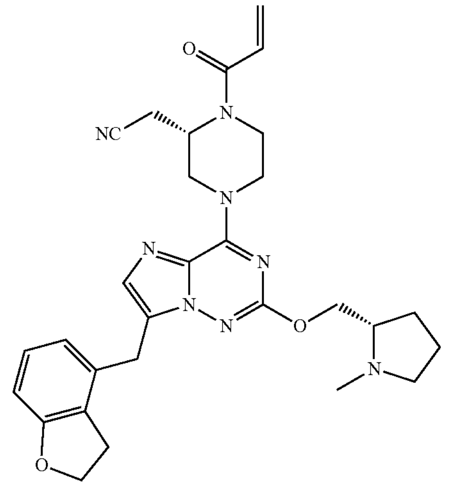
A10
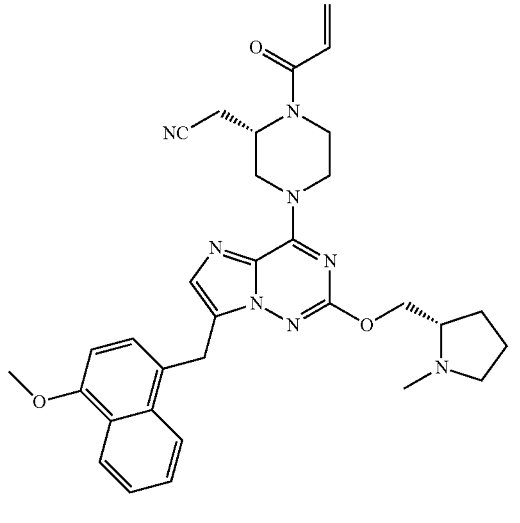
-continued
A11
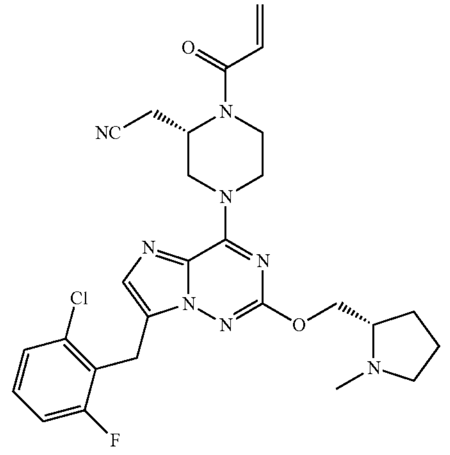
A12
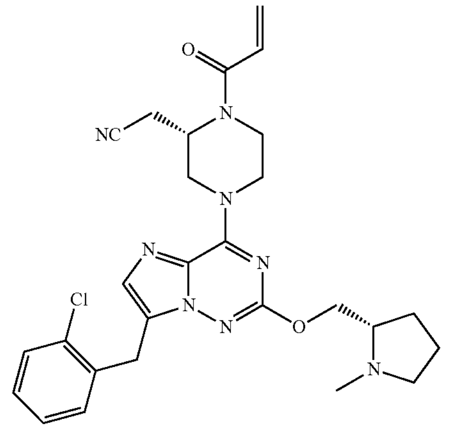
A13
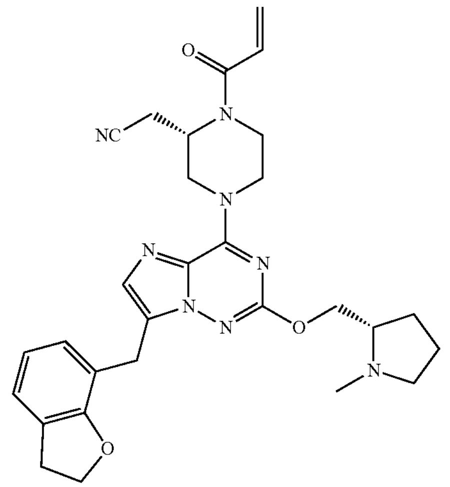

-continued
A14
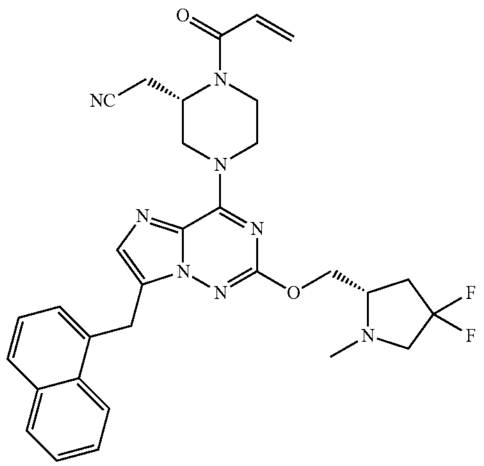
A15
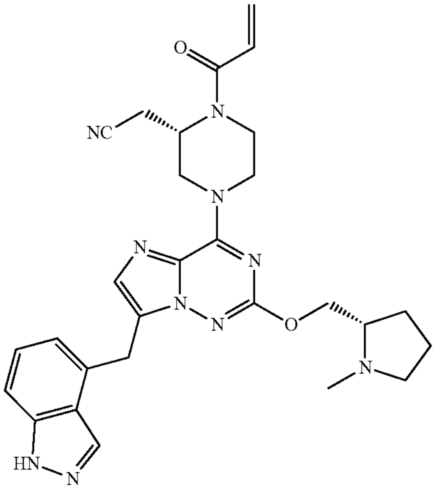
A16
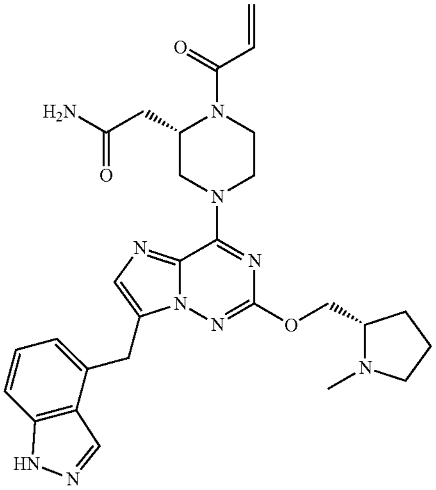
-continued
A17
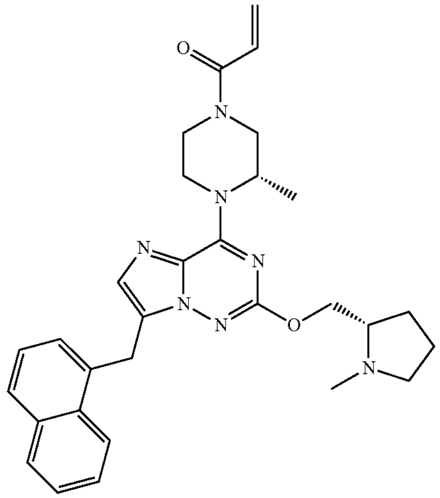
A18
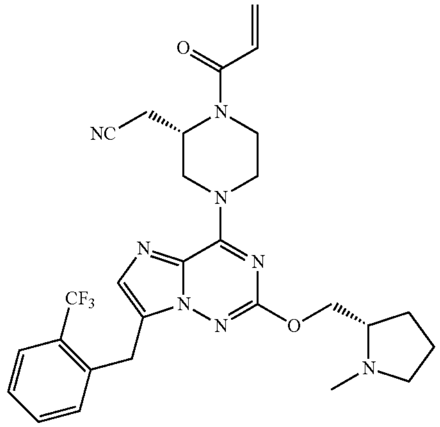
A19
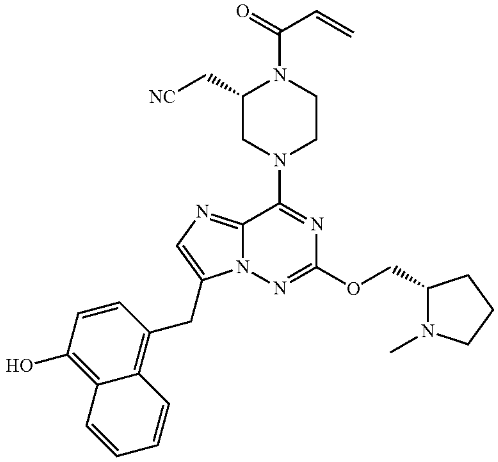

-continued
A20
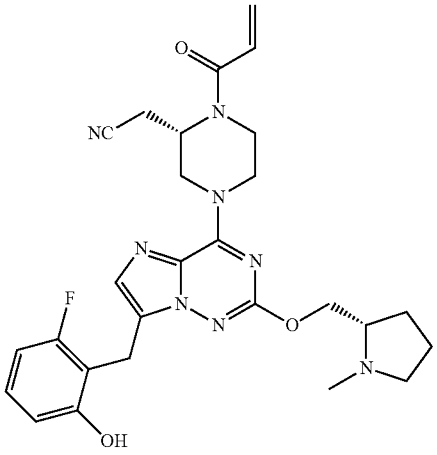
A21
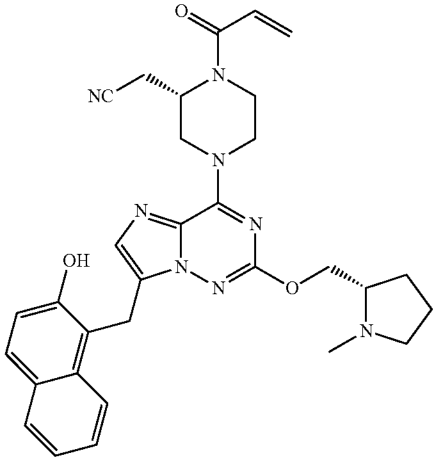
A22
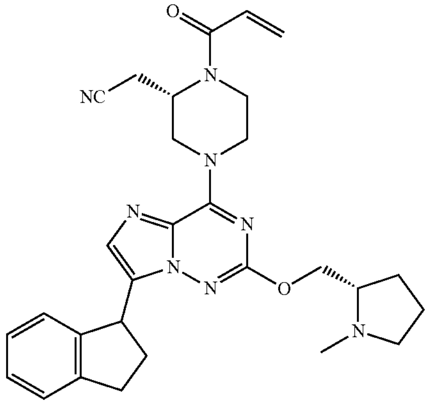
-continued
A23
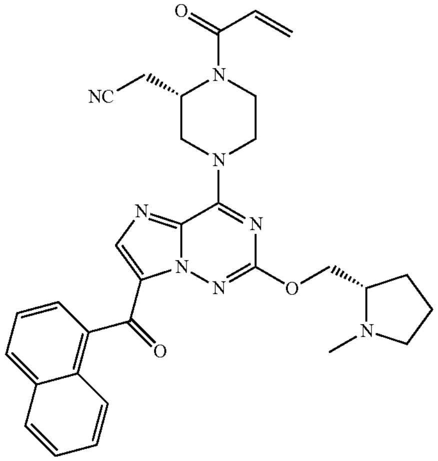
B1
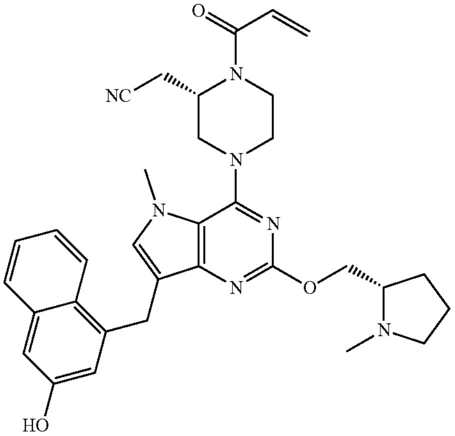
B2
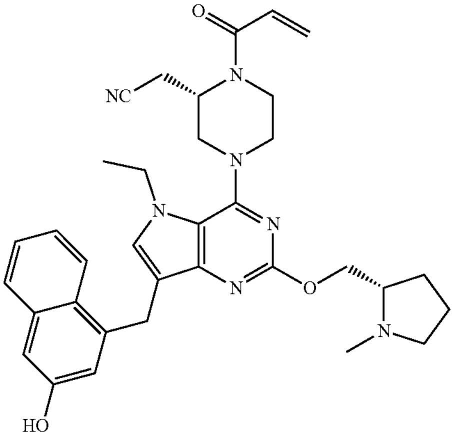

-continued

B3

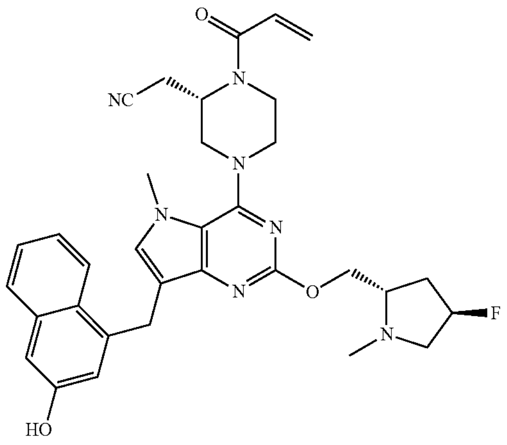

B4

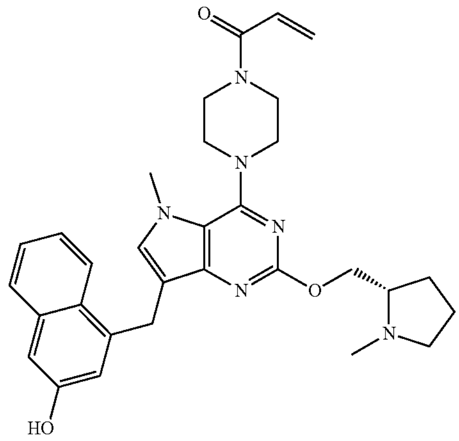

B5

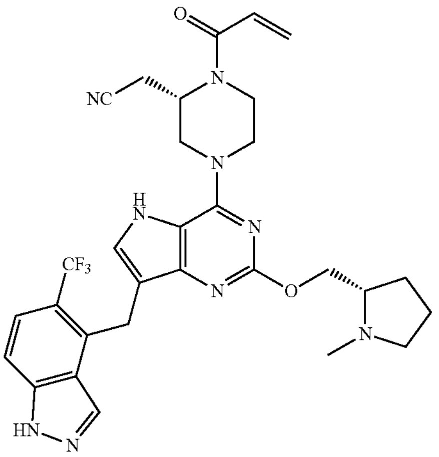

-continued

B6

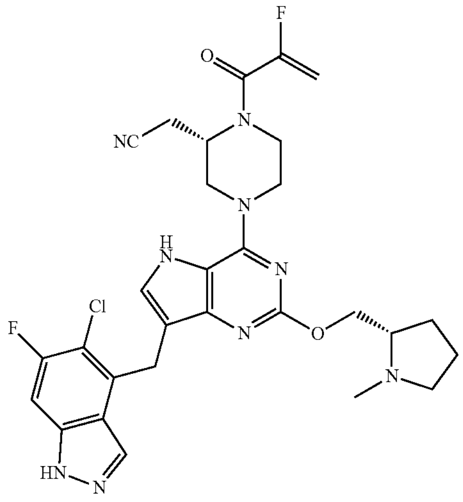

or a pharmaceutically acceptable salt thereof, or a stereoisomer thereof.

Aspect 18: A pharmaceutical composition comprising the compound of any of aspects 1-17 or a stereoisomer thereof, or a pharmaceutically acceptable salt thereof and a pharmaceutically acceptable excipient.

Aspect 19: A method of treating cancer, comprising administering a subject in need thereof the compound of any of aspects 1-17 or a stereoisomer thereof, or a pharmaceutically acceptable salt thereof.

DETAILED DESCRIPTION OF THE INVENTION

The following terms have the indicated meanings throughout the specification:

As used herein, including the appended claims, the singular forms of words such as . . . .

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as “a”, “an”, and “the”, include their corresponding plural references unless the context clearly indicates otherwise.

The term “or” is used to mean, and is used interchangeably with, the term “and/or” unless the context clearly dictates otherwise.

The term “alkyl” refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl (“n-Pr”), 2-propyl or isopropyl (“i-Pr”), 1-butyl or n-butyl (“n-Bu”), 2-methyl-1-propyl or isobutyl (“i-Bu”), 1-methylpropyl or s-butyl (“s-Bu”), 1, 1-dimethylethyl or t-butyl (“t-Bu”), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl groups. An alkyl group defined herein is optionally deuterated or tritiated.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1, 1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl and 3, 3-dimethyl-2-butyl.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl or halo $C_{1-4}$alkyl, but not limited to —$CF_3$, —$CH_2Cl$, —$CH_2CF_3$, —$CHCl_2$, —$CF_3$, and the like.

The term "alkenyl" refers to a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1, 3-dienyl, 2-methylbuta-1, 3-dienyl, hex-1-enyl, hex-2-enyl, hex-3-enyl, hex-4-enyl, and hexa-1, 3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from a monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4, 4], [4, 5], [5, 5], [5, 6] and [6, 6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5, 6] and [6, 6] ring systems.

The term "spiro cycloalkyl" refers to a cyclic structure which contains carbon atoms and is formed by at least two rings sharing one atom. The term "7 to 12 membered spiro cycloalkyl" refers to a cyclic structure which contains 7 to 12 carbon atoms and is formed by at least two rings sharing one atom.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contains at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

The term "benzo fused cycloalkyl" is a bicyclic fused cycloalkyl in which a 4- to 8-membered monocyclic cycloalkyl ring fused to a benzene ring. For example, a benzo fused cycloalkyl is

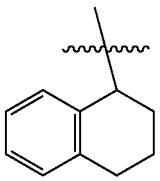
and
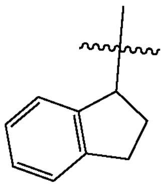

wherein the wavy lines indicate the points of attachment.

The term a "benzo fused cycloalkenyl" is a bicyclic fused cycloalkenyl in which a 4- to 8-membered monocyclic cycloalkenyl ring fused to a benzene ring.

The term a "benzo fused cycloalkynyl" is a bicyclic fused cycloalkynyl in which a 4- to 8-membered monocyclic cycloalkynyl ring fused to a benzene ring.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2, 3-dihydro-1H-indenyl, 1H-indenyl, 1, 2, 3, 4-tetralyl, dihydroindenyl (e.g., 2,3-dihydro-1H-indene), dihydronaphthyl (e.g., 1, 4-dihydronaphthyl), dihydroacenaphthylenyl, etc. Preferred embodiments are a 8 to 9 membered fused ring, which refer to cyclic structures containing 8 to 9 ring atoms within the above examples.

The term "aryl" used alone or in combination with other terms refers to a group selected from:

a) 5- and 6-membered carbocyclic aromatic rings, e.g., phenyl;

b) bicyclic ring systems such as 7- to 12-membered bicyclic ring systems, wherein at least one ring is carbocyclic and aromatic, e.g., naphthyl and indanyl; and, c) tricyclic ring systems such as 10- to 15-membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:

a) 5-, 6-, 7- or 8-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring (s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include, but not limited to, the following groups benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinyl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2, 4-pyrimidinyl, 3, 5-pyrimidinyl, 2, 4-imidazolyl, imidazopyridinyl, isoxazolyl, oxazolyl, thiazolyl, isothiazolyl, thiadiazolyl (such as 1, 2, 3-thiadiazolyl, 1, 2, 4-thiadiazolyl, or 1, 3, 4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1, 2, 3-oxadiazolyl, 1, 2, 4-oxadiazolyl, or 1, 3, 4-oxadiazolyl), phthalazinyl, pyrazinyl, pyridazinyl, pyrrolyl, triazolyl (such as 1, 2, 3-triazolyl, 1, 2, 4-triazolyl, or 1, 3, 4-triazolyl), quinolinyl, isoquinolinyl, pyrazolyl, pyrrolopyridinyl (such as 1H-pyrrolo[2, 3-b]pyridin-5-yl), pyrazolopyridinyl (such as 1H-pyrazolo[3, 4-b]pyridin-5-yl), benzoxazolyl (such as benzo[d]oxazol-6-yl), pteridinyl, purinyl, 1-oxa-2, 3-diazolyl, 1-oxa-2, 4-diazolyl, 1-oxa-2, 5-diazolyl, 1-oxa-3, 4-diazolyl, 1-thia-2, 3-diazolyl, 1-thia-2, 4-diazolyl, 1-thia-2, 5-diazolyl, 1-thia-3, 4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl), or carbazolyl (9H-carbazolyl).

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term “optionally oxidized sulfur” used herein refer to S, SO or $SO_2$.

The term “monocyclic heterocyclyl” refers to monocyclic groups in which at least one ring member (e.g., 1-3 heteroatoms, 1 or 2 heteroatoms) is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2, 5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1, 2-dithietanyl, 1, 3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1, 4-oxathianyl, 1, 4-dioxepanyl, 1, 4-oxathiepanyl, 1, 4-oxaazepanyl, 1, 4-dithiepanyl, 1, 4-thiazepanyl and 1, 4-diazepanyl, 1, 4-dithianyl, 1, 4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1, 4-dioxanyl, 1, 3-dioxolanyl, pyrazolinyl, pyrazolidinyl, dithianyl, dithiolanyl, pyrazolidinyl, imidazolinyl, pyrimidinonyl, or 1, 1-dioxo-thiomorpholinyl.

The term “Spiro heterocyclyl” refers to a 5 to 20-membered polycyclic heterocyclyl with rings connected through one common carbon atom (called a Spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/3-membered, 4-membered/4-membered, 3-membered/5-membered, 4-membered/5-membered, 4-membered/6-membered, 5-membered/5-membered, or 5-membered/6-membered mono-spiro heterocyclyl. Representative examples of spiro heterocyclyls include, but not limited to the following groups: 2, 3-dihydrospiro[indene-1, 2'-pyrrolidine] (e.g., 2, 3-dihydrospiro[indene-1, 2'-pyrrolidine]-1'-yl), 1, 3-dihydrospiro[indene-2, 2'-pyrrolidine] (e.g., 1, 3-dihydrospiro [indene-2, 2'-pyrrolidine]-1'-yl), azaspiro[2.4]heptane (e.g., 5-azaspiro[2.4]heptane-5-yl), 2-oxa-6-azaspiro[3.3]heptane (e.g., 2-oxa-6-azaspiro[3.3]heptan-6-yl), azaspiro[3.4]octane (e.g., 6-azaspiro[3.4]octane-6-yl), 2-oxa-6-azaspiro [3.4]octane (e.g., 2-oxa-6-azaspiro[3.4]octane-6-yl), azaspiro[3.4]octane (e.g., 6-azaspiro[3.4]octan-6-yl), azaspiro[3.4]octane (e.g., 6-azaspiro[3.4]octan-6-yl), 1, 7-dioxaspiro[4.5]decane, 2-oxa-7-aza-spiro[4.4]nonane (e.g., 2-oxa-7-aza-spiro[4.4]non-7-yl), 7-oxa-spiro[3.5] nonyl and 5-oxa-spiro[2.4]heptyl.

The term “fused heterocyclyl” refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl is divided into bicyclic, tricyclic, tetracyclic, or polycyclic fused heterocyclyl. The group can be attached to the remainder of the molecule through either ring.

Specifically, the term “bicyclic fused heterocyclyl” refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include, but not limited to, the following groups octahydrocyclopenta[c] pyrrole, octahydropyrrolo[3, 4-c]pyrrolyl, octahydroisoindolyl, isoindolinyl, octahydro-benzo[b][1, 4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl (e.g., 2,3-dihydrobenzofuran or 1,3-dihydrobenzofuran), dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, tetrahydropyrazolopyrimidinyl (e.g., 4, 5, 6, 7-tetrahydropyrazolo[1, 5-a]pyrimidin-3-yl), or benzoisoquinolinyl (e.g., 2,3-dihydro-TH-benzo[de]isoquinolinyl).

The term “benzo fused heterocyclyl” is a bicyclic fused heterocyclyl in which a monocyclic 4 to 9-membered heterocyclyl as defined herein (preferably 5- or 6-membered) fused to a benzene ring.

The term “bridged heterocyclyl” refers to a 5- to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups:

2-azabicyclo[2.2.1]heptyl, azabicyclo[3.1.0]hexyl, 2-azabicyclo[2.2.2]octyl and 2-azabicyclo[3.3.2]decyl.

If amine is substituted by $R^5$, it means that the nitrogen atom in structures of

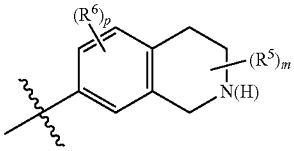

or

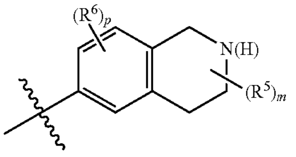

is not bonded to a hydrogen.

The term "at least one substituents" disclosed herein includes, for example, from 1 to 4, such as from 1 to 3, further as 1 or 2, substituents, provided the theory of valence is met. For example, "at least one substituents $R^{6d}$" disclosed herein includes from 1 to 4, such as from 1 to 3, further as 1 or 2, substituents selected from the list of $R^{6d}$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer (s). In some embodiments, the term "substantially pure" means that the target stereoisomer contains no more than 10%, for example, no more than 5%, such as no more than 1%, by weight of any other stereoisomer (s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H, et al. "*Chromatographic resolution of enantiomers: Selective review.*" *J. Chromatogr.*, 113 (3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthetic Schemes

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from room temperature to the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

The compounds disclosed herein can be prepared by following Scheme I to IV.

Scheme I

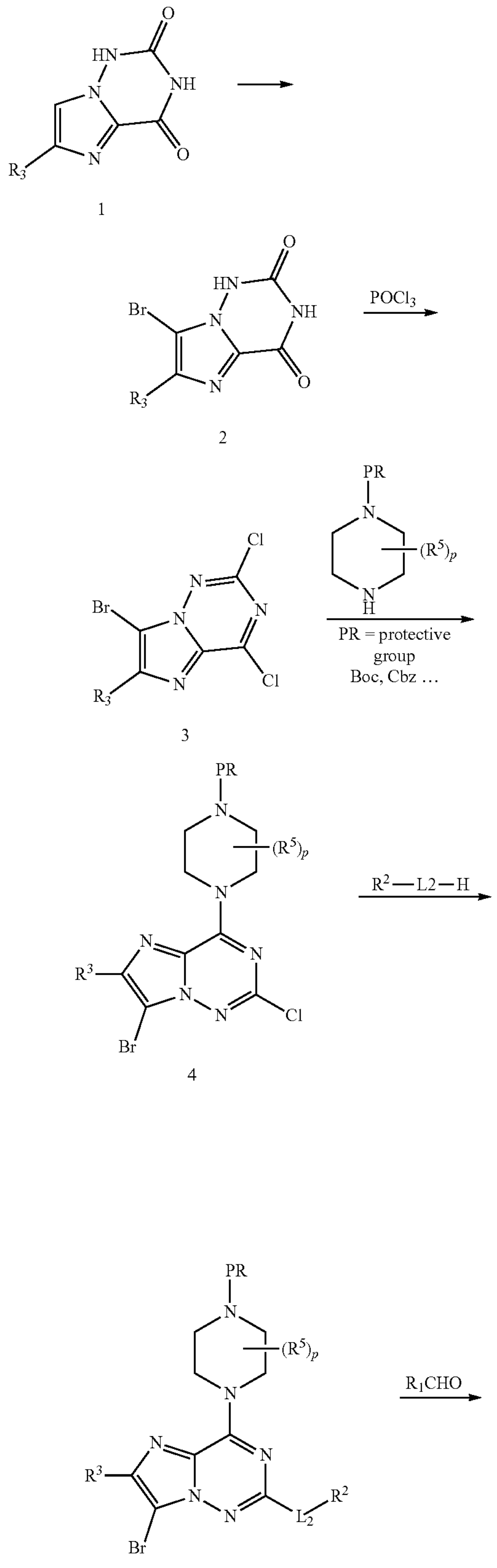

1

2

3

4

5

-continued

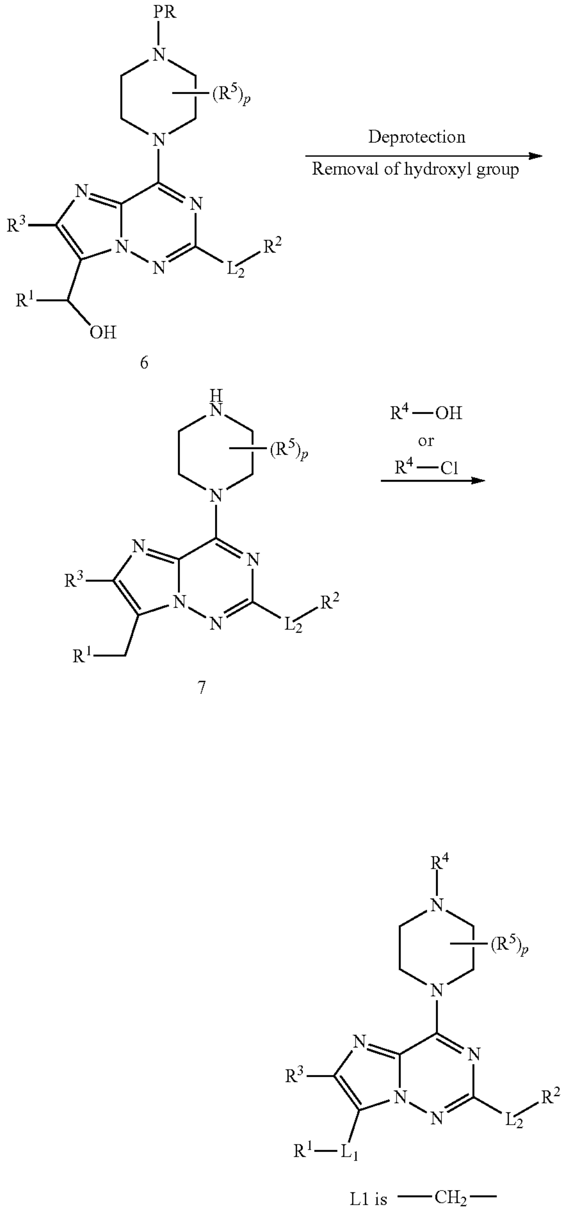

6

7

Formula I wherein R1 to R5, $L_1$ and $L_2$ are as defined with formula (I).

In scheme I, a commercially available compound 1, which is reacted with bromination reagent (such as NBS, $Br_2$ . . . ) to obtain compound 2; The dione compound 2 are chloridized by $POCl_3$ to form compound 3; One chlorine atom of compound 3 is replaced by protective amine to give the compound 4; then another chlorine atom react with $R^2L_2H$ under basic condition (such as NaH, t-BuOK . . . ) or Metal-catalyzed coupling reaction condition to obtain compound 5; which subsequently react with R1CHO under basic condition (such as n-Butyllithium, LDA . . . ) to form compound 6; The protected groups on the amine and the hydroxy group of compound 6 are removed to give the compound 7; then the compound 7 react with $R^4$—OH, $R^4$—Cl or $R^4OR^4$ to afford the formula I.

The compound 6 disclosed herein also can be prepared by following Scheme II.

Scheme II

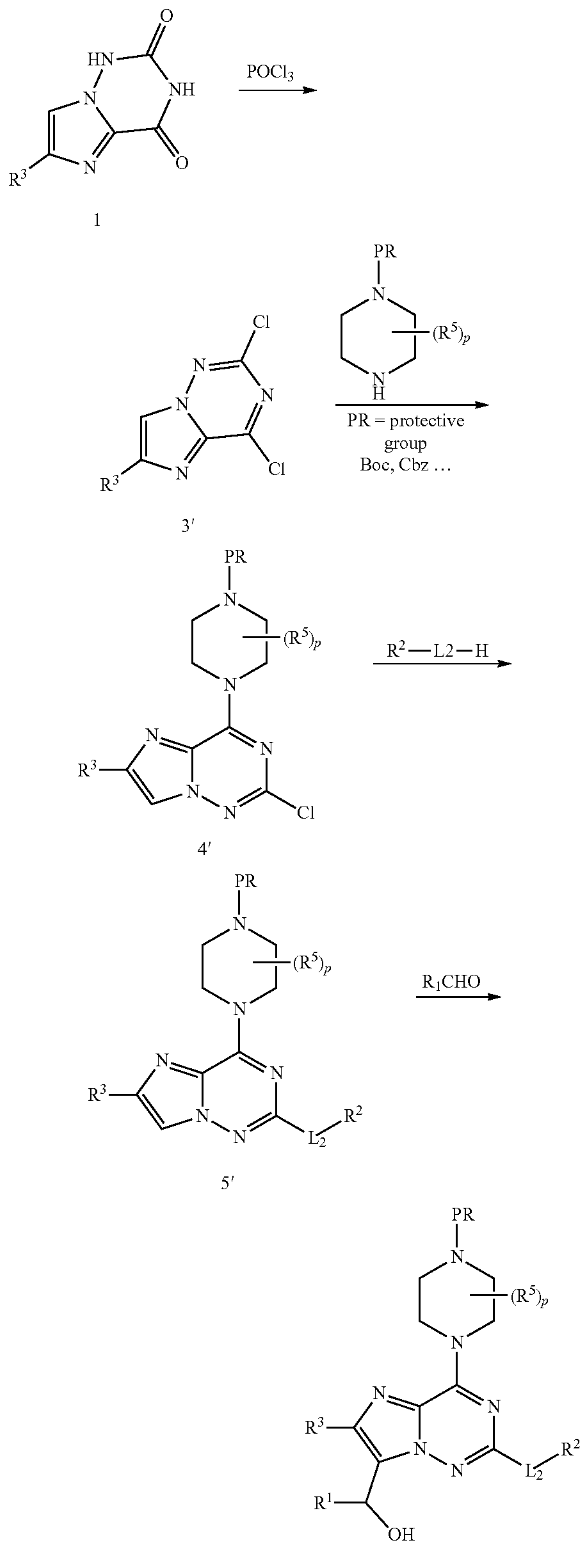

1

3'

4'

5'

6

In the scheme II, the compound 1 are chloridized by $POCl_3$ to form compound 3'; One chlorine atom of compound 3' is replaced by protective amine to give the compound 4'; then another chlorine atom react with $R^2L_2H$ under basic condition (such as NaH, t-BuOK . . . ) or Metal-catalyzed coupling reaction condition to obtain compound 5'; which subsequently react with R1CHO under basic condition (such as n-Butyllithium, LDA . . . ) to form compound 6.

The compound 7 disclosed herein also can be prepared by following Scheme III.

Scheme III

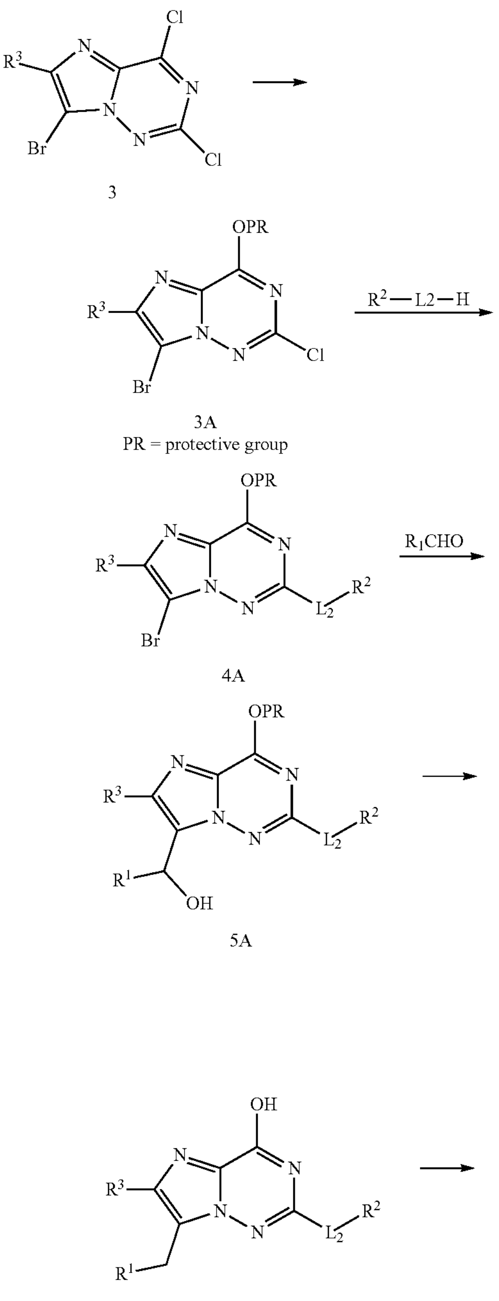

3

3A

PR = protective group

4A

5A

6A

-continued

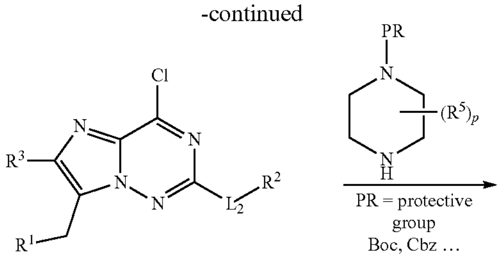

7A

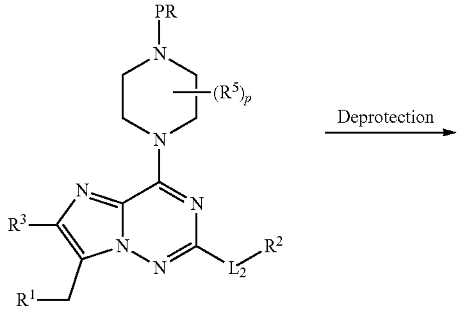

8A

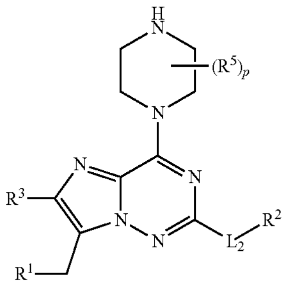

7

In the scheme III, One chlorine atom of compound 3 is replaced by protective group to give the compound 3A; then another chlorine atom react with $R^2L_2H$ under basic condition (such as NaH, t-BuOK . . . ) or Metal-catalyzed coupling reaction condition to obtain compound 4A; which subsequently react with R1CHO under basic condition (such as n-Butyllithium, LDA . . . ) to form compound 5A; The protective group and the hydroxy group of compound 5A are removed to give the compound 6A; the compound 6A is chloridized to form compound 7A. then react with protective amine to give the product 8A; remove the protective group to afford 7.

The compounds disclosed herein can be prepared by following Scheme IV.

Scheme IV.

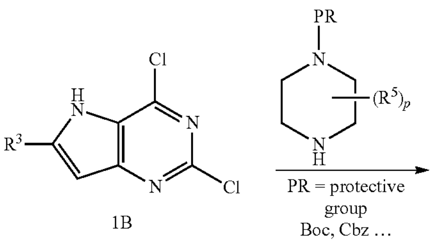

1B

-continued

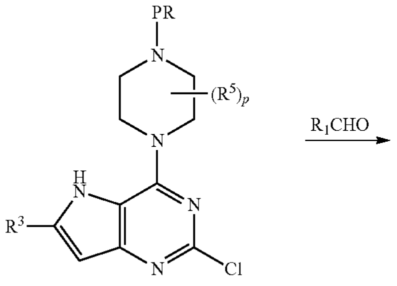

2B

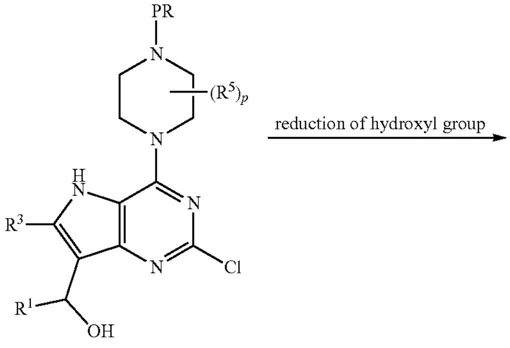

3B

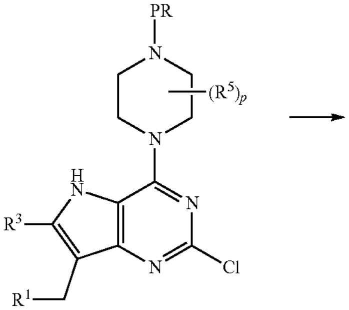

4B

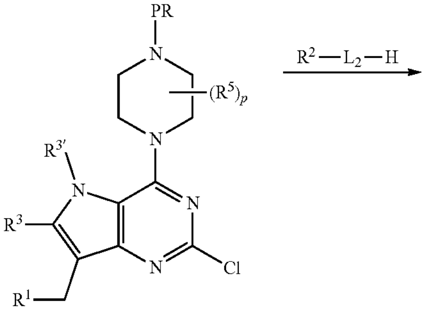

5B

-continued

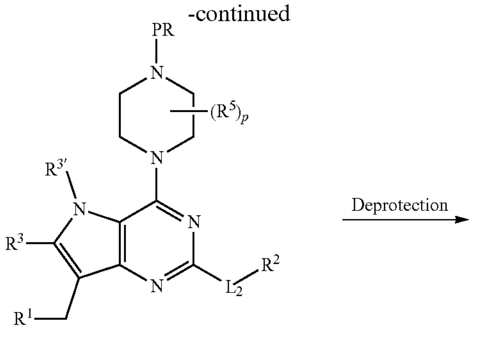

6B

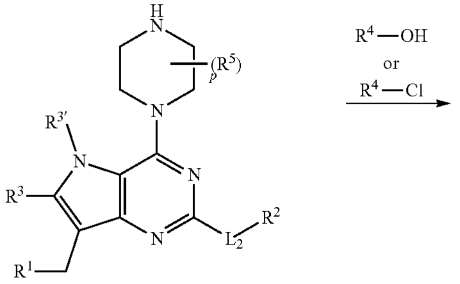

7B

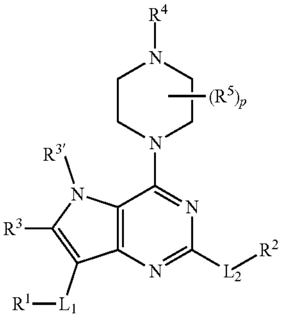

L1 is —$CH_2$— formula II wherein R1 to R5, $L_1$ and $L_2$ are as defined with formula (II).

In scheme IV, a commercially available compound 1B, which is reacted with protective amine to give compound 2B; which subsequently react with R1CHO under basic condition (such as $K_2CO_3$, t-BuOK, $NaOCH_3$ . . . ) to form compound 3B; then the hydroxy group of compound 3B is reduced to afford the compound 4B; replacing by $R^{3'}$ to give compound 5B; then the chlorine atom react with $R^2L_2H$ under basic condition (such as NaH, t-BuOK . . . ) or Metal-catalyzed coupling reaction condition to obtain compound 6B; remove the protective group of 6B to give compound 7B; Then the compound 7 react with $R^4$—OH, $R^4$—Cl or $R^4OR^4$ to afford the formula II

EXAMPLES

The examples below are intended to be purely exemplary and should not be considered to be limiting in any way. Unless otherwise specified, the experimental methods in the Examples described below are conventional methods. Unless otherwise specified, the reagents and materials are all commercially available. All solvents and chemicals employed are of analytical grade or chemical purity. Solvents are all redistilled before use. Anhydrous solvents are all prepared according to standard methods or reference methods. Silica gel (100-200 meshes) for column chromatography and silica gel (GF254) for thin-layer chromatography (TLC) are commercially available from Tsingdao Haiyang Chemical Co., Ltd. or Yantai Chemical Co., Ltd. of China; all are eluted with petroleum ether (60-90° C.)/ethyl acetate (v/v), and visualized by iodine or the solution of molybdphosphoric acid in ethanol unless otherwise specified. All extraction solvents, unless otherwise specified, are dried over anhydrous $Na_2SO_4$. $^1H$ NMR spectra are recorded on Bruck-400 nuclear magnetic resonance spectrometer with TMS (tetramethylsilane) as the internal standard. LC/MS data are recorded by using Agilent1100 High Performance Liquid Chromatography-Ion Trap Mass Spectrometer (LC-MSD Trap) equipped with a diode array detector (DAD) detected at 214 nm and 254 nm, and an ion trap (ESI source). All compound names except the reagents were generated by ChemDraw®.

In the following examples, the following abbreviations are used:

Ac Acetyl
AcOH Acetic acid
Aq Aqueous
Brine Saturated aqueous sodium chloride solution
Bn Benzyl
Boc Tert-butyloxycarbonyl
Cbz benzyloxycarbonyl
DMF N,N-Dimethylformamide
Dppf 1,1"-bis(diphenylphosphino)ferrocene
DBU 1,8-diazabicyclo[5.4.0]undec-7-ene
DCE 1,2-dichloroethane
DCM Dichloromethane
DIEA or DIPEA N,N-diisopropylethylamine
DMAP 4-N,N-dimethylaminopyridine
DMF N,N-dimethylformamide
DMSO Dimethyl sulfoxide
EA or EtOAc Ethyl acetate
eq equivalent
g Grams
h or hr Hour
HCl Hydrochloric acid
HPLC High-performance liquid chromatography
IPA 2-propanol
i-PrOH Isopropyl alcohol
mg Milligrams
mL Milliliters
Mmol Millimole
MeCN Acetonitrile
MeOH Methanol
Min Minutes
ms or MS Mass spectrum
NMR Nuclear magnetic resonance
Pd/C Palladium on carbon
PE Petroleum ether
PMB 4-Methoxybenzyl
PPA Polyphosphoric acid
Rt., RT. or rt. Room temperature
Ru-Phos/Ru-PHOS 2-dicyclohexylphosphino-2',6'-di-1-propoxy-1,1-biphenyl
SEM 2-trimethylsilylethoxymethoxy
TBSCl tert-Butyldimethylsilyl chloride
TEA Triethanolamine
TFA Trifluoroacetic acid THF Tetrahydrofuran THP tetrahydropyran TLC thin layer chromatography Synthesis Example 1: Compound A1 (S)-1-(4-(2-((1-methylpyrrolidin-2-yl)methoxy)-7-(naphthalen-1-ylmethyl)imidazo[2,1-f][1,2,4]triazin-4-yl)piperazin-1-yl)prop-2-en-1-one Step A: 2,4-dichloroimidazo[2,1-f][1,2,4]triazine

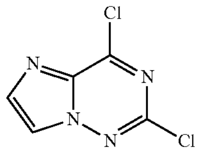

$POCl_3$ (50 g, 328.9 mmol) was added to a solution of imidazo[2,1-f][1,2,4]triazine-2,4(1H,3H)-dione (10 g, 65.8 mmol) in toluene (60 ml) at rt. Then DIEA (25 g, 193 mmol) was added dropwise at 60° C. The mixture was stirred at 90° C. overnight. The solvent was removed under reduced pressure. The residue was used in the next step directly.

Step B: tert-butyl 4-(2-chloroimidazo[2,1-f][1,2,4]triazin-4-yl)piperazine-1-carboxylate

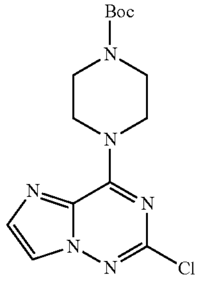 [SMILES: CC(C)(C)OC(=O)N1CCN(c2nc(Cl)nn3ccnc23)CC1]

Tert-butyl piperazine-1-carboxylate (12 g, 63.8 mmol) was dissolved in THF (60 mL) followed by addition of $K_2CO_3$ (26.4 g, 191.5 mmol) in water (50 ml). A mixture of 2,4-dichloroimidazo[2,1-f][1,2,4]triazine (12 g, 63.8 mmol) and DIEA (24.7 g, 191.5 mmol) in THF (60 ml) was added slowly. Then the reaction was stirred at room temperature for 2 h. The solvent was evaporated and the residue partitioned between EA (100 mL) and water (100 mL). The combined organic layers were washed with brine, dried over $Na_2SO_4$, filtered and concentrated. The residue was slurried with MeOH for overnight to give the target compound (9.3 g, 42%). $^1H$ NMR (400 MHz, $CD_3Cl$) δ 7.71 (d, J=0.9 Hz, 1H), 7.54 (s, 1H), 4.87 (s, 2H), 4.04 (s, 2H), 3.61 (s, 4H), 1.50 (s, 9H) ppm. MS: M/e 339 $(M+1)^+$.

Step C: tert-butyl (S)-4-(2-((1-methylpyrrolidin-2-yl)methoxy)imidazo[2,1-f][1,2,4]triazin-4-yl)piperazine-1-carboxylate

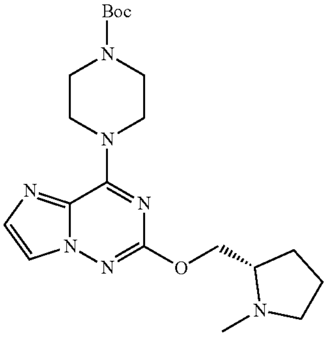 [SMILES: CN1CCC[C@H]1COc1nc(N2CCN(C(=O)OC(C)(C)C)CC2)c2nccn2n1]

To a solution of NaH (232 mg, 5.8 mmol, 60%) in THF (10 mL) at 0° C. was added (S)-(1-methylpyrrolidin-2-yl) methanol (414 mg, 3.6 mmol). After 30 min, a solution of the product of the step B (1 g, 2.9 mmol) in THF (5 mL) was added. Then the reaction was stirred at 60° C. for overnight. The mixture was cooled to room temperature, diluted with water (30 mL), extracted with EtOAc (60 mL×2). The combined organic layers were washed with brine, dried over $Na_2SO_4$, filtered and concentrated. The residue was purified by combi flash to give target compound (0.75 g, 62%). $^1H$ NMR (400 MHz, DMSO-d6) δ 7.96 (d, J=0.9 Hz, 1H), 7.54 (d, J=0.9 Hz, 1H), 4.77 (s, 2H), 4.21 (dd, J=10.5, 5.0 Hz, 1H), 4.05 (dd, J=10.5, 6.2 Hz, 1H), 3.91 (s, 2H), 3.50 (s, 4H), 2.95 (dt, J=8.9, 4.3 Hz, 1H), 2.56 (dd, J=13.2, 6.3 Hz, 1H), 2.35 (s, 3H), 2.19 (q, J=8.7 Hz, 1H), 1.95 (tt, J=12.0, 8.4 Hz, 1H), 1.74-1.54 (m, 3H), 1.43 (s, 9H) ppm. MS: M/e 418 $(M+1)^+$.

Step D: tert-butyl 4-(7-(hydroxy(naphthalen-1-yl)methyl)-2-(((S)-1-methylpyrrolidin-2-yl)methoxy)imidazo[2,1-f][1,2,4]triazin-4-yl)piperazine-1-carboxylate

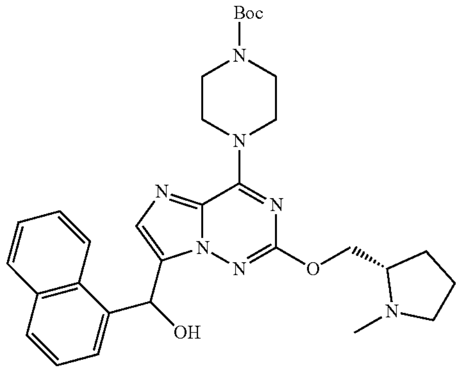 [SMILES: CN1CCC[C@H]1COc1nc(N2CCN(C(=O)OC(C)(C)C)CC2)c2ncc(C(O)c3cccc4ccccc34)n2n1]

To a solution of the product of the step C (500 mg, 1.2 mmol) in THF (10 mL) was added n-BuLi (1.12 mL, 2.8 mmol, 2.5M in hexane) drop wise maintaining the temperature between −75~−65° C. After 30 min, a mixture of 1-naphthaldehyde (224 mg, 1.44 mmol) in THF (2 mL) was added dropwise. The resulted mixture was stirred at −70° C.

for 1 h and then warmed to room temperature for 1 h. The reaction was quenched with saturated $NH_4Cl$ solution, extracted with EtOAc (60 mL×2). The combined organic lays were washed with brine, dried over $Na_2SO_4$, filtered, and concentrated. The residue was purified by combi flash to give target compound (500 mg, 71%). NMR (400 MHz, DMSO-d6) δ 8.13-8.09 (m, 1H), 7.97-7.92 (m, 1H), 7.87 (d, J=8.1 Hz, 1H), 7.72-7.64 (m, 1H), 7.55-7.41 (m, 3H), 7.30 (d, J=7.0 Hz, 1H), 6.77 (d, J=5.1 Hz, 1H), 6.27 (d, J=5.2 Hz, 1H), 5.76 (s, 1H), 4.73 (d, J=30.5 Hz, 2H), 4.16 (dd, J=10.7, 4.8 Hz, 1H), 4.03-3.78 (m, 3H), 3.47 (s, 4H), 2.96-2.86 (m, 1H), 2.26 (d, J=10.5 Hz, 3H), 2.13 (q, J=8.4 Hz, 1H), 1.96-1.74 (m, 1H), 1.71-1.46 (m, 3H), 1.42 (d, J=5.6 Hz, 9H) ppm. MS: M/e 574 $(M+1)^+$.

Step E: (S)-2-((1-methylpyrrolidin-2-yl)methoxy)-7-(naphthalen-1-ylmethyl)-4-(piperazin-1-yl)imidazo[2,1-f][1,2,4]triazine

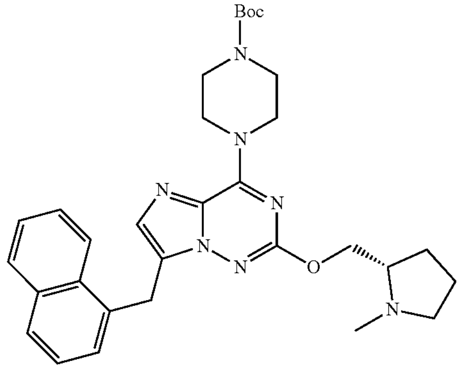 [SMILES: CN1CCC[C@H]1COc1nc(N2CCN(C(=O)OC(C)(C)C)CC2)c2ncc(Cc3cccc4ccccc34)n2n1]

To a mixture of the product of step D (100 mg) was added TFA (2 mL) and $Et_3SiH$ (2 mL). The reaction was heated at 25° C. overnight. The mixture was concentrated to dryness and the residue was used directly for next step without further purification. MS: M/e 458 $(M+1)^+$.

Step F: (S)-1-(4-(2-((1-methylpyrrolidin-2-yl)methoxy)-7-(naphthalen-1-ylmethyl)imidazo[2,1-f][1,2,4]triazin-4-yl)piperazin-1-yl)prop-2-en-1-one

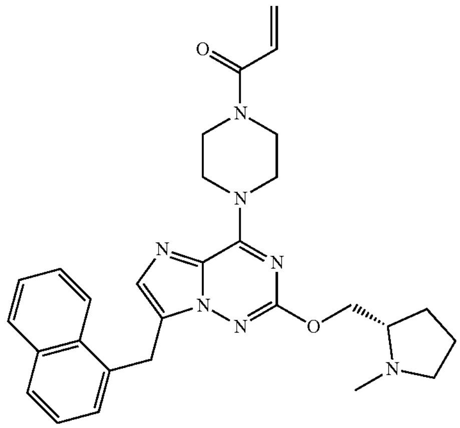 [SMILES: C=CC(=O)N1CCN(c2nc(OC[C@@H]3CCCN3C)nn3c(Cc4cccc5ccccc45)cnc23)CC1]

To a mixture of the product of the step E (50 mg, crude) in $CH_3CN$ (3 mL) was added saturated $NaHCO_3$ (0.5 mL) and followed by a solution of acryloyl chloride (6 mg, 0.07 mmol) in $CH_3CN$ (0.3 mL) at 0° C. The resulting mixture was stirred at room temperature for 30 min. The reaction was diluted with water, extracted with EA (60 mL), washed with brine, dried over $Na_2SO_4$, filtered, and concentrated. The residue was purified by prep-TLC to give the target compound (9 mg, 8% for two steps). 1H NMR (400 MHz, DMSO-d6) δ 8.19 (d, J=9.4 Hz, 1H), 7.98-7.90 (m, 1H), 7.83 (d, J=8.1 Hz, 1H), 7.52 (dd, J=9.1, 5.2 Hz, 2H), 7.46-7.36 (m, 2H), 7.31 (s, 1H), 6.84 (dd, J=16.7, 10.5 Hz, 1H), 6.16 (dd, J=16.7, 2.0 Hz, 1H), 5.73 (dd, J=10.4, 2.2 Hz, 1H), 4.78 (s, 2H), 4.63 (s, 2H), 4.26 (s, 1H), 4.13 (s, 1H), 3.93 (s, 2H), 3.84-3.63 (m, 4H), 3.02 (s, 1H), 2.67 (s, 1H), 2.37 (s, 4H), 1.94 (s, 1H), 1.74-1.67 (m, 3H) ppm. MS: M/e 512 $(M+1)^+$.

Example 2: Compound A2: (S)-1-(4-(7-((3-hydroxynaphthalen-1-yl)methyl)-2-((1-methylpyrrolidin-2-yl)methoxy)imidazo[2,1-f][1,2,4]triazin-4-yl)piperazin-1-yl)prop-2-en-1-one Step A: tert-butyl 4-(7-(hydroxy(3-hydroxynaphthalen-1-yl)methyl)-2-(((S)-1-methylpyrrolidin-2-yl)methoxy)imidazo[2,1-f][1,2,4]triazin-4-yl)piperazine-1-carboxylate

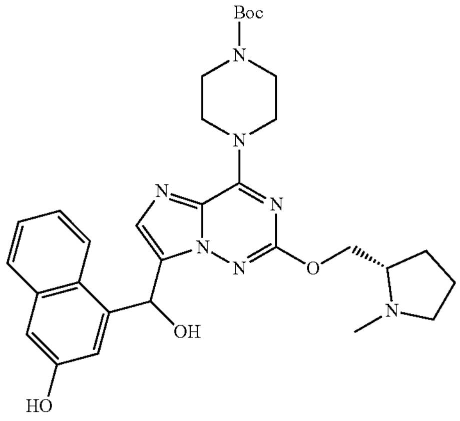 [SMILES: CN1CCC[C@H]1COc1nc(N2CCN(C(=O)OC(C)(C)C)CC2)c2ncc(C(O)c3cc(O)cc4ccccc34)n2n1]

To a solution of the product of tert-butyl (S)-4-(2-((1-methylpyrrolidin-2-yl)methoxy)imidazo[2,1-f][1,2,4]triazin-4-yl)piperazine-1-carboxylate (500 mg, 1.2 mmol) in THF (10 mL) was added n-BuLi (1.12 mL, 1.8 mmol, 2.5M in hexane) drop wise maintaining the temperature between −75~−65° C. After 30 min, a mixture of 3-hydroxy-1-naphthaldehyde (246 mg, 1.44 mmol) in THF (5 mL) was added drop wise. The resulted mixture was stirred at −70° C. for 1 h and then warmed to room temperature for 1 h. The reaction was quenched with saturated $NH_4Cl$ solution, extracted with EtOAc, washed with brine, dried over $Na_2SO_4$, filtered, and concentrated. The residue was purified by combi flash to give target compound (200 mg, 28%). MS: M/e 590 $(M+1)^+$.

Step B: (S)-4-((2-((1-methylpyrrolidin-2-yl)methoxy)-4-(piperazin-1-yl)imidazo[2,1-f][1,2,4]triazin-7-yl)methyl)naphthalen-2-ol

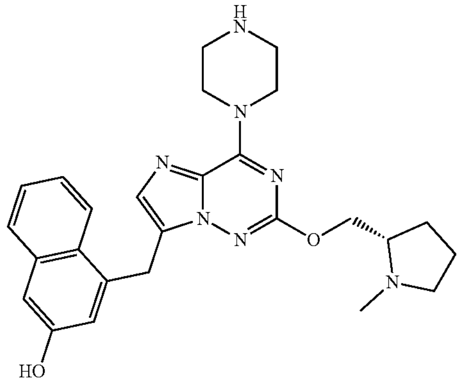 [SMILES: CN1CCC[C@H]1COc1nc(N2CCNCC2)c2ncc(Cc3cc(O)cc4ccccc34)n2n1]

To a mixture of the product of step A (200 mg) was added TFA (2 mL) and $Et_3SiH$ (2 mL). The reaction was stirred at 25° C. overnight. The mixture was concentrated to dryness. Water was added to dissolve the residue. The aqueous layer was adjusted to pH 12 with aqueous $K_2CO_3$ and extracted with EtOAc. The combined organic layers were dried over $Na_2SO_4$ and evaporated in vacuo to give the crude product (70 mg) MS: M/e 474 $(M+1)^+$.

Step C: (S)-1-(4-(7-((3-hydroxynaphthalen-1-yl)methyl)-2-((1-methylpyrrolidin-2-yl)methoxy)imidazo[2,1-f][1,2,4]triazin-4-yl)piperazin-1-yl)prop-2-en-1-one

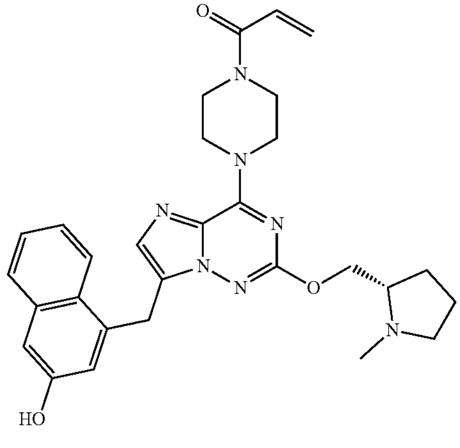 [SMILES: C=CC(=O)N1CCN(c2nc(OC[C@@H]3CCCN3C)nn3c(Cc4cc(O)cc5ccccc45)cnc23)CC1]

To a mixture of the product of the step B (70 mg, crude) in $CH_3CN$ (2 mL) was added saturated $NaHCO_3$ (15 mg) in water (1 ml) and followed by a solution of acryloyl chloride (15 mg, 0.16 mmol) in $CH_3CN$ (0.5 mL) at 0° C. The resulting mixture was stirred at room temperature for 30 min. The reaction was diluted with water and extracted with EA. The organic phase was washed with brine. The combined organic phases were dried over $Na_2SO_4$, filtered, and concentrated. The residue was purified by prep-TLC to give the target compound (8 mg, 10% for two steps). $^1H$ NMR (400 MHz, DMSO-d6) δ 9.64 (s, 1H), 8.04 (d, J=8.4 Hz, 1H), 7.70 (d, J=8.1 Hz, 1H), 7.39 (t, J=7.1 Hz, 2H), 7.29 (t, J=7.5 Hz, 1H), 7.02 (s, 1H), 6.93-6.76 (m, 2H), 6.17 (d, J=16.8 Hz, 1H), 5.74 (d, J=12.0 Hz, 1H), 4.81 (s, 2H), 4.57 (s, 2H), 4.35 (s, 2H), 3.95 (s, 2H), 3.83-3.65 (m, 4H), 2.99 (s, 2H), 2.67 (s, 1H), 2.43 (s, 1H), 2.23-1.55 (m, 6H). MS: M/e 528 $(M+1)^+$.

Example 3: Compound A3: 2-((S)-1-acryloyl-4-(7-(3-methoxynaphthalen-1-yl)-2-(((S)-1-methylpyrrolidin-2-yl)methoxy)imidazo[2,1-f][1,2,4]triazin-4-yl)piperazin-2-yl)acetonitrile Step A: benzyl (S)-4-(7-bromo-2-chloroimidazo[2,1-f][1,2,4]triazin-4-yl)-2-(cyanomethyl)piperazine-1-carboxylate

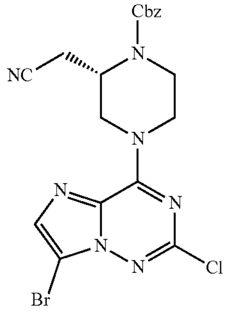 [SMILES: N#CC[C@H]1CN(c2nc(Cl)nn3c(Br)cnc23)CCN1C(=O)OCc1ccccc1]

Benzyl (S)-2-(cyanomethyl)piperazine-1-carboxylate hydrochloride (974 mg, 3.29 mmol) was added to a solution of 7-bromo-2,4-dichloroimidazo[2,1-f][1,2,4]triazine (1 g, 3.76 mmol), DIEA (1.2 g, 9.3 mmol) in THF (10 ml). Then the reaction was stirred at room temperature for 2 h. The reaction mixture was diluted in water and extracted with DCM. The combined organic extracts were washed with saturated aqueous NaCl, dried over $Na_2SO_4$, and concentrated. The crude product was purified by column chromatography on silica gel (EA:PE=1:2) to give the target compound (1.4 g, 86.8%). $^1H$ NMR (400 MHz, $CDCl_3$) δ 7.55 (s, 1H), 7.44-7.32 (m, 5H), 6.03 (s, 1H), 5.24-5.14 (m, 2H), 4.75 (s, 2H), 4.27 (s, 1H), 3.67-3.16 (m, 3H), 2.83-2.58 (m, 2H) ppm, MS: M/e 490 $(M+1)^+$.

Step B: benzyl (S)-4-(7-bromo-2-(((S)-1-methylpyrrolidin-2-yl)methoxy)imidazo[2,1-f][1,2,4]triazin-4-yl)-2-(cyanomethyl)piperazine-1-carboxylate

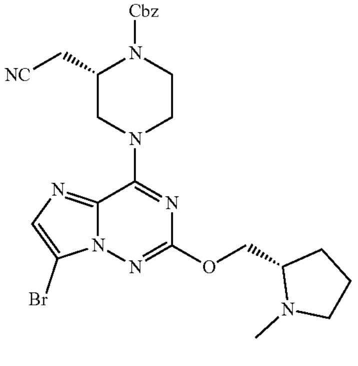 [SMILES: CN1CCC[C@H]1COc1nc(N2CCN(C(=O)OCc3ccccc3)[C@@H](CC#N)C2)c2ncc(Br)n2n1]

To a solution of NaH (74 mg, 1.84 mmol, 60%) in THF (5 mL) at 0° C. was added (S)-(1-methylpyrrolidin-2-yl) methanol (169 mg, 1.47 mmol). After 30 min, a solution of the product of the step A (600 mg, 1.23 mmol) in THF (5 mL) was added. Then the reaction was stirred at 60° C. for overnight. The mixture was cooled to room temperature, diluted with water, extracted with EtOAc. The combined organic layers were washed with brine, dried over $Na_2SO_4$, filtered and concentrated. The residue was purified by combi flash to give target compound (180 mg, 26%). MS: M/e 569 $(M+1)^+$.

Step C: benzyl (S)-2-(cyanomethyl)-4-(7-(3-methoxynaphthalen-1-yl)-2-(((S)-1-methylpyrrolidin-2-yl)methoxy)imidazo[2,1-f][1,2,4]triazin-4-yl) piperazine-1-carboxylate

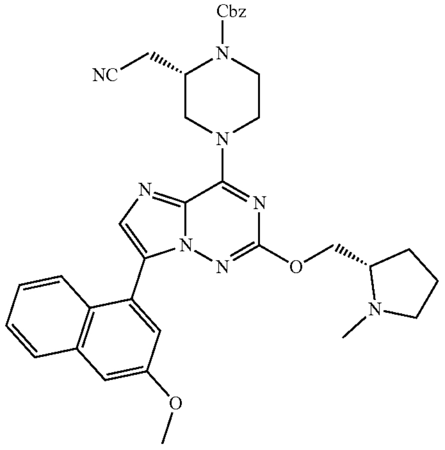 [SMILES: COc1cc(-c2cnc3c(N4CCN(C(=O)OCc5ccccc5)[C@@H](CC#N)C4)nc(OC[C@@H]4CCCN4C)nn23)c2ccccc2c1]

A flask was charged with $Pd(dppf)Cl_2$ (12.4 mg, 0.017 mmol), the product of the step B (100 mg, 0.17 mmol), (3-methoxynaphthalen-1-yl)boronic acid (38 mg, 0.19 mmol), $Na_2CO_3$ (22 mg, 0.2 mmol), dioxane (3 ml) and $H_2O$ (0.3 ml). The resulted mixture was stirred at 90° C. for 4 h and then cooled to room temperature. The reaction was quenched with water, extracted with EtOAc, washed with brine, dried over $Na_2SO_4$, filtered, and concentrated. The residue was purified by combi flash to give target compound (90 mg, 79%). MS: M/e 647 $(M+1)^+$.

Step D: 2-((S)-4-(7-(3-methoxynaphthalen-1-yl)-2-(((S)-1-methylpyrrolidin-2-yl)methoxy)imidazo[2,1-f][1,2,4]triazin-4-yl)piperazin-2-yl)acetonitrile

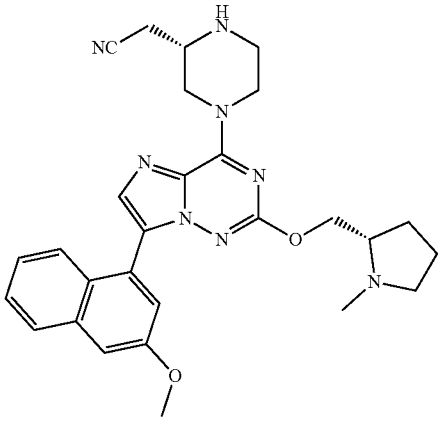 [SMILES: COc1cc(-c2cnc3c(N4CCN[C@@H](CC#N)C4)nc(OC[C@@H]4CCCN4C)nn23)c2ccccc2c1]

$BBr_3$ (1M in DCM, 0.61 ml) was added to a mixture of the product of step C (160 mg, 0.25 mmol) in DCM (2 mL) dropwise at −10° C. The reaction was stirred at −10° C. for 1 hour. The mixture was filtered and the filtrate cake was dried by oven. The filtrate cake (20 mg, crude) was used directly for next step without further purification. MS: M/e 513 $(M+1)^+$.

Step E: 2-((S)-1-acryloyl-4-(7-(3-methoxynaphthalen-1-yl)-2-(((S)-1-methylpyrrolidin-2-yl)methoxy) imidazo[2,1-f][1,2,4]triazin-4-yl)piperazin-2-yl)acetonitrile

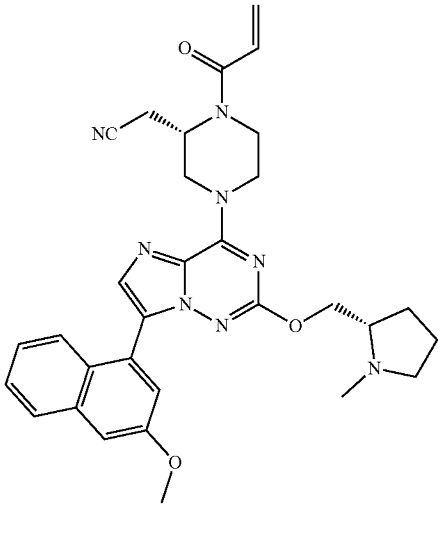 [SMILES: C=CC(=O)N1CCN(c2nc(OC[C@@H]3CCCN3C)nn3c(-c4cc(OC)cc5ccccc45)cnc23)C[C@@H]1CC#N]

To a mixture of the product of the step D (20 mg, crude) in $CH_3CN$ (1 mL) was added saturated $NaHCO_3$ (0.5 mL) and followed by a solution of acryloyl chloride (4 mg) in $CH_3CN$ (0.3 mL) at 0° C. The resulting mixture was stirred at room temperature for 30 min. The reaction was diluted with water, extracted with EA, washed with brine, dried over $Na_2SO_4$, filtered, and concentrated. The residue was purified by prep-TLC to give the target compound (1.7 mg, 10% for two steps). $^1H$ NMR (400 MHz, DMSO-d6) δ 7.93 (d, J=8.2 Hz, 1H), 7.83 (s, 1H), 7.61-7.48 (m, 3H), 7.34 (s, 2H), 6.93-6.85 (m, 1H), 6.23 (d, J=16.6 Hz, 1H), 5.82 (d, J=10.4 Hz, 1H), 5.03 (m, 2H), 4.17 (s, 2H), 3.88 (s, 3H), 3.67-3.44 (m, 5H), 3.17-2.76 (m, 6H), 2.07-1.38 (m, 6H) ppm. MS: M/e 567 $(M+1)^+$.

Example 4: Compound A4: 2-((S)-1-acryloyl-4-(2-(((S)-1-methylpyrrolidin-2-yl)methoxy)-7-(naphthalen-1-ylmethyl)imidazo[2,1-f][1,2,4]triazin-4-yl)piperazin-2-yl)acetonitrile Step A: 7-bromo-4-(tert-butoxy)-2-chloroimidazo[2,1-f][1,2,4]triazine

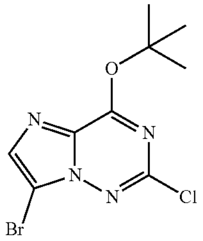 [SMILES: CC(C)(C)Oc1nc(Cl)nn2c(Br)cnc12]

To a solution of 7-bromo-2,4-dichloroimidazo[2,1-f][1,2,4]triazine (0.53 g, 2 mmol) in THF (6 mL) was added t-BuOLi (176 mg, 2.2 mmol) in portions. Then the mixture was stirred at room temperature for 0.4 h. The residue was purified by combi flash to give target compound (400 mg, 66%). $^1H$ NMR (400 MHz, $CDCl_3$) δ 7.67 (s, 1H), 1.78 (s, 9H) ppm.

Step B: (S)-7-bromo-4-(tert-butoxy)-2-((1-methylpyrrolidin-2-yl)methoxy)imidazo[2,1-f][1,2,4]triazine

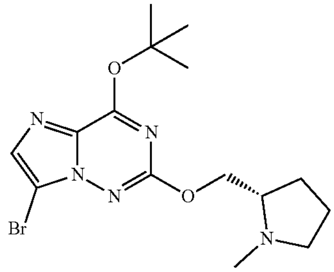 [SMILES: CN1CCC[C@H]1COc1nc(OC(C)(C)C)c2ncc(Br)n2n1]

To a solution of NaH (448 mg, 11.2 mmol, 60%) in THF (10 mL) at 0° C. was added (S)-(1-methylpyrrolidin-2-yl)methanol (0.7 g, 6.15 mmol). After 30 min, a solution of the product of the step A (1.6 g, 5.6 mmol) in THF (5 mL) was added. Then the reaction was stirred at 60° C. for 1 h. The mixture was cooled to room temperature, diluted with water (30 mL), extracted with EtOAc (60 mL×2). The combined organic layers were washed with brine, dried over $Na_2SO_4$, filtered and concentrated. The residue was purified by combi flash to give target compound (0.7 g, 33%). MS: M/e 384 $(M+1)^+$.

Step C: (4-(tert-butoxy)-2-(((S)-1-methylpyrrolidin-2-yl)methoxy)imidazo[2,1-f][1,2,4]triazin-7-yl)(naphthalen-1-yl)methanol

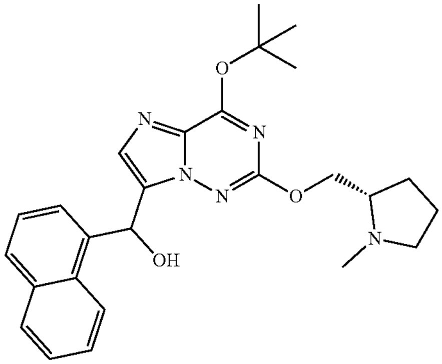 [SMILES: CN1CCC[C@H]1COc1nc(OC(C)(C)C)c2ncc(C(O)c3cccc4ccccc34)n2n1]

To a solution of the product of the step B (250 mg, 0.7 mmol) in THF (10 mL) was added n-BuLi (0.6 mL, 0.96 mmol, 1.6 M in hexane) dropwise maintaining the temperature between −75~−65° C. After 30 min, a mixture of 1-naphthaldehyde (120 mg, 0.77 mmol) in THF (2 mL) was added dropwise. The resulted mixture was stirred at −70° C. for 1 h and then warmed to room temperature for 1 h. The reaction was quenched with saturated $NH_4Cl$ solution, extracted with EtOAc (60 mL×2), washed with brine, dried over $Na_2SO_4$, filtered, and concentrated. The residue was purified by combi flash to give target compound (230 mg, 71%). MS: M/e 462 $(M+1)^+$.

Step D: (S)-2-((1-methylpyrrolidin-2-yl)methoxy)-7-(naphthalen-1-ylmethyl)imidazo[2,1-f][1,2,4]triazin-4-ol

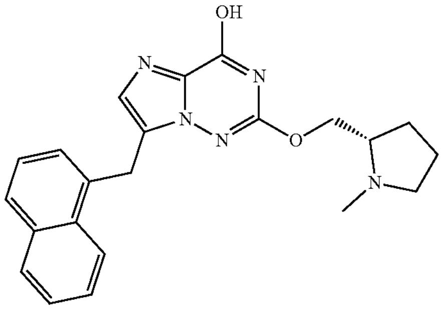 [SMILES: CN1CCC[C@H]1COc1nc(O)c2ncc(Cc3cccc4ccccc34)n2n1]

To a mixture of the product of step C (230 mg, 0.5 mmol) in DCM (4 mL) was added TFA (2 mL) and $Et_3SiH$ (2 mL). The reaction was heated at 25° C. overnight. The mixture was concentrated to dryness and the residue was used directly for next step without further purification. MS: M/e 390 $(M+1)^+$.

Step E: benzyl (S)-2-(cyanomethyl)-4-(2-(((S)-1-methylpyrrolidin-2-yl)methoxy)-7-(naphthalen-1-ylmethyl)imidazo[2,1-f][1,2,4]triazin-4-yl)piperazine-1-carboxylate

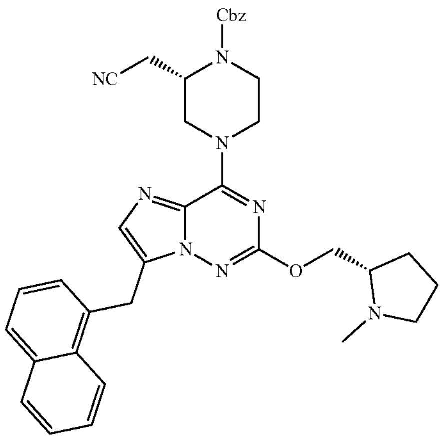 [SMILES: CN1CCC[C@H]1COc1nc(N2CCN(C(=O)OCc3ccccc3)[C@@H](CC#N)C2)c2ncc(Cc3cccc4ccccc34)n2n1]

To the residue of the step D (200 mg, crude) in toluene (10 mL) was added $POCl_3$ (465 mg, 3 mmol) and DIEA (258 mg, 2 mmol). The resulted mixture was stirred at 100° C. overnight. The mixture was concentrated to dryness, treated with THF (15 mL). Then DIEA (258 mg, 2 mmol) and benzyl (S)-2-(cyanomethyl)piperazine-1-carboxylate (130 mg, 0.5 mmol) were added and the reaction was stirred at room temperature for 3 hours. The reaction was quenched with saturated water, extracted with EtOAc (80 mL). The organic layer was washed with brine, dried over $Na_2SO_4$, filtered, and concentrated. The residue was purified by combi flash to give target compound (100 mg, 32% for two steps). MS: M/e 631 $(M+1)^+$.

Step F: 2-((S)-4-(2-(((S)-1-methylpyrrolidin-2-yl)methoxy)-7-(naphthalen-1-ylmethyl)imidazo[2,1-f][1,2,4]triazin-4-yl)piperazin-2-yl)acetonitrile

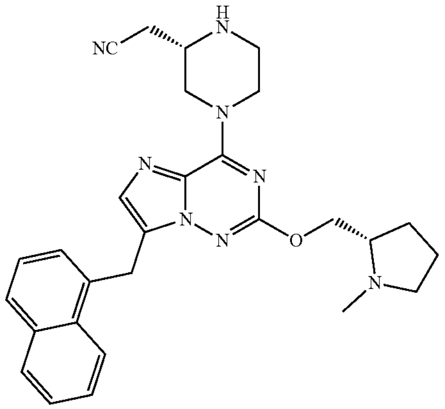 [SMILES: CN1CCC[C@H]1COc1nc(N2CCN[C@@H](CC#N)C2)c2ncc(Cc3cccc4ccccc34)n2n1]

To a mixture of the product of step E (50 mg, 0.079 mmol) in EtOH/THF (2.5 mL/2.5 mL) was added Pd/C (30 mg, 10% Pd). The reaction was stirred at room temperature under $H_2$ (balloon) for 8 h. The mixture was filtered, and the solid was washed with THF (5 mL). The filtrate was concentrated to dryness (50 mg) and the residue was used directly for next step without further purification. MS: M/e 497 $(M+1)^+$.

Step G: 2-((S)-1-acryloyl-4-(2-(((S)-1-methylpyrrolidin-2-yl)methoxy)-7-(naphthalen-1-ylmethyl)imidazo[2,1-f][1,2,4]triazin-4-yl)piperazin-2-yl)acetonitrile

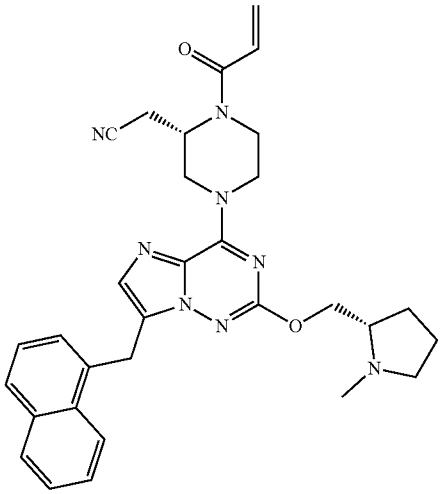 [SMILES: C=CC(=O)N1CCN(c2nc(OC[C@@H]3CCCN3C)nn3c(Cc4cccc5ccccc45)cnc23)C[C@@H]1CC#N]

To a mixture of the product of the step F (50 mg, crude) in $CH_3CN$ (3 mL) was added saturated $NaHCO_3$ (0.5 mL) and followed by a solution of acryloyl chloride (6 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (4 mg, 10% for two steps). $^1$HNMR (400 MHz, DMSO-$d_6$) δ 8.21 (d, J=7.6 Hz, 1H), 7.95 (d, J=8.0 Hz, 1H), 7.83 (d, J=8.0 Hz, 1H), 7.62-7.49 (m, 2H), 7.48-7.38 (m, 2H), 7.34 (s, 1H), 7.00-6.75 (m, 1H), 6.19 (d, J=16.4 Hz, 1H), 5.78 (d, J=10.8 Hz, 1H), 5.19-4.75 (m, 2H), 4.64 (s, 2H), 4.57-4.08 (m, 3H), 3.57-3.02 (m, 5H), 2.89-2.67 (m, 2H), 2.53-2.47 (m, 5H), 2.16-1.90 (m, 1H), 1.86-1.57 (m, 3H) ppm. MS: M/e 551 $(M+1)^+$.

Example 5: Compound A5: 2-((S)-1-acryloyl-4-(7-((3-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: 4-formylnaphthalen-2-yl pivalate

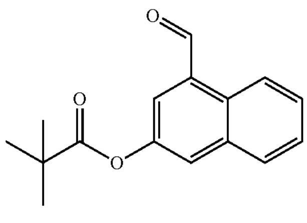 [SMILES: CC(C)(C)C(=O)Oc1cc(C=O)c2ccccc2c1]

To a solution of 3-hydroxy-1-naphthaldehyde (0.86 g, 5 mmol) in THF (10 mL) was added pyridine (790 mg, 10 mmol) and followed by dropwise of pivaloyl chloride (720 mg, 6 mmol). Then the mixture was stirred at room temperature for 16 h. The reaction was quenched with water, extracted with EtOAc (60 mL×2), washed with brine, dried over $Na_2SO_4$, filtered, and concentrated. The residue was purified by combi flash to give target compound (620 mg, 48%). MS: M/e 257 $(M+1)^+$.

Step B: 4-((4-(tert-butoxy)-2-(((S)-1-methylpyrrolidin-2-yl)methoxy)imidazo[2,1-f][1,2,4]triazin-7-yl)(hydroxy)methyl)naphthalen-2-yl pivalate

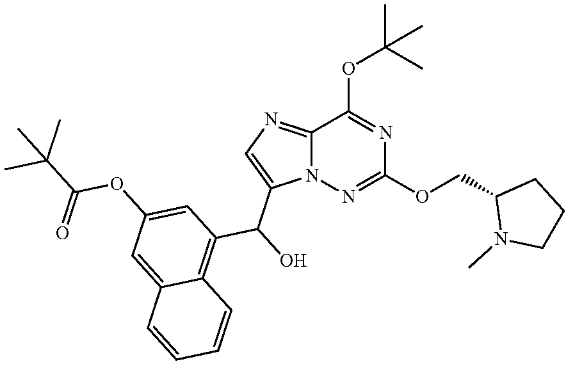 [SMILES: CN1CCC[C@H]1COc1nc(OC(C)(C)C)c2ncc(C(O)c3cc(OC(=O)C(C)(C)C)cc4ccccc34)n2n1]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (6 mL) was added n-BuLi (1 mL, 1.6 mmol) drop wise maintaining the temperature between −75~−65° C. After 30 min, a mixture of the product of the step A (307 mg, 1.2 mmol) in THF (1 mL) was added drop wise. The resulted mixture was stirred at −70° C. for 1 h and then warmed to room temperature for 3 h. The reaction was quenched with saturated $NH_4Cl$ solution, extracted with EtOAc (60 mL×2), washed with brine, dried over $Na_2SO_4$, filtered, and concentrated. The residue was purified by combi flash to give target compound (340 mg, 60%). MS: M/e 562 $(M+1)^+$.

Step C: (S)-4-((4-hydroxy-2-((1-methylpyrrolidin-2-yl)methoxy)imidazo[2,1-f][1,2,4]triazin-7-yl)methyl)naphthalen-2-yl pivalate

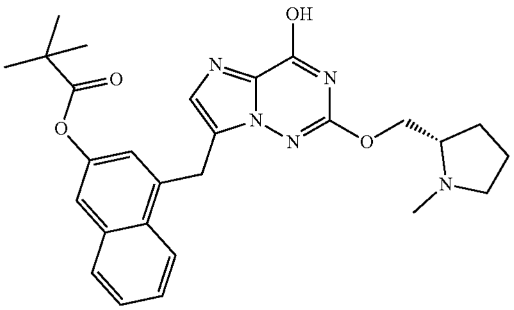 [SMILES: CN1CCC[C@H]1COc1nc(O)c2ncc(Cc3cc(OC(=O)C(C)(C)C)cc4ccccc34)n2n1]

To a mixture of the product of step B (340 mg, 0.6 mmol) in DCM (8 mL) was added TFA (2 mL) and $Et_3SiH$ (4 mL). The reaction was heated at 40° C. overnight. The mixture was concentrated to dryness and the residue was used directly for next step without further purification. MS: M/e 490 $(M+1)^+$.

Step D: benzyl (S)-2-(cyanomethyl)-4-(2-(((S)-1-methylpyrrolidin-2-yl)methoxy)-7-((3-(pivaloyloxy)naphthalen-1-yl)methyl)imidazo[2,1-f][1,2,4]triazin-4-yl)piperazine-1-carboxylate

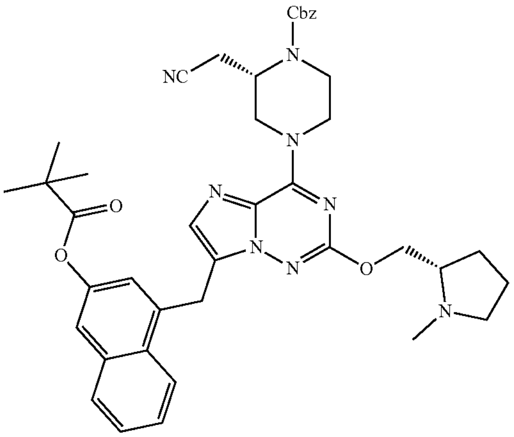 [SMILES: CN1CCC[C@H]1COc1nc(N2CCN(C(=O)OCc3ccccc3)[C@@H](CC#N)C2)c2ncc(Cc3cc(OC(=O)C(C)(C)C)cc4ccccc34)n2n1]

To the residue of the step C (crude) in toluene (10 mL) was added $POCl_3$ (567 mg, 3.6 mmol) and DIEA (314 mg, 2.44 mmol). The resulted mixture was stirred at 100° C. overnight. The mixture was concentrated to dryness, treated with THF (10 mL). Then DIEA (619 mg, 4.8 mmol) and benzyl (S)-2-(cyanomethyl)piperazine-1-carboxylate (155 mg, 0.6 mmol) were added and the reaction was stirred at room temperature for 16 hours. The reaction was quenched with saturated water, extracted with EtOAc (60 mL), washed with brine, dried over $Na_2SO_4$, filtered, and concentrated. The residue was purified by combi flash to give target compound (130 mg, 29% for two steps). MS: M/e 731 $(M+1)^+$.

Step E: 4-((4-((S)-3-(cyanomethyl)piperazin-1-yl)-2-(((S)-1-methylpyrrolidin-2-yl)methoxy)imidazo[2,1-f][1,2,4]triazin-7-yl)methyl)naphthalen-2-yl pivalate

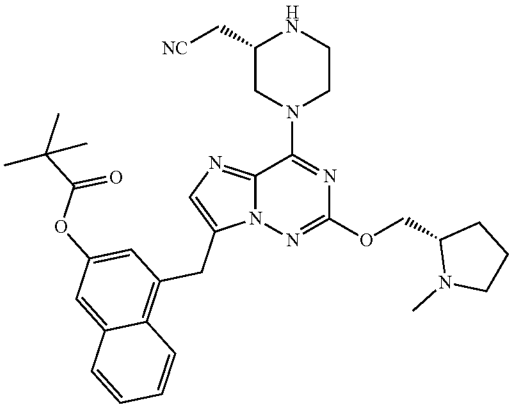 [SMILES: CN1CCC[C@H]1COc1nc(N2CCN[C@@H](CC#N)C2)c2ncc(Cc3cc(OC(=O)C(C)(C)C)cc4ccccc34)n2n1]

To a mixture of the product of step D (130 mg, 0.178 mmol) in EtOH/THF (6 mL/6 mL) was added Pd/C (100 mg, 10% Pd). The reaction was stirred at room temperature under $H_2$ (balloon) for 16 h. The mixture was filtered, and the solid was washed with DCM/MeOH (5 mL/5 mL). The filtrate was concentrated to dryness (100 mg) and the residue was used directly for next step without further purification. MS: M/e 597 $(M+1)^+$.

Step F: 4-((4-((S)-4-acryloyl-3-(cyanomethyl)piperazin-1-yl)-2-(((S)-1-methylpyrrolidin-2-yl)methoxy)imidazo[2,1-f][1,2,4]triazin-7-yl)methyl)naphthalen-2-yl pivalate

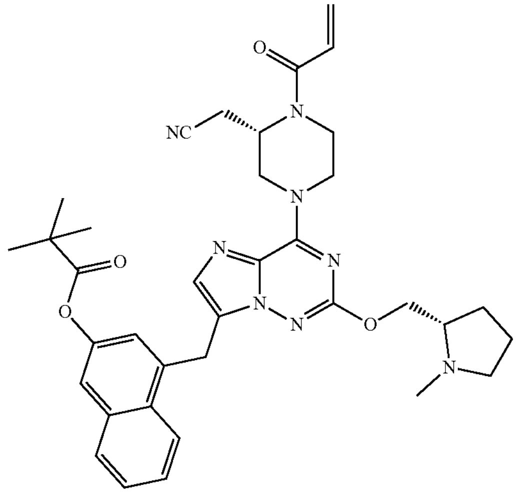 [SMILES: C=CC(=O)N1CCN(c2nc(OC[C@@H]3CCCN3C)nn3c(Cc4cc(OC(=O)C(C)(C)C)cc5ccccc45)cnc23)C[C@@H]1CC#N]

To a mixture of the 4-((4-((S)-3-(cyanomethyl)piperazin-1-yl)-2-(((S)-1-methylpyrrolidin-2-yl)methoxy)imidazo[2,1-f][1,2,4]triazin-7-yl)methyl)naphthalen-2-yl pivalate (40 mg, crude) in $CH_3CN$ (2 mL) was added saturated $NaHCO_3$ (1 mL) and followed by a solution of acryloyl chloride (6.6 mg, 0.1 mmol) in $CH_3CN$ (0.5 mL) at 0° C. The resulting mixture was stirred at room temperature for 1 hour. The reaction was diluted with water, extracted with EA. The organic layer was washed with brine, dried over $MgSO_4$, filtered, and concentrated. The residue was purified by prep-TLC to give the target compound 50 mg. MS: M/e 651 $(M+1)^+$.

Step G: 2-((S)-1-acryloyl-4-(7-((3-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

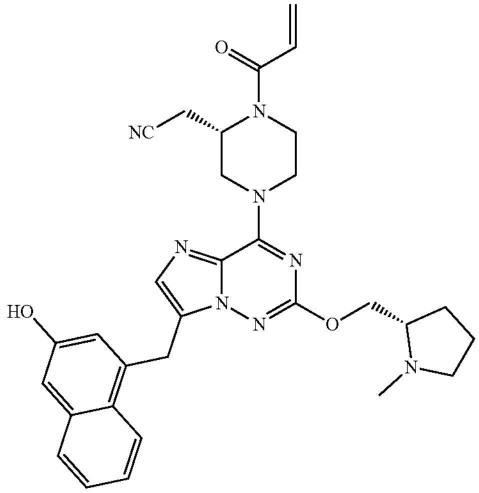 [SMILES: C=CC(=O)N1CCN(c2nc(OC[C@@H]3CCCN3C)nn3c(Cc4cc(O)cc5ccccc45)cnc23)C[C@@H]1CC#N]

To a mixture of the product of step F (50 mg) in THF (2 mL) was added NaOH (2 M, 1 ml). The reaction was stirred at rt for 2 hours. The mixture was adjusted pH to (4~5) with citric acid and the residue was extracted with EA. The combined organic layers were washed with brine, dried over $Na_2SO_4$ and concentrated. The residue was purified by prep-TLC to give the target compound (8 mg, 18%). 1H NMR (400 MHz, DMSO-d6) δ 8.08 (d, J=8.2 Hz, 1H), 7.70 (d, J=8.1 Hz, 1H), 7.54-7.40 (m, 2H), 7.32 (s, 1H), 7.05 (s, 1H), 6.96-6.83 (m, 2H), 6.20 (d, J=16.5 Hz, 1H), 5.81 (d, J=10.2 Hz, 1H), 4.89-5.06 (m, 2H), 4.58 (s, 5H), 4.16 (s, 1H), 3.33-3.50 (m, 4H), 2.70-3.07 (m, 8H), 2.10 (s, 1H), 1.51-1.74 (m, 3H) ppm. MS: M/e 567 $(M+1)^+$.

Example 6: Compound A6: 2-((S)-1-acryloyl-4-(7-((8-chloronaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(8-chloronaphthalen-1-yl)methanol

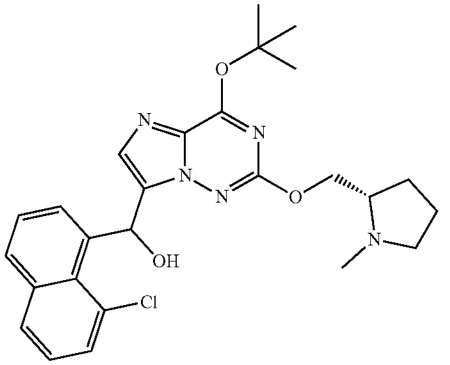 [SMILES: CN1CCC[C@H]1COc1nc(OC(C)(C)C)c2ncc(C(O)c3cccc4cccc(Cl)c34)n2n1]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (10 mL) was added n-BuLi (1 mL, 1.6 mmol) dropwise maintaining the temperature between −75~−65° C. After 30 min, a mixture of 8-chloro-1-naphthaldehyde (200 mg, 1.1 mmol) in THF (2 mL) was added dropwise. The resulted mixture was stirred at −70° C. for 1 h and then warmed to room temperature for 16 h. The reaction was quenched with saturated $NH_4Cl$ solution, extracted with EtOAc (50 mL×2). The combined organic layers were washed with brine, dried over $Na_2SO_4$, filtered, and concentrated. The residue was purified by combi flash to give the target compound (400 mg, 80%). MS: M/e 496 $(M+1)^+$.

Step B: (S)-7-((8-chloronaphthalen-1-yl)methyl)-2-((1-methylpyrrolidin-2-yl)methoxy)imidazo[2,1-f][1,2,4]triazin-4-ol

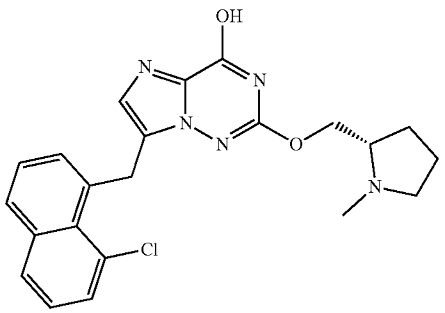 [SMILES: CN1CCC[C@H]1COc1nc(O)c2ncc(Cc3cccc4cccc(Cl)c34)n2n1]

To a mixture of the product of step A (400 mg, 0.8 mmol) in DCM (4 mL) was added TFA (4 mL) and $Et_3SiH$ (4 mL). The reaction was stirred at 25° C. overnight. The mixture was concentrated to dryness and the residue was used directly for next step without further purification. MS: M/e 424 $(M+1)^+$.

Step C: benzyl (S)-4-(7-((8-chloronaphthalen-1-yl)methyl)-2-(((S)-1-methylpyrrolidin-2-yl)methoxy)imidazo[2,1-f][1,2,4]triazin-4-yl)-2-(cyanomethyl)piperazine-1-carboxylate

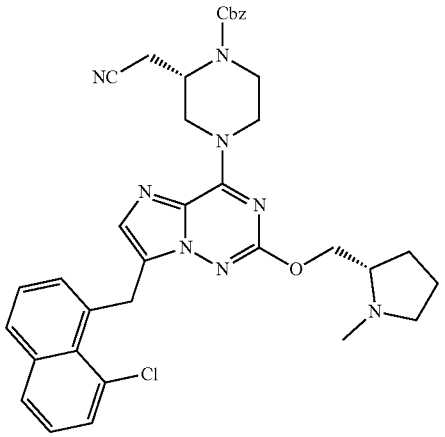 [SMILES: CN1CCC[C@H]1COc1nc(N2CCN(C(=O)OCc3ccccc3)[C@@H](CC#N)C2)c2ncc(Cc3cccc4cccc(Cl)c34)n2n1]

To the above residue of the step B (crude) in toluene (8 mL) was added $POCl_3$ (1 g, 6.5 mmol) and DIEA (428 mg, 3.23 mmol). The resulting mixture was stirred at 100° C. overnight. The mixture was concentrated to dryness, treated with THF (15 mL). Then DIEA (825 mg, 6.4 mmol) and benzyl (S)-2-(cyanomethyl)piperazine-1-carboxylate (209 mg, 0.8 mmol) were added and the reaction was stirred at room temperature for 3 hours. The reaction was quenched with water, extracted with EtOAc (80 mL). The organic layer was washed with brine, dried over $Na_2SO_4$, filtered, and concentrated. The residue was purified by combi flash to give target compound (40 mg, 6% for two steps). MS: M/e 665 $(M+1)^+$.

Step D: 2-((S)-4-(7-((8-chloronaphthalen-1-yl)methyl)-2-(((S)-1-methylpyrrolidin-2-yl)methoxy)imidazo[2,1-f][1,2,4]triazin-4-yl)piperazin-2-yl)acetonitrile

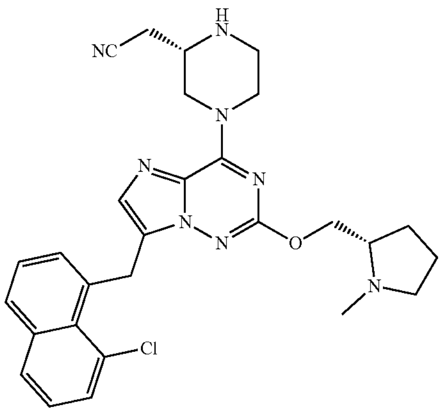 [SMILES: CN1CCC[C@H]1COc1nc(N2CCN[C@@H](CC#N)C2)c2ncc(Cc3cccc4cccc(Cl)c34)n2n1]

To a mixture of the product of step C (30 mg, 0.05 mmol) in DCM (5 mL) at −70° C. was added 1N $BBr_3$ in DCM (0.1 mL, 0.1 mmol). The reaction was slowly warmed to room temperature for 2 hours. Another portion of 1N $BBr_3$ in DCM (0.1 mL, 0.1 mmol) was added and stirred overnight. The reaction was diluted with water, extracted with DCM (60 mL). The organic layer was washed with brine, dried over $Na_2SO_4$, filtered, and concentrated to give the target compound (20 mg, crude) which was used directly for next step without further purification. MS: M/e 531 $(M+1)^+$.

Step E: 2-((S)-1-acryloyl-4-(7-((8-chloronaphthalen-1-yl)methyl)-2-(((S)-1-methylpyrrolidin-2-yl)methoxy)imidazo[2,1-f][1,2,4]triazin-4-yl)piperazin-2-yl)acetonitrile

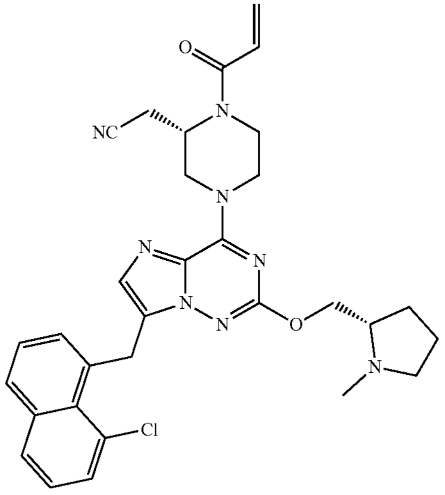 [SMILES: C=CC(=O)N1CCN(c2nc(OC[C@@H]3CCCN3C)nn3c(Cc4cccc5cccc(Cl)c45)cnc23)C[C@@H]1CC#N]

To a mixture of the product of the step D (20 mg, crude) in $CH_3CN$ (4 mL) was added saturated $NaHCO_3$ (0.3 mL) and followed by a solution of acryloyl chloride (6 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (0.4 mg, 1.3% for two steps). $^1$HNMR (400 MHz, $CD_3OD$) δ 7.94-7.86 (m, 2H), 7.60-7.35 (m, 4H), 6.90-6.75 (m, 2H), 6.24-6.22 (m, 1H), 5.90-5.76 (m, 1H), 5.69 (dd, J=3.6 Hz, 8.8 Hz 1H), 5.25-4.95 (m, 4H), 4.65-4.55 (m, 1H), 4.40-4.26 (m, 2H), 4.25-4.10 (m, 1H), 3.70-3.55 (m, 1H), 3.14-3.04 (m, 2H), 2.95-2.70 (m, 3H), 2.48 (s, 3H), 2.42-2.30 (m, 1H), 2.13-1.98 (m, 1H), 1.86-1.65 (m, 3H) ppm. MS: M/e 586 $(M+1)^+$.

Example 7: Compound A07: 2-((S)-1-acryloyl-4-(7-((8-methylnaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(8-methylnaphthalen-1-yl)methanol

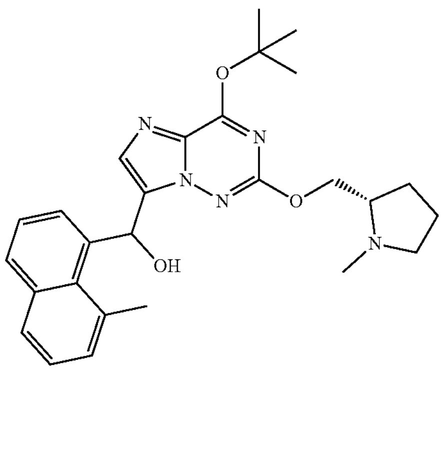 [SMILES: Cc1cccc2cccc(C(O)c3cnc4c(OC(C)(C)C)nc(OC[C@@H]5CCCN5C)nn34)c12]

To a solution of (S)-7-bromo-4-(tert-butoxy)-2-((1-methylpyrrolidin-2-yl)methoxy)imidazo[2,1-f][1,2,4]triazine (550 mg, 1.43 mmol) in THF (10 mL) was added n-BuLi (1.43 mL, 1.6 mmol) dropwise maintaining the temperature between −75~−65° C. After 30 min, a mixture of 8-methyl-1-naphthaldehyde (294 mg, 1.72 mmol) in THF (2 mL) was added dropwise. The resulted mixture was stirred at −70° C. for 1 h and then warmed to room temperature for 16 h. The reaction was quenched with saturated $NH_4Cl$ solution, extracted with EtOAc (50 mL×2). The combined organic layers were washed with brine, dried over $Na_2SO_4$, filtered, and concentrated. The residue was purified by combi flash to give target compound (340 mg, 50%). MS: M/e 476 $(M+1)^+$.

Step B: (S)-7-((8-methylnaphthalen-1-yl)methyl)-2-((1-methylpyrrolidin-2-yl)methoxy)imidazo[2,1-f][1,2,4]triazin-4-ol

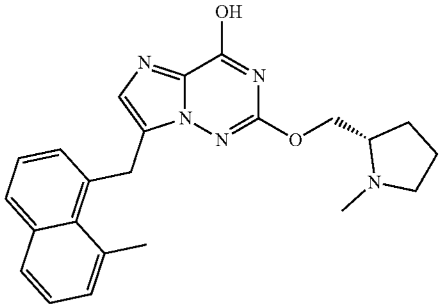 [SMILES: Cc1cccc2cccc(Cc3cnc4c(O)nc(OC[C@@H]5CCCN5C)nn34)c12]

To a mixture of the product of step A (340 mg, 0.715 mmol) in DCM (4 mL) was added TFA (4 mL) and $Et_3SiH$ (4 mL). The reaction was heated at 25° C. for 3 hours. The mixture was concentrated to dryness and the residue was used directly for next step without further purification. MS: M/e 404 $(M+1)^+$.

Step C: benzyl (S)-2-(cyanomethyl)-4-(7-((8-methylnaphthalen-1-yl)methyl)-2-(((S)-1-methylpyrrolidin-2-yl)methoxy)imidazo[2,1-f][1,2,4]triazin-4-yl)piperazine-1-carboxylate

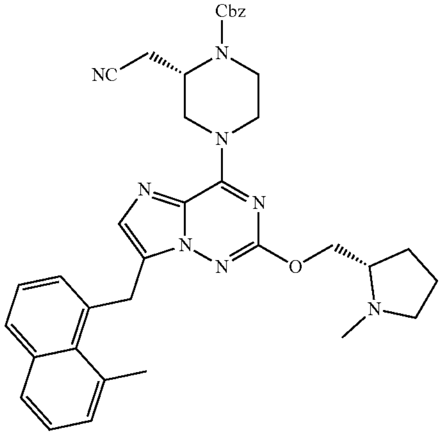 [SMILES: Cc1cccc2cccc(Cc3cnc4c(N5CCN(C(=O)OCc6ccccc6)[C@@H](CC#N)C5)nc(OC[C@@H]5CCCN5C)nn34)c12]

To the residue of the step B (crude) in toluene (8 mL) was added $POCl_3$ (868 mg, 5.6 mmol) and DIEA (360 mg, 2.8 mmol). The resulted mixture was stirred at 100° C. overnight. The mixture was concentrated to dryness, treated with THF (15 mL). Then DIEA (720 mg, 5.6 mmol) and benzyl (S)-2-(cyanomethyl)piperazine-1-carboxylate (217 mg, 0.84 mmol) were added and the reaction was stirred at room temperature for 2 hours. The reaction was quenched with water, extracted with EtOAc (60 mL×2). The combined organic layers were washed with brine, dried over $Na_2SO_4$, filtered, and concentrated. The residue was purified by combi flash to give target compound (120 mg, 26% for two steps). MS: M/e 645 $(M+1)^+$.

Step D: 2-((S)-4-(7-((8-methylnaphthalen-1-yl)methyl)-2-(((S)-1-methylpyrrolidin-2-yl)methoxy)imidazo[2,1-f][1,2,4]triazin-4-yl)piperazin-2-yl)acetonitrile

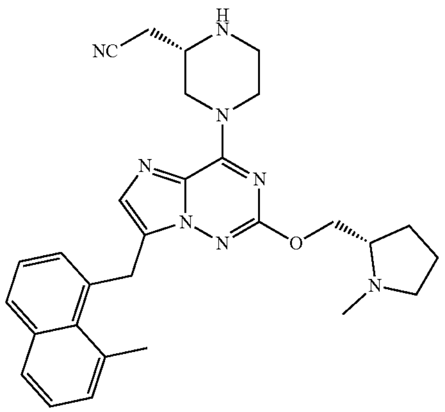 [SMILES: Cc1cccc2cccc(Cc3cnc4c(N5CCN[C@@H](CC#N)C5)nc(OC[C@@H]5CCCN5C)nn34)c12]

To a mixture of the product of step C (120 mg, 0.186 mmol) in EtOH/THF (5 mL/5 mL) was added Pd/C (80 mg, 10% Pd). The reaction was stirred at room temperature under $H_2$ (balloon) for 16 h. The suspension was filtered, and the solid was washed with MeOH (5 mL). The filtrate was concentrated to dryness (90 mg) and the residue was used directly for next step without further purification. MS: M/e 511 $(M+1)^+$.

Step E: 2-((S)-1-acryloyl-4-(7-((8-methylnaphthalen-1-yl)methyl)-2-(((S)-1-methylpyrrolidin-2-yl)methoxy)imidazo[2,1-f][1,2,4]triazin-4-yl)piperazin-2-yl)acetonitrile

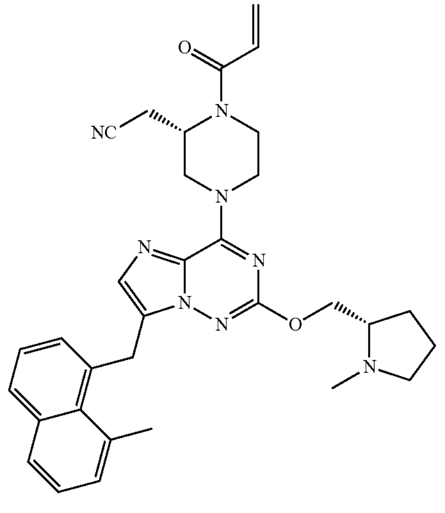 [SMILES: C=CC(=O)N1CCN(c2nc(OC[C@@H]3CCCN3C)nn3c(Cc4cccc5cccc(C)c45)cnc23)C[C@@H]1CC#N]

To a mixture of the product of the step D (90 mg, crude) in $CH_3CN$ (4 mL) was added saturated $NaHCO_3$ (0.5 mL) and followed by a solution of acryloyl chloride (16 mg, 0.17 mmol) in $CH_3CN$ (0.3 mL) at 0° C. The resulting mixture was stirred at room temperature for one hour. The reaction was diluted with water, extracted with EA (60 mL×2). The combined organic phases were washed with brine, dried over $Na_2SO_4$, filtered, and concentrated. The residue was purified by prep-TLC to give the target compound (25 mg, 24% for two steps). $^1$HNMR (400 MHz, DMSO-d6) δ 7.90-7.76 (m, 2H), 7.44-7.31 (m, 2H), 7.32-7.23 (m, 2H), 6.95-6.75 (m, 2H), 6.19 (d, J=17.6 Hz 1H), 5.78 (dd, J=10.8 Hz 1H), 5.15-4.83 (m, 2H), 4.78 (s, 2H), 4.55-3.94 (m, 3H), 3.90-3.40 (m, 2H), 3.15-2.85 (m, 5H), 2.76-2.71 (m, 4H), 2.31 (s, 3H), 2.24-2.10 (m, 1H), 1.96-1.83 (m, 1H), 1.80-1.50 (m, 3H) ppm. MS: M/e 565 $(M+1)^+$.

Example 8: Compound A8: 2-((S)-1-acryloyl-4-(2-(((S)-1-methylpyrrolidin-2-yl)methoxy)-7-(naphthalen-2-ylmethyl)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(naphthalen-2-yl)methanol

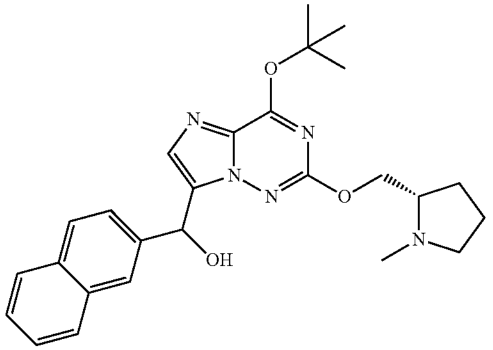 [SMILES: CN1CCC[C@H]1COc1nc(OC(C)(C)C)c2ncc(C(O)c3ccc4ccccc4c3)n2n1]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (10 mL) was added n-BuLi (1 mL, 1.6 mmol) dropwise maintaining the temperature between −75~−65° C. After 30 min, a mixture of 2-naphthaldehyde (170 mg, 1.1 mmol) in THF (2 mL) was added drop wise. The resulted mixture was stirred at −70° C. for 1 h and then warmed to room temperature for 1 h. The reaction was quenched with saturated $NH_4Cl$ solution, extracted with EtOAc (60 mL×2). The combined organic layers were washed with brine, dried over $Na_2SO_4$, filtered, and concentrated. The residue was purified by combi flash to give target compound (150 mg, 32%). MS: M/e 462 $(M+1)^+$.

Step B: (S)-2-((1-methylpyrrolidin-2-yl)methoxy)-7-(naphthalen-2-ylmethyl)imidazo[2,1-f][1,2,4]triazin-4-ol

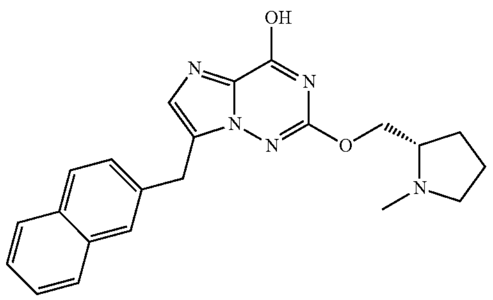 [SMILES: CN1CCC[C@H]1COc1nc(O)c2ncc(Cc3ccc4ccccc4c3)n2n1]

To a mixture of the product of step A (150 mg, 0.32 mmol) in DCM (2 mL) was added TFA (2 mL) and $Et_3SiH$ (2 mL). The reaction was stirred at 25° C. for 5 hours. The mixture was concentrated to dryness and the residue was used directly for next step without further purification. MS: M/e 390 $(M+1)^+$.

Step C: benzyl (S)-2-(cyanomethyl)-4-(2-(((S)-1-methylpyrrolidin-2-yl)methoxy)-7-(naphthalen-2-ylmethyl)imidazo[2,1-f][1,2,4]triazin-4-yl)piperazine-1-carboxylate

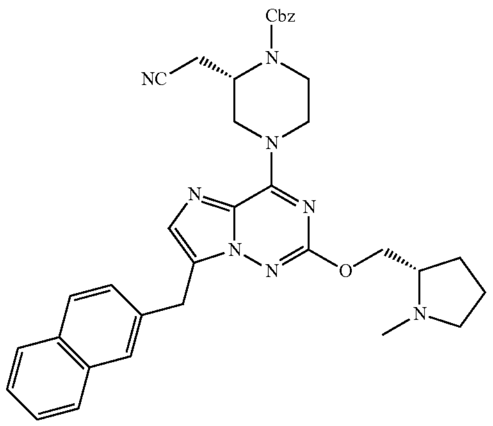 [SMILES: CN1CCC[C@H]1COc1nc(N2CCN(C(=O)OCc3ccccc3)[C@@H](CC#N)C2)c2ncc(Cc3ccc4ccccc4c3)n2n1]

To the above residue of the step B (200 mg, crude) in $POCl_3$ (4 mL) was added triethylamine hydrochloride (137 mg, 1 mmol). The resulted mixture was stirred at 120° C. in a sealed tube overnight. The mixture was concentrated to dryness, treated with THF (6 mL). Then DIEA (340 mg, 2.64 mmol) and benzyl (S)-2-(cyanomethyl)piperazine-1-carboxylate (85 mg, 0.33 mmol) were added and the reaction was stirred at room temperature for 3 hours. The reaction was quenched with water, extracted with EtOAc (60 mL×2). The combined organic layers were washed with brine, dried over $Na_2SO_4$, filtered, and concentrated. The residue was purified by combi flash to give target compound (60 mg, 29% for two steps). MS: M/e 631 $(M+1)^+$.

Step D: 2-((S)-4-(2-(((S)-1-methylpyrrolidin-2-yl)methoxy)-7-(naphthalen-2-ylmethyl)imidazo[2,1-f][1,2,4]tri zin-4-yl)piperazin-2-yl)acetonitrile

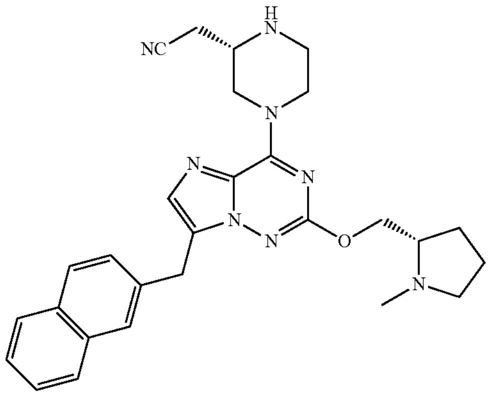 [SMILES: CN1CCC[C@H]1COc1nc(N2CCN[C@@H](CC#N)C2)c2ncc(Cc3ccc4ccccc4c3)n2n1]

To a mixture of the product of step C (60 mg, 0.095 mmol) in EtOH/THF (3 mL/3 mL) was added Pd/C (50 mg, 10% Pd). The reaction was stirred at room temperature under $H_2$ (balloon) for overnight. The mixture was filtered, and the solid was washed with DCM/MeOH (20 mL/1 mL). The filtrate was concentrated to dryness (40 mg) and the residue was used directly for next step without further purification. MS: M/e 497 $(M+1)^+$.

Step E: 2-((S)-1-acryloyl-4-(2-(((S)-1-methylpyrrolidin-2-yl)methoxy)-7-(naphthalen-2-ylmethyl)imidazo[2,1-f][1,2,4]triazin-4-yl)piperazin-2-yl)acetonitrile

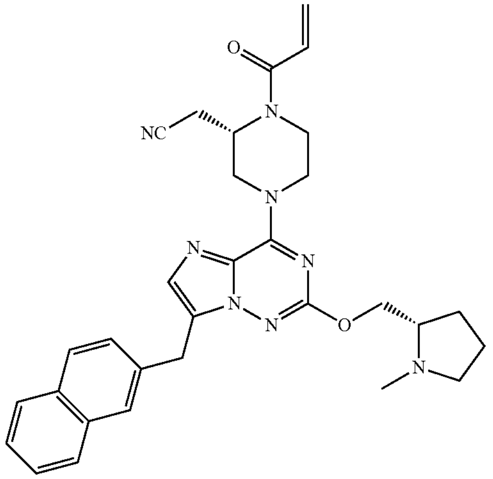 [SMILES: C=CC(=O)N1CCN(c2nc(OC[C@@H]3CCCN3C)nn3c(Cc4ccc5ccccc5c4)cnc23)C[C@@H]1CC#N]

To a mixture of the product of the step D (40 mg, crude) in $CH_3CN$ (5 mL) was added saturated $NaHCO_3$ (0.5 mL) and followed by a solution of acryloyl chloride (9 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (8 mg, 15% for two steps).

$^1$HNMR (400 MHz, DMSO-$d_6$) δ 7.92-7.70 (m, 4H), 7.54-7.33 (m, 4H), 6.90-6.79 (m, 1H), 6.17 (d, J=16.4 Hz, 1H), 5.76 (d, J=9.6 Hz, 1H), 5.15-4.75 (m, 2H), 4.65-4.39 (m, 1H), 4.33 (s, 2H), 4.26-3.77 (m, 3H), 3.54-3.36 (m, 2H), 3.19-2.67 (m, 6H), 2.28 (s, 3H), 2.16-2.04 (m, 1H), 1.95-1.76 (m, 1H), 1.74-1.50 (m, 2H) ppm. MS: M/e 551 $(M+1)^+$.

Example 9: Compound A09: 2-((S)-1-acryloyl-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazin-2-yl)acetonitrile Step A: 7-bromo-4-(tert-butoxy)-2-chloroimidazo[2,1-f][1,2,4]triazine

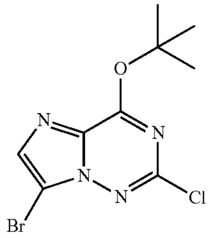 [SMILES: CC(C)(C)Oc1nc(Cl)nn2c(Br)cnc12]

To a cooled solution of 7-bromo-2,4-dichloroimidazo[2,1-f][1,2,4]triazine (2 g, 7.5 mmol) in THF (20 mL) at 0° C. was added with tert-butyllithium (660 mg, 8.3 mmol) in portions. After addition, the reaction mixture was stirred at r.t. for 30 minutes. The solution was quenched with ice water, extracted with EA. The organic layer was washed with brine, dried over $Na_2SO_4$, filtered, and concentrated. The crude was purified by Combi Flash (PE:EA=9:1) to get the product (1.4 g, 64%). MS: M/e 305 (M+1)+

Step B: (S)-7-bromo-4-(tert-butoxy)-2-((1-methylpyrrolidin-2-yl)methoxy)imidazo[2,1-f][1,2,4]triazine

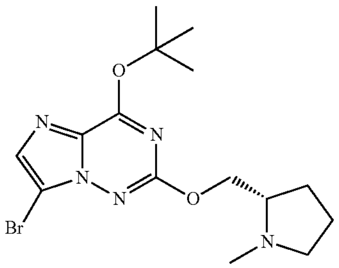 [SMILES: CN1CCC[C@H]1COc1nc(OC(C)(C)C)c2ncc(Br)n2n1]

NaH (276 mg, 6.9 mmol) was added to a solution of (S)-(1-methylpyrrolidin-2-yl)methanol (637 mg, 5.5 mmol) in THF (20 mL). After stirred at r.t. for 30 mins, 7-bromo-4-(tert-butoxy)-2-chloroimidazo[2,1-f][1,2,4]triazine (1.4 g, 4.6 mmol) in THF (5 mL) was added dropwise. The resulting mixture was transferred to an oil bath at 60° C. and stirred for 30 mins at 60° C. The solution was quenched with $NH_4Cl$ solution (5 mL) and extracted with EA (15 mL). The organic layer was dried, concentrated and purified by Combi Flash (DCM:$NH_3$ (7M in Methanol)=20:1) to get the product (0.9 g, 51%). $^1$H NMR (400 MHz, DMSO-d6) δ 7.73 (s, 1H), 4.29-4.33 (m, 1H), 4.19-4.15 (m, 1H), 2.95 (d, J=8.0 Hz, 1H), 2.66-2.63 (m, 1H), 2.38 (s, 3H), 2.19-2.14 (m, 1H), 1.95-1.91 (m, 1H), 1.69 (s, 9H), 1.68-1.62 (m, 3H) ppm. MS: M/e 384 (M+1)+

Step C: (4-(tert-butoxy)-2-(((S)-1-methylpyrrolidin-2-yl)methoxy)imidazo[2,1-f][1,2,4]triazin-7-yl)(2,3-dihydrobenzofuran-4-yl)methanol

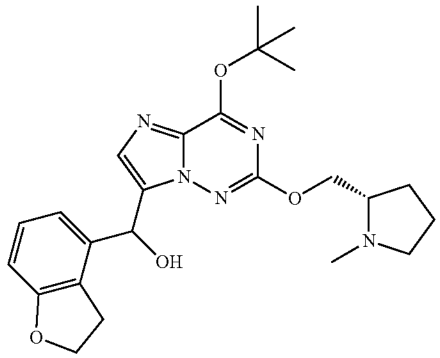

To a cooled solution of (S)-7-bromo-4-(tert-butoxy)-2-((1-methylpyrrolidin-2-yl)methoxy)imidazo[2,1-f][1,2,4]triazine (300 mg, 0.78 mmol) in THF (5 mL) at −78° C. was added with n-BuLi (1.6 M in n-hexane, 0.7 mL, 1.12 mmol) dropwise. After stirred for 30 inns, 2,3-dihydrobenzofuran-4-carbaldehyde (139 mg, 0.9 mmol) in THF (3 mL) was added dropwise. The resulting mixture was stirred gradually to r.t overnight. The solution was quenched with $NH_4Cl$ solution (5 mL) and extracted with EA (15 mL). The organic layer was dried, concentrated and purified by Combi Flash (DCM:$NH_3$ (7 M in Methanol)=100:3) to get the product (290 mg, 82%). MS: M/e 454 (M+1)+

Step D: (S)-7-((2,3-dihydrobenzofuran-4-yl)methyl)-2-((1-methylpyrrolidin-2-yl)methoxy)imidazo[2,1-f][1,2,4]triazin-4-ol

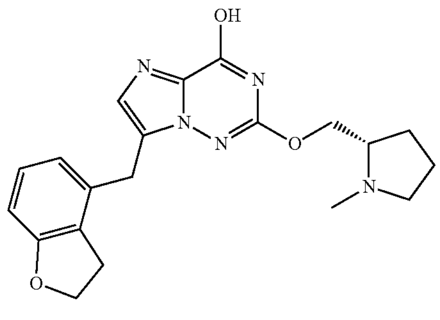 [SMILES: CN1CCC[C@H]1COc1nc(O)c2ncc(Cc3cccc4c3CCO4)n2n1]

$Et_3SiH$ (2 mL) and TFA (2 mL) were added to a solution of (4-(tert-butoxy)-2-(((S)-1-methylpyrrolidin-2-yl)methoxy)imidazo[2,1-f][1,2,4]triazin-7-yl)(2,3-dihydrobenzofuran-4-yl)methanol (290 mg, 0.6 mmol) in DCM (2 mL). The solution was stirred at r.t for 6 hrs, and then heated at 40° C. overnight. The solvent was evaporated under oil pump, then co-distilled with toluene. The crude product was used in the next step directly (240 mg, crude). MS: M/e 382 $(M+1)^+$ Step E: (S)-4-chloro-7-((2,3-dihydrobenzofuran-4-yl)methyl)-2-((1-methylpyrrolidin-2-yl)methoxy)imidazo[2,1-f][1,2,4]triazine

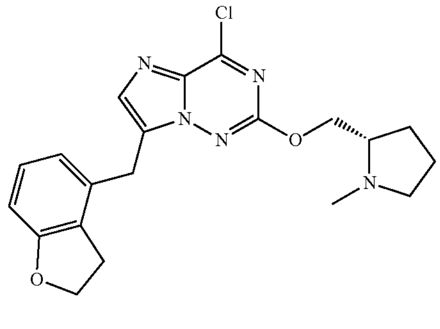 [SMILES: CN1CCC[C@H]1COc1nc(Cl)c2ncc(Cc3cccc4c3CCO4)n2n1]

A sealed tube charged with (S)-7-((2,3-dihydrobenzofuran-4-yl)methyl)-2-((1-methylpyrrolidin-2-yl)methoxy)imidazo[2,1-f][1,2,4]triazin-4-ol (190 mg, 0.5 mmol), $Et_3N\cdot HCl$ (138 mg, 1 mmol) and $POCl_3$ (8 mL) was heated at 120° C. overnight. After cooled down, the solvent was evaporated under oil pump and co-distilled with toluene to get the crude product, which was use directly in the next step (200 mg, crude). MS: M/e 400 $(M+1)^+$.

Step F: benzyl (S)-2-(cyanomethyl)-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazine-1-carboxylate

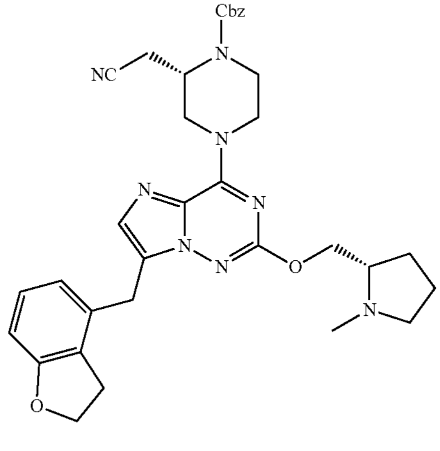 [SMILES: CN1CCC[C@H]1COc1nc(N2CCN(C(=O)OCc3ccccc3)[C@@H](CC#N)C2)c2ncc(Cc3cccc4c3CCO4)n2n1]

Benzyl (S)-2-(cyanomethyl)piperazine-1-carboxylate (208 mg, 0.8 mmol) was added to a solution of (S)-4-chloro-7-((2,3-dihydrobenzofuran-4-yl)methyl)-2-((1-methylpyrrolidin-2-yl)methoxy)imidazo[2,1-f][1,2,4]triazine (200 mg, 0.52 mmol) in THF (20 mL), followed with DIEA (520 mg, 4 mmol). The reaction mixture was stirred at r.t. for 1 hour. The solution was added with water (10 mL) and extracted with EA (15 mL). The organic layer was dried over $Na_2SO_4$, concentrated and purified by Combi Flash (DCM:$NH_3$ (7M in MeOH)=100:7) to give the product (150 mg, 48%). MS: M/e 623 $(M+1)^+$.

Step G: 2-((S)-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazin-2-yl)acetonitrile

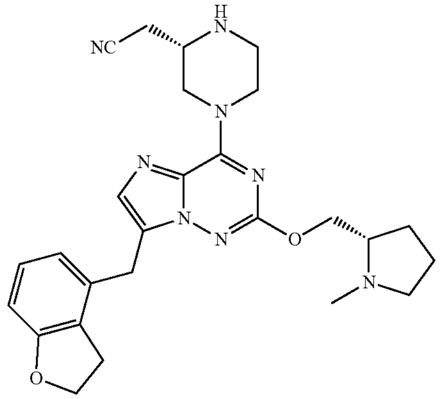 [SMILES: CN1CCC[C@H]1COc1nc(N2CCN[C@@H](CC#N)C2)c2ncc(Cc3cccc4c3CCO4)n2n1]

A solution of benzyl (S)-2-(cyanomethyl)-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazine-1-carboxylate (75 mg, 0.12 mmol) and Pd/C (wet, 10%, 50 mg) in THF/EtOH (2 mL/2 mL) was stirred at r.t. under $H_2$ balloon overnight. The catalyst was filtered and the filtrate was concentrated to get the crude product, which was used directly (55 mg, crude). MS: M/e 489 $(M+1)^+$ Step H: 2-((S)-1-acryloyl-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazin-2-yl)acetonitrile

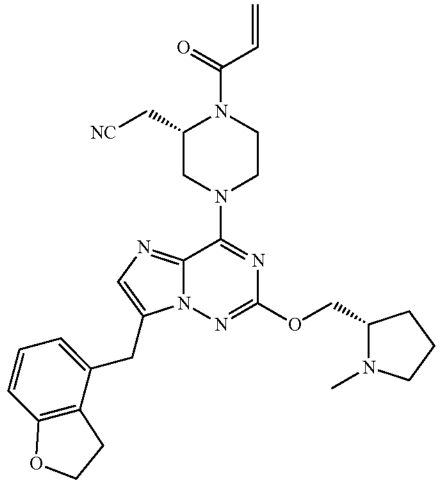 [SMILES: C=CC(=O)N1CCN(c2nc(OC[C@@H]3CCCN3C)nn3c(Cc4cccc5c4CCO5)cnc23)C[C@@H]1CC#N]

$NaHCO_3$ solution (saturated, 0.5 mL) was added to a solution of 2-((S)-4-(7-((2,3-dihydrobenzofuran-4-yl)methyl)-2-(((S)-1-methylpyrrolidin-2-yl)methoxy)imidazo[2,1-f][1,2,4]triazin-4-yl)piperazin-2-yl)acetonitrile (30 mg, crude) in $CH_3CN$ (5 mL), followed with acryloyl chloride (7 mg, 0.07 mmol). The reaction mixture was stirred at r.t. for 1 hr. The solution was evaporated, added with water (4 mL) and extracted with EA (8 mL). The organic layer was dried, concentrated and purified by prep-TLC (DCM:$NH_3$ (7M in MeOH)=10:1) to get the product (6 mg, 18%). $^1H$ NMR (400 MHz, $CD_3OD$) δ 7.31 (s, 1H), 7.00 (t, J=8.0 Hz, 1H), 6.82 (br.s, 1H), 6.67 (d, J=8.0 Hz, 1H), 6.59 (d, J=8.0 Hz, 1H), 6.28 (d, J=16.0 Hz, 1H), 5.83 (d, J=8.0 Hz, 1H), 5.12 (br.s, 1H), 4.59 (s, 2H), 4.51 (t, J=8.0 Hz, 2H), 4.40 (br.s, 2H), 4.35-4.29 (m, 2H), 4.15 (s, 2H), 3.63-3.48 (m, 2H), 3.24 (s, 1H), 3.14 (d, J=8.0 Hz, 2H), 3.02 (s, 1H), 2.88 (s, 2H), 2.61 (s, 3H), 2.19-2.00 (m, 2H), 1.87-1.60 (m, 3H) ppm. MS: M/e 543 $(M+1)^+$.

Example 10: Compound A10: 2-((S)-1-acryloyl-4-(7-((4-methoxynaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(4-methoxynaphthalen-1-yl)methanol

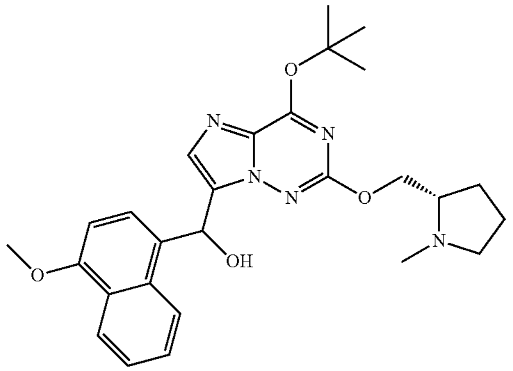 [SMILES: COc1ccc(C(O)c2cnc3c(OC(C)(C)C)nc(OC[C@@H]4CCCN4C)nn23)c2ccccc12]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (5 mL) was added n-BuLi (0.94 mL, 1.5 mmol) dropwise maintaining the temperature between −75~−65° C. After 30 min, a mixture of 4-methoxy-1-naphthaldehyde (223.2 mg, 1.2 mmol) in THF (5 mL) was added dropwise. The resulted mixture was stirred at −70° C. for 1 h and then warmed to room temperature for 1 h. The reaction was quenched with saturated $NH_4Cl$ solution, extracted with EtOAc. The organic layer was washed with brine, dried over $Na_2SO_4$, filtered, and concentrated. The residue was purified by combi flash to give target compound (320 mg, 65%). MS: M/e 492 $(M+1)^+$.

Step B: (S)-7-((4-methoxynaphthalen-1-yl)methyl)-2-((1-methylpyrrolidin-2-yl)methoxy)imidazo[2,1-f][1,2,4]triazin-4-ol

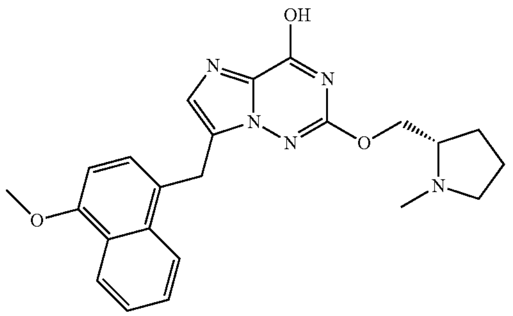 [SMILES: COc1ccc(Cc2cnc3c(O)nc(OC[C@@H]4CCCN4C)nn23)c2ccccc12]

To a mixture of the product of step A (250 mg) in DCE (2 mL) was added TFA (2 mL) and $Et_3SiH$ (2 mL). The reaction was stirred at 25° C. overnight. The mixture was concentrated to dryness. The residue was used directly for next step without further purification. MS: M/e 420 $(M+1)^+$.

Step C: benzyl (S)-2-(cyanomethyl)-4-(7-((4-methoxynaphthalen-1-yl)methyl)-2-(((S)-1-methylpyrrolidin-2-yl)methoxy)imidazo[2,1-f][1,2,4]triazin-4-yl)piperazine-1-carboxylate

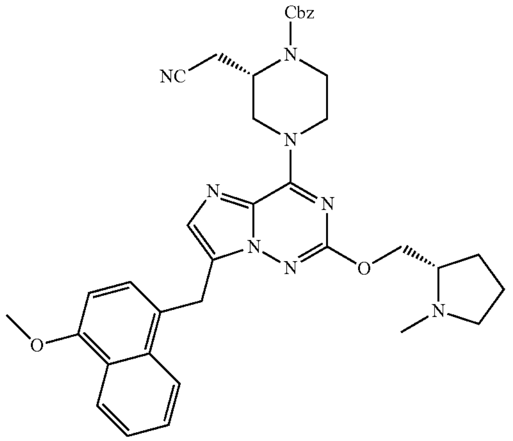 [SMILES: COc1ccc(Cc2cnc3c(N4CCN(C(=O)OCc5ccccc5)[C@@H](CC#N)C4)nc(OC[C@@H]4CCCN4C)nn23)c2ccccc12]

To the above residue of the step B (200 mg, crude) in $POCl_3$ (3 mL) was added triethylamine hydrochloride (204 mg, 1.5 mmol). The resulted mixture was stirred at 120° C. overnight. The mixture was concentrated to dryness, treated with THF (5 mL). Then DIEA (177 mg, 1.5 mmol) and benzyl (S)-2-(cyanomethyl)piperazine-1-carboxylate (130 mg, 0.5 mmol) were added and the reaction was stirred at room temperature for 2 hours. The reaction was quenched with water, extracted with EtOAc (80 mL). The organic layer was washed with brine, dried over $Na_2SO_4$, filtered, and concentrated. The residue was purified by combi flash to give target compound (75 mg, 24% for two steps). MS: M/e 661 $(M+1)^+$.

Step D: 2-((S)-4-(7-((4-methoxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

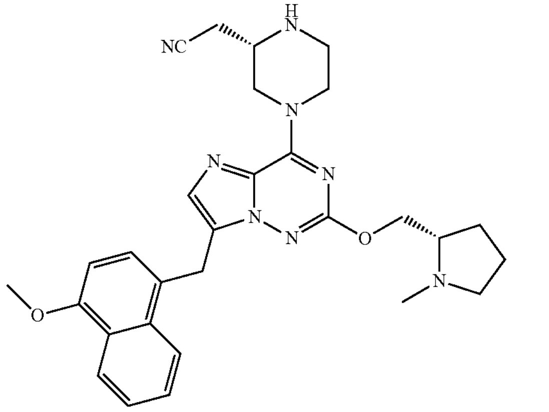 [SMILES: COc1ccc(Cc2cnc3c(N4CCN[C@@H](CC#N)C4)nc(OC[C@@H]4CCCN4C)nn23)c2ccccc12]

To a mixture of the product of step C (60 mg) in EtOH/THF (2 mL/2 mL) was added Pd/C (10 mg, 10% Pd). The reaction was stirred at room temperature under $H_2$ (balloon) for 8 h. The mixture was filtered, and the solid was washed with THF (5 mL). The filtrate was concentrated to dryness (40 mg) and the residue was used directly for next step without further purification. MS: M/e 527 $(M+1)^+$.

Step E: 2-((S)-1-acryloyl-4-(7-((4-methoxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

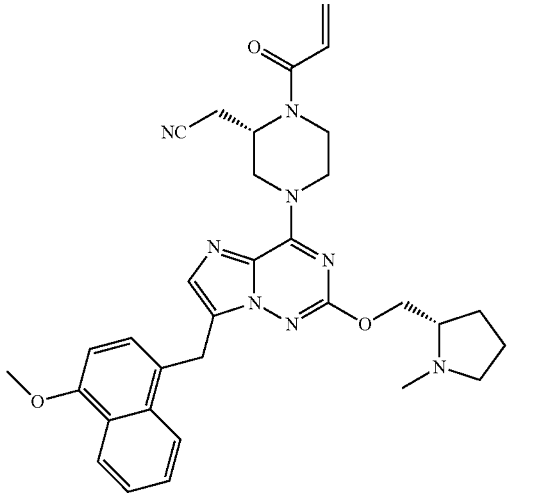 [SMILES: C=CC(=O)N1CCN(c2nc(OC[C@@H]3CCCN3C)nn3c(Cc4ccc(OC)c5ccccc45)cnc23)C[C@@H]1CC#N]

To a mixture of the product of the step D (40 mg, crude) in $CH_3CN$ (2 mL) was added saturated $NaHCO_3$ (0.5 mL) and followed by a solution of acryloyl chloride (8 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (2.17 mg, 10% for two steps). 1H NMR (400 MHz, DMSO-d6) δ 8.19 (d, J=7.5 Hz, 1H), 8.10 (d, J=9.0 Hz, 1H), 7.58-7.45 (m, 2H), 7.34 (d, J=7.6 Hz, 1H), 7.25 (s, 1H), 6.89 (d, J=7.8 Hz, 2H), 6.18 (d, J=16.4 Hz, 1H), 5.77 (d, J=10.3 Hz, 1H), 4.85 (s, 2H), 4.52 (s, 2H), 4.24 (s, 1H), 4.10 (s, 1H), 3.94 (s, 3H), 3.30 (s, 3H), 2.94 (s, 5H), 2.31 (s, 4H), 2.17 (s, 1H), 1.91 (s, 1H), 1.67 (s, 3H) ppm. MS: M/e 581 $(M+1)^+$.

Example 11: Compound A11: 2-((S)-1-acryloyl-4-(7-(2-chloro-6-fluorobenzyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(2-chloro-6-fluorophenyl)methanol

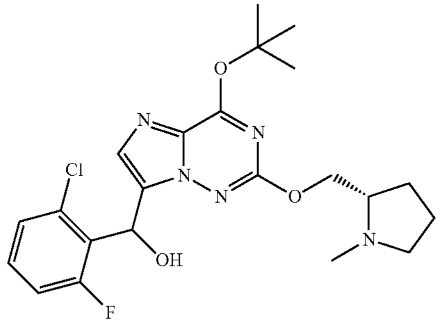 [SMILES: CN1CCC[C@H]1COc1nc(OC(C)(C)C)c2ncc(C(O)c3c(F)cccc3Cl)n2n1]

To a solution of (S)-7-bromo-4-(tert-butoxy)-2-((1-methylpyrrolidin-2-yl)methoxy)imidazo[2,1-f][1,2,4]triazine (300 mg, 0.78 mmol) in THF (8 mL) was added a solution of n-BuLi (1.6M, 0.69 mL, 1.1 mmol) dropwise maintaining the temperature between −75~−65° C. After 1 h, a suspension of the 2-chloro-6-fluorobenzaldehyde (148 mg, 0.93 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3). The combined organic phases were washed with brine, dried over $Na_2SO_4$, filtered, and concentrated. The residue was purified by prep-TLC to give the target compound (150 mg, 41.5%). MS: M/e 464 $(M+1)^+$.

Step B: (S)-7-(2-chloro-6-fluorobenzyl)-2-((1-methylpyrrolidin-2-yl)methoxy)imidazo[2,1-f][1,2,4]triazin-4-ol

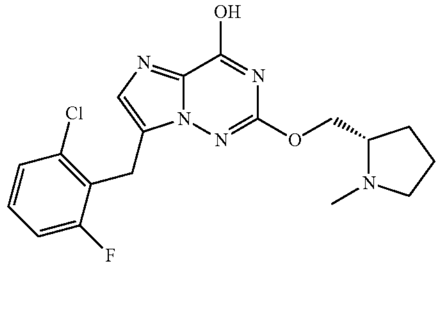

To a solution of the product of step A (150 mg, 0.323 mmol) in DCM (5 mL) was added TFA (5 mL) and $Et_3SiH$ (5 mL). The reaction mixture was stirred at 40° C. overnight. The mixture was concentrated in vacuo. The residue was added $NaHCO_3$ solution (1 M, 10 mL) and extracted with ethyl acetate. The combined organic extracts were dried over sodium sulfate, filtered and evaporated. The residue was purified by preparative TLC to afforded the title product (180 mg 100%). MS: m/e 392 $(M+1)^+$.

Step C: (S)-4-chloro-7-(2-chloro-6-fluorobenzyl)-2-((1-methylpyrrolidin-2-yl)methoxy)imidazo[2,1-f][1,2,4]triazine

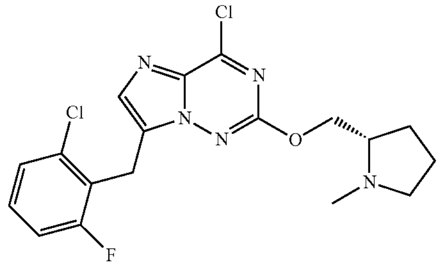 [SMILES: CN1CCC[C@H]1COc1nc(Cl)c2ncc(Cc3c(F)cccc3Cl)n2n1]

To a solution of (S)-7-(2-chloro-6-fluorobenzyl)-2-((1-methylpyrrolidin-2-yl)methoxy)imidazo[2,1-f][1,2,4]triazin-4-ol (180 mg, 0.46 mmol) in $POCl_3$ (10 mL) was added Triethylamine Hydrochloride (137 mg, 1 mmol). The mixture was sealed and stirred at 110° C. overnight. The mixture was cooled down to rt and concentrated in vacuo. The residue was directly used in next step. MS: m/e 410 $(M+1)^+$.

Step D: 2-((S)-4-(7-(2-chloro-6-fluorobenzyl)-2-(((S)-1-methylpyrrolidin-2-yl)methoxy)imidazo[2,1-f][1,2,4]triazin-4-yl)piperazin-2-yl acetonitrile

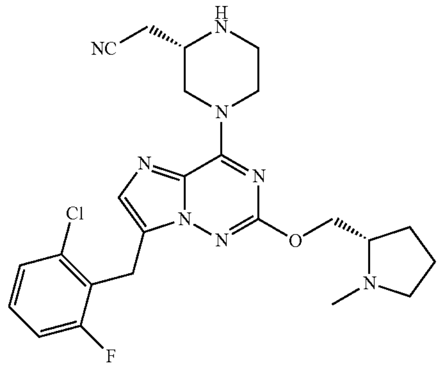 [SMILES: CN1CCC[C@H]1COc1nc(N2CCN[C@@H](CC#N)C2)c2ncc(Cc3c(F)cccc3Cl)n2n1]

The product from step C in acetonitrile (10 mL) was slowly added a solution of (S)-2-(piperazin-2-yl)acetonitrile (125 mg, 1 mmol) and DIEA (258 mg, 2 mmol) in acetonitrile (2 ml). The mixture was stirred at r.t. for 2 h. The mixture was directly used in next step. MS: m/e 499 $(M+1)^+$.

Step E: 2-((S)-1-acryloyl-4-(7-(2-chloro-6-fluorobenzyl)-2-(((S)-1-methylpyrrolidin-2-yl)methoxy)imidazo[2,1-f][1,2,4]triazin-4-yl)piperazin-2-yl acetonitrile

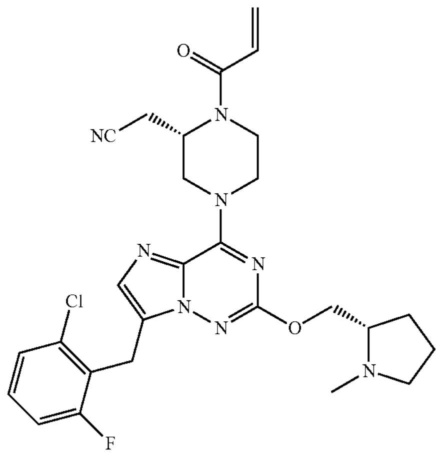 [SMILES: C=CC(=O)N1CCN(c2nc(OC[C@@H]3CCCN3C)nn3c(Cc4c(F)cccc4Cl)cnc23)C[C@@H]1CC#N]

The mixture from step D was added $NaHCO_3$ solution (1 M, 10 mL). Acryloyl chloride (90 mg, 0.1 mol) was added slowly to the mixture. The reaction was stirred at r.t. for 2 h. The resulting mixture was extracted with ethyl acetate. The combined organic extracts were dried over sodium sulfate, filtered and evaporated. Purification by prep-TLC to afford the title product (1.1 mg, 0.4% for 3 steps) 1H NMR (400 MHz, DMSO-d6) δ 7.33 (br.s, 2H), 7.16 (br.s, 2H), 6.85 (s, 1H), 6.28 (d, J=16.4 Hz, 1H), 5.83 (d, J=9.6 Hz, 1H), 4.75 (s, 1H), 4.53 (d, J=7.3 Hz, 1H), 4.37 (s, 2H), 4.15 (s, 1H), 3.88 (s, 1H), 3.71 (s, 1H), 3.58-3.49 (m, 1H), 3.13 (s, 1H), 3.06 (s, 3H), 2.89 (s, 1H), 2.83-2.74 (m, 3H), 2.41 (s, 1H), 2.19 (s, 1H), 2.03 (s, 2H), 1.29 (s, 3H) ppm. MS: M/e 553 $(M+1)^+$.

Example 12: Compound A12: 2-((S)-1-acryloyl-4-(7-(2-chlorobenzyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(2-chlorophenyl)methanol

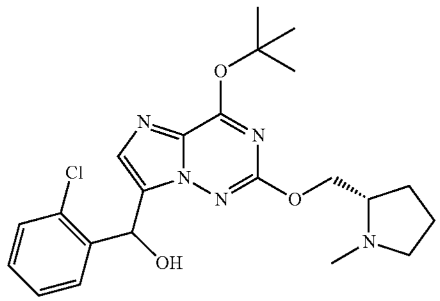 [SMILES: CN1CCC[C@H]1COc1nc(OC(C)(C)C)c2ncc(C(O)c3ccccc3Cl)n2n1]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (8 mL) was added a solution of n-BuLi (1.6M, 0.94 mL, 1.5 mmol) dropwise maintaining the temperature between −75~−65° C. After 1 h, a suspension of the 2-chlorobenzaldehyde (168 mg, 1.2 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3). The combined organic phases were washed with brine, dried over $Na_2SO_4$, filtered, and concentrated. The residue was purified by prep-TLC to give the target compound (420 mg, 94.3%). MS: M/e 446 $(M+1)^+$.

Step B: (S)-7-(2-chlorobenzyl)-2-((1-methylpyrrolidin-2-yl)methoxy)imidazo[2,1-f][1,2,4]triazin-4-ol

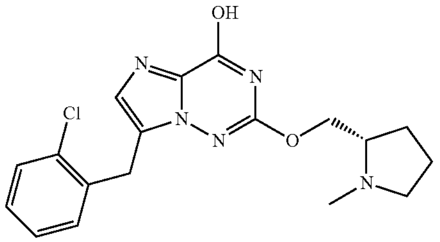 [SMILES: CN1CCC[C@H]1COc1nc(O)c2ncc(Cc3ccccc3Cl)n2n1]

To a solution of (4-(tert-butoxy)-2-(((S)-1-methylpyrrolidin-2-yl)methoxy)imidazo[2,1-f][1,2,4]triazin-7-yl)(2-chlorophenyl)methanol (420 mg, 0.94 mmol) in DCM (10 mL) was added TFA (5 mL) and $Et_3SiH$ (5 mL). The reaction mixture was stirred at 40° C. overnight. The mixture was concentrated in vacuo. The residue was added $NaHCO_3$ solution (1 M, 10 mL) and extracted with ethyl acetate. The combined organic extracts were dried over sodium sulfate, filtered and evaporated. The residue was purified by preparative TLC to afforded the title product (200 mg 56.8%). MS: m/e 374 $(M+1)^+$.

Step C: (S)-4-chloro-7-(2-chlorobenzyl)-2-((1-methylpyrrolidin-2-yl)methoxy)imidazo[2,1-f][1,2,4]triazine

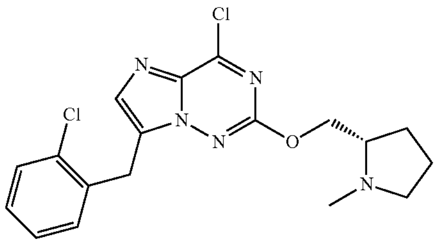 [SMILES: CN1CCC[C@H]1COc1nc(Cl)c2ncc(Cc3ccccc3Cl)n2n1]

To a solution of (S)-7-(2-chlorobenzyl)-2-((1-methylpyrrolidin-2-yl)methoxy)imidazo[2,1-f][1,2,4]triazin-4-ol (130 mg, 0.35 mmol) in $POCl_3$ (5 mL) was added Triethylamine Hydrochloride (137 mg, 1 mmol). The mixture was sealed and stirred at 110° C. overnight. The mixture was cooled down to rt and concentrated in vacuo. The residue was directly used in next step. MS: m/e 392 $(M+1)^+$.

Step D: 2-((S)-4-(7-(2-chlorobenzyl)-2-(((S)-1-methylpyrrolidin-2-yl)methoxy)imidazo[2,1-f][1,2,4]triazin-4-yl)piperazin-2-yl)acetonitrile

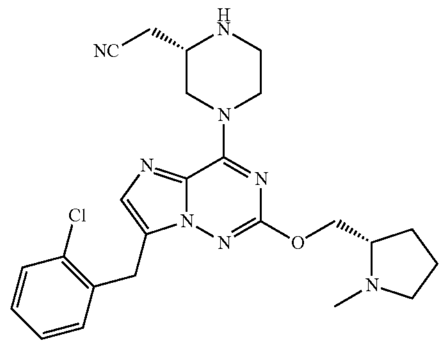 [SMILES: CN1CCC[C@H]1COc1nc(N2CCN[C@@H](CC#N)C2)c2ncc(Cc3ccccc3Cl)n2n1]

The product of step C in acetonitrile (10 mL) was slowly added a solution of (S)-2-(piperazin-2-yl)acetonitrile (125 mg, 1 mmol) and DIEA (258 mg, 2 mmol) in acetonitrile (2 ml). The mixture was stirred at rt for 2 h. The mixture was directly used in next step. MS: m/e 481 $(M+1)^+$.

Step E: 2-((S)-1-acryloyl-4-(7-(2-chlorobenzyl)-2-(((S)-1-methylpyrrolidin-2-yl)methoxy)imidazo[2,1-f][1,2,4]triazin-4-yl)piperazin-2-yl)acetonitrile

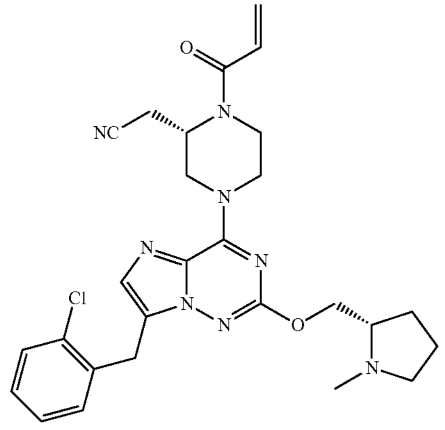 [SMILES: C=CC(=O)N1CCN(c2nc(OC[C@@H]3CCCN3C)nn3c(Cc4ccccc4Cl)cnc23)C[C@@H]1CC#N]

The mixture of product of step D was added $NaHCO_3$ solution (1 M, 10 mL). Acryloyl chloride (90 mg, 0.1 mol) was added slowly to the mixture. The reaction was stirred at r.t. for 2 h. The resulting mixture was extracted with ethyl acetate. The combined organic extracts were dried over sodium sulfate, filtered and evaporated. The residue was purified by prep-TLC to afford the title product (3.2 mg, 1.7% for 3 steps) 1H NMR (400 MHz, DMSO-d6) δ 7.42 (d, J=7.2 Hz, 1H), 7.32 (s, 1H), 7.25 (d, J=4.3 Hz, 3H), 6.82 (s, 1H), 6.29 (d, J=16.5 Hz, 1H), 5.83 (d, J=10.4 Hz, 1H), 4.72 (s, 1H), 4.50 (dd, J=12.2, 7.3 Hz, 1H), 4.34 (s, 2H), 4.18 (s, 1H), 3.84 (s, 1H), 3.69 (s, 1H), 3.26-3.15 (m, 3H), 3.03 (s, 3H), 2.90 (s, 1H), 2.79 (s, 2H), 2.36 (s, 1H), 2.19 (s, 1H), 2.05 (s, 2H), 1.29 (s, 3H) ppm. MS: M/e 536 $(M+1)^+$.

Example 13: Compound A13: 2-((S)-1-acryloyl-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(2,3-dihydrobenzofuran-7-yl)methanol

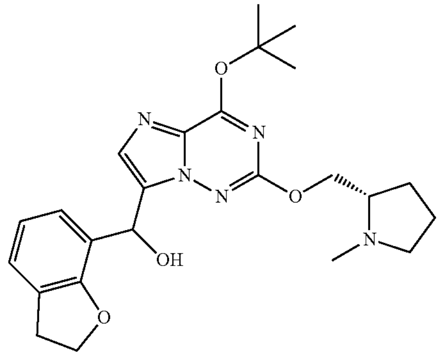 [SMILES: CN1CCC[C@H]1COc1nc(OC(C)(C)C)c2ncc(C(O)c3cccc4c3OCC4)n2n1]

To a cooled solution of (S)-7-bromo-4-(tert-butoxy)-2-((1-methylpyrrolidin-2-yl)methoxy)imidazo[2,1-f][1,2,4]triazine (300 mg, 0.78 mmol) in THF (8 mL) at −78° C. was added with n-BuLi (1.6 M in n-hexane, 0.7 mL, 1.2 mmol) dropwise. After stirred for 30 mins, 2,3-dihydrobenzofuran-7-carbaldehyde (139 mg, 0.9 mmol) in THF (1 mL) was added dropwise. The resulting mixture was stirred gradually to r.t. overnight. The solution was quenched with $NH_4Cl$ solution (5 mL) and extracted with EA (15 mL). The organic layer was dried, concentrated and purified by CombiFlash (DCM:$NH_3$·MeOH=4%) to get the product (280 mg, 79%). MS: M/e 454 $(M+1)^+$.

Step B: (S)-7-((2,3-dihydrobenzofuran-7-yl)methyl)-2-((1-methylpyrrolidin-2-yl)methoxy)imidazo[2,1-f][1,2,4]triazin-4-ol

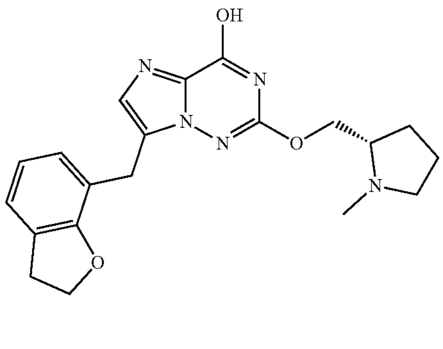 [SMILES: CN1CCC[C@H]1COc1nc(O)c2ncc(Cc3cccc4c3OCC4)n2n1]

$Et_3SiH$ (2 mL) and TFA (2 mL) were added to a solution of (4-(tert-butoxy)-2-(((S)-1-methylpyrrolidin-2-yl)methoxy)imidazo[2,1-f][1,2,4]triazin-7-yl)(2,3-dihydrobenzofuran-7-yl)methanol (280 mg, 0.6 mmol) in DCM (2 mL). The solution was heated at 40° C. overnight. The solvent was evaporated under oil pump, then co-distilled with toluene. The crude product was used in the next step directly (235 mg, crude). MS: M/e 382 $(M+1)^+$.

Step C: (S)-4-chloro-7-((2,3-dihydrobenzofuran-7-yl)methyl)-2-((1-methylpyrrolidin-2-yl)methoxy)imidazo[2,1-f][1,2,4]triazine

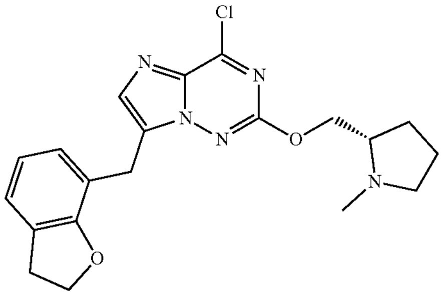 [SMILES: CN1CCC[C@H]1COc1nc(Cl)c2ncc(Cc3cccc4c3OCC4)n2n1]

A sealed tube charged with (S)-7-((2,3-dihydrobenzofuran-7-yl)methyl)-2-((1-methylpyrrolidin-2-yl)methoxy)imidazo[2,1-f][1,2,4]triazin-4-ol (235 mg, 0.6 mmol), $Et_3N$·HCl (106 mg, 1.2 mmol) and $POCl_3$ (5 mL) was heated at 120° C. overnight. After cooled down, the solvent was evaporated under oil pump and co-distilled with toluene to get the crude product, which was use directly in the next step (240 mg, crude). MS: M/e 400 $(M+1)^+$.

Step D: benzyl (S)-2-(cyanomethyl)-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazine-1-carboxylate

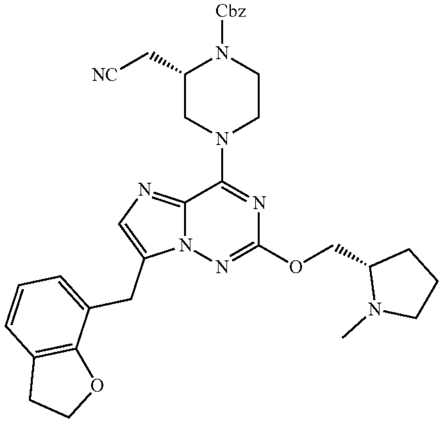 [SMILES: CN1CCC[C@H]1COc1nc(N2CCN(C(=O)OCc3ccccc3)[C@@H](CC#N)C2)c2ncc(Cc3cccc4c3OCC4)n2n1]

Benzyl (S)-2-(cyanomethyl)piperazine-1-carboxylate (259 mg, 1.0 mmol) was added to a solution of (S)-4-chloro-7-((2,3-dihydrobenzofuran-7-yl)methyl)-2-((1-methylpyrrolidin-2-yl)methoxy)imidazo[2,1-f][1,2,4]triazine (190 mg, 0.5 mmol) in THF (10 mL), followed with DIEA (516 mg, 4 mmol). The reaction mixture was stirred at r.t. for 1 hour. The solution was quenched with water (5 mL) and extracted with EA (10 mL). The organic layer was dried over $Na_2SO_4$, concentrated and purified by CombiFlash (DCM:$NH_3$ (7M in MeOH)=10:1) to give the product (100 mg, 34%). MS: M/e 623 $(M+1)^+$.

Step E: 2-((S)-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazin-2-yl)acetonitrile

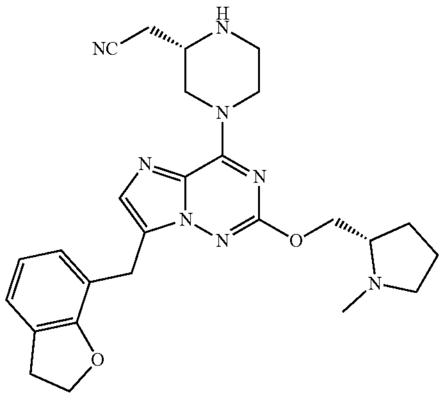 [SMILES: CN1CCC[C@H]1COc1nc(N2CCN[C@@H](CC#N)C2)c2ncc(Cc3cccc4c3OCC4)n2n1]

A suspension of benzyl (S)-2-(cyanomethyl)-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazine-1-carboxylate (100 mg, 0.16 mmol) and Pd/C (wet, 10%, 100 mg) in THF/EtOH (4 mL/4 mL) was stirred at r.t. under $H_2$ balloon overnight. The catalyst was filtered and the filtrate was concentrated to get the crude product, which was used directly (60 mg, 76%). MS: M/e 489 $(M+1)^+$ Step F: 2-((S)-1-acryloyl-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazin-2-yl)acetonitrile

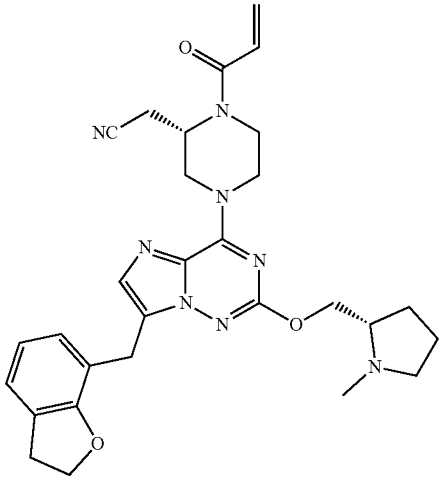 [SMILES: C=CC(=O)N1CCN(c2nc(OC[C@@H]3CCCN3C)nn3c(Cc4cccc5c4OCC5)cnc23)C[C@@H]1CC#N]

$NaHCO_3$ solution (saturated, 0.5 mL) was added to a solution of 2-((S)-4-(7-((2,3-dihydrobenzofuran-7-yl)methyl)-2-(((S)-1-methylpyrrolidin-2-yl)methoxy)imidazo[2,1-f][1,2,4]triazin-4-yl)piperazin-2-yl)acetonitrile (60 mg, 0.12 mmol) in $CH_3CN$ (5 mL), acryloyl chloride (17 mg, 0.18 mmol) was added. The reaction mixture was stirred at r.t for 1 hr. The solution was evaporated, added with water (4 mL) and extracted with EA (10 mL). The organic layer was dried, concentrated and purified by prep-TLC (DCM: $NH_3$ (7M in MeOH)=9:1) to get the product (6 mg, 9%). $^1H$ NMR (400 MHz, $CD_3OD$) δ 7.25 (s, 1H), 7.08 (t, J=8.0 Hz, 1H), 6.93 (d, J=8.0 Hz, 1H), 6.81 (br.s, 1H), 6.73 (t, J=8.0 Hz, 1H), 6.28 (d, J=16.0 Hz, 1H), 5.83 (d, J=12.0 Hz, 1H), 5.12 (br.s, 1H), 4.59-4.51 (m, 3H), 4.37 (s, 2H), 4.10 (s, 3H), 3.6-3.47 (m, 2H), 3.22-3.18 (m, 4H), 2.87 (s, 3H), 2.56 (s, 3H), 2.50 (s, 1H), 2.12-2.10 (m, 1H), 1.87-1.78 (m, 4H) ppm. MS: M/e 543 $(M+1)^+$ Example 14: Compound A14: 2-((S)-1-acryloyl-4-(2-(((S)-4,4-difluoro-1-methylpyrrolidin-2-yl)methoxy)-7-(naphthalen-1-ylmethyl)imidazo[2,1-f][1,2,4]triazin-4-yl)piperazin-2-yl)acetonitrile Step A: (S)-7-bromo-4-(tert-butoxy)-2-((4,4-difluoro-1-methylpyrrolidin-2-yl)methoxy)imidazo[2,1-f][1,2,4]triazine

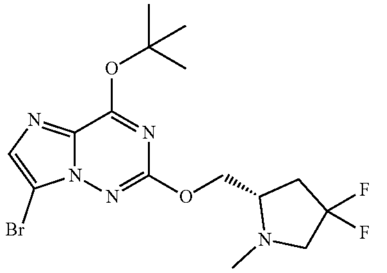 [SMILES: CN1CC(F)(F)C[C@H]1COc1nc(OC(C)(C)C)c2ncc(Br)n2n1]

To a solution of (S)-(4,4-difluoro-1-methylpyrrolidin-2-yl)methanol (500 mg, 3.3 mmol) in THF (5 mL) was added NaH (264 mg, 60%, 6.6 mmol) at 0° C. and the mixture was stirred for 5 min. Then the solution of 7-bromo-4-(tert-butoxy)-2-chloroimidazo[2,1-f][1,2,4]triazine (1.0 g, 3.3 mmol) in THF (5 mL) was added and the resulted mixture was stirred at 60° C. for 1 hour. The mixture was cooled and then poured into $H_2O$ (20 mL). The mixture was extracted with EA (20 mL×3). The combined organic phases were washed with brine (20 mL×3), dried over $Na_2SO_4$ and concentrated under reduced pressure. The residue was purified by column chromatography to obtain the title compound (825 mg, yield: 60%). MS: M/e 420 $(M+1)^+$.

Step B: (4-(tert-butoxy)-2-(((S)-4,4-difluoro-1-methylpyrrolidin-2-yl)methoxy)imidazo[2,1-f][1,2,4]triazin-7-yl)(naphthalen-1-yl)methanol

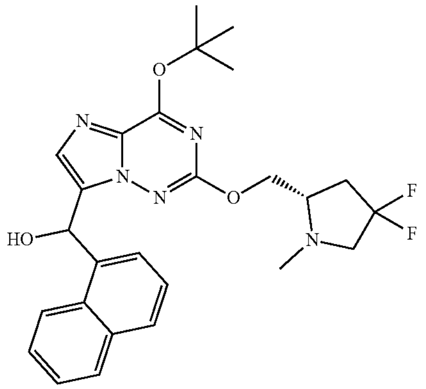 [SMILES: CN1CC(F)(F)C[C@H]1COc1nc(OC(C)(C)C)c2ncc(C(O)c3cccc4ccccc34)n2n1]

To a solution of (S)-7-bromo-4-(tert-butoxy)-2-((4,4-difluoro-1-methylpyrrolidin-2-yl)methoxy)imidazo[2,1-f][1,2,4]triazine (825 mg, 1.97 mmol) in THF (5 mL) was added n-BuLi (1.6 M, 2.5 mL, 4.0 mmol) at −78° C. in N2 atmosphere. The mixture was stirred at −78° C. for 30 min. Then the solution of 1-naphthaldehyde (624 mg, 4.0 mmol) in THF (4 mL) was added to the system at −78° C. The reaction was stirred for 30 min, and then warmed to room temperature and stirred for 30 min. The reaction mixture was quenched with saturated $NH_4Cl$ (20 mL) at room temperature and extracted with EA (20 mL×2). The combined organic phases were washed with brine (20 mL×3), dried over $Na_2SO_4$ and concentrated under reduced pressure. The residue was purified by column chromatography to obtain the title compound (590 mg, yield: 61%). MS: M/e 498 $(M+1)^+$.

Step C: (S)-2-((4,4-difluoro-1-methylpyrrolidin-2-yl)methoxy)-7-(naphthalen-1-ylmethyl)imidazo[2,1-f][1,2,4]triazin-4-ol

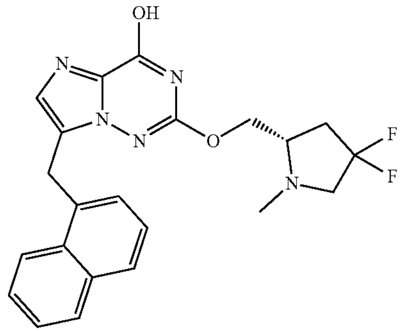 [SMILES: CN1CC(F)(F)C[C@H]1COc1nc(O)c2ncc(Cc3cccc4ccccc34)n2n1]

(4-(tert-butoxy)-2-(((S)-4,4-difluoro-1-methylpyrrolidin-2-yl)methoxy)imidazo[2,1-f][1,2,4]triazin-7-yl)(naphthalen-1-yl)methanol (590 mg, 1.19 mmol) in TFA (5 mL) was added $Et_3SiH$ (5 mL) and the mixture was stirred at 40° C. for 16 hrs. The reaction mixture was concentrated under reduced pressure. The residue was treated with HCl (5 mL, 4M), extracted with DCM (5 mL×3). The aqueous layer was basified by NaOH (4M) to pH~10 and extracted with DCM/IPA (5:1, 10 mL×5). The combined organic phases were washed with brine (20 mL×3), dried over $Na_2SO_4$, concentrated and purified by column chromatography to obtain the title compound (350 mg, yield: 69%). MS: M/e 426 $(M+1)^+$.

Step D: (S)-4-chloro-2-((4,4-difluoro-1-methylpyrrolidin-2-yl)methoxy)-7-(naphthalen-1-ylmethyl)imidazo[2,1-f][1,2,4]triazine

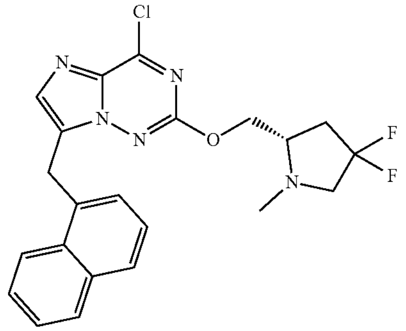 [SMILES: CN1CC(F)(F)C[C@H]1COc1nc(Cl)c2ncc(Cc3cccc4ccccc34)n2n1]

A mixture of (S)-2-((4,4-difluoro-1-methylpyrrolidin-2-yl)methoxy)-7-(naphthalen-1-ylmethyl)imidazo[2,1-f][1,2,4]triazin-4-ol (120 mg, 0.28 mmol) and $Et_3NHCl$ (500 mg, 3.6 mmol) in $POCl_3$ (5 mL) was stirred at 100° C. for 16 hrs. The mixture was concentrated, diluted with 5 mL of THF and the resulted mixture was used for the next step directly. MS: M/e 444 $(M+1)^+$.

Step E: 2-((S)-4-(2-(((S)-4,4-difluoro-1-methylpyrrolidin-2-yl)methoxy)-7-(naphthalen-1-ylmethyl)imidazo[2,1-f][1,2,4]triazin-4-yl)piperazin-2-yl)acetonitrile

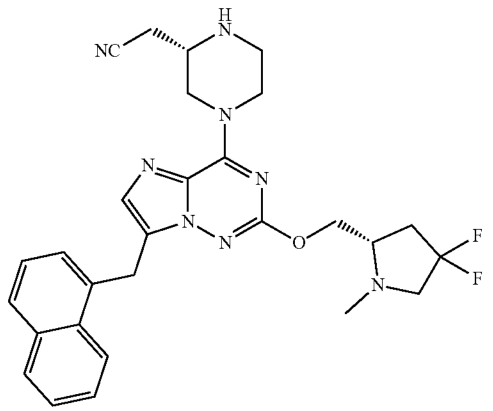 [SMILES: CN1CC(F)(F)C[C@H]1COc1nc(N2CCN[C@@H](CC#N)C2)c2ncc(Cc3cccc4ccccc34)n2n1]

To a solution of (S)-4-chloro-2-((4,4-difluoro-1-methylpyrrolidin-2-yl)methoxy)-7-(naphthalen-1-ylmethyl)imidazo[2,1-f][1,2,4]triazine in THF (5 mL) was added DIEA (500 mg, 3.87 mmol) and followed by a solution of (S)-2-(piperazin-2-yl)acetonitrile (71 mg, 0.568 mmol) in DCM (1.5 mL) at rt. The resulted mixture was stirred at rt for 2 hrs. The mixture was concentrated and diluted with DCM (20 mL). The mixture was washed with brine (10 mL×2), dried over $Na_2SO_4$, concentrated and purified by prep-HPLC to obtain the title compound (55 mg, yield: 30% for 2 steps). MS: M/e 533 $(M+1)^+$.

Step F: 2-((S)-1-acryloyl-4-(2-(((S)-4,4-difluoro-1-methylpyrrolidin-2-yl)methoxy)-7-(naphthalen-1-ylmethyl)imidazo[2,1-f][1,2,4]triazin-4-yl)piperazin-2-yl)acetonitrile

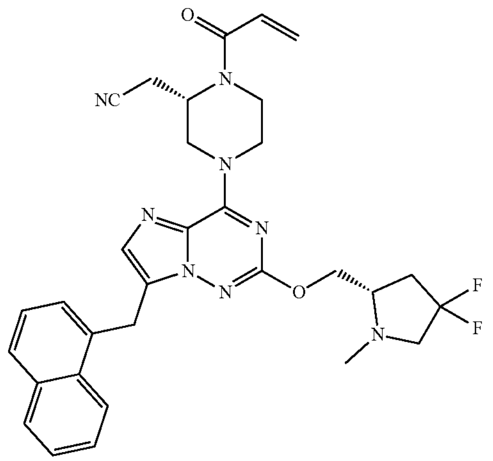 [SMILES: C=CC(=O)N1CCN(c2nc(OC[C@@H]3CC(F)(F)CN3C)nn3c(Cc4cccc5ccccc45)cnc23)C[C@@H]1CC#N]

To a mixture of 2-((S)-4-(2-(((S)-4,4-difluoro-1-methylpyrrolidin-2-yl)methoxy)-7-(naphthalen-1-ylmethyl)imidazo[2,1-f][1,2,4]triazin-4-yl)piperazin-2-yl)acetonitrile (55 mg, 0.085 mmol) and $NaHCO_3/H_2O$ (200 mg, 1 mL) in MeCN (1 mL) was added a solution of acryloyl chloride (25 mg, 0.27 mmol) in MeCN (1 mL) in drops. The resulted mixture was stirred at rt for 2 hrs. The mixture was diluted with 10 mL of EA and washed with brine (5 mL×3). The combined organic phases were dried over $Na_2SO_4$, concentrated and purified by prep-TLC (PE/EA=1:2) to obtain the title compound (18 mg, yield: 27%). $^1H$ NMR (400 MHz, DMSO-d6) δ 8.19 (d, J=7.2 Hz, 1H), 7.92 (d, J=8.8 Hz, 1H), 7.81 (d, J=7.2 Hz, 1H), 7.58-7.46 (m, 2H), 7.46-7.34 (m, 2H), 7.28 (s, 1H), 6.80 (dd, J=16.4, 10.4 Hz, 1H), 6.15 (d, J=16.4 Hz, 1H), 5.74 (d, J=10.4 Hz, 1H), 5.46-4.77 (m, 2H), 4.63 (s, 2H), 4.40-4.03 (m, 3H), 3.84-3.46 (m, 1H), 3.47-3.17 (m, 3H), 3.04-2.55 (m, 5H), 2.46-2.37 (m, 1H), 2.32 (s, 3H), 2.25-2.05 (m, 1H) ppm. MS: M/e 587 $(M+1)^+$.

Example 15: Compound A15: 2-((S)-4-(7-((1H-indazol-4-yl)methyl)-2-(((S)-1-methylpyrrolidin-2-yl)methoxy)imidazo[2,1-f][1,2,4]triazin-4-yl)-1-acryloylpiperazin-2-yl)acetonitrile Step A: tert-butyl 4-((4-(tert-butoxy)-2-(((S)-1-methylpyrrolidin-2-yl)methoxy)imidazo[2,1-f][1,2,4]triazin-7-yl)(hydroxy)methyl)-1H-indazole-1-carboxylate

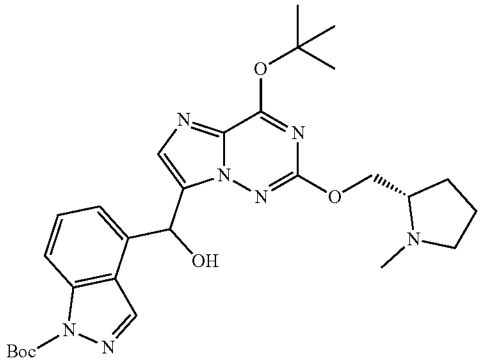 [SMILES: CN1CCC[C@H]1COc1nc(OC(C)(C)C)c2ncc(C(O)c3cccc4c3cnn4C(=O)OC(C)(C)C)n2n1]

To a cooled solution of (S)-7-bromo-4-(tert-butoxy)-2-((1-methylpyrrolidin-2-yl)methoxy)imidazo[2,1-f][1,2,4]triazine (300 mg, 0.78 mmol) in THF (8 mL) at −78° C. was added with n-BuLi (1.6 M in n-hexane, 0.7 mL, 1.2 mmol) dropwise. After stirred for 30 mins, tert-butyl 4-formyl-1H-indazole-1-carboxylate (231 mg, 0.9 mmol) in THF (2 mL) was added dropwise. The resulting mixture was stirred gradually to r.t overnight. The solution was quenched with $NH_4Cl$ solution (5 mL) and extracted with EA (15 mL). The organic layer was dried, concentrated and purified by CombiFlash (DCM:$NH_3$ (7M in MeOH)=10:1) to get the product (230 mg, 53%). MS: M/e 552 $(M+1)^+$.

Step B: (S)-7-((1H-indazol-4-yl)methyl)-2-((1-methylpyrrolidin-2-yl)methoxy)imidazo[2,1-f][1,2,4]triazin-4-ol

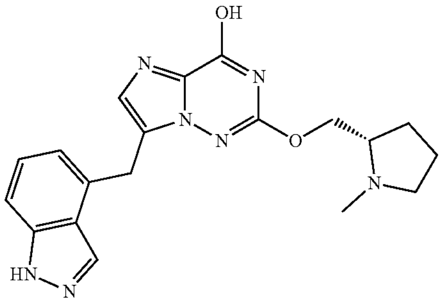 [SMILES: CN1CCC[C@H]1COc1nc(O)c2ncc(Cc3cccc4[nH]ncc34)n2n1]

$Et_3SiH$ (2 mL) and TFA (2 mL) were added to a solution of tert-butyl 4-((4-(tert-butoxy)-2-(((S)-1-methylpyrrolidin-2-yl)methoxy)imidazo[2,1-f][1,2,4]triazin-7-yl)(hydroxy)methyl)-1H-indazole-1-carboxylate (230 mg, 0.4 mmol) in DCM (2 mL). The solution was heated at 80° C. overnight. The solvent was evaporated under oil pump, then azeotrope with toluene. The crude product was used in the next step directly (160 mg, crude). MS: M/e 380 $(M+1)^+$.

Step C: (S)-7-((1H-indazol-4-yl)methyl)-4-chloro-2-((1-methylpyrrolidin-2-yl)methoxy)imidazo[2,1-f][1,2,4]triazine

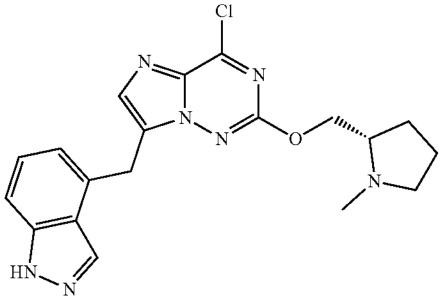 [SMILES: CN1CCC[C@H]1COc1nc(Cl)c2ncc(Cc3cccc4[nH]ncc34)n2n1]

A sealed tube charged with (S)-7-((1H-indazol-4-yl)methyl)-2-((1-methylpyrrolidin-2-yl)methoxy)imidazo[2,1-f][1,2,4]triazin-4-ol (160 mg, 0.4 mmol), $Et_3N{\cdot}HCl$ (222 mg, 1.6 mmol) and $POCl_3$ (8 mL) was heated at 120° C. overnight. After cooled down, the solvent was evaporated under oil pump and co-distilled with toluene to get the crude product, which was use directly in the next step (160 mg, crude). MS: M/e 398 $(M+1)^+$.

Step D: benzyl (S)-4-(7-((1H-indazol-4-yl)methyl)-2-(((S)-1-methylpyrrolidin-2-yl)methoxy)imidazo[2,1-f][1,2,4]triazin-4-yl)-2-(cyanomethyl)piperazine-1-carboxylate

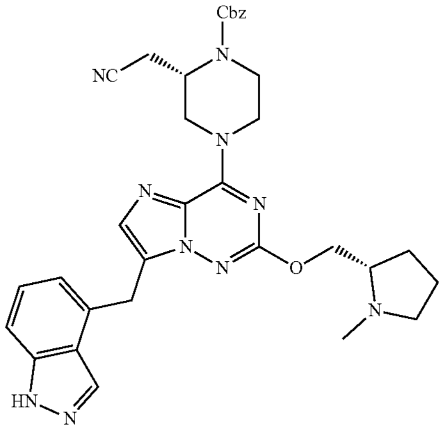 [SMILES: CN1CCC[C@H]1COc1nc(N2CCN(C(=O)OCc3ccccc3)[C@@H](CC#N)C2)c2ncc(Cc3cccc4[nH]ncc34)n2n1]

Benzyl (S)-2-(cyanomethyl)piperazine-1-carboxylate (207 mg, 0.8 mmol) was added to a solution of (S)-7-((1H-indazol-4-yl)methyl)-4-chloro-2-((1-methylpyrrolidin-2-yl)methoxy)imidazo[2,1-f][1,2,4]triazine (160 mg, 0.4 mmol) in THF (10 mL), followed with DIEA (413 mg, 3.2 mmol). The reaction mixture was stirred at r.t for 1 hour. The solution was added with water (5 mL) and extracted with EA (10 mL). The organic layer was dried over $Na_2SO_4$, concentrated and purified by CombiFlash (DCM:$NH_3$ (7M in MeOH)=20:3) to give the product (80 mg, 32%). MS: M/e 621 $(M+1)^+$.

Step E: tert-butyl 4-((4-((S)-4-((benzyloxy)carbonyl)-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate

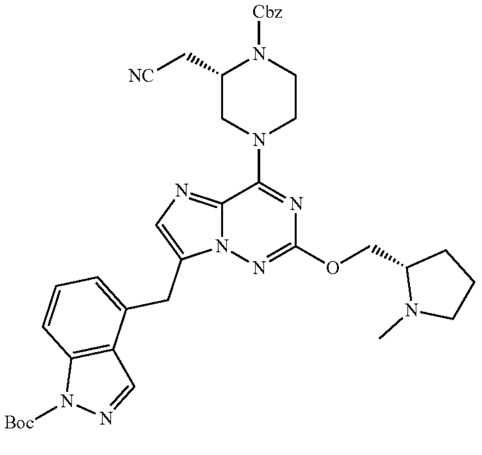 [SMILES: CN1CCC[C@H]1COc1nc(N2CCN(C(=O)OCc3ccccc3)[C@@H](CC#N)C2)c2ncc(Cc3cccc4c3cnn4C(=O)OC(C)(C)C)n2n1]

$(Boc)_2O$ (34 mg, 0.16 mmol) was added to a solution of benzyl (S)-4-(7-((1H-indazol-4-yl)methyl)-2-(((S)-1-methylpyrrolidin-2-yl)methoxy)imidazo[2,1-f][1,2,4]triazin-4-yl)-2-(cyanomethyl)piperazine-1-carboxylate (80 mg, 0.13 mmol), DMAP (2 mg) and triethylamine (20 mg, 0.2 mmol) in DCM (5 mL). The reaction mixture was stirred at r.t for 2 hrs, then concentrated and purified by CombiFlash (DCM: MeOH=8%) to give the product (35 mg, 38%) MS: M/e 721 $(M+1)^+$.

Step F: tert-butyl 4-((4-((S)-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate

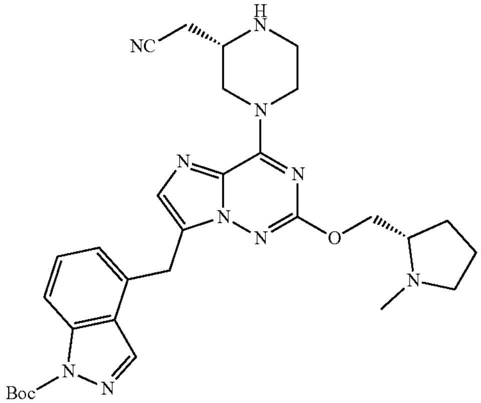 [SMILES: CN1CCC[C@H]1COc1nc(N2CCN[C@@H](CC#N)C2)c2ncc(Cc3cccc4c3cnn4C(=O)OC(C)(C)C)n2n1]

A solution of tert-butyl 4-((4-((S)-4-((benzyloxy)carbonyl)-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate (35 mg, 0.05 mmol) and Pd/C (wet, 10%, 23 mg) in THF/EtOH (3 mL/3 mL) was stirred at r.t under $H_2$ balloon overnight. The catalyst was filtered out and the filtrate was concentrated to get the crude product, which was used directly (20 mg, 71%). MS: M/e 587 $(M+1)^+$.

Step G: tert-butyl 4-((4-((S)-4-acryloyl-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate

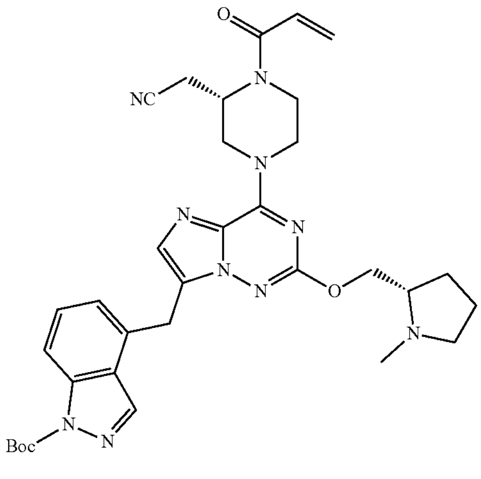 [SMILES: C=CC(=O)N1CCN(c2nc(OC[C@@H]3CCCN3C)nn3c(Cc4cccc5c4cnn5C(=O)OC(C)(C)C)cnc23)C[C@@H]1CC#N]

$NaHCO_3$ solution (saturated, 0.3 mL) was added to a solution of tert-butyl 4-((4-((S)-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate (20 mg, 0.03 mmol) in $CH_3CN$ (3 mL), followed with acryloyl chloride (5 mg, 0.06 mmol). The reaction mixture was stirred at r.t for 1 hr. The solution was evaporated, added with water (2 mL) and extracted with EA (5 mL). The organic layer was dried, concentrated and used in the next step directly (20 mg, crude). MS: M/e 641 $(M+1)^+$.

Step H: 2-((S)-4-(7-((1H-indazol-4-yl)methyl)-2-(((S)-1-methylpyrrolidin-2-yl)methoxy)imidazo[2,1-f][1,2,4]triazin-4-yl)-1-acryloylpiperazin-2-yl)acetonitrile

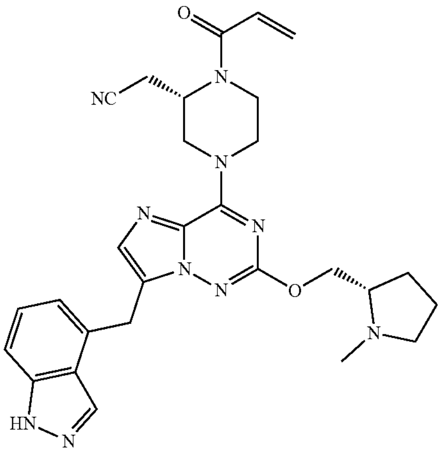 [SMILES: C=CC(=O)N1CCN(c2nc(OC[C@@H]3CCCN3C)nn3c(Cc4cccc5[nH]ncc45)cnc23)C[C@@H]1CC#N]

TFA (0.2 mL) was added to a solution of tert-butyl 4-((4-((S)-4-acryloyl-3-(cyanomethyl)piperazin-1-yl)-2-(((S)-1-methylpyrrolidin-2-yl)methoxy)imidazo[2,1-f][1,2,4]triazin-7-yl)methyl)-1H-indazole-1-carboxylate (20 mg, 0.03 mmol) in DCM (3 mL). After stirred at r.t for 1 hr, the solution was added with water, extracted with DCM and washed with $NaHCO_3$ solution. The organic layer was dried, concentrated and purified by prep-TLC (DCM:$NH_3$ (7M in MeOH)=10:1) to get the product (6 mg, 38%). $^1H$ NMR (400 MHz, $CD_3OD$) δ 8.12 (s, 1H), 7.45 (s, 1H), 7.42 (d, J=8.0 Hz, 1H), 7.30 (t, J=8.0 Hz, 1H), 6.97 (d, J=8.0 Hz, 1H), 6.81 (br.s, 1H), 6.28 (d, J=16.0 Hz, 1H), 5.83 (d, J=8.0 Hz, 1H), 5.09 (s, 1H), 4.62 (s, 1H), 4.57 (s, 3H), 4.42-4.37 (m, 1H), 4.15 (s, 1H), 3.78-3.48 (m, 5H), 3.20 (s, 2H), 2.97 (s, 3H), 2.91-2.85 (m, 2H), 2.28-1.94 (m, 4H) ppm. MS: M/e 541 $(M+1)^+$.

Example 16: Compound A16: 2-((S)-4-(7-((1H-indazol-4-yl)methyl)-2-(((S)-1-methylpyrrolidin-2-yl)methoxy)imidazo[2,1-f][1,2,4]triazin-4-yl)-1-acryloylpiperazin-2-yl)acetamide

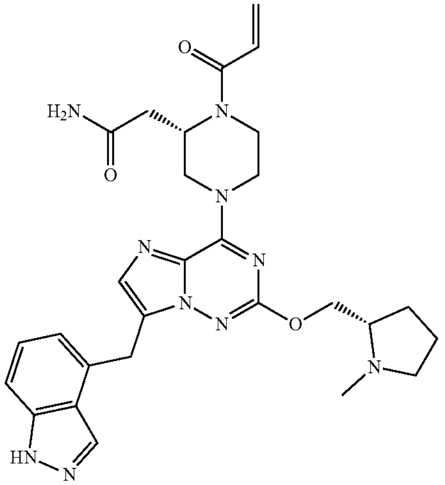 [SMILES: C=CC(=O)N1CCN(c2nc(OC[C@@H]3CCCN3C)nn3c(Cc4cccc5[nH]ncc45)cnc23)C[C@@H]1CC(N)=O]

The compound A16 was separated when purified compound A15 by prep-TLC. $^1H$ NMR (400 MHz, $CD_3OD$) δ 8.12 (s, 1H), 7.43 (s, 1H), 7.41 (s, 1H), 7.30 (t, J=8.0 Hz, 1H), 6.98 (d, J=8.0 Hz, 1H), 6.80-6.77 (m, 1H), 6.24 (d, J=16.0 Hz, 2H), 5.78 (d, J=8.0 Hz, 1H), 5.34-5.24 (m, 1H), 4.60 (s, 1H), 4.56 (s, 3H), 4.43-4.38 (m, 1H), 4.13 (s, 1H), 3.78-3.48 (m, 4H), 3.13 (s, 2H), 3.05 (s, 3H), 2.62-2.59 (m, 2H), 2.21-1.94 (m, 5H) ppm. MS: M/e 559 $(M+1)^+$ Example 17: Compound A17: 1-((S)-3-methyl-4-(2-(((S)-1-methylpyrrolidin-2-yl)methoxy)-7-(naphthalen-1-ylmethyl)imidazo[2,1-f][1,2,4]triazin-4-yl)piperazin-1-yl)prop-2-en-1-one Step A: tert-butyl (S)-4-(7-bromo-2-chloroimidazo[2,1-f][1,2,4]triazin-4-yl)-3-methylpiperazine-1-carboxylate

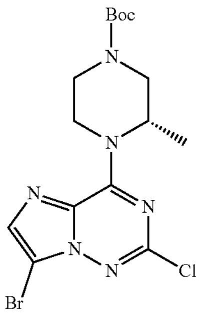 [SMILES: C[C@H]1CN(C(=O)OC(C)(C)C)CCN1c1nc(Cl)nn2c(Br)cnc12]

tert-butyl (S)-3-methylpiperazine-1-carboxylate (880 mg, 4.45 mmol) was dissolved in THF (5 mL). A mixture of 7-bromo-2,4-dichloroimidazo[2,1-f][1,2,4]triazine (1 g, 4 mmol) and DIEA (774 mg, 6 mmol) in THF (5 ml) was added slowly. Then the reaction was stirred at room temperature for 2 h. The solvent was evaporated and the residue partitioned between EA (100 mL) and water (100 mL). The combined organic layers were washed with brine, dried over $Na_2SO_4$, filtered and concentrated. The residue was purified by column chromatography on silica gel (eluting with ethyl acetate/PE, 0-30%) to give the target compound (1.3 g, 81%). MS: M/e 431 $(M+1)^+$.

Step B: tert-butyl (S)-4-(7-bromo-2-(((S)-1-methylpyrrolidin-2-yl)methoxy)imidazo[2,1-f][1,2,4]triazin-4-yl)-3-methylpiperazine-1-carboxylate

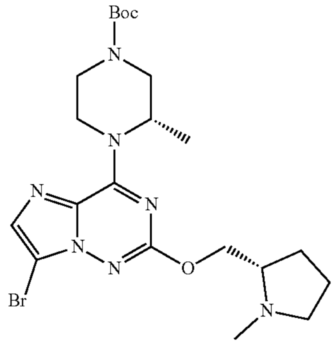 [SMILES: C[C@H]1CN(C(=O)OC(C)(C)C)CCN1c1nc(OC[C@@H]2CCCN2C)nn2c(Br)cnc12]

To a solution of NaH (60 mg, 1.5 mmol, 60%) in THF (5 mL) at 0° C. was added (S)-(1-methylpyrrolidin-2-yl)methanol (138 mg, 1.2 mmol). After 30 min, a solution of the product of the step A (430 mg, 1 mmol) in THF (5 mL) was added. Then the reaction was stirred at 60° C. overnight. The mixture was cooled to room temperature, diluted with water (30 mL), extracted with EtOAc (60 mL×2). The combined organic layers were washed with brine, dried over $Na_2SO_4$, filtered and concentrated. The residue was purified by combi flash to give target compound (320 mg, 63%). $^1H$ NMR (400 MHz, DMSO-d6) δ 7.68 (s, 1H), 4.28 (s, 1H), 4.01 (s, 1H), 3.85 (d, J=12.2 Hz, 1H), 3.60 (s, 1H), 3.09 (d, J=107.9 Hz, 4H), 2.58 (s, 1H), 2.24-2.11 (m, 1H), 2.02-1.87 (m, 1H), 1.74-1.54 (m, 4H), 1.43 (s, 9H), 1.24 (s, 3H) ppm. MS: M/e 510 $(M+1)^+$ Step C: tert-butyl (3S)-4-(7-(hydroxy(naphthalen-1-yl)methyl)-2-(((S)-1-methylpyrrolidin-2-yl)methoxy)imidazo[2,1-f][1,2,4]triazin-4-yl)-3-methylpiperazine-1-carboxylate

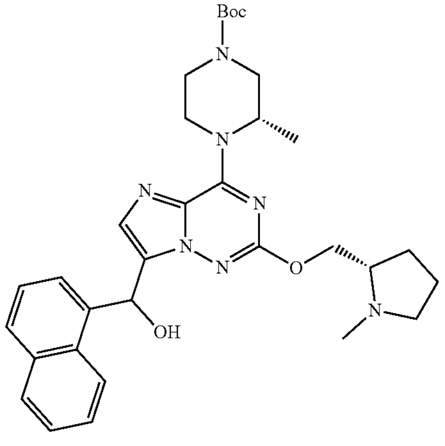 [SMILES: C[C@H]1CN(C(=O)OC(C)(C)C)CCN1c1nc(OC[C@@H]2CCCN2C)nn2c(C(O)c3cccc4ccccc34)cnc12]

To a solution of the product of the step B (100 mg, 0.19 mmol) in THF (10 mL) was added n-BuLi (0.2 mL, 0.294 mmol, 1.6M in hexane) dropwise maintaining the temperature between −75~−65° C. After 30 min, a mixture of 1-naphthaldehyde (36 mg, 0.23 mmol) in THF (2 mL) was added dropwise. The resulted mixture was stirred at −70° C. for 1 h and then warmed to room temperature for 1 h. The reaction was quenched with saturated $NH_4Cl$ solution, extracted with EtOAc (60 mL×2). The combined organic layers were washed with brine, dried over $Na_2SO_4$, filtered, and concentrated. The residue was purified by combi flash to give target compound (90 mg, 78%). MS: M/e 588 $(M+1)^+$.

Step D: 4-((S)-2-methylpiperazin-1-yl)-2-(((S)-1-methylpyrrolidin-2-yl)methoxy)-7-(naphthalen-1-ylmethyl)imidazo[2,1-f][1,2,4]triazine

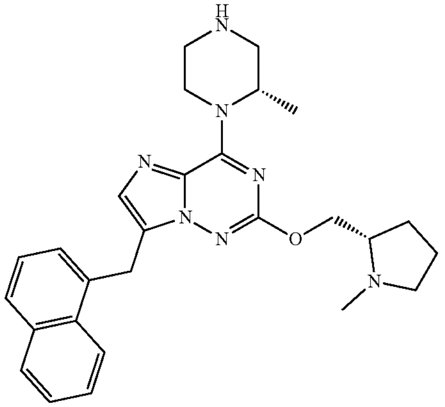 [SMILES: C[C@H]1CNCCN1c1nc(OC[C@@H]2CCCN2C)nn2c(Cc3cccc4ccccc34)cnc12]

To a mixture of the product of step C (90 mg) in TFA (1 mL) was added DCE (1 ml) and $Et_3SiH$ (1 mL). The reaction was heated at 25° C. overnight. The mixture was concentrated to dryness and the residue was used directly for next step without further purification. MS: M/e 472 $(M+1)^+$.

Step E: 1-((S)-3-methyl-4-(2-(((S)-1-methylpyrrolidin-2-yl)methoxy)-7-(naphthalen-1-ylmethyl)imidazo[2,1-f][1,2,4]triazin-4-yl)piperazin-1-yl)prop-2-en-1-one

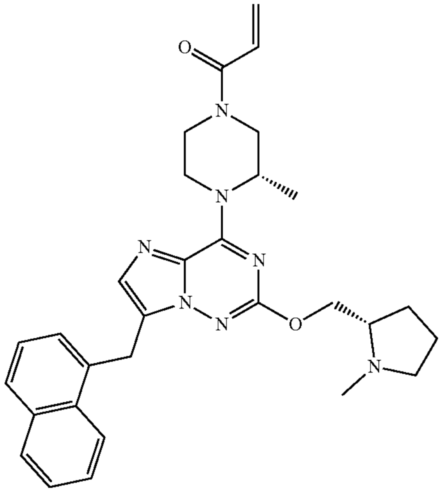 [SMILES: C=CC(=O)N1CCN(c2nc(OC[C@@H]3CCCN3C)nn3c(Cc4cccc5ccccc45)cnc23)[C@@H](C)C1]

To a mixture of the product of the step D (80 mg, crude) in $CH_3CN$ (3 mL) was added saturated $NaHCO_3$ (1 mL) and followed by a solution of acryloyl chloride (18 mg, 0.2 mmol) in $CH_3CN$ (0.3 mL) at 0° C. The resulting mixture was stirred at room temperature for 30 min. The reaction was diluted with water, extracted with EA (60 mL), washed with brine, dried over $Na_2SO_4$, filtered, and concentrated. The residue was purified by prep-TLC to give the target compound (18 mg, 20% for two steps). $^1H$ NMR (400 MHz, DMSO-d6) δ 8.19 (d, J=6.2 Hz, 1H), 7.94 (d, J=7.7 Hz, 1H), 7.83 (d, J=7.9 Hz, 1H), 7.57-7.49 (m, 2H), 7.47-7.25 (m, 3H), 6.94-6.76 (m, 1H), 6.18 (d, J=15.7 Hz, 1H), 5.74 (d, J=10.5 Hz, 1H), 4.63 (s, 2H), 4.22-4.05 (m, 4H), 3.62-3.48 (m, 1H), 3.18-2.87 (m, 4H), 2.58 (s, 2H), 2.30 (s, 3H), 2.18 (s, 1H), 1.94-1.85 (m, 1H), 1.67-1.52 (m, 3H), 1.21 (d, J=14.4 Hz, 3H) ppm. MS: M/e 526 $(M+1)^+$.

Example 18: Compound A18: 2-((S)-1-acryloyl-4-(2-(((S)-1-methylpyrrolidin-2-yl)methoxy)-7-(2-(trifluoromethyl)benzyl)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(2-(trifluoromethyl)phenyl)methanol

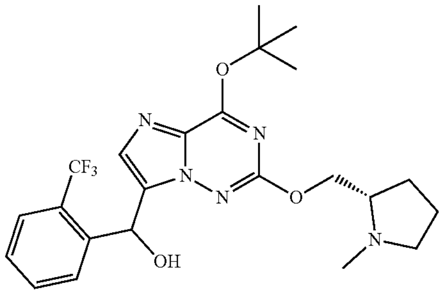 [SMILES: CN1CCC[C@H]1COc1nc(OC(C)(C)C)c2ncc(C(O)c3ccccc3C(F)(F)F)n2n1]

To a solution of (S)-7-bromo-4-(tert-butoxy)-2-((1-methylpyrrolidin-2-yl)methoxy)imidazo[2,1-f][1,2,4]triazine (200 mg, 0.5 mmol) in THF (8 mL) was added a solution of n-BuLi (1.6M, 0.77 mL, 1 mmol) drop wise maintaining the temperature between −75~−65° C. After 1 h, a suspension of the 2-(trifluoromethyl)benzaldehyde (174 mg, 1 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3). The combined organic layers were washed with brine, dried over $Na_2SO_4$, filtered, and concentrated. The residue was purified by prep-TLC to give the target compound (210 mg, 87.8%). MS: M/e 480 $(M+1)^+$.

Step B: (S)-2-((1-methylpyrrolidin-2-yl)methoxy)-7-(2-(trifluoromethyl)benzyl)imidazo[2,1-f][1,2,4]triazin-4-ol

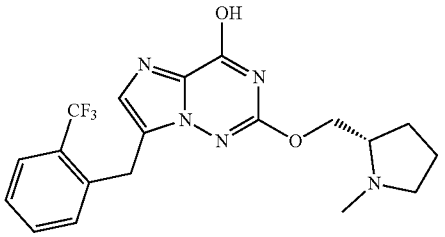 [SMILES: CN1CCC[C@H]1COc1nc(O)c2ncc(Cc3ccccc3C(F)(F)F)n2n1]

To a solution of (4-(tert-butoxy)-2-(((S)-1-methylpyrrolidin-2-yl)methoxy)imidazo[2,1-f][1,2,4]triazin-7-yl)(2-(trifluoromethyl)phenyl)methanol (310 mg, 0.67 mmol) in DCM (10 mL) was added TFA (5 mL) and $Et_3SiH$ (5 mL). The reaction mixture was stirred at 40° C. overnight. The mixture was concentrated in vacuo. The residue was added $NaHCO_3$ solution (1 M, 10 mL) and extracted with ethyl acetate. The combined organic extracts were dried over sodium sulfate, filtered and evaporated. Purification by preparative TLC to afforded the title product (200 mg 65.7%). MS: m/e 408 $(M+1)^+$.

Step C: (S)-4-chloro-2-((1-methylpyrrolidin-2-yl)methoxy)-7-(2-(trifluoromethyl)benzyl)imidazo[2,1-f][1,2,4]triazine

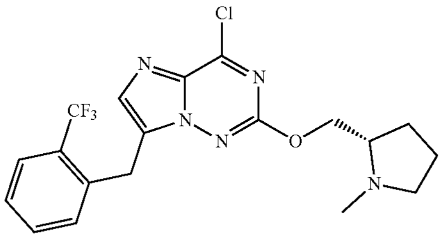 [SMILES: CN1CCC[C@H]1COc1nc(Cl)c2ncc(Cc3ccccc3C(F)(F)F)n2n1]

To a solution of (S)-2-((1-methylpyrrolidin-2-yl)methoxy)-7-(2-(trifluoromethyl)benzyl)imidazo[2,1-f][1,2,4]triazin-4-ol (200 mg, 0.49 mmol) in $POCl_3$ (5 mL) was added Triethylamine Hydrochloride (137 mg, 1 mmol). The mixture was sealed and stirred at 110° C. for overnight. The mixture was cooled down to rt and concentrated in vacuo. The residue was directly used in next step. MS: m/e 426 $(M+1)^+$.

Step D: 2-((S)-4-(2-(((S)-1-methylpyrrolidin-2-yl)methoxy)-7-(2-(trifluoromethyl)benzyl)imidazo[2,1-f][1,2,4]triazin-4-yl)piperazin-2-yl)acetonitrile

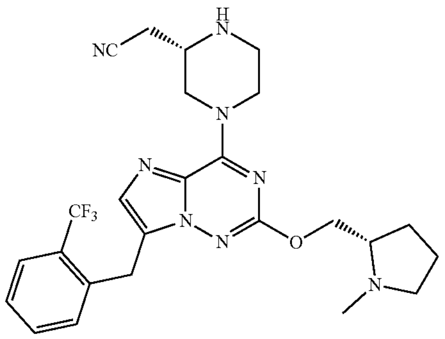 [SMILES: CN1CCC[C@H]1COc1nc(N2CCN[C@@H](CC#N)C2)c2ncc(Cc3ccccc3C(F)(F)F)n2n1]

The product of step C in acetonitrile (10 mL) was slowly added a solution of (S)-2-(piperazin-2-yl)acetonitrile (125 mg, 1 mmol) and DIEA (258 mg, 2 mmol) in acetonitrile (2 ml). The mixture was stirred at rt for 2 h. The mixture was directly used in next step. MS: m/e 515 $(M+1)^+$.

Step E: 2-((S)-1-acryloyl-4-(2-(((S)-1-methylpyrrolidin-2-yl)methoxy)-7-(2-(trifluoromethyl)benzyl)imidazo[2,1-f][1,2,4]triazin-4-yl)piperazin-2-yl)acetonitrile

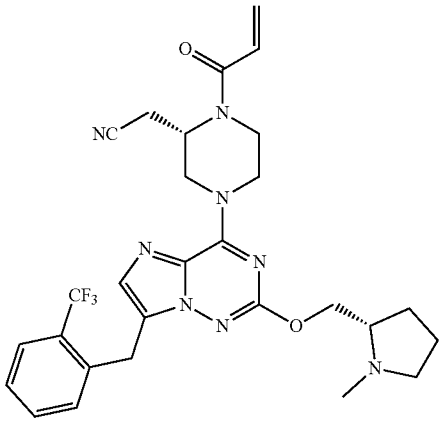 [SMILES: C=CC(=O)N1CCN(c2nc(OC[C@@H]3CCCN3C)nn3c(Cc4ccccc4C(F)(F)F)cnc23)C[C@@H]1CC#N]

The mixture of the product of step D was added $NaHCO_3$ solution (1 M, 10 mL). Acryloyl chloride (90 mg, 0.1 mol) was added slowly to the mixture. The reaction was stirred at rt for 2 h. The resulting mixture was extracted with ethyl acetate. The combined organic extracts were dried over sodium sulfate, filtered and evaporated. Purification by preparative TLC to afford the title product (1.2 mg, 0.43% for 3 steps) 1H NMR (400 MHz, $CD_3OD$) δ 7.74 (d, J=7.7 Hz, 1H), 7.52 (t, J=7.2 Hz, 1H), 7.44 (t, J=7.3 Hz, 1H), 7.28 (d, J=7.3 Hz, 1H), 7.24 (s, 1H), 6.82 (s, 1H), 6.29 (d, J=16.7 Hz, 1H), 5.84 (d, J=10.1 Hz, 1H), 5.34 (s, 1H), 5.10 (s, 1H), 4.69 (s, 1H), 4.51-4.44 (m, 1H), 4.42 (s, 2H), 3.82 (s, 1H), 3.70-3.61 (m, 4H), 3.21 (s, 1H), 3.02 (s, 3H), 2.91 (s, 1H), 2.34 (s, 1H), 2.25-2.13 (m, 2H), 2.05-1.93 (m, 3H), 1.60 (s, 1H) ppm. MS: M/e 569 $(M+1)^+$.

Example 19: Compound A19: 2-((S)-1-acryloyl-4-(7-((4-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: 2-((S)-4-(7-((4-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

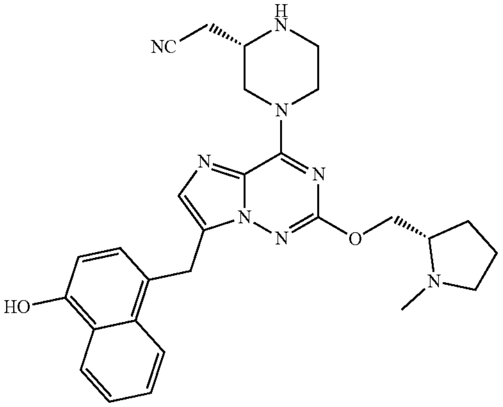 [SMILES: CN1CCC[C@H]1COc1nc(N2CCN[C@@H](CC#N)C2)c2ncc(Cc3ccc(O)c4ccccc34)n2n1]

benzyl (S)-2-(cyanomethyl)-4-(7-((4-methoxynaphthalen-1-yl)methyl)-2-(((S)-1-methylpyrrolidin-2-yl)methoxy)imidazo[2,1-f][1,2,4]triazin-4-yl)piperazine-1-carboxylate (50 mg, 0.075 mmol) was dissolved in DCM (3 ml) followed by addition of $BBr_3$ (1M in DCM, 2.3 ml, 2.27 mmol). The mixture was stirred at rt for 2 hours. The reaction was concentrated to dryness (40 mg) and the residue was used directly for next step without further purification. MS: M/e 513 $(M+1)^+$.

Step B: 2-((S)-1-acryloyl-4-(7-((4-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

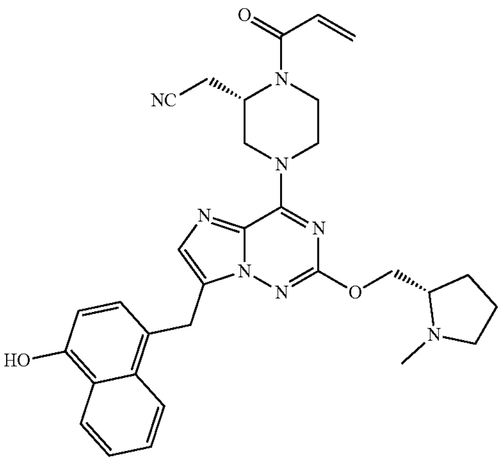 [SMILES: C=CC(=O)N1CCN(c2nc(OC[C@@H]3CCCN3C)nn3c(Cc4ccc(O)c5ccccc45)cnc23)C[C@@H]1CC#N]

To a mixture of the product of the step A (100 mg, crude) in $CH_3CN$ (2 mL) was added saturated $NaHCO_3$ (1 mL) and followed by a solution of acryloyl chloride (20 mg, 0.22 mmol) in $CH_3CN$ (0.5 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (1.9 mg, 10% for two steps). $^1H$ NMR (400 MHz, DMSO-d6) δ 10.08 (s, 1H), 9.71 (s, 1H), 8.18 (d, J=8.0 Hz, 1H), 8.04 (d, J=8.0 Hz, 1H), 7.51-5.40 (m, 2H), 7.29 (s, 1H), 7.20 (d, J=7.4 Hz, 1H), 6.83-6.51 (m, 2H), 6.20 (d, J=16.6 Hz, 1H), 5.79 (d, J=10.1 Hz, 1H), 5.07-4.98 (m, 2H), 4.68-4.54 (m, 1H), 4.50 (s, 3H), 4.10 (s, 1H), 3.79 (s, 2H), 3.10-3.01 (m, 4H), 2.92 (d, J=3.2 Hz, 6H), 2.20 (s, 1H), 2.05-1.89 (m, 3H) ppm. MS: M/e 567 $(M+1)^+$.

Example 20: Compound A20: 2-((S)-1-acryloyl-4-(7-(2-fluoro-6-hydroxybenzyl)-2-(((S)-1-methylpyrrolidin-2-yl)methoxy)imidazo[2,1-f][1,2,4]triazin-4-yl)piperazin-2-yl)acetonitrile Step A: (2-(benzyloxy)-6-fluorophenyl)(4-(tert-butoxy)-2-(((S)-1-methylpyrrolidin-2-yl)methoxy)imidazo[2,1-f][1,2,4]triazin-7-yl)methanol

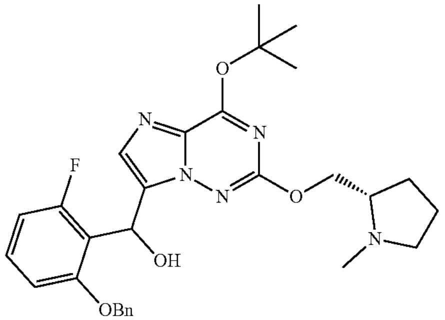 [SMILES: CN1CCC[C@H]1COc1nc(OC(C)(C)C)c2ncc(C(O)c3c(F)cccc3OCc3ccccc3)n2n1]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (10 mL) was added n-BuLi (1 mL, 1.6 mmol) dropwise maintaining the temperature between −75~−65° C. After 30 min, a mixture of 2-(benzyloxy)-6-fluorobenzaldehyde (276 mg, 1.2 mmol) in THF (2 mL) was added dropwise. The resulted mixture was stirred at −70° C. for 1 h and then warmed to room temperature for 16 h. The reaction was quenched with saturated $NH_4Cl$ solution, extracted with EtOAc (50 mL×2). The combined organic layers were washed with brine, dried over $Na_2SO_4$, filtered, and concentrated. The residue was purified by combi flash to give target compound (320 mg, 63%). MS: M/e 536 $(M+1)^+$.

Step B: (S)-7-(2-(benzyloxy)-6-fluorobenzyl)-2-((1-methylpyrrolidin-2-yl)methoxy)imidazo[2,1-f][1,2,4]triazin-4-ol

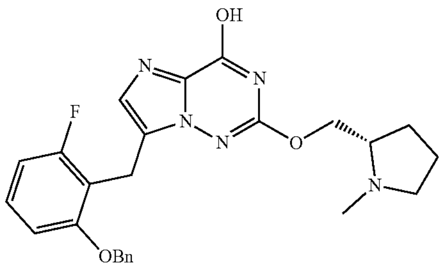 [SMILES: CN1CCC[C@H]1COc1nc(O)c2ncc(Cc3c(F)cccc3OCc3ccccc3)n2n1]

To a mixture of the product of step A (320 mg) in DCE (3 mL) was added TFA (3 mL) and $Et_3SiH$ (3 mL). The reaction was stirred at 25° C. overnight. The mixture was concentrated to dryness and the residue was used directly for next step without further purification. MS: M/e 464 $(M+1)^+$.

Step C: (S)-7-(2-(benzyloxy)-6-fluorobenzyl)-4-chloro-2-((1-methylpyrrolidin-2-yl)methoxy)imidazo[2,1-f][1,2,4]triazine

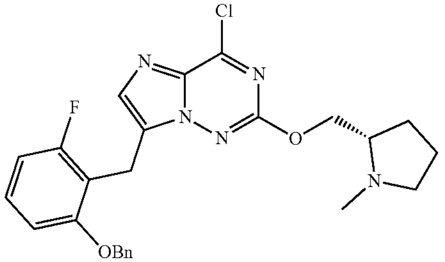 [SMILES: CN1CCC[C@H]1COc1nc(Cl)c2ncc(Cc3c(F)cccc3OCc3ccccc3)n2n1]

The product of step B (120 mg, 0.26 mmol) was dissolved in $POCl_3$ (2 ml) followed by addition of triethylamine hydrochloride (106 mg, 0.78 mmol). The reaction was heated at 100° C. overnight. The mixture was concentrated to dryness and the residue was used directly for next step without further purification (100 mg, crude). MS: M/e 482 $(M+1)^+$.

Step D: benzyl (S)-4-(7-(2-(benzyloxy)-6-fluorobenzyl)-2-(((S)-1-methylpyrrolidin-2-yl)methoxy)imidazo[2,1-f][1,2,4]triazin-4-yl)-2-(cyanomethyl)piperazine-1-carboxylate

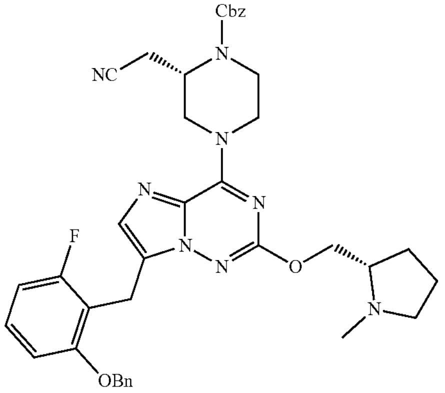 [SMILES: CN1CCC[C@H]1COc1nc(N2CCN(C(=O)OCc3ccccc3)[C@@H](CC#N)C2)c2ncc(Cc3c(F)cccc3OCc3ccccc3)n2n1]

The product of step C (100 mg, 0.21 mmol) was dissolved in THF (3 ml), then DIEA (81 mg, 0.63 mmol) and benzyl (S)-2-(cyanomethyl)piperazine-1-carboxylate (59 mg, 0.23 mmol) were added and the reaction was stirred at room temperature for 3 hours. The reaction was quenched with saturated water, extracted with EtOAc (80 mL). The organic layer was washed with brine, dried over $Na_2SO_4$, filtered, and concentrated. The residue was purified by combi flash to give target compound (40 mg, 10% over two steps). MS: M/e 705 $(M+1)^+$.

Step E: 2-((S)-4-(7-(2-fluoro-6-hydroxybenzyl)-2-(((S)-1-methylpyrrolidin-2-yl)methoxy)imidazo[2,1-f][1,2,4]triazin-4-yl)piperazin-2-yl)acetonitrile

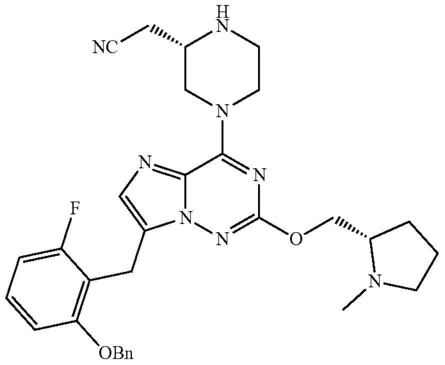 [SMILES: CN1CCC[C@H]1COc1nc(N2CCN[C@@H](CC#N)C2)c2ncc(Cc3c(F)cccc3OCc3ccccc3)n2n1]

The product of step D (40 mg) was dissolved in a mixture of EtOH (2 mL) and THF (2 ml) followed by addition of Pd/C (10 mg, 10%). The reaction mixture was hydrogenated at balloon with stirring for overnight, and filtered through a pad of Celite. The filtrate was evaporated to afford the target compound (40 mg, crude) which was used directly for next step without further purification. MS: M/e 481 $(M+1)^+$.

Step F: 2-((S)-1-acryloyl-4-(7-(2-fluoro-6-hydroxybenzyl)-2-(((S)-1-methylpyrrolidin-2-yl)methoxy)imidazo[2,1-f][1,2,4]triazin-4-yl)piperazin-2-yl)acetonitrile

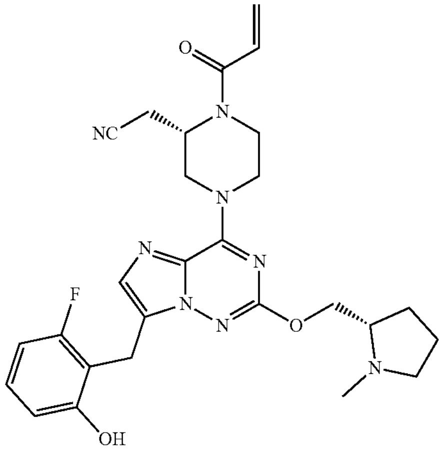 [SMILES: C=CC(=O)N1CCN(c2nc(OC[C@@H]3CCCN3C)nn3c(Cc4c(O)cccc4F)cnc23)C[C@@H]1CC#N]

To a mixture of the product of the step E (50 mg, crude) in $CH_3CN$ (1 mL) was added saturated $NaHCO_3$ (1 mL) and followed by a solution of acryloyl chloride (10 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (0.5 mg, 3% for two steps). 1H NMR (400 MHz, cd3od) δ 7.20-7.04 (m, 2H), 6.80 (s, 1H), 6.69-6.53 (m, 2H), 6.28 (d, J=17.3 Hz, 1H), 5.83 (d, J=10.3 Hz, 1H), 5.09 (s, 1H), 4.80 (s, 2H), 4.54-4.49 (m, 1H), 4.17 (s, 3H), 3.96-3.87 (m, 1H), 3.84-3.74 (m, 1H), 3.53-3.48 (m, 2H), 3.29-3.17 (m, 2H), 3.08 (s, 3H), 2.88-2.65 (m, 3H), 2.47-2.40 (m, 1H), 2.21-2.08 (m, 3H) ppm. MS: M/e 535 $(M+1)^+$.

Example 21: Compound A21: 2-((S)-1-acryloyl-4-(7-((2-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile Step A: (4-(tert-butoxy)-2-(((S)-1-methylpyrrolidin-2-yl)methoxy)imidazo[2,1-f][1,2,4]triazin-7-yl)(2-methoxynaphthalen-1-yl)methanol

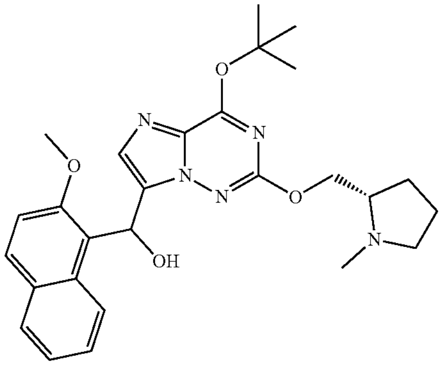 [SMILES: COc1ccc2ccccc2c1C(O)c1cnc2c(OC(C)(C)C)nc(OC[C@@H]3CCCN3C)nn12]

To a solution of (S)-7-bromo-4-(tert-butoxy)-2-((1-methylpyrrolidin-2-yl)methoxy)imidazo[2,1-f][1,2,4]triazine (383 mg, 1 mmol) in THF (10 mL) was added n-BuLi (1 mL, 1.6 mmol) dropwise maintaining the temperature between −75~−65° C. After 30 min, a mixture of 2-methoxy-1-naphthaldehyde (223 mg, 1.2 mmol) in THF (2 mL) was added dropwise. The resulted mixture was stirred at −70° C. for 1 h and then warmed to room temperature for 16 h. The reaction was quenched with saturated $NH_4Cl$ solution, extracted with EtOAc (50 mL×2). The combined organic layers were washed with brine, dried over $Na_2SO_4$, filtered, and concentrated. The residue was purified by combi flash to give target compound (340 mg, 69%). MS: M/e 492 $(M+1)^+$.

Step B: (S)-7-((2-methoxynaphthalen-1-yl)methyl)-2-((1-methylpyrrolidin-2-yl)methoxy)imidazo[2,1-f][1,2,4]triazin-4-ol

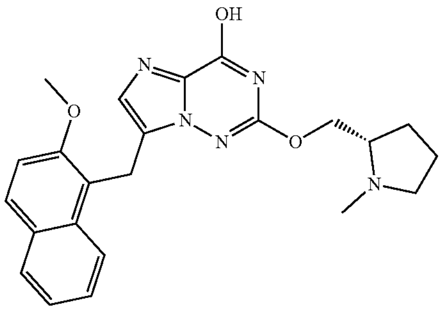 [SMILES: COc1ccc2ccccc2c1Cc1cnc2c(O)nc(OC[C@@H]3CCCN3C)nn12]

To a mixture of the product of step A (340 mg, 0.8 mmol) in DCE (3 mL) was added TFA (3 mL) and $Et_3SiH$ (3 mL). The reaction was heated at 25° C. overnight. The mixture was concentrated to dryness and the residue was used directly for next step without further purification. MS: M/e 420 $(M+1)^+$.

Step C: benzyl (S)-2-(cyanomethyl)-4-(7-((2-methoxynaphthalen-1-yl)methyl)-2-(((S)-1-methylpyrrolidin-2-yl)methoxy)imidazo[2,1-f][1,2,4]triazin-4-yl)piperazine-1-carboxylate

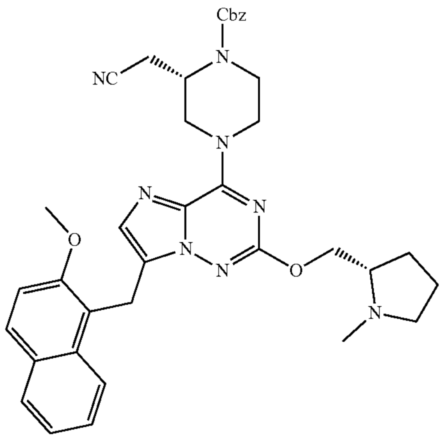 [SMILES: COc1ccc2ccccc2c1Cc1cnc2c(N3CCN(C(=O)OCc4ccccc4)[C@@H](CC#N)C3)nc(OC[C@@H]3CCCN3C)nn12]

To the residue of the step B (300 mg, crude) in $POCl_3$ (4 mL) was added triethylamine hydrochloride (292 mg, 2.15 mmol). The resulted mixture was stirred at 100° C. overnight. The mixture was concentrated to dryness, treated with THF (15 mL). Then DIEA (387 mg, 2.04 mmol) and benzyl (S)-2-(cyanomethyl)piperazine-1-carboxylate (194 mg, 0.75 mmol) were added and the reaction was stirred at room temperature for 2 hours. The reaction was quenched with water, extracted with EtOAc (80 mL). The organic layer was washed with brine, dried over $Na_2SO_4$, filtered, and concentrated. The residue was purified by combi flash to give target compound (130 mg, 27% for two steps). MS: M/e 661 $(M+1)^+$.

Step D: 2-((S)-4-(7-((2-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

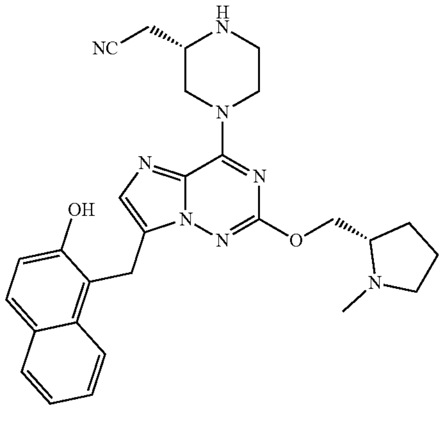 [SMILES: CN1CCC[C@H]1COc1nc(N2CCN[C@@H](CC#N)C2)c2ncc(Cc3c(O)ccc4ccccc34)n2n1]

To a mixture of the product of step C (30 mg, 0.05 mmol) in DCM (3 mL) at rt was added 1N $BBr_3$ in DCM (0.5 mL, 0.5 mmol). The reaction was stirred at room temperature for 2 hours. The reaction was filtered, the filtered cake was washed with MTBE to give the target compound (20 mg, crude) which was used directly for next step without further purification. MS: M/e 513 $(M+1)^+$.

Step E: 2-((S)-1-acryloyl-4-(7-((2-hydroxynaphthalen-1-yl)methyl)-2-(((S)-1-methylpyrrolidin-2-yl)methoxy)imidazo[2,1-f][1,2,4]triazin-4-yl)piperazin-2-yl)acetonitrile

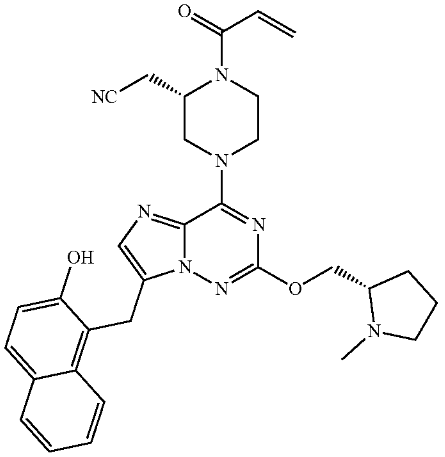 [SMILES: C=CC(=O)N1CCN(c2nc(OC[C@@H]3CCCN3C)nn3c(Cc4c(O)ccc5ccccc45)cnc23)C[C@@H]1CC#N]

To a mixture of the product of the step D (20 mg, crude) in $CH_3CN$ (1 mL) was added saturated $NaHCO_3$ (0.5 mL) and followed by a solution of acryloyl chloride (6 mg, 0.1 mmol) in $CH_3CN$ (0.3 mL) at 0° C. The resulting mixture was stirred at room temperature for 30 min. The reaction was diluted with water, extracted with EA. The organic layer was washed with brine, dried over $Na_2SO_4$, filtered, and concentrated. The residue was purified by prep-TLC to give the target compound (2.25 mg, 10% for two steps). 1H NMR (400 MHz, DMSO-d6) δ 10.01 (s, 1H), 7.95 (d, J=7.8 Hz, 1H), 7.87 (d, J=7.8 Hz, 1H), 7.80 (d, J=8.7 Hz, 1H), 7.47 (t, J=7.3 Hz, 1H), 7.34 (d, J=6.9 Hz, 3H), 6.71-6.91 (m, 2H), 6.24 (d, J=16.5 Hz, 1H), 5.84 (d, J=9.7 Hz, 1H), 5.19-4.85 (m, 2H), 4.80-4.71 (m, 2H), 4.55 (s, 2H), 4.18 (s, 1H), 3.92 (s, 1H), 3.67 (s, 1H), 3.21 (s, 2H), 3.11-2.84 (m, 6H), 2.38 (s, 2H), 2.07-1.83 (m, 3H) ppm. MS: M/e 567 $(M+1)^+$.

Example 22: Compound A22: 2-((2S)-1-acryloyl-4-(7-(2,3-dihydro-1H-inden-1-yl)-2-(((S)-1-methylpyrrolidin-2-yl)methoxy)imidazo[2,1-f][1,2,4]triazin-4-yl)piperazin-2-yl)acetonitrile Step A: 1-(4-(tert-butoxy)-2-(((S)-1-methylpyrrolidin-2-yl)methoxy)imidazo[2,1-f][1,2,4]triazin-7-yl)-2,3-dihydro-1H-inden-1-ol

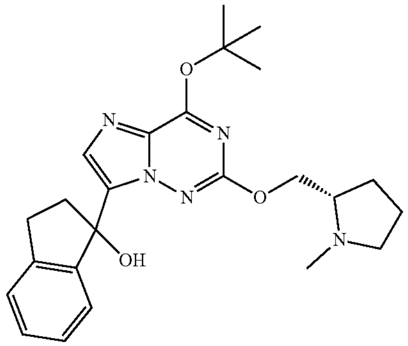 [SMILES: CN1CCC[C@H]1COc1nc(OC(C)(C)C)c2ncc(C3(O)CCc4ccccc43)n2n1]

To a cooled solution of (S)-7-bromo-4-(tert-butoxy)-2-((1-methylpyrrolidin-2-yl)methoxy)imidazo[2,1-f][1,2,4]triazine (400 mg, 1.1 mmol) in THF (8 mL) at −78° C. was added with n-BuLi (1.6 M in n-hexane, 1.0 mL, 1.6 mmol) dropwise. After stirred for 30 mins, 2,3-dihydro-1H-inden-1-one (174 mg, 1.3 mmol) in THF (2 mL) was added dropwise. The resulting mixture was stirred gradually to r.t overnight. The solution was quenched with $NH_4Cl$ solution (5 mL) and extracted with EA (10 mL). The organic layer was dried, concentrated and purified by Combi-Flash (DCM:$NH_3$ (7 M in methanol)=25:2) to get the product (275 mg, 60%). MS: M/e 438 $(M+1)^+$.

Step B: (S)-7-(1H-inden-3-yl)-2-((1-methylpyrrolidin-2-yl)methoxy)imidazo[2,1-f][1,2,4]triazin-4-ol

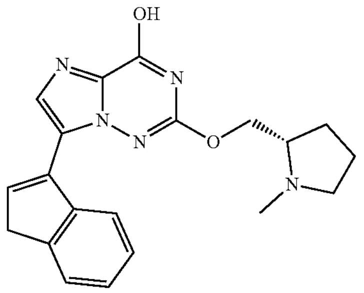 [SMILES: CN1CCC[C@H]1COc1nc(O)c2ncc(C3=CCc4ccccc43)n2n1]

$Et_3SiH$ (1 mL) and TFA (1 mL) were added to a solution of 1-(4-(tert-butoxy)-2-(((S)-1-methylpyrrolidin-2-yl)methoxy)imidazo[2,1-f][1,2,4]triazin-7-yl)-2,3-dihydro-1H-inden-1-ol (335 mg, 0.8 mmol) in DCM (2 mL). The solution was stirred at r.t overnight. The solvent was evaporated under oil pump, then azeotrope with toluene. The crude product was used in the next step directly (250 mg, crude). MS: M/e 364 $(M+1)^+$.

Step C: (S)-4-chloro-7-(1H-inden-3-yl)-2-((1-methylpyrrolidin-2-yl)methoxy)imidazo[2,1-f][1,2,4]triazine

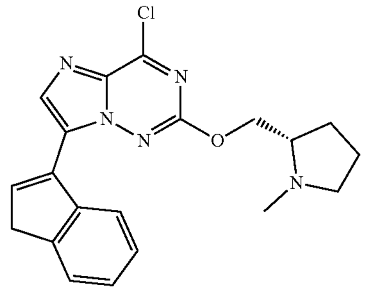 [SMILES: CN1CCC[C@H]1COc1nc(Cl)c2ncc(C3=CCc4ccccc43)n2n1]

A solution of (S)-7-(1H-inden-3-yl)-2-((1-methylpyrrolidin-2-yl)methoxy)imidazo[2,1-f][1,2,4]triazin-4-ol (250 mg, 0.7 mmol) and $Et_3N{\cdot}HCl$ (193 mg, 1.4 mmol) in $POCl_3$ (5 mL) was heated at 100° C. overnight. After cooled down, the solvent was evaporated under oil pump and co-distilled with toluene to get the crude product, which was use directly in the next step (120 mg, crude). MS: M/e 382 $(M+1)^+$.

Step D: benzyl (S)-4-(7-(1H-inden-3-yl)-2-(((S)-1-methylpyrrolidin-2-yl)methoxy)imidazo[2,1-f][1,2,4]triazin-4-yl)-2-(cyanomethyl)piperazine-1-carboxylate

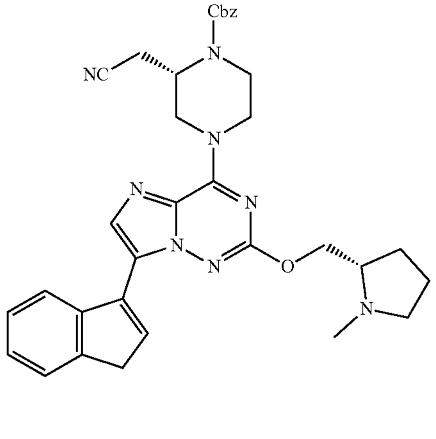 [SMILES: CN1CCC[C@H]1COc1nc(N2CCN(C(=O)OCc3ccccc3)[C@@H](CC#N)C2)c2ncc(C3=CCc4ccccc43)n2n1]

To a solution of (S)-4-chloro-7-(1H-inden-3-yl)-2-((1-methylpyrrolidin-2-yl)methoxy)imidazo[2,1-f][1,2,4]triazine (120 mg, 0.3 mmol) in THF (5 mL) was added DIEA (310 mg, 0.4 mmol) and benzyl (S)-2-(cyanomethyl)piperazine-1-carboxylate (156 mg, 0.6 mmol). The reaction mixture was stirred at r.t for 1 hour. The solution was added water (5 mL) and extracted with EA (10 mL). The organic layer was dried over $Na_2SO_4$, concentrated and purified by preparative TLC (DCM:$NH_3$ (7M in MeOH)=10:1) to give the product (100 mg, 53%). MS: M/e 605 $(M+1)^+$.

Step E: 2-((2S)-4-(7-(2,3-dihydro-1H-inden-1-yl)-2-(((S)-1-methylpyrrolidin-2-yl)methoxy)imidazo[2,1-f][1,2,4]triazin-4-yl)piperazin-2-yl)acetonitrile

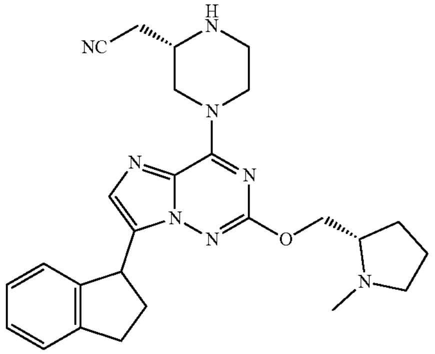 [SMILES: CN1CCC[C@H]1COc1nc(N2CCN[C@@H](CC#N)C2)c2ncc(C3CCc4ccccc43)n2n1]

A suspension of benzyl (S)-4-(7-(1H-inden-3-yl)-2-(((S)-1-methylpyrrolidin-2-yl)methoxy)imidazo[2,1-f][1,2,4]triazin-4-yl)-2-(cyanomethyl)piperazine-1-carboxylate (100 mg, 0.16 mmol) and Pd/C (wet, 10%, 100 mg) in THF/EtOH (5 mL/5 mL) was stirred at r.t under $H_2$ balloon overnight. The catalyst was filtered out and the filtrate was concentrated to get the crude product, which was used directly (40 mg, 51%). MS: M/e 473 $(M+1)^+$.

Step F: 2-((2S)-1-acryloyl-4-(7-(2,3-dihydro-1H-inden-1-yl)-2-(((S)-1-methylpyrrolidin-2-yl)methoxy)imidazo[2,1-f][1,2,4]triazin-4-yl)piperazin-2-yl)acetonitrile

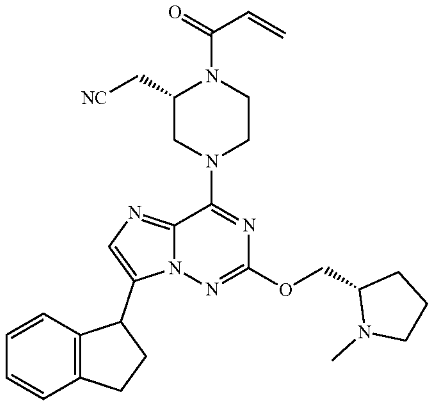 [SMILES: C=CC(=O)N1CCN(c2nc(OC[C@@H]3CCCN3C)nn3c(C4CCc5ccccc54)cnc23)C[C@@H]1CC#N]

$NaHCO_3$ solution (saturated, 0.5 mL) was added to a solution of 2-((2S)-4-(7-(2,3-dihydro-1H-inden-1-yl)-2-(((S)-1-methylpyrrolidin-2-yl)methoxy)imidazo[2,1-f][1,2,4]triazin-4-yl)piperazin-2-yl)acetonitrile (40 mg, 0.1 mmol) in $CH_3CN$ (5 mL), followed with acryloyl chloride (19 mg, 0.2 mmol). The reaction mixture was stirred at r.t for 1 hr. The solution was evaporated, added water (4 mL) and extracted with EA (10 mL). The organic layer was dried, concentrated and purified by preparative TLC (DCM:$NH_3$ (7M in MeOH)=10:1) to get the product (5 mg, 11%). $^1H$ NMR (400 MHz, $CD_3OD$) δ 7.31 (d, J=8.0 Hz, 1H), 7.22-7.19 (m, 2H), 7.13-7.06 (m, 2H), 6.89-6.79 (m, 1H), 6.29 (d, J=16.0 Hz, 1H), 5.84 (d, J=8.0 Hz, 1H), 5.10 (br.s, 1H), 4.69 (s, 1H), 4.50-4.45 (m, 1H), 4.17-3.59 (m, 2H), 3.22-2.90 (m, 9H), 2.70-2.60 (m, 2H), 2.32-2.03 (m, 6H), 1.60-1.40 (m, 4H). ppm. MS: M/e 527 $(M+1)^+$.

Example 23: Compound A23: 2-((S)-4-(7-(1-naphthoyl)-2-(((S)-1-methylpyrrolidin-2-yl)methoxy)imidazo[2,1-f][1,2,4]triazin-4-yl)-1-acryloylpiperazin-2-yl)acetonitrile Step A: (S)-(4-(tert-butoxy)-2-((1-methylpyrrolidin-2-yl)methoxy)imidazo[2,1-f][1,2,4]triazin-7-yl)(naphthalen-1-yl)methanone

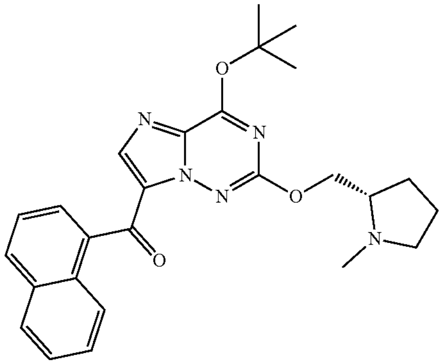 [SMILES: CN1CCC[C@H]1COc1nc(OC(C)(C)C)c2ncc(C(=O)c3cccc4ccccc34)n2n1]

(4-(tert-butoxy)-2-(((S)-1-methylpyrrolidin-2-yl)methoxy)imidazo[2,1-f][1,2,4]triazin-7-yl)(naphthalen-1-yl)methanol (250 mg, 0.54 mmol) was dissolved in DCM (5 mL) followed by addition of DMP (300 mg, 0.70 mmol) batchwise. The reaction was stirred at 25° C. for 2 hours. The reaction was quenched with water, extracted with EtOAc (80 mL). The organic layer was washed with brine, dried over $Na_2SO_4$, filtered, and concentrated. The residue was purified by combi flash to give target compound (160 mg, 64%). MS: M/e 460 $(M+1)^+$.

Step B: (S)-(4-hydroxy-2-((1-methylpyrrolidin-2-yl)methoxy)imidazo[2,1-f][1,2,4]triazin-7-yl)(naphthalen-1-yl)methanone

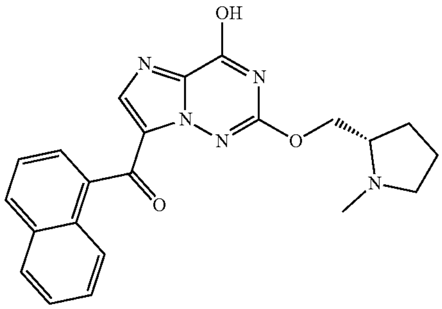 [SMILES: CN1CCC[C@H]1COc1nc(O)c2ncc(C(=O)c3cccc4ccccc34)n2n1]

To the product of step A (120 mg, 0.26 mmol) in DCM (5 mL) was added TFA (0.5 ml). The mixture was stirred at rt overnight. The mixture was concentrated to dryness and used in the next step directly without purification. MS: M/e 404 $(M+1)^+$.

Step C: tert-butyl(S)-4-(7-(1-naphthoyl)-2-(((S)-1-methylpyrrolidin-2-yl)methoxy)imidazo[2,1-f][1,2,4]triazin-4-yl)-2-(cyanomethyl)piperazine-1-carboxylate

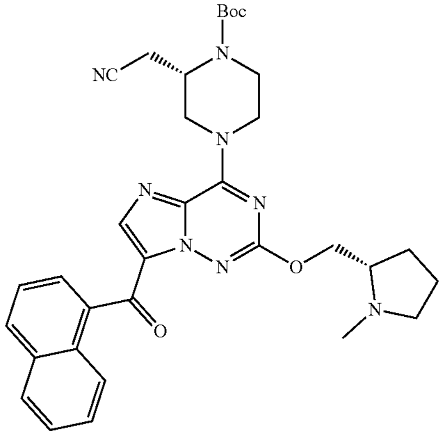 [SMILES: CN1CCC[C@H]1COc1nc(N2CCN(C(=O)OC(C)(C)C)[C@@H](CC#N)C2)c2ncc(C(=O)c3cccc4ccccc34)n2n1]

To the residue of the step B (50 mg, crude) in $POCl_3$ (3 mL) was added triethylamine hydrochloride (50 mg). The resulted mixture was stirred at 100° C. overnight. The mixture was concentrated to dryness, treated with THF (5 mL). Then DIEA (50 mg, 0.36 mmol) and tert-butyl (S)-2-(cyanomethyl)piperazine-1-carboxylate (26 mg, 0.12 mmol) were added and the reaction was stirred at room temperature for 2 hours. The reaction was quenched with water, extracted with EtOAc, washed with brine, dried over $Na_2SO_4$, filtered, and concentrated. The residue was purified by combi flash to give target compound (70 mg, 40% for two steps). MS: M/e 611 $(M+1)^+$.

Step D: 2-((S)-4-(7-(1-naphthoyl)-2-(((S)-1-methylpyrrolidin-2-yl)methoxy)imidazo[2,1-f][1,2,4]triazin-4-yl)piperazin-2-yl)acetonitrile

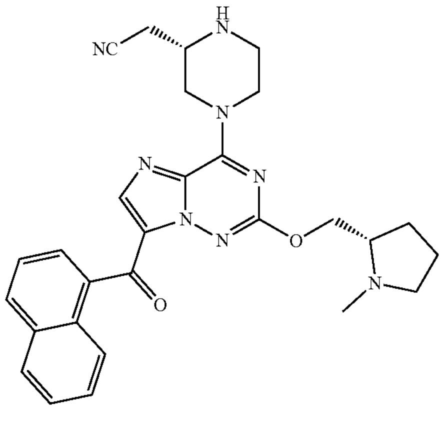 [SMILES: CN1CCC[C@H]1COc1nc(N2CCN[C@@H](CC#N)C2)c2ncc(C(=O)c3cccc4ccccc34)n2n1]

To a mixture of the product of step D (70 mg, crude) in DCM (2 mL) was added TFA (0.5 ml). The reaction was stirred at room temperature for 2 h. The solvent was removed under reduced pressure and the residue was used directly for next step without further purification. MS: M/e 511 $(M+1)^+$.

Step E: 2-((S)-4-(7-(1-naphthoyl)-2-(((S)-1-methylpyrrolidin-2-yl)methoxy)imidazo[2,1-f][1,2,4]triazin-4-yl)-1-acryloylpiperazin-2-yl)acetonitrile

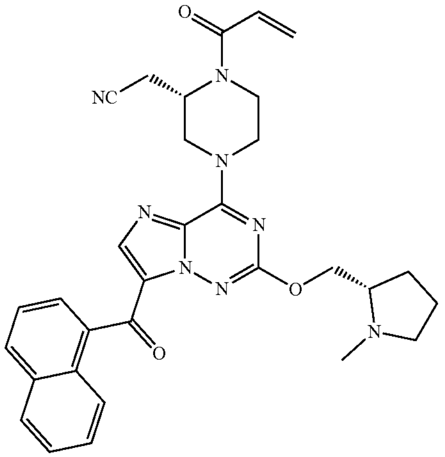 [SMILES: C=CC(=O)N1CCN(c2nc(OC[C@@H]3CCCN3C)nn3c(C(=O)c4cccc5ccccc45)cnc23)C[C@@H]1CC#N]

To a mixture of the product of the step D (50 mg, crude) in $CH_3CN$ (3 mL) was added saturated $NaHCO_3$ (0.5 mL) and followed by a solution of acryloyl chloride (9 mg, 0.1 mmol) in $CH_3CN$ (0.3 mL) at 0° C. The resulting mixture was stirred at room temperature for 30 min. The reaction was diluted with water, extracted with EA (60 mL). The organic layer was washed with brine, dried over $Na_2SO_4$, filtered, and concentrated. The residue was purified by prep-TLC to give the target compound (13 mg, 46% for two steps). 1H NMR (400 MHz, DMSO-d6) δ 8.17 (d, J=7.7 Hz, 1H), 8.07-8.04 (m, 3H), 7.73 (d, J=6.9 Hz, 1H), 7.67-7.52 (m, 3H), 6.86 (s, 1H), 6.20 (d, J=16.6 Hz, 1H), 5.80 (d, J=9.4 Hz, 1H), 4.98 (br.s, 2H), 4.52 (s, 1H), 4.18 (s, 1H), 3.65-3.61 (m, 4H), 3.29-3.20 (m, 3H), 3.00-2.91 (m, 3H), 2.33 (s, 3H), 1.79-1.73 (m, 3H), 1.48 (s, 1H). MS: M/e 565 $(M+1)^+$.

Example 24: Compound B1: 2-((S)-1-acryloyl-4-(7-((3-hydroxynaphthalen-1-yl)methyl)-5-methyl-2-(((S)-1-methylpyrrolidin-2-yl)methoxy)-5H-pyrrolo[3,2-d]pyrimidin-4-yl)piperazin-2-yl)acetonitrile Step A: benzyl (S)-4-(2-chloro-5H-pyrrolo[3,2-d]pyrimidin-4-yl)-2-(cyanomethyl)piperazine-1-carboxylate

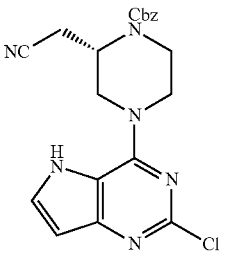 [SMILES: N#CC[C@H]1CN(c2nc(Cl)nc3cc[nH]c23)CCN1C(=O)OCc1ccccc1]

A mixture of 2,4-dichloro-5H-pyrrolo[3,2-d]pyrimidine (2.5 g, 0.013 mol), benzyl (S)-2-(cyanomethyl)piperazine-1-carboxylate (3.44 g, 0.013 mol) and DIEA (5.15 g, 0.040 mol) in THF (50 ml) was stirred at 70° C. overnight. After completed, the solution was concentrated, diluted with EA (50 ml) and then washed with brine (20 ml). The organic layer was dried and concentrated under reduced pressure. The resulting residue was purified by flash column chromatography with 50%-100% EA in PE to afford product (1.7 g, 31%). MS: M/e 411 $(M+1)^+$.

Step B: benzyl (2S)-4-(7-((3-(benzyloxy)naphthalen-1-yl)(hydroxy)methyl)-2-chloro-5H-pyrrolo[3,2-d]pyrimidin-4-yl)-2-(cyanomethyl)piperazine-1-carboxylate

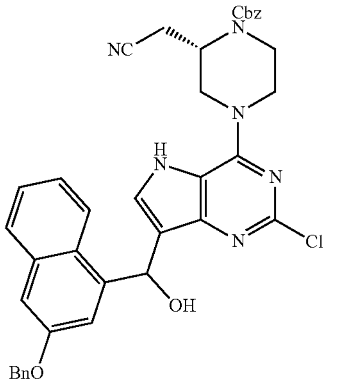 [SMILES: N#CC[C@H]1CN(c2nc(Cl)nc3c(C(O)c4cc(OCc5ccccc5)cc5ccccc45)c[nH]c23)CCN1C(=O)OCc1ccccc1]

A mixture of benzyl (S)-4-(2-chloro-5H-pyrrolo[3,2-d]pyrimidin-4-yl)-2-(cyanomethyl)piperazine-1-carboxylate (1 g, 2.43 mmol), 3-(benzyloxy)-1-naphthaldehyde (0.96 g, 3.66 mmol) and $K_2CO_3$ (0.5 g, 3.62 mmol) in MeCN (12 ml), $H_2O$ (10 ml) and MeOH (2 ml) was stirred at 40° C. for 3 days. The mixture was poured into $H_2O$ (20 ml), extracted with EA (20 ml×2). The organic layer was washed with brine (10 ml), dried and concentrated. The resulting residue was purified by flash with 10%-100% EA in PE to afford product (0.4 g, 24%). MS: M/e 673 $(M+1)^+$.

Step C: benzyl (S)-4-(7-((3-(benzyloxy)naphthalen-1-yl)methyl)-2-chloro-5H-pyrrolo[3,2-d]pyrimidin-4-yl)-2-(cyanomethyl)piperazine-1-carboxylate

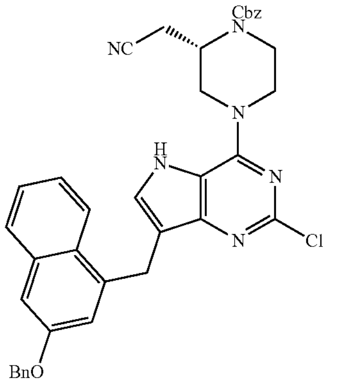 [SMILES: N#CC[C@H]1CN(c2nc(Cl)nc3c(Cc4cc(OCc5ccccc5)cc5ccccc45)c[nH]c23)CCN1C(=O)OCc1ccccc1]

A solution of benzyl (2S)-4-(7-((3-(benzyloxy)naphthalen-1-yl)(hydroxy)methyl)-2-chloro-5H-pyrrolo[3,2-d]pyrimidin-4-yl)-2-(cyanomethyl)piperazine-1-carboxylate (500 mg, 0.74 mmol) in TFA (5 ml), triethylsilane (5 ml) and DCE (5 ml) was stirred at rt for 1 h. After completed, the mixture was concentrated under reduced pressure. The residue was purified by flash column chromatography with 0-60% EA in PE to afford product (0.42 g, 86%). MS: M/e 657 $(M+1)^+$.

Step D: benzyl (S)-4-(7-((3-(benzyloxy)naphthalen-1-yl)methyl)-2-chloro-5-methyl-5H-pyrrolo[3,2-d]pyrimidin-4-yl)-2-(cyanomethyl)piperazine-1-carboxylate

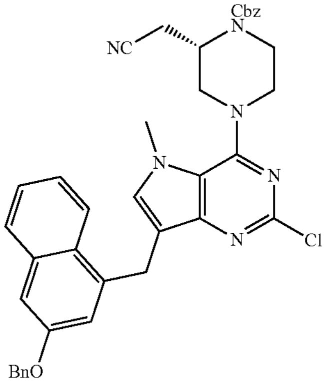 [SMILES: Cn1cc(Cc2cc(OCc3ccccc3)cc3ccccc23)c2nc(Cl)nc(N3CCN(C(=O)OCc4ccccc4)[C@@H](CC#N)C3)c21]

A mixture of benzyl (S)-4-(7-((3-(benzyloxy)naphthalen-1-yl)methyl)-2-chloro-5H-pyrrolo[3,2-d]pyrimidin-4-yl)-2-(cyanomethyl)piperazine-1-carboxylate (0.41 g, 0.62 mmol) and NaH (60%, 50 mg, 1.25 mmol) in DMF (10 ml) was stirred at rt for 10 min. MeI (0.13 g, 0.92 mmol) was added and stirred at rt for 1.5 h. After completed, the solution was quenched with $H_2O$ (10 ml) and then extracted with EA (20 ml×2). The organic layer was dried and concentrated under reduced pressure. The resulting residue was purified by flash column chromatography with 0-60% EA in PE to afford product (0.35 g, 84%). MS: M/e 671 $(M+1)^+$.

Step E: benzyl (S)-4-(7-((3-(benzyloxy)naphthalen-1-yl)methyl)-5-methyl-2-(((S)-1-methylpyrrolidin-2-yl)methoxy)-5H-pyrrolo[3,2-d]pyrimidin-4-yl)-2-(cyanomethyl)piperazine-1-carboxylate

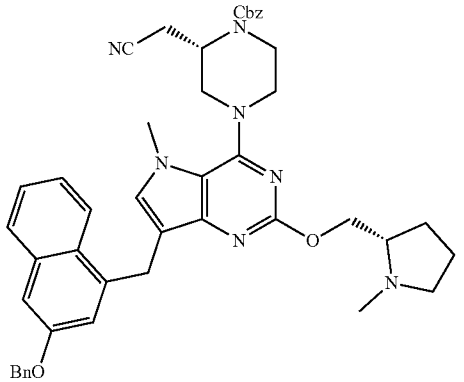 [SMILES: CN1CCC[C@H]1COc1nc(N2CCN(C(=O)OCc3ccccc3)[C@@H](CC#N)C2)c2c(n1)c(Cc1cc(OCc3ccccc3)cc3ccccc13)cn2C]

A mixture of benzyl (S)-4-(7-((3-(benzyloxy)naphthalen-1-yl)methyl)-2-chloro-5-methyl-5H-pyrrolo[3,2-d]pyrimidin-4-yl)-2-(cyanomethyl)piperazine-1-carboxylate (0.32 g, 0.48 mmol), (S)-(1-methylpyrrolidin-2-yl)methanol (82.3 mg, 0.72 mmol), $Pd_2dba_3$ (131 mg, 0.14 mmol) RuPhos (67 mg, 0.14 mmol) and $Cs_2CO_3$ (311 mg, 0.95 mmol) in dioxane (10 ml) was stirred at 120° C. overnight. After completed, the mixture was poured into water (15 ml) and extracted with EA (20 ml×2). The organic layer was washed with brine (10 ml), dried and concentrated under reduced pressure. The resulting residue was purified by flash column chromatography with 0-10% MeOH in DCM to afford product (170 mg, 48%). MS: M/e 750 $(M+1)^+$.

Step F: 2-((S)-4-(7-((3-hydroxynaphthalen-1-yl)methyl)-5-methyl-2-(((S)-1-methylpyrrolidin-2-yl)methoxy)-5H-pyrrolo[3,2-d]pyrimidin-4-yl)piperazin-2-yl)acetonitrile

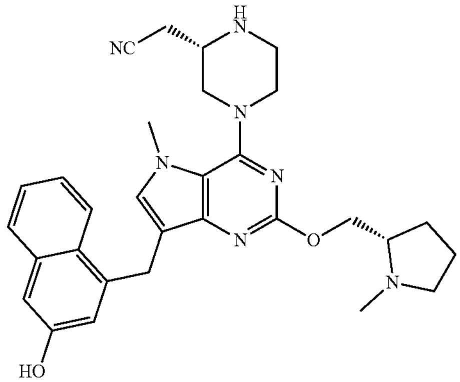 [SMILES: CN1CCC[C@H]1COc1nc(N2CCN[C@@H](CC#N)C2)c2c(n1)c(Cc1cc(O)cc3ccccc13)cn2C]

A mixture of benzyl (S)-4-(7-((3-(benzyloxy)naphthalen-1-yl)methyl)-5-methyl-2-(((S)-1-methylpyrrolidin-2-yl)methoxy)-5H-pyrrolo[3,2-d]pyrimidin-4-yl)-2-(cyanomethyl)piperazine-1-carboxylate (170 mg, 0.23 mmol) and Pd/C (150 mg) in THF (10 ml) and MeOH (10 ml) was stirred at rt for 2 days under $H_2$ atmosphere. After completed, the mixture was filtered through diatomite. The filtrate was concentrated under reduced pressure to afford product (119 mg, 100%) as a crude, which was used directly for the next step without further purification. MS: M/e 526 $(M+1)^+$.

Step G: 2-((S)-1-acryloyl-4-(7-((3-hydroxynaphthalen-1-yl)methyl)-5-methyl-2-(((S)-1-methylpyrrolidin-2-yl)methoxy)-5H-pyrrolo[3,2-d]pyrimidin-4-yl)piperazin-2-yl)acetonitrile

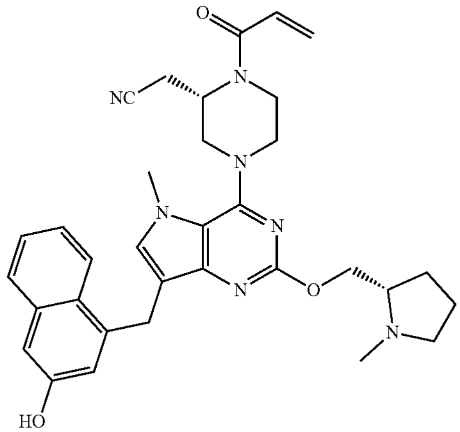 [SMILES: C=CC(=O)N1CCN(c2nc(OC[C@@H]3CCCN3C)nc3c(Cc4cc(O)cc5ccccc45)cn(C)c23)C[C@@H]1CC#N]

To a mixture of 2-((S)-4-(7-((3-hydroxynaphthalen-1-yl)methyl)-5-methyl-2-(((S)-1-methylpyrrolidin-2-yl)methoxy)-5H-pyrrolo[3,2-d]pyrimidin-4-yl)piperazin-2-yl)acetonitrile (119 mg, 0.23 mmol) in MeCN (8 ml) at rt, was added aq. $NaHCO_3$ (sat., 0.3 mL) and then acryloyl chloride (30 mg, 0.33 mmol). The mixture was stirred at rt for 30 min. Then LiOH (20 mg, 0.83 mmol) in $H_2O$ (1 ml) was added to the above solution and stirred at rt for 1 h. The mixture was poured into water and then extracted with EA (15 ml×3). The organic layer was dried and concentrated. The residue was purified by prep-TLC to afford product (4.07 mg). $^1H$ NMR (400 MHz, $CD_3OD$) δ 8.00 (d, J=8.3 Hz, 1H), 7.64 (d, J=8.0 Hz, 1H), 7.48-7.30 (m, 2H), 7.25 (t, J=7.5 Hz, 1H), 7.21 (s, 1H), 6.99 (s, 1H), 6.88 (s, 1H), 6.29 (d, J=16.2 Hz, 1H), 5.83 (d, J=9.7 Hz, 1H), 4.79 (d, J=12.5 Hz, 1H), 4.63-4.54 (m, 1H), 4.42 (s, 2H), 4.08-3.94 (m, 2H), 3.90 (s, 3H), 3.87-3.83 (m, 1H), 3.62-3.55 (m, 1H), 3.50-3.37 (m, 2H), 3.13 (s, 2H), 2.96 (s, 3H), 2.41-2.29 (m, 1H), 2.21-2.13 (m, 1H), 2.08-2.01 (m, 2H), 1.32-1.27 (m, 4H) ppm. MS: M/e 580 $(M+1)^+$.

Example 25: Compound B2: 2-((S)-1-acryloyl-4-(5-ethyl-7-((3-hydroxynaphthalen-1-yl)methyl)-2-(((S)-1-methylpyrrolidin-2-yl)methoxy)-5H-pyrrolo[3,2-d]pyrimidin-4-yl)piperazin-2-yl)acetonitrile Step A: benzyl (S)-4-(2-chloro-5H-pyrrolo[3,2-d]pyrimidin-4-yl)-2-(cyanomethyl)piperazine-1-carboxylate

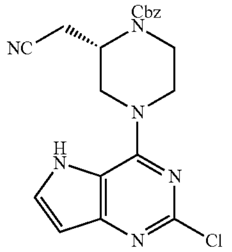 [SMILES: N#CC[C@H]1CN(c2nc(Cl)nc3cc[nH]c23)CCN1C(=O)OCc1ccccc1]

A mixture of 2,4-dichloro-5H-pyrrolo[3,2-d]pyrimidine (5 g, 0.027 mol), benzyl (S)-2-(cyanomethyl)piperazine-1-carboxylate (6.9 g, 0.027 mol) and DIEA (10 g, 0.078 mol) in THF (50 ml) was stirred at 70° C. overnight. After completed, the solution was concentrated, diluted with EA (50 ml) and then washed with brine (20 ml). The organic layer was dried and concentrated under reduced pressure. The resulting residue was purified by flash column chromatography with 50%-100% EA in PE to afford product (11 g, 100%). $^1H$ NMR (400 MHz, DMSO-d6) δ 11.58 (s, 1H), 7.65 (s, 1H), 7.50-7.27 (m, 5H), 6.43 (s, 1H), 5.22-5.08 (m, 2H), 4.60 (s, 1H), 4.29 (d, J=11.6 Hz, 2H), 3.99 (d, J=10.9 Hz, 1H), 3.60-3.35 (m, 3H), 3.05-2.87 (m, 1H) ppm. MS: M/e 411 $(M+1)^+$.

Step B: benzyl (2S)-4-(2-chloro-7-(hydroxy(3-(pivaloyloxy)naphthalen-1-yl)methyl)-5H-pyrrolo[3,2-d]pyrimidin-4-yl)-2-(cyanomethyl)piperazine-1-carboxylate

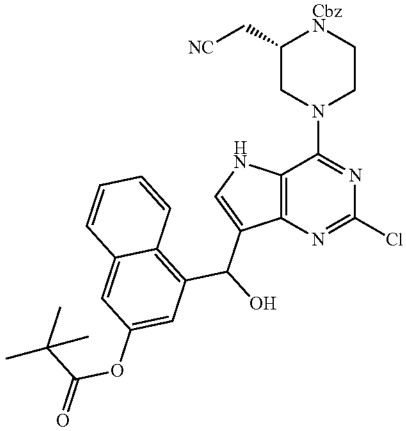 [SMILES: CC(C)(C)C(=O)Oc1cc(C(O)c2c[nH]c3c(N4CCN(C(=O)OCc5ccccc5)[C@@H](CC#N)C4)nc(Cl)nc23)c2ccccc2c1]

A mixture of benzyl (S)-4-(2-chloro-5H-pyrrolo[3,2-d]pyrimidin-4-yl)-2-(cyanomethyl)piperazine-1-carboxylate (1.85 g, 4.5 mmol), 4-formylnaphthalen-2-yl pivalate (1.15 g, 4.5 mmol) and $K_2CO_3$ (0.93 g, 6.7 mmol) in MeCN (20 ml) and $H_2O$ (20 ml) was stirred at 45° C. for 3 days. The mixture was poured into $H_2O$ (20 ml), extracted with EA (25 ml×2). The organic layer was washed with brine (10 ml), dried and concentrated. The resulting residue was purified by flash with 10%-100% EA in PE to afford product (1.5 g, 50%). $^1$H NMR (400 MHz, DMSO-d6) δ 11.42 (s, 1H), 7.98 (d, J=8.3 Hz, 1H), 7.91 (d, J=8.2 Hz, 1H), 7.64 (s, 1H), 7.58 (s, 1H), 7.50-7.43 (m, 1H), 7.42-7.31 (m, 5H), 7.08 (d, J=13.2 Hz, 1H), 6.68 (s, 1H), 5.22-5.06 (m, 2H), 4.58 (s, 1H), 4.34-4.17 (m, 2H), 3.96 (d, J=11.4 Hz, 1H), 3.63-3.35 (m, 5H), 3.05-2.86 (m, 2H), 1.38 (s, 9H) ppm. MS: M/e 667 $(M+1)^+$.

Step C: benzyl (S)-4-(2-chloro-7-((3-(pivaloyloxy)naphthalen-1-yl)methyl)-5H-pyrrolo[3,2-d]pyrimidin-4-yl)-2-(cyanomethyl)piperazine-1-carboxylate

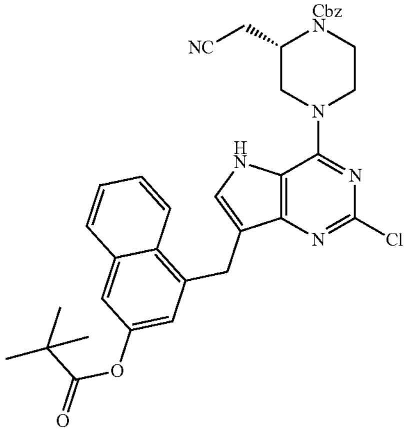 [SMILES: CC(C)(C)C(=O)Oc1cc(Cc2c[nH]c3c(N4CCN(C(=O)OCc5ccccc5)[C@@H](CC#N)C4)nc(Cl)nc23)c2ccccc2c1]

A solution of benzyl (2S)-4-(2-chloro-7-(hydroxy(3-(pivaloyloxy)naphthalen-1-yl)methyl)-5H-pyrrolo[3,2-d]pyrimidin-4-yl)-2-(cyanomethyl)piperazine-1-carboxylate (500 mg, 0.75 mmol) in TFA (2 ml), triethylsilane (2 ml) and DCE (2 ml) was stirred at rt for 30 min. After completed, the mixture was poured into aq. $NaHCO_3$ (30 ml), extracted with DCM (20 ml×2). The organic layer was washed with brine (10 ml), dried and concentrated under reduced pressure to afford product (0.6 g, 100%, crude), which was used directly for the next step without further purification. MS: M/e 651 $(M+1)^+$.

Step D: benzyl (S)-4-(2-chloro-5-ethyl-7-((3-(pivaloyloxy)naphthalen-1-yl)methyl)-5H-pyrrolo[3,2-d]pyrimidin-4-yl)-2-(cyanomethyl)piperazine-1-carboxylate

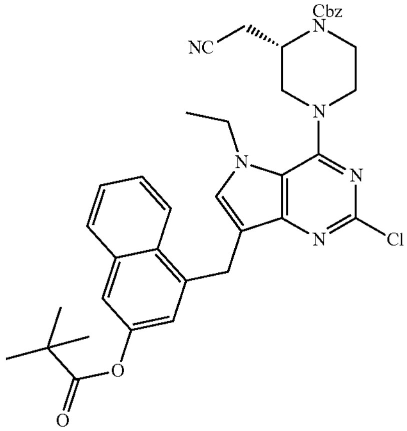 [SMILES: CCn1cc(Cc2cc(OC(=O)C(C)(C)C)cc3ccccc23)c2nc(Cl)nc(N3CCN(C(=O)OCc4ccccc4)[C@@H](CC#N)C3)c21]

To a stirred mixture of benzyl (S)-4-(2-chloro-7-((3-(pivaloyloxy)naphthalen-1-yl)methyl)-5H-pyrrolo[3,2-d]pyrimidin-4-yl)-2-(cyanomethyl)piperazine-1-carboxylate (0.27 g, 0.41 mmol) and $K_2CO_3$ (86 mg, 0.62 mmol) in DMF (8 ml), was added iodoethane (0.13 g, 0.83 mmol) and then stirred at rt for 4 h. After completed, the solution was poured into $H_2O$ (10 ml) and then extracted with EA (15 ml×2). The organic layer was dried and concentrated under reduced pressure. The resulting residue was purified by flash column chromatography with 10%-60% EA in PE to afford product (0.2 g, 71%). MS: M/e 679 $(M+1)^+$.

Step E: benzyl (S)-2-(cyanomethyl)-4-(5-ethyl-2-(((S)-1-methylpyrrolidin-2-yl)methoxy)-7-((3-(pivaloyloxy)naphthalen-1-yl)methyl)-5H-pyrrolo[3,2-d]pyrimidin-4-yl)piperazine-1-carboxylate

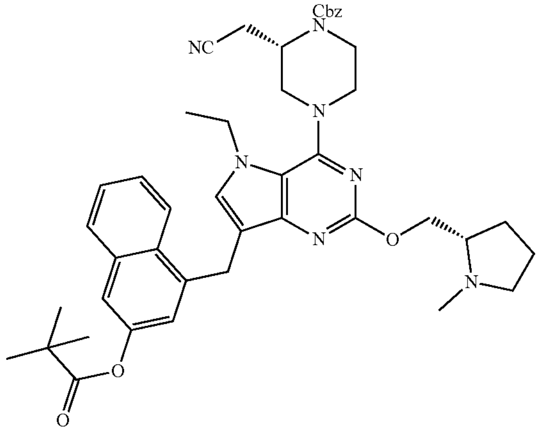 [SMILES: CCn1cc(Cc2cc(OC(=O)C(C)(C)C)cc3ccccc23)c2nc(OC[C@@H]3CCCN3C)nc(N3CCN(C(=O)OCc4ccccc4)[C@@H](CC#N)C3)c21]

A mixture of benzyl (S)-4-(2-chloro-5-ethyl-7-((3-(pivaloyloxy)naphthalen-1-yl)methyl)-5H-pyrrolo[3,2-d]pyrimidin-4-yl)-2-(cyanomethyl)piperazine-1-carboxylate (0.2 g, 0.29 mmol), (S)-(1-methylpyrrolidin-2-yl)methanol (68 mg, 0.59 mmol), $Pd_2dba_3$ (81 mg, 0.089 mmol) RuPhos (41 mg, 0.088 mmol) and $Cs_2CO_3$ (192 mg, 0.59 mmol) in dioxane (10 ml) was stirred at 120° C. overnight. After completed, the mixture was poured into water (15 ml) and extracted with EA (20 ml×2). The organic layer was washed with brine (10 ml), dried and concentrated under reduced pressure. The resulting residue was purified by prep-TLC with DCM:MeOH (10:1) to afford product (60 mg, 27%). MS: M/e 758 $(M+1)^+$.

Step F: 4-((4-((S)-3-(cyanomethyl)piperazin-1-yl)-5-ethyl-2-(((S)-1-methylpyrrolidin-2-yl)methoxy)-5H-pyrrolo[3,2-d]pyrimidin-7-yl)methyl)naphthalen-2-yl pivalate

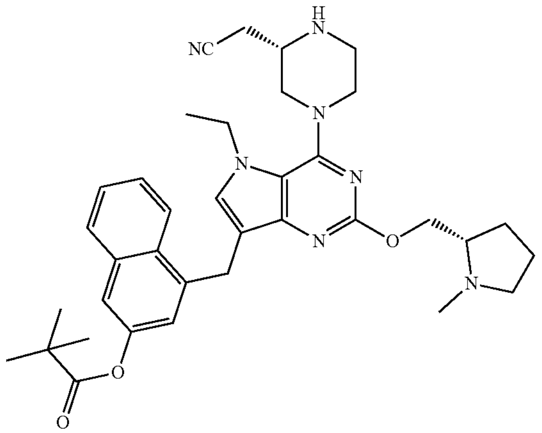 [SMILES: CCn1cc(Cc2cc(OC(=O)C(C)(C)C)cc3ccccc23)c2nc(OC[C@@H]3CCCN3C)nc(N3CCN[C@@H](CC#N)C3)c21]

A mixture of benzyl (S)-2-(cyanomethyl)-4-(5-ethyl-2-(((S)-1-methylpyrrolidin-2-yl)methoxy)-7-((3-(pivaloyloxy)naphthalen-1-yl)methyl)-5H-pyrrolo[3,2-d]pyrimidin-4-yl)piperazine-1-carboxylate (60 mg, 0.079 mmol) and Pd/C (60 mg) in THF (5 ml) and MeOH (10 ml) was stirred at rt overnight under $H_2$ atmosphere. After completed, the mixture was filtered through diatomite. The filtrate was concentrated under reduced pressure to afford product (45 mg, 91%), which was used directly for the next step without further purification. MS: M/e 624 $(M+1)^+$.

Step G: 2-((S)-1-acryloyl-4-(5-ethyl-7-((3-hydroxynaphthalen-1-yl)methyl)-2-(((S)-1-methylpyrrolidin-2-yl)methoxy)-5H-pyrrolo[3,2-d]pyrimidin-4-yl)piperazin-2-yl)acetonitrile

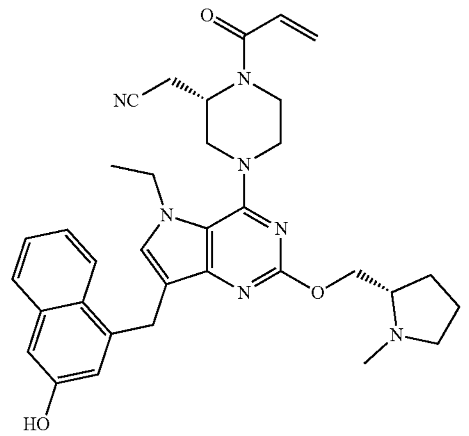 [SMILES: C=CC(=O)N1CCN(c2nc(OC[C@@H]3CCCN3C)nc3c(Cc4cc(O)cc5ccccc45)cn(CC)c23)C[C@@H]1CC#N]

To a mixture of 4-((4-((S)-3-(cyanomethyl)piperazin-1-yl)-5-ethyl-2-(((S)-1-methylpyrrolidin-2-yl)methoxy)-5H-pyrrolo[3,2-d]pyrimidin-7-yl)methyl)naphthalen-2-yl pivalate (45 mg, 0.072 mmol) in MeCN (8 ml) at rt, was added aq. $NaHCO_3$ (sat., 0.3 mL) and then acryloyl chloride (13 mg, 0.14 mmol). The mixture was stirred at rt for 30 min. Then LiOH (20 mg, 0.83 mmol) in $H_2O$ (1 ml) was added to the above solution and stirred at rt for 1 h. The mixture was poured into water and then extracted with EA (15 ml×3). The organic layer was dried and concentrated. The residue was purified by prep-TLC to afford product (3.81 mg). $^1H$ NMR (400 MHz, DMSO-d6) δ 9.86 (s, 1H), 9.60 (s, 1H), 8.10 (d, J=9.1 Hz, 1H), 7.67 (d, J=8.2 Hz, 1H), 7.54 (s, 1H), 7.37 (t, J=7.4 Hz, 1H), 7.26 (t, J=7.5 Hz, 1H), 6.97 (d, J=7.2 Hz, 2H), 6.19 (d, J=16.4 Hz, 1H), 5.78 (d, J=10.1 Hz, 1H), 4.65-4.57 (m, 1H), 4.55-4.48 (m, 1H), 4.33 (s, 2H), 4.28-4.02 (m, 3H), 3.89-3.49 (m, 7H), 3.24-2.85 (m, 7H), 2.29-2.10 (m, 1H), 2.06-1.82 (m, 3H), 1.23-1.19 (t, 3H) ppm. MS: M/e 594 $(M+1)^+$.

Example 26: Compound B3: 2-((S)-1-acryloyl-4-(2-(((2S,4R)-4-fluoro-1-methylpyrrolidin-2-yl)methoxy)-7-((3-hydroxynaphthalen-1-yl)methyl)-5-methyl-5H-pyrrolo[3,2-d]pyrimidin-4-yl)piperazin-2-yl)acetonitrile Step A: ((2S,4R)-4-fluoro-1-methylpyrrolidin-2-yl)methanol

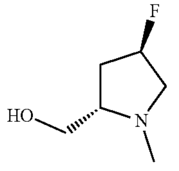

To a stirred solution of 1-(tert-butyl) 2-methyl (2S,4R)-4-fluoropyrrolidine-1,2-dicarboxylate (1 g, 4.0 mmol) in THF (15 ml) was added LAH (0.3 g, 7.9 mmol) in several portions. The mixture was then stirred at 50° C. overnight. After completed, the mixture was cooled to rt and quenched with $Na_2SO_4 10H_2O$, which was then filtered through diatomite. The filtrate was concentrated under reduced pressure to afford product (0.54 g, 100%), which was used directly for the next step without further purification. MS: M/e 134 $(M+1)^+$.

Step B: benzyl (S)-4-(2-chloro-5-methyl-7-((3-(pivaloyloxy)naphthalen-1-yl)methyl)-5H-pyrrolo[3,2-d]pyrimidin-4-yl)-2-(cyanomethyl)piperazine-1-carboxylate

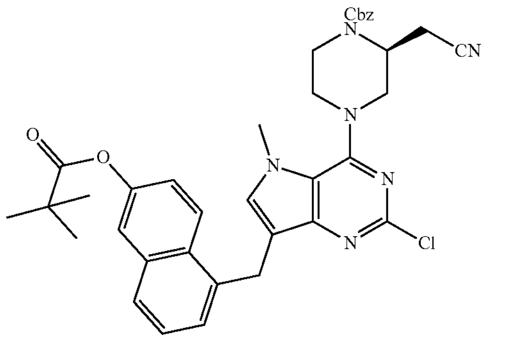 [SMILES: Cn1cc(Cc2cccc3cc(OC(=O)C(C)(C)C)ccc23)c2nc(Cl)nc(N3CCN(C(=O)OCc4ccccc4)[C@@H](CC#N)C3)c21]

To a stirred mixture of benzyl (S)-4-(2-chloro-7-((3-(pivaloyloxy)naphthalen-1-yl)methyl)-5H-pyrrolo[3,2-d]pyrimidin-4-yl)-2-(cyanomethyl)piperazine-1-carboxylate (0.98 g, 1.5 mmol, crude) and $K_2CO_3$ (410 mg, 3 mmol) in DMF (10 ml), was added iodomethane (0.57 g, 4 mmol) and then stirred at rt for 2.5 h. After completed, the solution was poured into $H_2O$ (15 ml) and then extracted with EA (20 ml×2). The organic layer was dried and concentrated under reduced pressure. The resulting residue was purified by flash column chromatography with 0-60% EA in PE to afford product (0.93 g, 92%). MS: M/e 665 $(M+1)^+$.

Step C: benzyl (S)-2-(cyanomethyl)-4-(2-(((2S,4R)-4-fluoro-1-methylpyrrolidin-2-yl)methoxy)-5-methyl-7-((3-(pivaloyloxy)naphthalen-1-yl)methyl)-5H-pyrrolo[3,2-d]pyrimidin-4-yl)piperazine-1-carboxylate

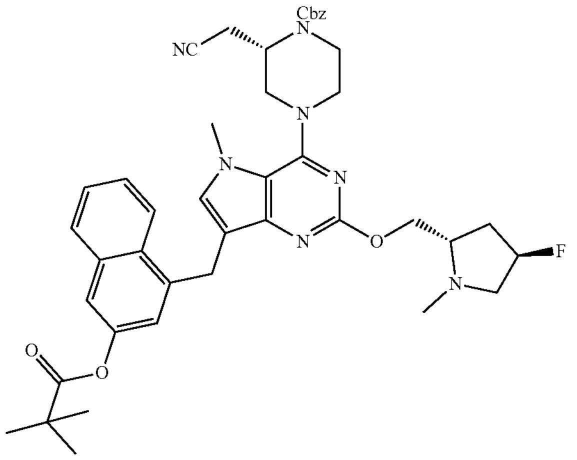

A mixture of benzyl (S)-4-(2-chloro-5-methyl-7-((3-(pivaloyloxy)naphthalen-1-yl)methyl)-5H-pyrrolo[3,2-d]pyrimidin-4-yl)-2-(cyanomethyl)piperazine-1-carboxylate (0.25 g, 0.38 mmol), ((2S,4R)-4-fluoro-1-methylpyrrolidin-2-yl)methanol (100 mg, 0.75 mmol), $Pd_2dba_3$ (103 mg, 0.11 mmol) RuPhos (53 mg, 0.11 mmol) and $Cs_2CO_3$ (245 mg, 0.75 mmol) in dioxane (10 ml) was stirred at 100° C. overnight. After completed, the mixture was poured into water (15 ml) and extracted with EA (20 ml×2). The organic layer was washed with brine (10 ml), dried and concentrated under reduced pressure. The resulting residue was purified by prep-TLC with DCM:MeOH (10:1) to afford crude product (50 mg), which was used directly for the next step without further purification. MS: M/e 762 $(M+1)^+$.

Step D: 4-((4-((S)-3-(cyanomethyl)piperazin-1-yl)-2-(((2S,4R)-4-fluoro-1-methylpyrrolidin-2-yl)methoxy)-5-methyl-5H-pyrrolo[3,2-d]pyrimidin-7-yl)methyl)naphthalen-2-yl pivalate

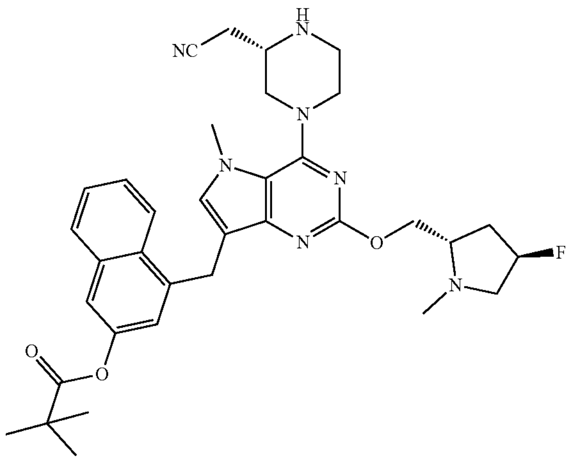 [SMILES: CN1C[C@H](F)C[C@H]1COc1nc(N2CCN[C@@H](CC#N)C2)c2c(n1)c(Cc1cc(OC(=O)C(C)(C)C)cc3ccccc13)cn2C]

A mixture of benzyl (S)-2-(cyanomethyl)-4-(2-(((2S,4R)-4-fluoro-1-methylpyrrolidin-2-yl)methoxy)-5-methyl-7-((3-(pivaloyloxy)naphthalen-1-yl)methyl)-5H-pyrrolo[3,2-d]pyrimidin-4-yl)piperazine-1-carboxylate (50 mg, crude) and Pd/C (50 mg) in THF (5 ml) and MeOH (5 ml) was stirred at rt overnight under $H_2$ atmosphere. After completed, the mixture was filtered through diatomite. The filtrate was concentrated under reduced pressure to afford product (40 mg, crude), which was used directly for the next step without further purification. MS: M/e 628 $(M+1)^+$.

Step E: 2-((S)-1-acryloyl-4-(2-(((2S,4R)-4-fluoro-1-methylpyrrolidin-2-yl)methoxy)-7-((3-hydroxynaphthalen-1-yl)methyl)-5-methyl-5H-pyrrolo[3,2-d]pyrimidin-4-yl)piperazin-2-yl)acetonitrile

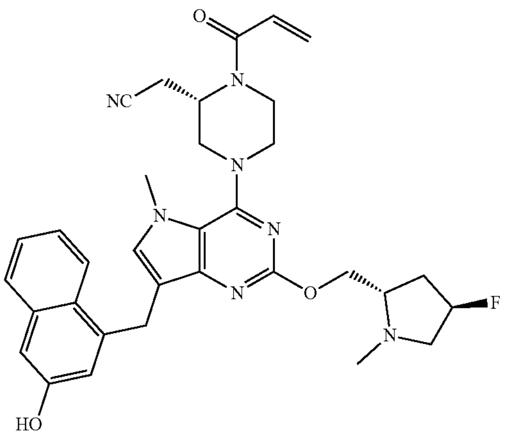 [SMILES: C=CC(=O)N1CCN(c2nc(OC[C@@H]3C[C@@H](F)CN3C)nc3c(Cc4cc(O)cc5ccccc45)cn(C)c23)C[C@@H]1CC#N]

To a mixture of 4-((4-((S)-3-(cyanomethyl)piperazin-1-yl)-2-(((2S,4R)-4-fluoro-1-methylpyrrolidin-2-yl)methoxy)-5-methyl-5H-pyrrolo[3,2-d]pyrimidin-7-yl)methyl)naphthalen-2-yl pivalate (40 mg, crude) in MeCN (8 ml) at rt, was added aq. $NaHCO_3$ (sat., 0.3 mL) and then acryloyl chloride (12 mg, 0.13 mmol). The mixture was stirred at rt for 30 min. Then LiOH (20 mg, 0.83 mmol) in $H_2O$ (1 ml) was added to the above solution and stirred at rt for 1 h. The mixture was poured into water and then extracted with EA (15 ml×3). The organic layer was dried and concentrated. The residue was purified by prep-TLC to afford product (1.14 mg). $^1H$ NMR (400 MHz, DMSO-d6) δ 9.60 (s, 1H), 8.11 (t, J=10.0 Hz, 1H), 7.67 (d, J=8.1 Hz, 1H), 7.35 (d, J=7.0 Hz, 2H), 7.26-7.19 (m, 2H), 6.98 (s, 2H), 6.18 (d, J=16.8 Hz, 1H), 5.78 (d, J=11.4 Hz, 1H), 5.32 (s, 2H), 4.31 (s, 2H), 3.86 (s, 3H), 3.80-3.61 (m, 5H), 3.51 (s, 1H), 3.05-2.92 (m, 5H), 2.01-1.96 (m, 5H), 1.51-1.40 (m, 2H) ppm. MS: M/e 598 $(M+1)^+$.

Example 27: Compound B4: (S)-1-(4-(7-((3-hydroxynaphthalen-1-yl)methyl)-5-methyl-2-((1-methylpyrrolidin-2-yl)methoxy)-5H-pyrrolo[3,2-d]pyrimidin-4-yl)piperazin-1-yl)prop-2-en-1-one Step A: benzyl 4-(2-chloro-5H-pyrrolo[3,2-d]pyrimidin-4-yl)piperazine-1-carboxylate

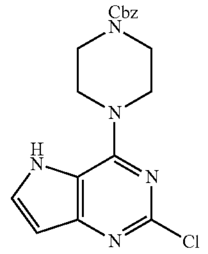 [SMILES: O=C(OCc1ccccc1)N1CCN(c2nc(Cl)nc3cc[nH]c23)CC1]

A mixture of 2,4-dichloro-5H-pyrrolo[3,2-d]pyrimidine (5 g, 0.027 mol), benzyl piperazine-1-carboxylate (6.44 g, 0.029 mol) and DIEA (6.86 g, 0.053 mol) in THF (50 ml) was stirred at 70° C. overnight. After completed, the solution was concentrated, diluted with EA (50 ml) and then washed with brine (20 ml). The organic layer was dried and concentrated under reduced pressure. The resulting residue was purified by flash column chromatography with 30%-100% EA in PE to afford product (8.45 g, 85%). $^1H$ NMR (400 MHz, DMSO-d6) δ 11.63 (s, 1H), 7.64 (s, 1H), 7.39 (d, J=5.9 Hz, 4H), 7.36-7.30 (m, 1H), 6.42 (s, 1H), 5.13 (s, 2H), 3.79 (s, 4H), 3.59 (s, 4H) ppm. MS: M/e 372 $(M+1)^+$.

Step B: benzyl 4-(2-chloro-7-(hydroxy(3-(pivaloyloxy)naphthalen-1-yl)methyl)-5H-pyrrolo[3,2-d]pyrimidin-4-yl)piperazine-1-carboxylate

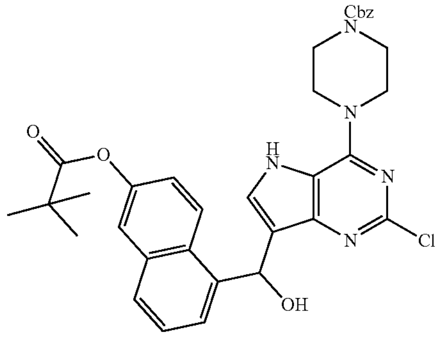 [SMILES: CC(C)(C)C(=O)Oc1ccc2c(C(O)c3c[nH]c4c(N5CCN(C(=O)OCc6ccccc6)CC5)nc(Cl)nc34)cccc2c1]

A mixture of benzyl 4-(2-chloro-5H-pyrrolo[3,2-d]pyrimidin-4-yl)piperazine-1-carboxylate (1 g, 2.7 mmol), 4-formylnaphthalen-2-yl pivalate (0.83 g, 3.2 mmol) and $K_2CO_3$ (0.56 g, 4.1 mmol) in MeCN (20 ml) and $H_2O$ (10 ml) was stirred at 45° C. overnight. The mixture was poured into $H_2O$ (20 ml), extracted with EA (25 ml×2). The organic layer was washed with brine (10 ml), dried and concentrated. The resulting residue was purified by flash with 0-100% EA in PE to afford product (0.45 g, 27%). MS: M/e 628 $(M+1)^+$.

Step C: benzyl 4-(2-chloro-7-((3-(pivaloyloxy)naphthalen-1-yl)methyl)-5H-pyrrolo[3,2-d]pyrimidin-4-yl)piperazine-1-carboxylate

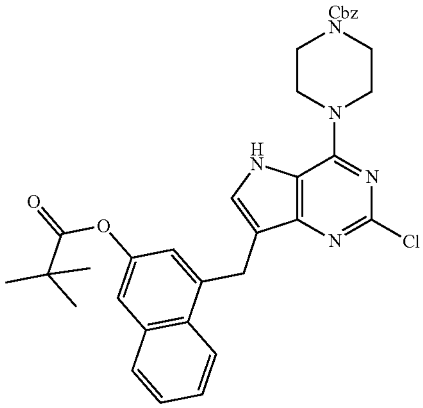 [SMILES: CC(C)(C)C(=O)Oc1cc(Cc2c[nH]c3c(N4CCN(C(=O)OCc5ccccc5)CC4)nc(Cl)nc23)c2ccccc2c1]

A solution of benzyl 4-(2-chloro-7-(hydroxy(3-(pivaloyloxy)naphthalen-1-yl)methyl)-5H-pyrrolo[3,2-d]pyrimidin-4-yl)piperazine-1-carboxylate (450 mg, 0.72 mmol) in TFA (2 ml), triethylsilane (2 ml) and DCE (2 ml) was stirred at rt for 30 min. After completed, the mixture was poured into aq. $NaHCO_3$ (30 ml), extracted with DCM (20 ml×2). The organic layer was washed with brine (10 ml), dried and concentrated under reduced pressure to afford product (0.43 g, 98%), which was used directly for the next step without further purification. MS: M/e 612 $(M+1)^+$.

Step D: benzyl 4-(2-chloro-5-methyl-7-((3-(pivaloyloxy)naphthalen-1-yl)methyl)-5H-pyrrolo[3,2-d]pyrimidin-4-yl)piperazine-1-carboxylate

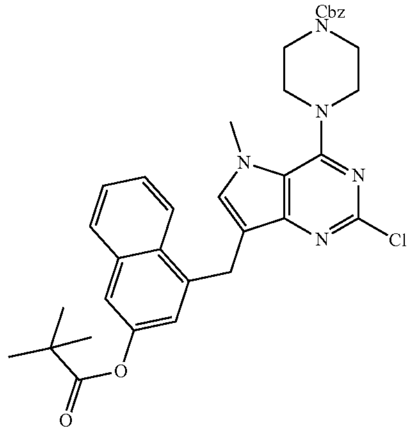 [SMILES: Cn1cc(Cc2cc(OC(=O)C(C)(C)C)cc3ccccc23)c2nc(Cl)nc(N3CCN(C(=O)OCc4ccccc4)CC3)c21]

To a stirred mixture of benzyl 4-(2-chloro-7-((3-(pivaloyloxy)naphthalen-1-yl)methyl)-5H-pyrrolo[3,2-d]pyrimidin-4-yl)piperazine-1-carboxylate (0.43 g, 0.70 mmol) and $K_2CO_3$ (150 mg, 1.09 mmol) in DMF (5 ml), was added iodomethane (0.15 g, 1.06 mmol) and then stirred at rt for 2 h. After completed, the solution was poured into $H_2O$ (10 ml) and then extracted with EA (15 ml×2). The organic layer was dried and concentrated under reduced pressure. The resulting residue was purified by flash column chromatography with 10%-50% EA in PE to afford product (0.44 g, 100%). MS: M/e 626 $(M+1)^+$.

Step E: benzyl (S)-4-(5-methyl-2-((1-methylpyrrolidin-2-yl)methoxy)-7-((3-(pivaloyloxy)naphthalen-1-yl)methyl)-5H-pyrrolo[3,2-d]pyrimidin-4-yl)piperazine-1-carboxylate

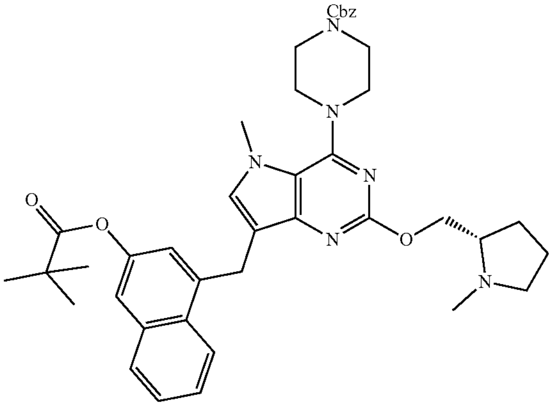

A mixture of benzyl 4-(2-chloro-5-methyl-7-((3-(pivaloyloxy)naphthalen-1-yl)methyl)-5H-pyrrolo[3,2-d]pyrimidin-4-yl)piperazine-1-carboxylate (0.44 g, 0.70 mmol), (S)-(1-methylpyrrolidin-2-yl)methanol (160 mg, 1.39 mmol), $Pd_2dba_3$ (190 mg, 0.21 mmol), RuPhos (100 mg, 0.21 mmol) and $Cs_2CO_3$ (460 mg, 1.41 mmol) in dioxane (10 ml) was stirred at 100° C. overnight. After completed, the mixture was poured into water (15 ml) and extracted with EA (20 ml×2). The organic layer was washed with brine (10 ml), dried and concentrated under reduced pressure. The resulting residue was purified by flash column chromatography with 0-10% MeOH in DCM to afford crude product (250 mg), which was used directly foe the next step without further purification. MS: M/e 705 $(M+1)^+$.

Step F: (S)-4-((5-methyl-2-((1-methylpyrrolidin-2-yl)methoxy)-4-(piperazin-1-yl)-5H-pyrrolo[3,2-d]pyrimidin-7-yl)methyl)naphthalen-2-yl pivalate

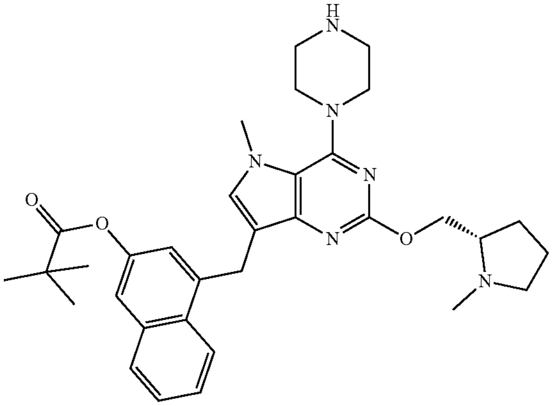 [SMILES: CN1CCC[C@H]1COc1nc(N2CCNCC2)c2c(n1)c(Cc1cc(OC(=O)C(C)(C)C)cc3ccccc13)cn2C]

A mixture of benzyl (S)-4-(5-methyl-2-((1-methylpyrrolidin-2-yl)methoxy)-7-((3-(pivaloyloxy)naphthalen-1-yl)methyl)-5H-pyrrolo[3,2-d]pyrimidin-4-yl)piperazine-1-carboxylate (250 mg, 0.35 mmol, crude) and Pd/C (50 mg) in THF (10 ml) and MeOH (10 ml) was stirred at rt overnight under $H_2$ atmosphere. After completed, the mixture was filtered through diatomite. The filtrate was concentrated under reduced pressure to afford product (190 mg, crude), which was used directly for the next step without further purification. MS: M/e 571 $(M+1)^+$.

Step G: (S)-1-(4-(7-((3-hydroxynaphthalen-1-yl) methyl)-5-methyl-2-((1-methylpyrrolidin-2-yl) methoxy)-5H-pyrrolo[3,2-d]pyrimidin-4-yl)piperazin-1-yl)prop-2-en-1-one

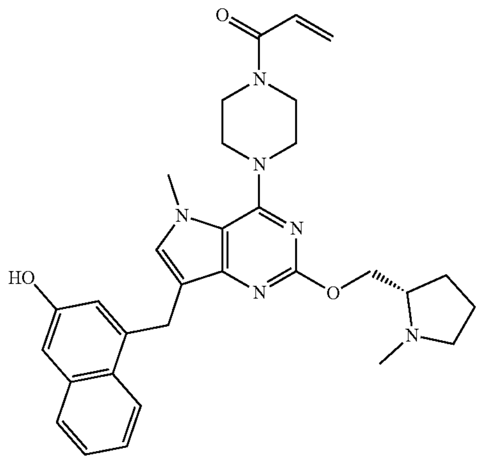 [SMILES: C=CC(=O)N1CCN(c2nc(OC[C@@H]3CCCN3C)nc3c(Cc4cc(O)cc5ccccc45)cn(C)c23)CC1]

To a mixture of (S)-4-((5-methyl-2-((1-methylpyrrolidin-2-yl)methoxy)-4-(piperazin-1-yl)-5H-pyrrolo[3,2-d]pyrimidin-7-yl)methyl)naphthalen-2-yl pivalate (190 mg, crude) in MeCN (2 ml) and THF (6 ml) at rt, was added aq. $NaHCO_3$ (sat., 0.5 mL) and then acryloyl chloride (61 mg, 0.67 mmol). The mixture was stirred at rt for 30 min. Then LiOH (60 mg, 2.5 mmol) in $H_2O$ (2 ml) was added to the above solution and stirred at rt for 2 h. The mixture was poured into water and then extracted with EA (15 ml×3). The organic layer was dried and concentrated. The residue was purified by prep-TLC to afford product (1.83 mg). $^1H$ NMR (400 MHz, DMSO-d6) δ 9.61 (s, 1H), 8.10 (d, J=8.3 Hz, 1H), 7.67 (d, J=8.1 Hz, 1H), 7.37 (t, J=6.0 Hz, 1H), 7.34 (s, 1H), 7.26 (t, J=7.4 Hz, 1H), 6.98 (s, 2H), 6.83 (dd, J=16.5, 10.5 Hz, 1H), 6.13 (d, J=14.3 Hz, 1H), 5.71 (d, J=11.7 Hz, 1H), 4.56 (d, J=48.6 Hz, 2H), 4.31 (s, 2H), 3.83 (s, 3H), 3.80-3.68 (m, 6H), 3.09-2.77 (m, 6H), 2.30-2.12 (m, 2H), 2.06-1.96 (m, 2H), 1.93-1.78 (m, 2H) ppm. MS: M/e 541 $(M+1)^+$.

Example 28: Compound B5: 2-((S)-1-acryloyl-4-(2-(((S)-1-methylpyrrolidin-2-yl) methoxy)-7-((5-(trifluoromethyl)-1H-indazol-4-yl)methyl)-5H-pyrrolo[3,2-d]pyrimidin-4-yl)piperazin-2-yl)acetonitrile Step A: 4-bromo-1-(tetrahydro-2H-pyran-2-yl)-5-(trifluoromethyl)-1H-indazole

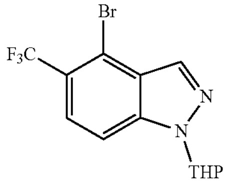

To a cooled solution of 4-bromo-5-(trifluoromethyl)-1H-indazole (2 g, 7.6 mmol) in $CH_3CN$ (20 mL) at 0° C. was added with DHP (1.9 g, 22.7 mmol), followed with PTSA (152 mg, 0.8 mmol). The resulting mixture was stirred at r.t overnight. The solvent was evaporated, then added with water (8 mL) and extracted with EA (15 mL). The organic layer was dried, concentrated and purified by CombiFlash (PE:EA=9:1) to get the product (2.3 g, 88%). MS: We 349 $(M+1)^+$ Step B: 1-(tetrahydro-2H-pyran-2-yl)-5-(trifluoromethyl)-1H-indazole-4-carbaldehyde

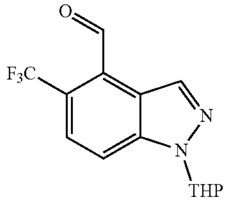

n-BuLi (1.6 M in THF, 4.8 mL) was added to a solution of 4-bromo-1-(tetrahydro-2H-pyran-2-yl)-5-(trifluoromethyl)-1H-indazole (2.2 g, 6.3 mmol) in THF (25 mL) at −78° C. dropwise. After addition, the solution was stirred for 30 mins, followed with morpholine-4-carbaldehyde (1.1 g, 9.5 mmol) in THF (5 mL) was added. The solution was stirred gradually to r.t for 2 hrs. The reaction mixture was quenched with $NH_4Cl$ solution and extracted with EA. The organic layer was dried, concentrated and purified by CombiFlash (PE:EA=9:1) to get the product (1.3 g, 70%). MS: We 299 $(M+1)^+$.

Step C: benzyl (S)-4-(2-chloro-5H-pyrrolo[3,2-d]pyrimidin-4-yl)-2-(cyanomethyl)piperazine-1-carboxylate

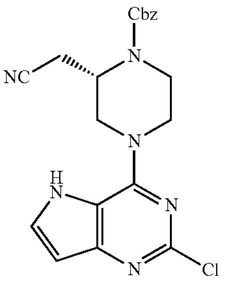 [SMILES: N#CC[C@H]1CN(c2nc(Cl)nc3cc[nH]c23)CCN1C(=O)OCc1ccccc1]

A solution of 2,4-dichloro-5H-pyrrolo[3,2-d]pyrimidine (20 g, 106 mmol), benzyl (S)-2-(cyanomethyl)piperazine-1-carboxylate (30.2 g, 117 mmol) and DIEA (20.5 g, 159 mmol) in THF (200 mL) was heated at 60° C. overnight. The solution was cooled down, added with water and extracted with EA. The organic layer was dried, concentrated and purified by gel column (PE:EA=1:2) to get the product (44 g, 100%). MS: We 411 $(M+1)^+$.

Step D: tert-butyl (S)-4-(4-((benzyloxy)carbonyl)-3-(cyanomethyl)piperazin-1-yl)-2-chloro-5H-pyrrolo[3,2-d]pyrimidine-5-carboxylate

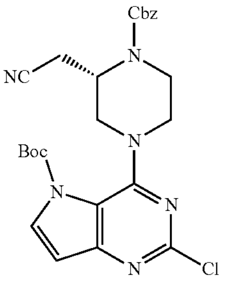 [SMILES: CC(C)(C)OC(=O)n1ccc2nc(Cl)nc(N3CCN(C(=O)OCc4ccccc4)[C@@H](CC#N)C3)c21]

DMAP (147 mg, 1.2 mmol) was added to a solution of benzyl (S)-4-(2-chloro-5H-pyrrolo[3,2-d]pyrimidin-4-yl)-2-(cyanomethyl)piperazine-1-carboxylate (5 g, 12 mmol) and $(Boc)_2O$ (3.1 g, 14 mmol) in DCM (50 mL). The solution was stirred at r.t overnight, concentrated and purified by CombiFlash (PE:EA=50%) to get the product (6.2 g, 100%). MS: M/e 511 (M+1)+

Step E: tert-butyl 4-((S)-4-((benzyloxy)carbonyl)-3-(cyanomethyl)piperazin-1-yl)-2-(((S)-1-methylpyrrolidin-2-yl)methoxy)-5H-pyrrolo[3,2-d]pyrimidine-5-carboxylate

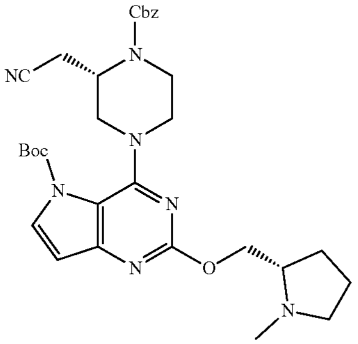 [SMILES: CN1CCC[C@H]1COc1nc(N2CCN(C(=O)OCc3ccccc3)[C@@H](CC#N)C2)c2c(ccn2C(=O)OC(C)(C)C)n1]

A solution of the product of the step D (9.1 g, 17.8 mmol), (S)-(1-methylpyrrolidin-2-yl)methanol (4.1 g, 36 mmol), $Pd_2(dba)_3$ (4.9 g, 5.4 mmol), RuPhos (2.5 g, 5.4 mmol) and $Cs_2CO_3$ (11.6 g, 35.6 mmol) in dioxane (100 mL) was heated at 100° C. under $N_2$ atmosphere overnight. The solution was cooled down, evaporated, added with EA, slurried and filtered. The filtrated was washed with brine, dried, concentrated and purified by CombiFlash (DCM:$NH_3$ (7M in MeOH)=10:1) to give the product (5.1 g, 49%). MS: M/e 590 $(M+1)^+$ Step F: benzyl (S)-2-(cyanomethyl)-4-(2-(((S)-1-methylpyrrolidin-2-yl)methoxy)-5H-pyrrolo[3,2-d]pyrimidin-4-yl)piperazine-1-carboxylate

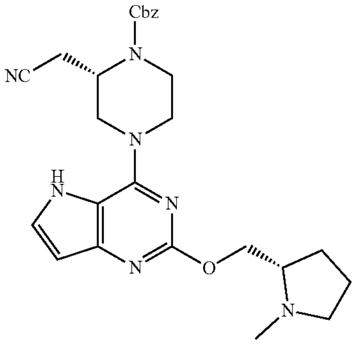 [SMILES: CN1CCC[C@H]1COc1nc(N2CCN(C(=O)OCc3ccccc3)[C@@H](CC#N)C2)c2[nH]ccc2n1]

TFA (10 mL) was added to a solution of tert-butyl 4-((S)-4-((benzyloxy)carbonyl)-3-(cyanomethyl)piperazin-1-yl)-2-(((S)-1-methylpyrrolidin-2-yl)methoxy)-5H-pyrrolo[3,2-d]pyrimidine-5-carboxylate (5.1 g, 8.7 mmol) in DCM (50 mL). The reaction mixture was stirred at r.t overnight, then evaporated, added with water, basified with $NaHCO_3$ solution to pH=7-8. After extracted with DCM, the organic layer was dried, concentrated and purified by CombiFlash (DCM:$NH_3$ (7M in MeOH)=25:2) to get the product (2.1 g, 50%). MS: M/e 490 $(M+1)^+$.

Step G: benzyl (2S)-2-(cyanomethyl)-4-(7-(hydroxy (1-(tetrahydro-2H-pyran-2-yl)-5-(trifluoromethyl)-1H-indazol-4-yl)methyl)-2-(((S)-1-methylpyrrolidin-2-yl)methoxy)-5H-pyrrolo[3,2-d]pyrimidin-4-yl) piperazine-1-carboxylate

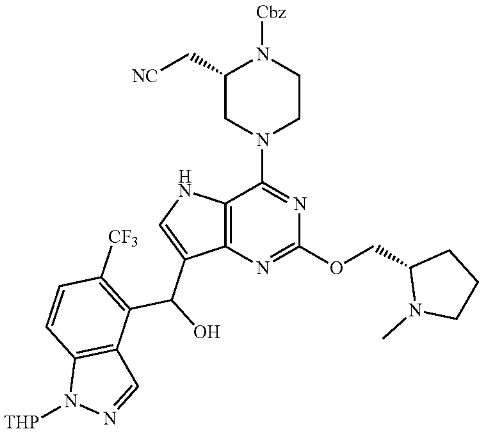

A solution of benzyl (S)-2-(cyanomethyl)-4-(2-(((S)-1-methylpyrrolidin-2-yl)methoxy)-5H-pyrrolo[3,2-d]pyrimidin-4-yl)piperazine-1-carboxylate (500 mg, 1 mmol), 1-(tetrahydro-2H-pyran-2-yl)-5-(trifluoromethyl)-1H-indazole-4-carbaldehyde (298 mg, 1 mmol) and $K_2CO_3$ (276 mg, 2 mmol) in $CH_3CN/H_2O$ (1:1, 6 mL) was heated at 50° C. overnight. The mixture was extracted with EA, dried, concentrated and purified by CombiFlash (DCM:$NH_3$ (7 M in methanol)=25:2) to get the product (237 mg, 29%). $^1$H NMR (400 MHz, DMSO-d6) δ 11.02 (s, 1H), 8.40 (s, 1H), 7.80 (d, J=8.0 Hz, 1H), 7.66 (d, J=8.0 Hz, 1H), 7.39-7.35 (m, 5H), 7.03-6.97 (m, 1H), 6.57 (s, 1H), 6.15 (s, 1H), 5.90 (d, J=12.0 Hz, 1H), 5.17-5.12 (m, 2H), 4.57 (s, 1H), 4.22 (br.s, 2H), 4.07-3.87 (m, 4H), 3.75 (s, 1H), 3.35 (s, 1H), 3.25 (s, 1H), 2.90 (s, 3H), 2.40-2.31 (m, 4H), 2.15 (s, 1H), 2.01-1.91 (m, 3H), 1.66-1.58 (m, 6H) ppm. MS: M/e 788 $(M+1)^+$.

Step H: benzyl (S)-2-(cyanomethyl)-4-(2-(((S)-1-methylpyrrolidin-2-yl)methoxy)-7-((5-(trifluoromethyl)-1H-indazol-4-yl)methyl)-5H-pyrrolo[3,2-d] pyrimidin-4-yl)piperazine-1-carboxylate

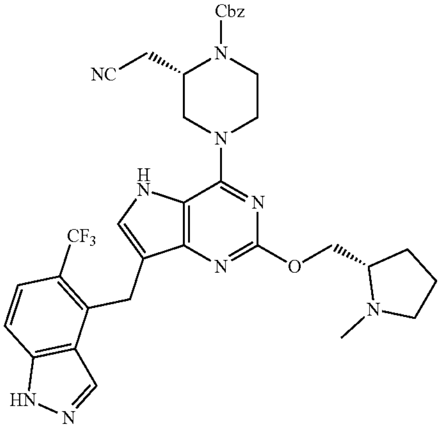 [SMILES: CN1CCC[C@H]1COc1nc(N2CCN(C(=O)OCc3ccccc3)[C@@H](CC#N)C2)c2[nH]cc(Cc3c(C(F)(F)F)ccc4[nH]ncc34)c2n1]

TFA (0.5 mL) was added to a solution of benzyl (2S)-2-(cyanomethyl)-4-(7-(hydroxy(1-(tetrahydro-2H-pyran-2-yl)-5-(trifluoromethyl)-1H-indazol-4-yl)methyl)-2-(((S)-1-methylpyrrolidin-2-yl)methoxy)-5H-pyrrolo[3,2-d] pyrimidin-4-yl)piperazine-1-carboxylate (50 mg, 0.06 mmol) in DCM (3 mL). It was stirred at 30° C. for 3 hrs. The solvent was evaporated. The residue was dissolved in DCM (3 mL) and washed with $NaHCO_3$ solution (3 mL). The organic layer was dried and concentrated to get the intermediate. It was dissolved in DCE (2 mL), then added with $Et_3SiH$ (0.5 mL) and TFA (0.5 mL), and heated at 30° C. overnight. The reaction mixture was evaporated, added with DCM, and washed with $NaHCO_3$ solution. The crude product was purified by preparative TLC (DCM:$NH_3$ (7 M in methanol)=25:2 to get the product (13 mg, 30%). MS: M/e 688 $(M+1)^+$.

Step I: 2-((S)-4-(2-(((S)-1-methylpyrrolidin-2-yl) methoxy)-7-((5-(trifluoromethyl)-1H-indazol-4-yl) methyl)-5H-pyrrolo[3,2-d]pyrimidin-4-yl)piperazin-2-yl)acetonitrile

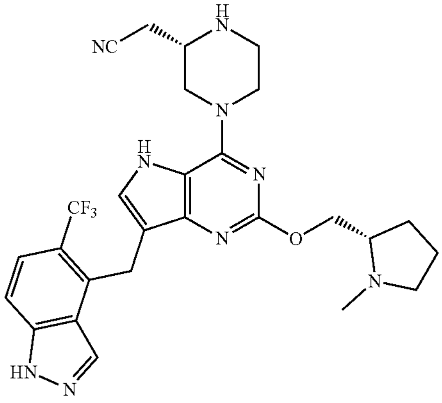 [SMILES: CN1CCC[C@H]1COc1nc(N2CCN[C@@H](CC#N)C2)c2[nH]cc(Cc3c(C(F)(F)F)ccc4[nH]ncc34)c2n1]

Pd/C (10%, wet, 20 mg) was added to a solution of benzyl (S)-2-(cyanomethyl)-4-(2-(((S)-1-methylpyrrolidin-2-yl) methoxy)-7-((5-(trifluoromethyl)-1H-indazol-4-yl)methyl)-5H-pyrrolo[3,2-d]pyrimidin-4-yl)piperazine-1-carboxylate (13 mg, 0.02 mmol) in EtOH/THF (1:1, 2 mL). It was stirred under $H_2$ balloon at r.t for 2 hrs. The catalyst was filtered out and the filtrate was concentrated to get the product. (10 mg, crude) MS: M/e 554 $(M+1)^+$ Step J: 2-((S)-1-acryloyl-4-(2-(((S)-1-methylpyrrolidin-2-yl)methoxy)-7-((5-(trifluoromethyl)-1H-indazol-4-yl)methyl)-5H-pyrrolo[3,2-d]pyrimidin-4-yl)piperazin-2-yl)acetonitrile

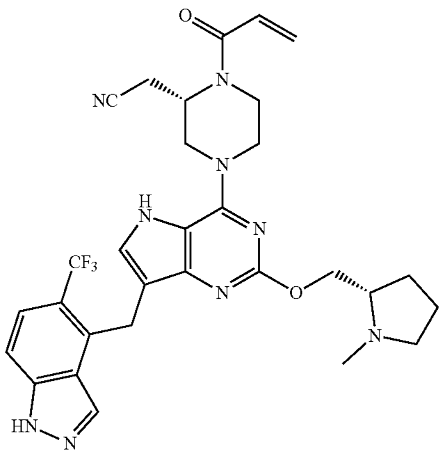 [SMILES: C=CC(=O)N1CCN(c2nc(OC[C@@H]3CCCN3C)nc3c(Cc4c(C(F)(F)F)ccc5[nH]ncc45)c[nH]c23)C[C@@H]1CC#N]

$NaHCO_3$ solution (saturated, 0.2 mL) was added to a solution of 2-((S)-4-(2-(((S)-1-methylpyrrolidin-2-yl)methoxy)-7-((5-(trifluoromethyl)-1H-indazol-4-yl)methyl)-5H-pyrrolo[3,2-d]pyrimidin-4-yl)piperazin-2-yl)acetonitrile (10 mg, crude) in $CH_3CN$ (2 mL), followed with acryloyl chloride (1.3 mg, 0.02 mmol). The reaction mixture was stirred at r.t for 10 mins. The solution was evaporated, added with water (2 mL) and extracted with EA (4 mL). The organic layer was dried, concentrated and purified by preparative TLC (DCM:$NH_3$ (7M in MeOH)=8:1) to get the product (1 mg, 10%). $^1H$ NMR (400 MHz, $CD_3OD$) δ 8.09 (s, 1H), 7.72 (d, J=12.0 Hz, 1H), 7.59 (d, J=8.0 Hz, 1H), 6.77 (s, 1H), 6.30 (d, J=16.0 Hz, 1H), 5.85 (s, 1H), 5.34 (s, 1H), 4.62 (s, 1H), 4.54 (s, 2H), 4.38 (s, 1H), 4.12 (s, 1H), 3.97 (s, 1H), 3.75 (s, 2H), 3.13 (s, 3H), 2.96-2.85 (m, 3H), 2.44 (s, 1H), 2.19-2.04 (m, 6H), 1.61 (s, 1H) ppm. MS: M/e 608 $(M+1)^+$.

Example 29: Compound B6: 2-((S)-4-(7-((5-chloro-6-fluoro-1H-indazol-4-yl)methyl)-2-(((S)-1-methylpyrrolidin-2-yl)methoxy)-5H-pyrrolo[3,2-d]pyrimidin-4-yl)-1-(2-fluoroacryloyl)piperazin-2-yl)acetonitrile Step A: 4-bromo-5-chloro-6-fluoro-1-(tetrahydro-2H-pyran-2-yl)-1H-indazole

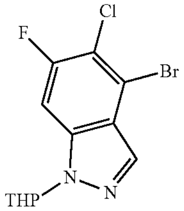

To a cooled solution of 4-bromo-5-chloro-6-fluoro-1H-indazole (2 g, 8.0 mmol) in $CH_3CN$ (20 mL) at 0° C. was added with DHP (2 g, 24 mmol), followed with PTSA (138 mg, 0.80 mmol). The resulting mixture was stirred at r.t overnight. The solvent was evaporated, then added with water (8 mL) and extracted with EA (15 mL). The organic layer was dried, concentrated and purified by CombiFlash (PE:EA=9:1) to get the product (2.4 g, 89.73%). MS: M/e 333 (M+1)+

Step B: methyl 5-chloro-6-fluoro-1-(tetrahydro-2H-pyran-2-yl)-1H-indazole-4-carboxylate

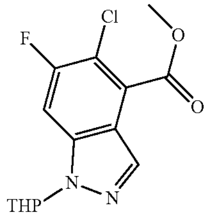

A solution of 4-bromo-5-chloro-6-fluoro-1-(tetrahydro-2H-pyran-2-yl)-1H-indazole (2.4 g, 7.2 mmol), Pd(dppf)$Cl_2$ (0.53 g, 0.72 mmol) and TEA (2.18 g, 21.6 mmol) in MeOH (50 mL) was stirred under CO (6 atm) atmosphere at 90° C. overnight. The solution was cooled down, added with water and extracted with EA. The organic layer was dried, concentrated and purified by gel column (PE:EA=1:2) to get the product (2.13 g, 94.42%). MS: M/e 313 (M+1)+

Step C: (5-chloro-6-fluoro-1-(tetrahydro-2H-pyran-2-yl)-1H-indazol-4-yl)methanol

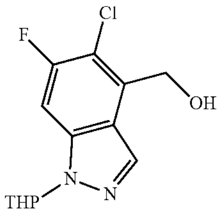

To a solution of methyl 5-chloro-6-fluoro-1-(tetrahydro-2H-pyran-2-yl)-1H-indazole-4-carboxylate (2.13 g, 6.81 mmol) in THF (20 mL) was added LAH (0.39 g, 10.21 mmol) portionwise and stirred at r.t for 2 h. The mixture was cooled down, quenched with ice, extracted with EA. The organic layer was dried, concentrated and purified by gel column (PE:EA=1:2) to get the product (1.72 g, 88.68%). MS: M/e 285 (M+1)+

Step D: 5-chloro-6-fluoro-1-(tetrahydro-2H-pyran-2-yl)-1H-indazole-4-carbaldehyde

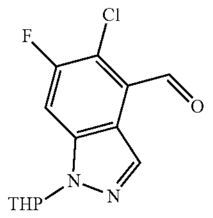

To a solution of (5-chloro-6-fluoro-1-(tetrahydro-2H-pyran-2-yl)-1H-indazol-4-yl)methanol (1.72 g, 6.03 mmol) in DCM (15 mL) was added Dess-Martin periodinane (3.07 g, 7.24 mmol) portionwise and stirred at r.t for 3 h. The mixture was quenched with $NaHCO_3$ solution, extracted with DCM. The organic layer was dried, concentrated and purified by gel column (PE:EA=1:1) to get the product (1.65 g, 96.61%). MS: M/e 283 (M+1)+

Step E: benzyl (2S)-4-(7-((5-chloro-6-fluoro-1-(tetrahydro-2H-pyran-2-yl)-1H-indazol-4-yl)(hydroxy)methyl)-2-(((S)-1-methylpyrrolidin-2-yl)methoxy)-5H-pyrrolo[3,2-d]pyrimidin-4-yl)-2-(cyanomethyl)piperazine-1-carboxylate

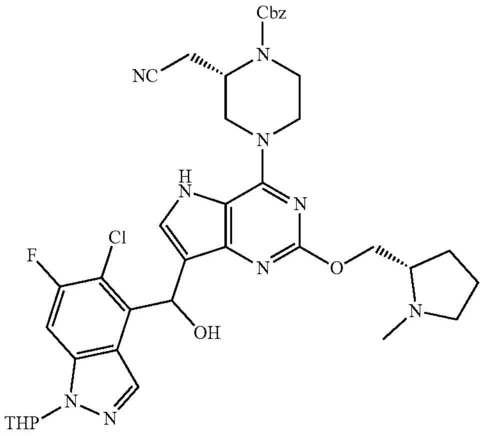

A solution of benzyl (S)-2-(cyanomethyl)-4-(2-(((S)-1-methylpyrrolidin-2-yl)methoxy)-5H-pyrrolo[3,2-d]pyrimidin-4-yl)piperazine-1-carboxylate (500 mg, 1 mmol), 5-chloro-6-fluoro-1-(tetrahydro-2H-pyran-2-yl)-1H-indazole-4-carbaldehyde (289 mg, 1 mmol) and $K_2CO_3$ (282 mg, 2 mmol) in $CH_3CN/H_2O$ (1:1, 6 mL) was heated at 50° C. overnight. The mixture was extracted with EA, dried, concentrated and purified by Combi-Flash (DCM:$NH_3$ (7M in MeOH)=25:2) to get the product (420 mg, 53.32%). MS: M/e 772 $(M+1)^+$.

Step F: benzyl (S)-4-(7-((5-chloro-6-fluoro-1H-indazol-4-yl)methyl)-2-(((S)-1-methylpyrrolidin-2-yl)methoxy)-5H-pyrrolo[3,2-d]pyrimidin-4-yl)-2-(cyanomethyl)piperazine-1-carboxylate

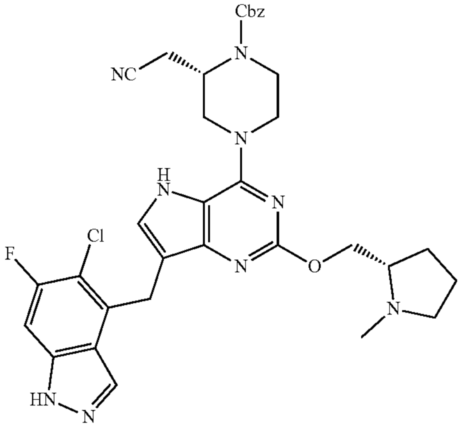 [SMILES: CN1CCC[C@H]1COc1nc(N2CCN(C(=O)OCc3ccccc3)[C@@H](CC#N)C2)c2[nH]cc(Cc3c(Cl)c(F)cc4[nH]ncc34)c2n1]

TFA (0.5 mL) was added to a solution of benzyl (2S)-4-(7-((5-chloro-6-fluoro-1-(tetrahydro-2H-pyran-2-yl)-1H-indazol-4-yl)(hydroxy)methyl)-2-(((S)-1-methylpyrrolidin-2-yl)methoxy)-5H-pyrrolo[3,2-d]pyrimidin-4-yl)-2-(cyanomethyl)piperazine-1-carboxylate (50 mg, 0.06 mmol) in DCM (3 mL) and stirred at r.t for 3 hrs. The solvent was evaporated. The residue was dissolved in DCM (3 mL) and washed with $NaHCO_3$ solution (3 mL). The organic layer was dried and concentrated to get the intermediate. It was dissolved in DCE (2 mL), then added with $Et_3SiH$ (0.5 mL) and TFA (0.5 mL), and heated at 30° C. overnight. The reaction mixture was evaporated, added with DCM, and washed with $NaHCO_3$ solution. The crude product was purified by preparative TLC (DCM:$NH_3$ (7M in MeOH)=25:2) to get the product (20 mg, 45.95%). MS: M/e 672 $(M+1)^+$.

Step G: 2-((S)-4-(7-((5-chloro-6-fluoro-1H-indazol-4-yl)methyl)-2-(((S)-1-methylpyrrolidin-2-yl)methoxy)-5H-pyrrolo[3,2-d]pyrimidin-4-yl)piperazin-2-yl)acetonitrile

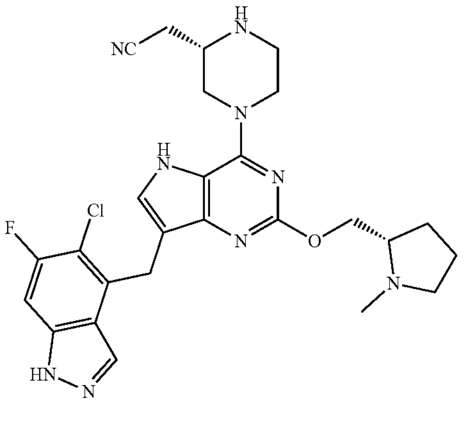 [SMILES: CN1CCC[C@H]1COc1nc(N2CCN[C@@H](CC#N)C2)c2[nH]cc(Cc3c(Cl)c(F)cc4[nH]ncc34)c2n1]

Pd/C (10%, wet, 20 mg) was added to a solution of the product of the step F (20 mg, 0.03 mmol) in EtOH/THF (1:1, 2 mL). It was stirred under $H_2$ balloon at r.t for 2 hrs. The catalyst was filtered and the filtrate was concentrated to get the product. (12 mg, 74.94) MS: M/e 538 $(M+1)^+$.

Step H: 2-((S)-4-(7-((5-chloro-6-fluoro-1H-indazol-4-yl)methyl)-2-(((S)-1-methylpyrrolidin-2-yl)methoxy)-5H-pyrrolo[3,2-d]pyrimidin-4-yl)-1-(2-fluoroacryloyl)piperazin-2-yl)acetonitrile

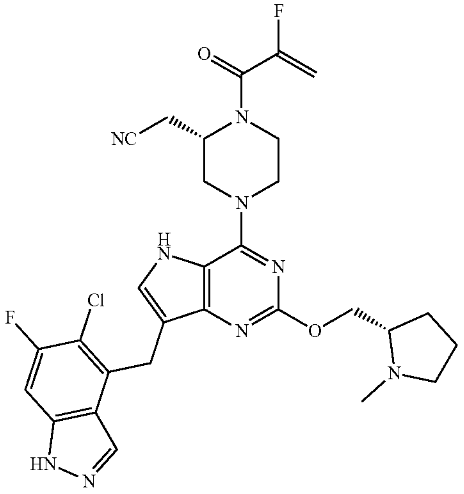 [SMILES: C=C(F)C(=O)N1CCN(c2nc(OC[C@@H]3CCCN3C)nc3c(Cc4c(Cl)c(F)cc5[nH]ncc45)c[nH]c23)C[C@@H]1CC#N]

A mixture of 2-((S)-4-(7-((5-chloro-6-fluoro-1H-indazol-4-yl)methyl)-2-(((S)-1-methylpyrrolidin-2-yl)methoxy)-5H-pyrrolo[3,2-d]pyrimidin-4-yl)piperazin-2-yl)acetonitrile (12 mg, 0.0372 mmol), 2-fluoroacrylic acid (4 mg, 0.0446 mmol), T3P (solution in DMF, 0.743 mmol) and TEA (8 mg, 0.0743) in THF was stirred at r.t for 5 h, the mixture was quenched with water (5 mL) and extracted with EA (20 mL). The organic layer was dried, concentrated and purified by preparative TLC (DCM:$NH_3$ (7M in MeOH)=8:1) to get the product (3 mg, 13.25%). $^1H$ NMR (400 MHz, $CD_3OD$) δ 13.30 (s, 1H), 11.38 (s, 1H), 10.44 (s, 1H), 10.06 (s, 1H), 8.29 (s, 1H), 7.44 (d, J=9.1 Hz, 1H), 7.26 (s, 1H), 5.48-5.18 (m, 2H), 4.66-4.56 (m, 1H), 4.56-4.44 (m, 2H), 4.44-4.34 (m, 3H), 3.83-3.73 (m, 1H), 3.62-3.56 (m, 1H), 3.44-3.32 (m, 4H), 2.93 (s, 4H), 2.38-2.18 (m, 2H), 2.09-2.02 (m, 1H), 1.98-1.91 (m, 1H), 1.87-1.79 (m, 1H) ppm. MS: M/e 610 $(M+1)^+$.

Biochemical Functional Assay

The KRAS (aa 1-169) G12C, C51S, C80L, C118S with a His-tag was expressed, purified and loaded with GDP in house. All protein and substrate solutions were prepared in assay buffer containing 25 mM HEPES pH7.5, 10 mM $MgCl_2$, and 0.01% Triton X-100. Purified GDP-loaded KRAS (aa 1-169) G12C, C51S, C80L, C118S protein was pre-incubated with a serially diluted compound at 24° C. for 3 hrs. Purified SOS1 (aa 564-1049) protein, GTPYS (Sigma) and GST-cRaf RBD (aa 1-149) were then added to each well and incubated at 24° C. for additional 3 hrs. This addition initiates the nucleotide exchange reaction and transition of inactive GDP loaded KRAS G12C to active GTPγS KRAS G12C which binds to GST-cRaf RBD. Following the incubation, Mab Anti-6HIS-Tb cryptate (Cisbio) and Mab Anti GST-XL665 (Cisbio) were added and further incubated at 24° C. for 3 hrs. The binding interaction between active GTPγS KRAS G12C and GST-cRaf RBD brings the Tb and XL665 into close proximity enabling an increased FRET signal (Ex337 nm, Em665 nm/620 nm). The inhibition percentage of nucleotide exchange reaction in presence of increasing concentrations of compounds was calculated based on the ratio of fluorescence at 665 nm to that at 620 nm detected on a BMG PHERAstar FSX instrument. The IC50 value of each compound was calculated from fitting the data to the four-parameter logistic model by Dotmatics.

TABLE 1

| Compounds A series | | | |
|---|---|---|---|
| Compound No. | IC50 (nmol) | Compound No. | IC50 (nmol) |
| A1 | 3280 | A2 | 427 |
| A3 | >10 uM | A4 | 46.7 |
| A5 | 29 | A6 | 100 |
| A7 | 47.8 | A8 | 7700 |
| A9 | 1060 | A10 | 187 |
| A11 | 215 | A12 | 217 |
| A13 | 101 | A14 | 506 |
| A15 | 1180 | A16 | >10 uM |
| A17 | 2930 | A18 | 235 |
| A19 | 9.6 | A20 | 19.1 |
| A21 | 20.8 | A22 | 201 |
| A23 | 489 | | |

TABLE 2

| Compounds B series | | | |
|---|---|---|---|
| Compound No. | IC50 (nmol) | Compound No. | IC50 (nmol) |
| B1 | 6.2 | B2 | 13 |
| B3 | 20.3 | B4 | 329 |
| B5 | 64.1 | B6 | 639 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula (I) or (II):

(I)

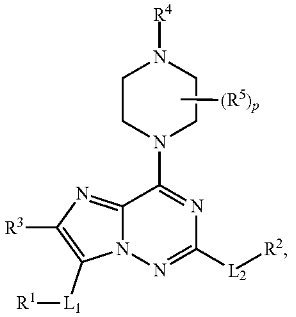

-continued (II)

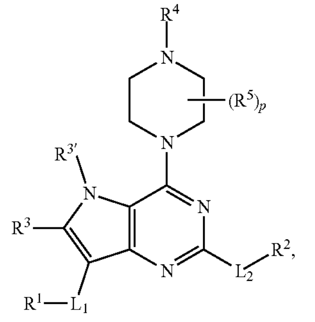

or a pharmaceutically acceptable salt thereof, or a stereoisomer thereof, wherein $L_1$ and $L_2$ are each independently selected from the group consisting of a single bond, —CO—NH—, —NH—CO—, —O—, —$NR^a$—, —$NR^a(CH_2)_m$—, —S—, —$(CH_2)_m$—, —O—$(CH_2)_m$—, —O—CH($R^a$)—, —CH($R^a$)—, —CH($R^a$) $(CH_2)_m$—, —$(CH_2)_m$—O—, —C(O)—, —$SO_2$—, cycloalkylene, oxetandiyl, tetrahydrofurandiyl, tetrahydropyrandiyl, azetidindiyl, pyrrilidindiyl, piperidindiyl, and piperizindiyl;

$R^1$ is selected from the group consisting of phenyl, naphthalenyl, indanyl, fluorenyl, indazolyl, dihydroacenaphthylenyl, quinolinyl, isoquinolinyl, indolyl, 2,3-dihydrobenzofuranyl, benzoimidazolyl, 1,3-dihydroisobenzofuranyl, benzofuranyl, carbazolyl, benzoisoquinolinyl, benzoisoindolyl, and dihydroindenyl, wherein each of said phenyl, naphthalenyl, indanyl, fluorenyl, indazolyl, dihydroacenaphthylenyl, quinolinyl, isoquinolinyl, indolyl, 2,3-dihydrobenzofuranyl or dihydroindenyl is optionally substituted with at least one $R^6$ selected from the group consisting of —$C_{1-8}$alkyl, —$C_{1-8}$alkoxy, -halo$C_{1-8}$ alkyl, oxo, halogen, hydroxy, —$NH_2$, and $C_{3-6}$ cycloalkyl, wherein each $R^6$ is identical or different when $R_1$ is substituted with more than one $R^6$;

$R^2$ is selected from the group consisting of —$NR^bR^c$, cycloalkyl, heterocyclyl, aryl, and heteroaryl, each of said cycloalkyl, heterocyclyl, aryl, or heteroaryl is optionally substituted with at least one $R^6$, wherein each $R^6$ is identical or different when $R^2$ is substituted with more than one $R^6$, and each $R^6$ is selected from the group consisting of —$C_{1-8}$alkyl, halogen, hydroxy, oxo, —$C_{1-8}$alkoxy, —$NR^bR^c$, cycloalkyl, heterocyclyl, aryl, and heteroaryl, wherein said —$C_{1-8}$alkyl, —$C_{1-8}$alkoxy, cycloalkyl, heterocyclyl, aryl, or heteroaryl is optionally substituted with at least one halogen, hydroxy, amino, CN, cycloalkyl, heterocyclyl, aryl or heteroaryl, or two $R^6$, when on two adjacent carbon atoms of a phenyl ring, together with the two intervening carbon atoms to which they are attached, form a 5- to 8-membered ring comprising 0, 1 or 2 heteroatoms independently selected from the group consisting of nitrogen, oxygen and optionally oxidized sulfur as ring member(s);

$R^3$ is selected from the group consisting of hydrogen, halogen, oxo, —$C_{1-8}$alkyl, —$C_{2-8}$alkenyl, —$C_{2-8}$alkynyl, cycloalkyl, heterocyclyl, aryl, and heteroaryl, and each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^{3'}$ is selected from the group consisting of hydrogen, oxo, —$C_{1-8}$alkyl, —$C_{2-8}$alkenyl, —$C_{2-8}$alkynyl, cycloalkyl, heterocyclyl, aryl, and heteroaryl, and each of said —$C_{1-8}$alkyl, —$C_{2-8}$alkenyl, —$C_{2-8}$alkynyl, cycloalkyl, heterocyclyl, aryl, or heteroaryl is optionally substituted with halogen, hydroxy, —$C_{1-8}$alkoxy, cycloalkyl, heterocyclyl, aryl, or heteroaryl;

$R^4$ is selected from the group consisting of

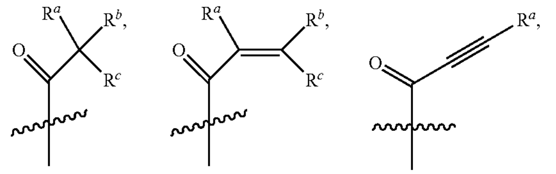

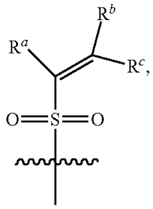

and

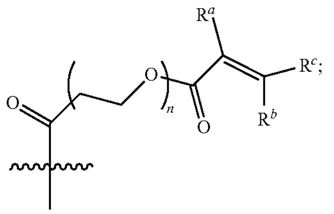

$R^5$ is selected from the group consisting of hydrogen, halogen, —$C_{1-8}$alkyl, —$C_{2-8}$alkenyl, —$C_{2-8}$alkynyl, oxo, —$NR^bR^c$, —$(CH_2)_m$—CO—$NR^dR^e$, cycloalkyl, heterocyclyl, aryl, heteroaryl and —$(CH_2)_m$—CN;

$R^a$, $R^b$ and $R^c$ are each independently selected from the group consisting of hydrogen, deuterium (D), cyano (CN), halogen, hydroxy, —$C_{1-8}$alkoxy, —$C_{1-8}$alkyl, —$C_{2-8}$alkenyl, —$C_{2-8}$alkynyl, cycloalkyl, heterocyclyl, aryl, heteroaryl, —$NR^dR^e$, and —CO—$NR^dR^c$, and each of said —$C_{1-8}$alkyl, —$C_{2-8}$alkenyl, —$C_{2-8}$alkynyl, cycloalkyl, heterocyclyl, aryl, or heteroaryl is optionally substituted with $R^f$; or ($R^a$ and $R^b$), ($R^a$ and $R^c$) or ($R^b$ and $R^c$) together with the atom(s) to which they are attached, form a 4- to 6-membered ring, said ring is optionally substituted with at least one $R^g$;

each $R^f$ is selected from the group consisting of halogen, hydroxy, oxo, —$C_{1-8}$alkoxy, —$NR^dR^e$, —CO—$NR^dR^e$, —$NR^d$—CO—$R^e$, cycloalkyl, heterocyclyl, aryl, and heteroaryl, wherein each said —$C_{1-8}$alkoxy, cycloalkyl, heterocyclyl, aryl, or heteroaryl is optionally substituted with halogen, hydroxy or —$C_{1-4}$alkyl;

$R^d$, $R^e$ and $R^g$ are each independently selected from the group consisting of hydrogen, deuterium (D), halogen, oxo, and —$C_{1-8}$alkyl, and each said —$C_{1-8}$alkyl is optionally substituted with at least one halogen, oxo, —$CF_3$ or —$COCH_3$;

p is independently 0, 1, 2, 3 or 4; and each m and n are independently 0, 1, 2, 3, 4, 5 or 6.

2. The compound according to claim 1, wherein $R^1$ is selected from the group consisting of
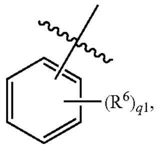
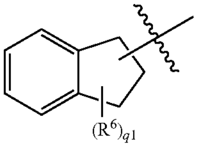
,
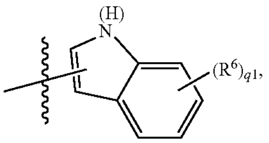
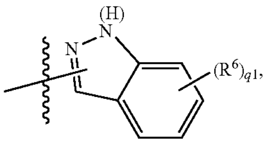
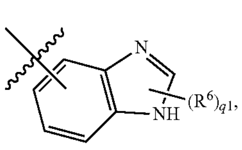
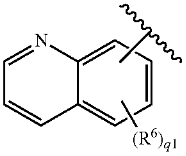
,
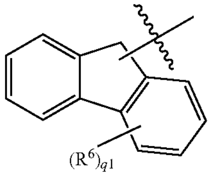
,
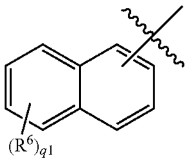
,
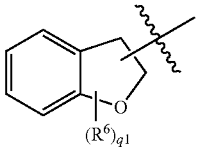
,
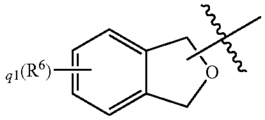
,
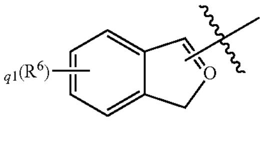
,
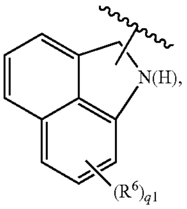
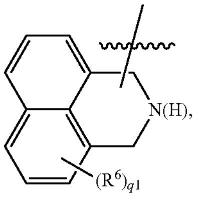
and
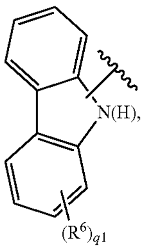
wherein $R^6$ is selected from the group consisting of F, Br, Cl, OH, $—OCH_2$, oxo, $—CH_2CN$, $—NH_2$, $—CF_3$, $—CF_2H$,
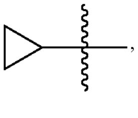 [SMILES: *C1CC1]
,
$CH_2CH_3$, and $CH_3$; and wherein q1 is 0, 1 or 2.
3. The compound according to claim 1, wherein $R^1$ is selected from the group consisting of
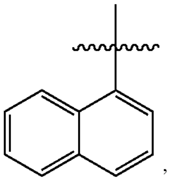
,
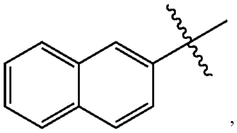
,
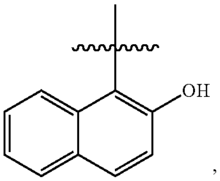
,
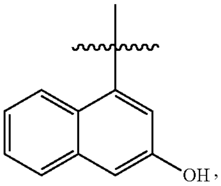
,
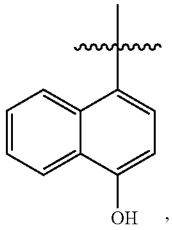
,
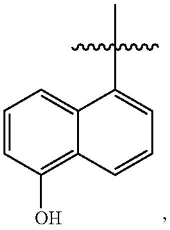
,
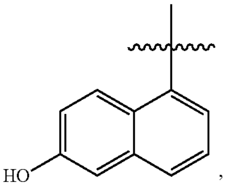
,
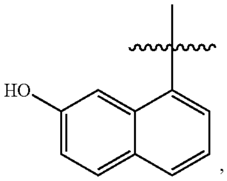
,
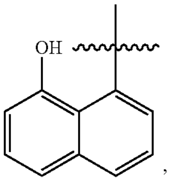
,
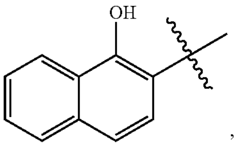
,
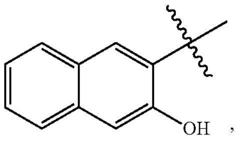
,
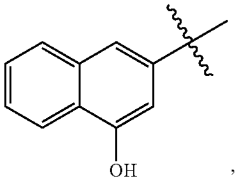
,
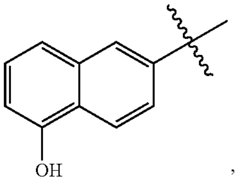
,
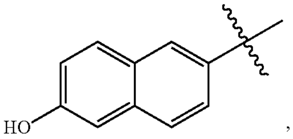
,
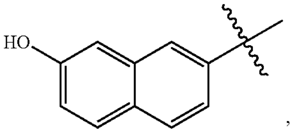
,
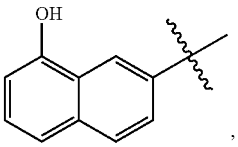
,
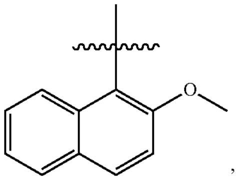
,
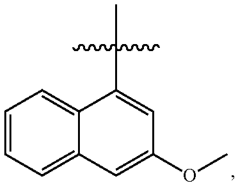
, -continued
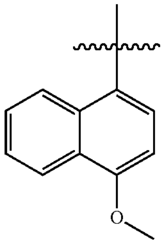, 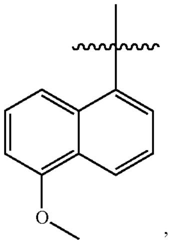,
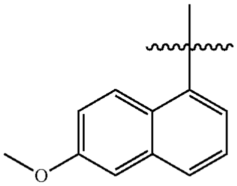, 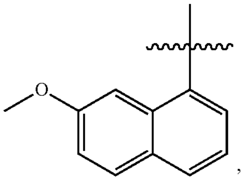,
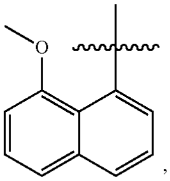, 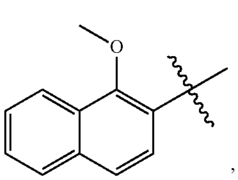,
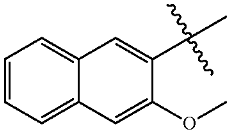, 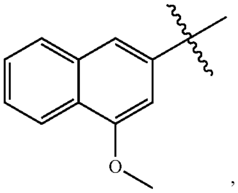,
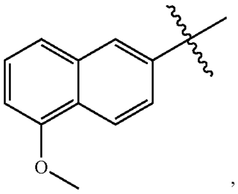, 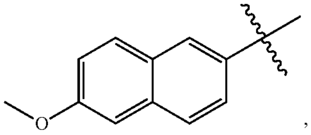,
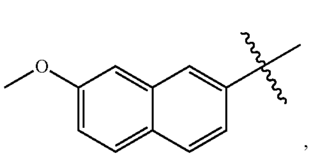, 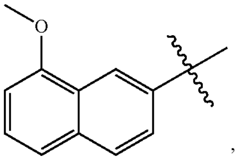,
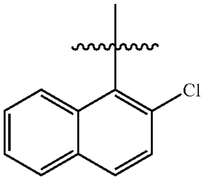, 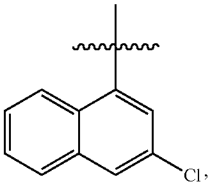,
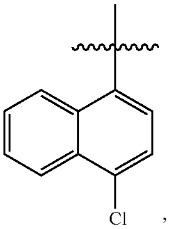, 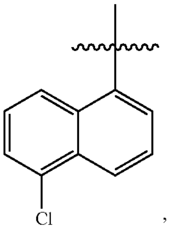,
-continued
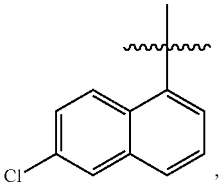, 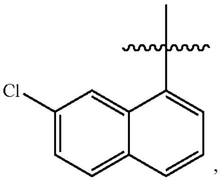,
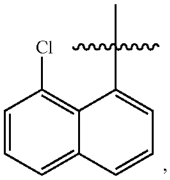, 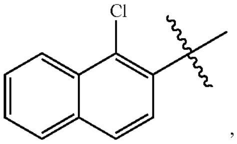,
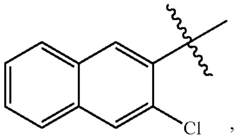, 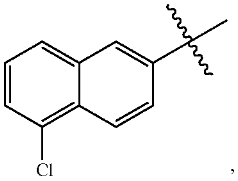,
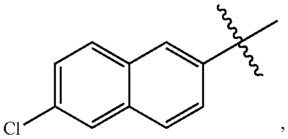,
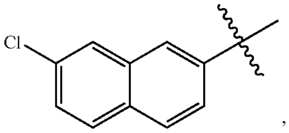, 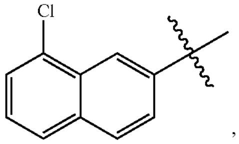,
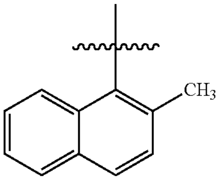, 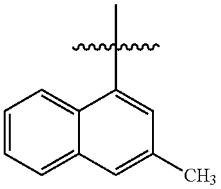,
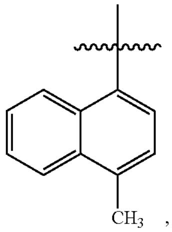, 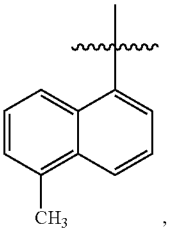,
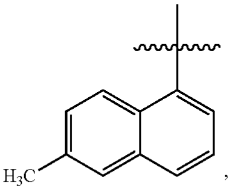, 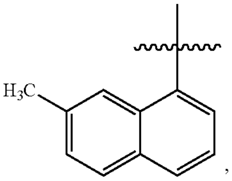,
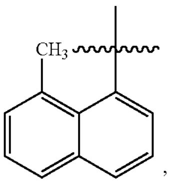, 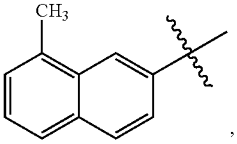, -continued
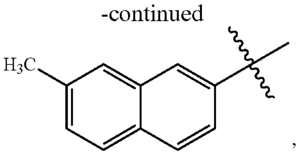,
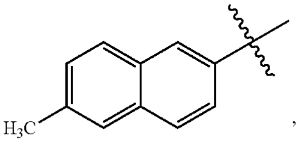,
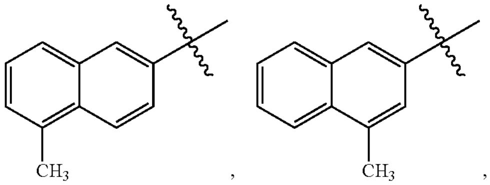, ,
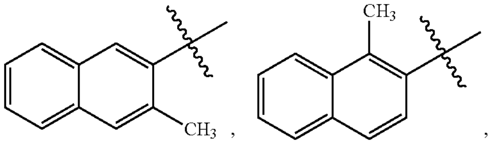, ,
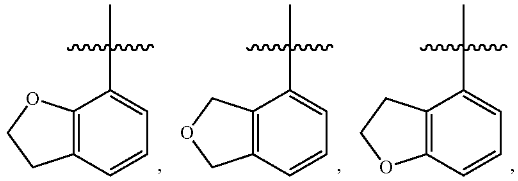, , ,
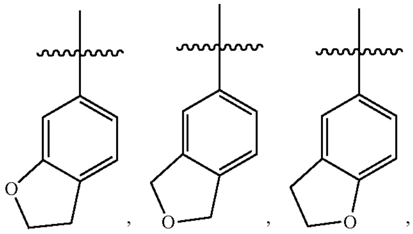, , ,
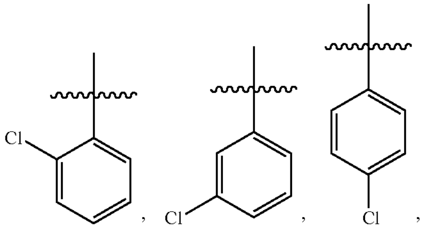, , ,
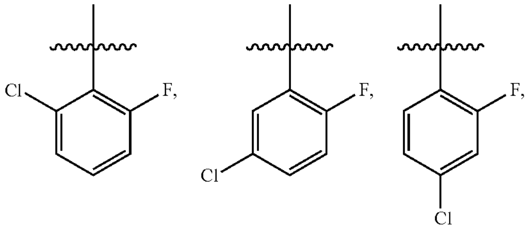
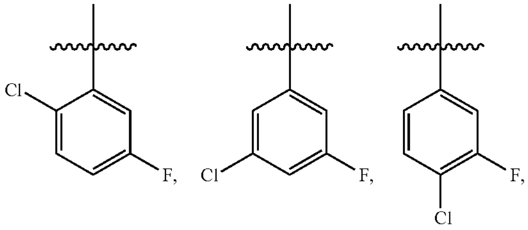
-continued
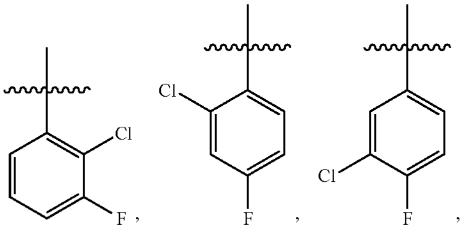, , ,
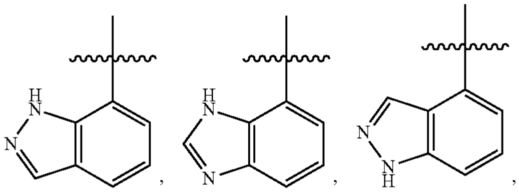, , ,
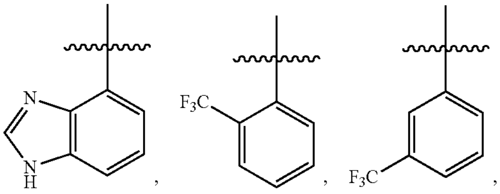, , ,
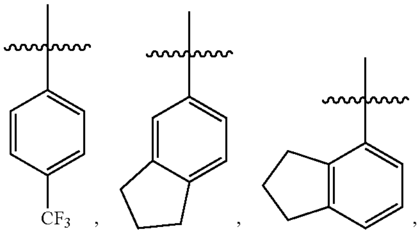, , ,
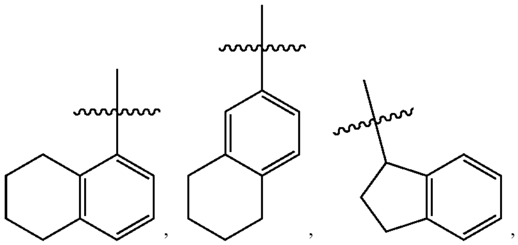, , ,
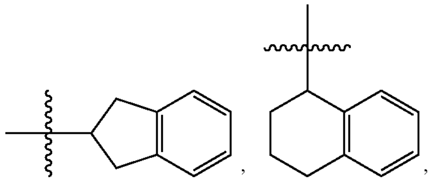, ,
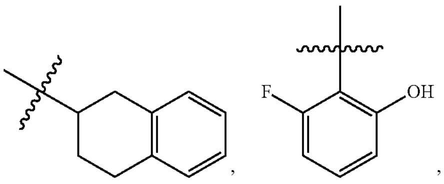, ,
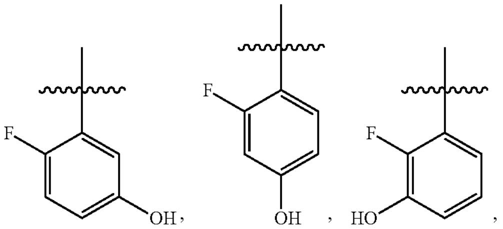, , , -continued
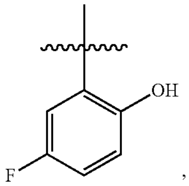,
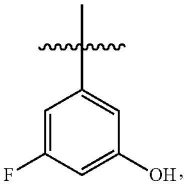,
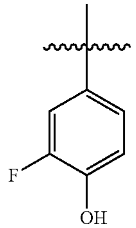,
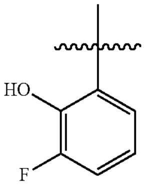,
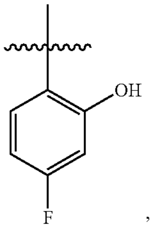,
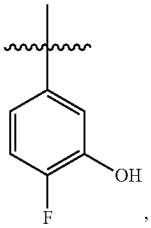,
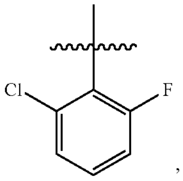,
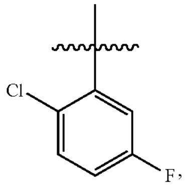,
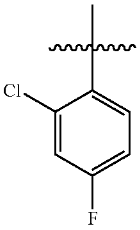,
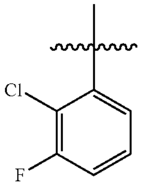,
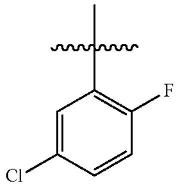,
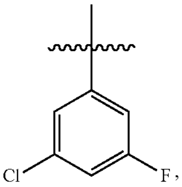,
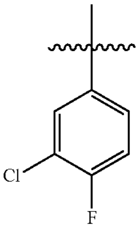,
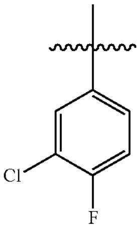,
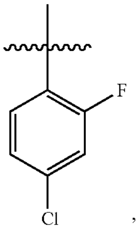,
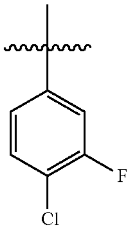,
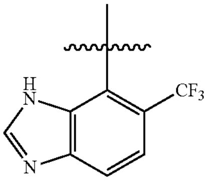,
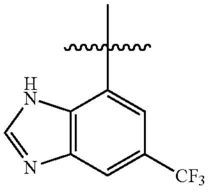,
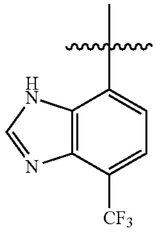,
-continued
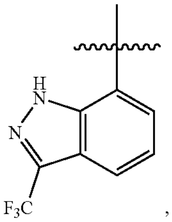,
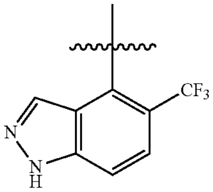,
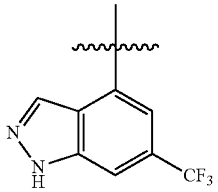,
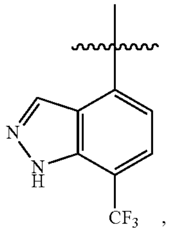,
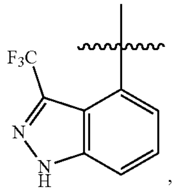,
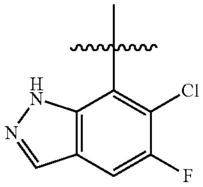,
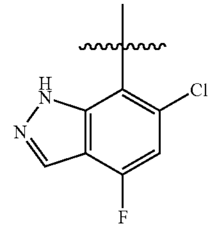,
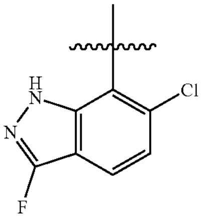,
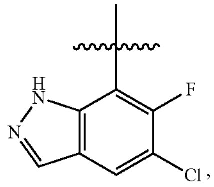,
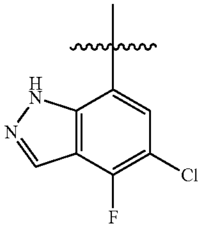,
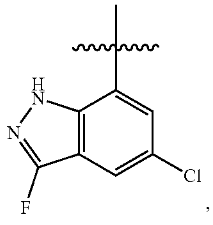,
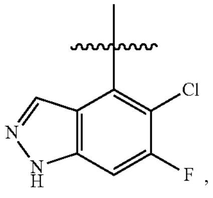,
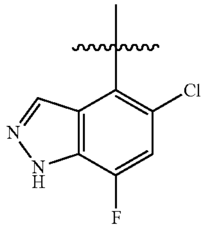,
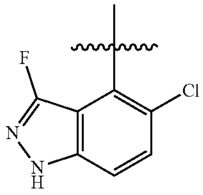, -continued

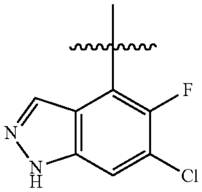,
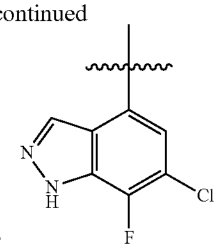, and
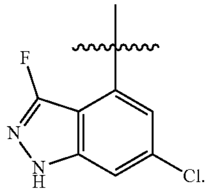.

4. The compound according to claim 1, wherein $L_1$ is selected from the group consisting of a single bond, —CO—NH—, —$CH_2$—, —$CH_2CH_2$—, —$CH_2CH_2CH_2$—, —C(O)—, and —$CH(CH_3)$—.

5. The compound according to claim 1, wherein $L_2$ is selected from the group consisting of a single bond, —O—, —O—$(CH_2)_m$—, —O—$CH(R^a)$—, —O—$CH(R^a)$—$(CH_2)_m$—, cyclopropylene, azetidindiyl, and —$NR^a(CH_2)_m$—, wherein m is 1 or 2; and $R^a$ is selected from the group consisting of hydrogen, methyl, and deuterium(D).

6. The compound according to claim 1, wherein $L_2$ is selected from the group consisting of a single bond, —O—$CH_2$—, —O—$CH_2CH_2$—, —O—$CH_2CH_2CH_2$—, —O—, —O—$CH(CH_3)$—, —NH—$CH_2$—, —NH—$CH_2CH_2$—, —O—$CH(CH_3)CH_2$—,

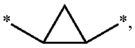, 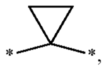, 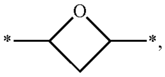,
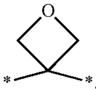, 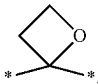, 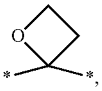, and
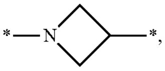, and wherein the asterisks * refer to the linking positions.

7. The compound according to claim 1, wherein $R^2$ is selected from the group consisting of

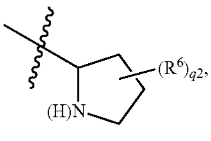, 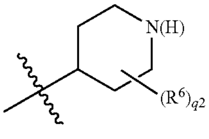,
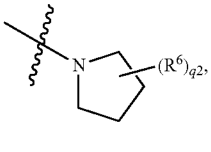,

—$NR^bR^c$,

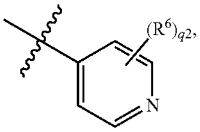, 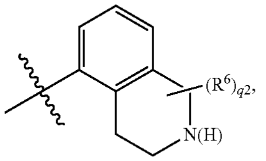, and
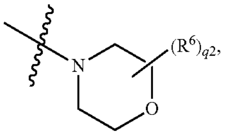, wherein each $R^6$ is selected from the group consisting of halogen, hydroxy, —$C_{1-8}$alkyl, —$C_{1-8}$alkoxy and heterocyclyl, wherein the —$C_{1-8}$alkyl is optionally substituted with hydroxy or halogen; each q2 is 0, 1, 2 or 3; $R^b$ and $R^c$ are independently hydrogen, deuterium(D), halogen, or —$C_{1-8}$alkyl.

8. The compound according to claim 7, wherein $R^6$ is selected from the group consisting of $CH_3$, OH, $CH_2OH$, F, —$CHF_2$, —$OCH_3$, Cl, Br, and

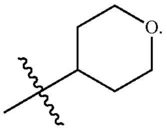 [SMILES: *C1CCOCC1].

9. The compound according to claim 1, wherein $R^2$ is selected from the group consisting of

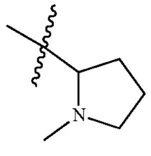, 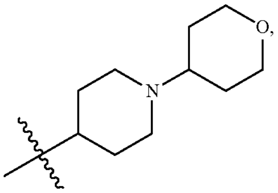,
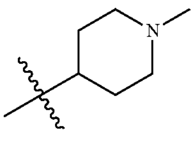, 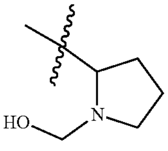, 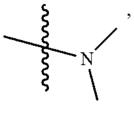,
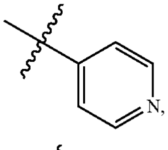, 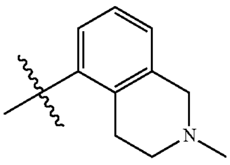,
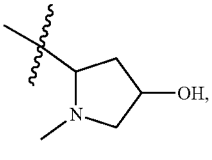, 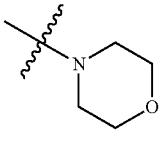, -continued

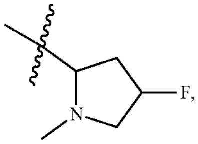 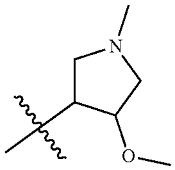 , 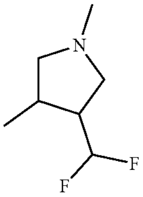 ,

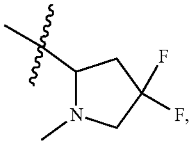 and 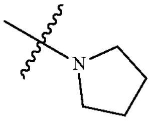 .

10. The compound according to claim 1, wherein $R^3$ is selected from the group consisting of hydrogen, halogen, oxo, and —$C_{1-8}$alkyl.

11. The compound according to claim 1, wherein $R^4$ is

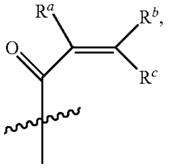

wherein $R^a$ is selected from the group consisting of hydrogen, deuterium(D), halogen, —$C_{1-8}$alkyl and —$C_{1-8}$alkoxy, said —$C_{1-8}$alkyl or —$C_{1-8}$alkoxy is optionally substituted with at least one halogen, hydroxy, —$C_{1-8}$alkoxy, or —$NR^d$-$COR^e$;

$R^b$ is selected from the group consisting of hydrogen and —$C_{1-8}$alkyl;

$R^c$ is selected from the group consisting of hydrogen, halogen, —$C_{1-8}$alkyl, —CN, —$NR^dR^e$, —CO—$NR^dR^e$, and heteroaryl, wherein said —$C_{1-8}$alkyl is optionally substituted with at least one $R^f$;

each $R^f$ is selected from the group consisting of halogen, hydroxy, —$NR^dR^e$, —$C_{1-8}$alkoxy, and 4- to 7-membered heterocyclyl, wherein each said —$C_{1-8}$alkoxy or 4- to 7-membered heterocyclyl is optionally substituted with halogen, hydroxy or —$C_{1-4}$alkyl; and $R^d$ and $R^e$ are each independently hydrogen, deuterium (D), halogen or —$C_{1-8}$alkyl, wherein said —$C_{1-8}$alkyl is optionally substituted with at least one halogen or —$COCH_3$.

12. The compound according to claim 1, wherein $R^4$ is selected from the group consisting of

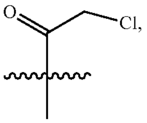 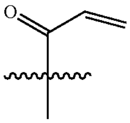 ,

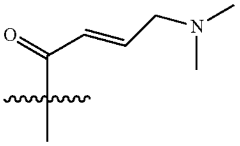 , 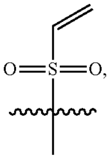

-continued

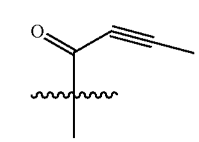 , 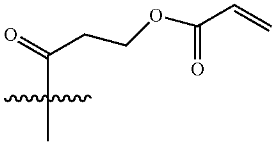 ,

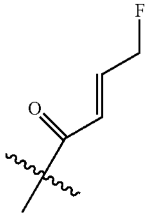 , 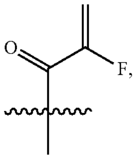 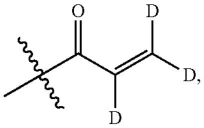

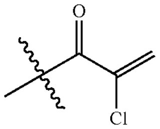 , 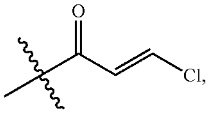

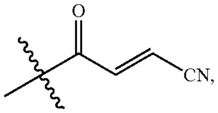 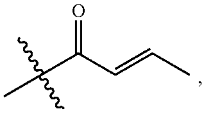 ,

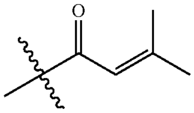 , 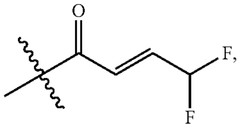

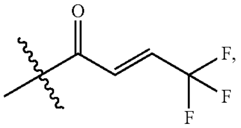 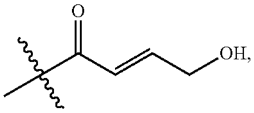

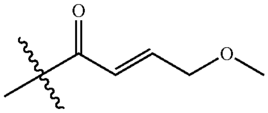 , 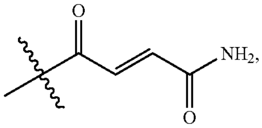

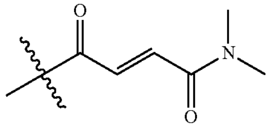 , 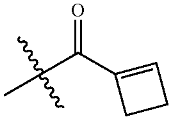 ,

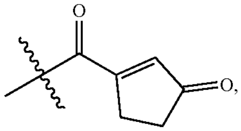 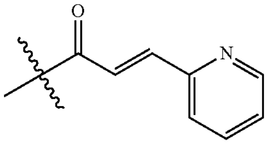 ,

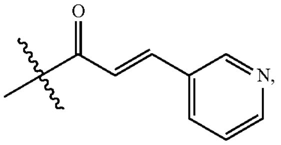

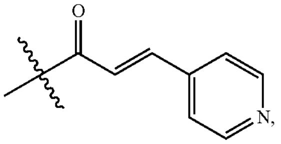

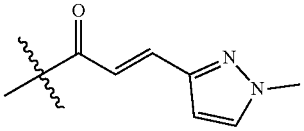 ,

-continued

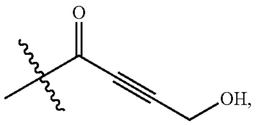

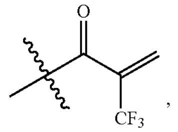

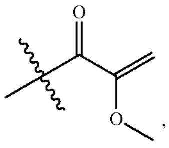

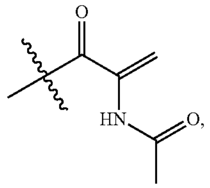

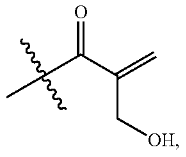

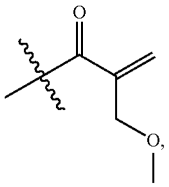

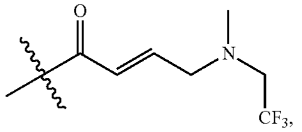

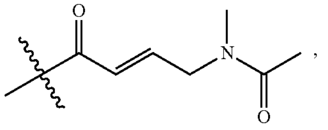

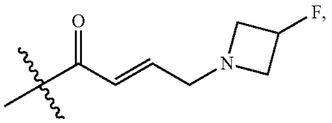

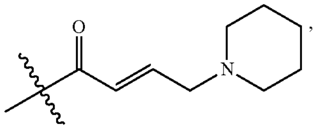

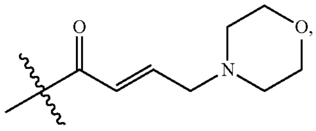

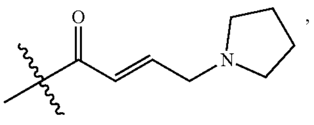

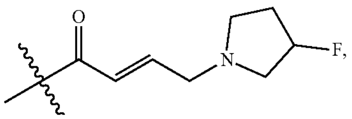

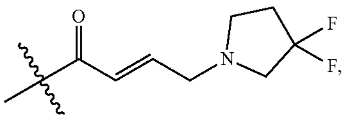

and

-continued

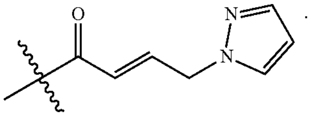

13. The compound according to claim 1, wherein $R^5$ is selected from the group consisting of hydrogen, halogen, $—C_{1-8}$alkyl, $—NR^bR^c$, $—(CH_2)_m—C(O)—NR^dR^e$, and $—(CH_2)_m—CN$, each $R^b$ and $R^c$ are independently hydrogen, $—C_{1-8}$alkyl, $—C_{2-8}$alkenyl, $—C_{2-8}$alkynyl, cycloalkyl, heterocyclyl, aryl, or heteroaryl; or ($R^b$ and $R^c$) together with the atom(s) to which they are attached form a 4- to 6-membered ring, said ring is optionally substituted with at least one $R^g$;

$R^d$, $R^e$ and $R^g$ are each independently hydrogen, deuterium (D), halogen, oxo, or $—C_{1-8}$alkyl; and each m is independently 0, 1, 2, or 3.

14. The compound according to claim 1, wherein $R^5$ is selected from the group consisting of $—CH_3$, $—C_2H_5$, $—C_3H_7$, $—C_4H_9$, $—C_5H_{11}$, $—(CH_2)_m—C(O)—NR^dR^c$, $—(CH_2)_m—CN$, and hydrogen, wherein each m is 0 or 1; and p is 1.

15. A compound selected from the group consisting of

A1

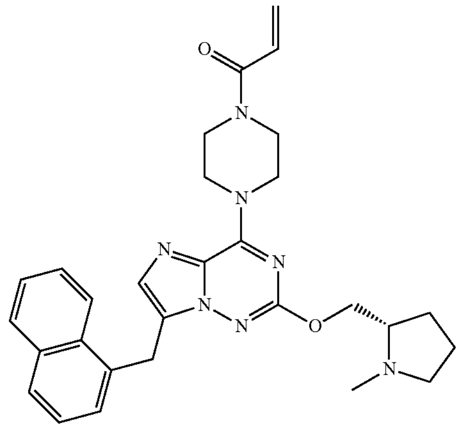

A2

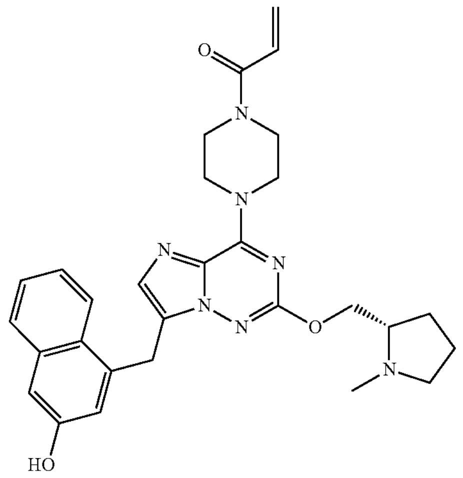

-continued
A3
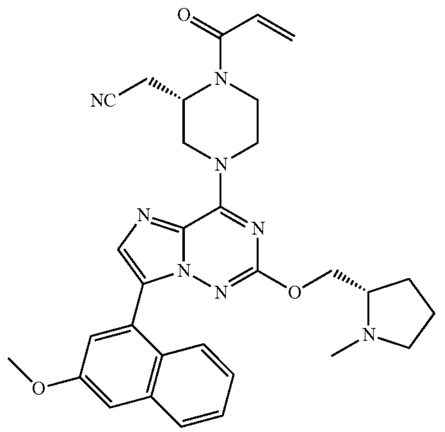
A4
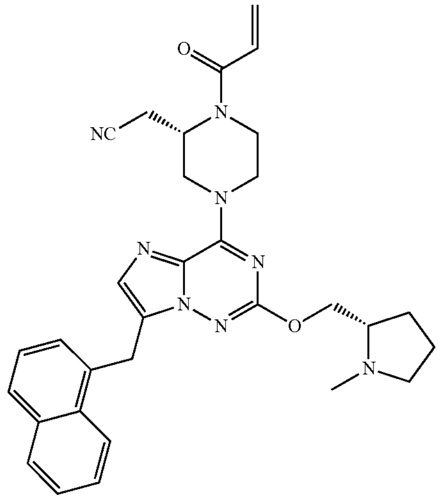
A5
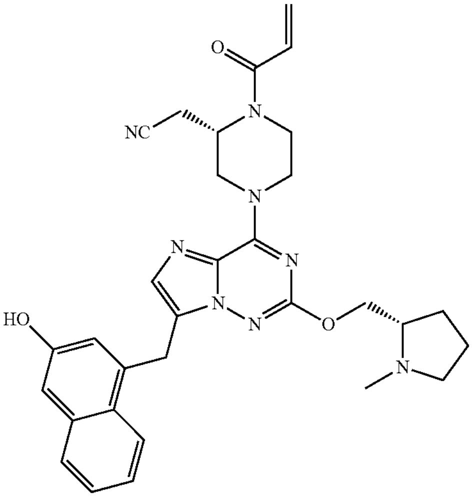
-continued
A6
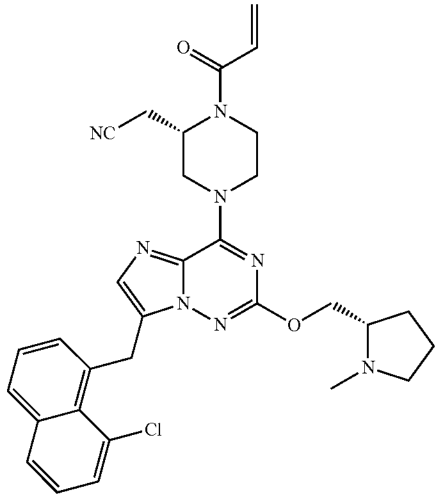
A7
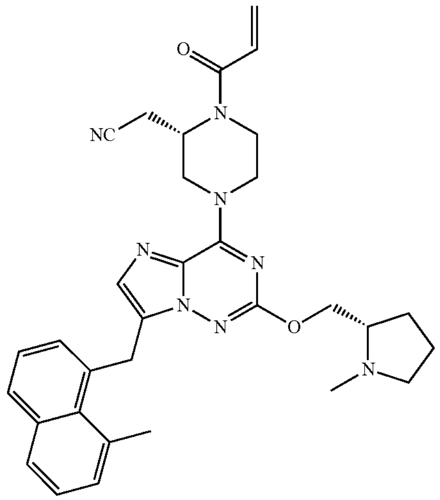
A8
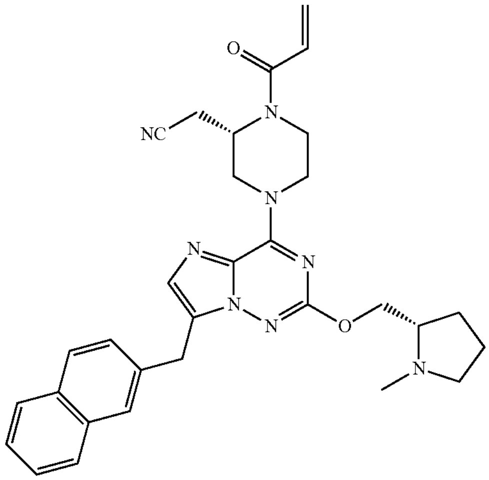

-continued
A9
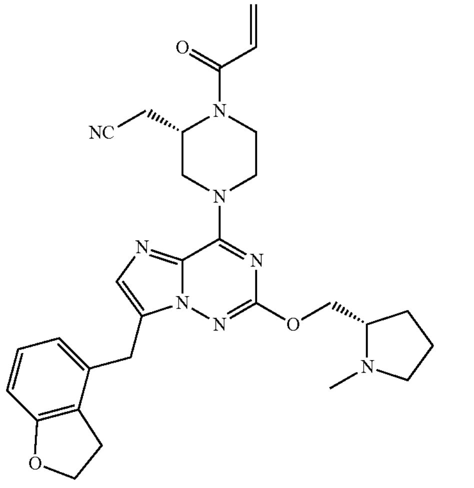
A10
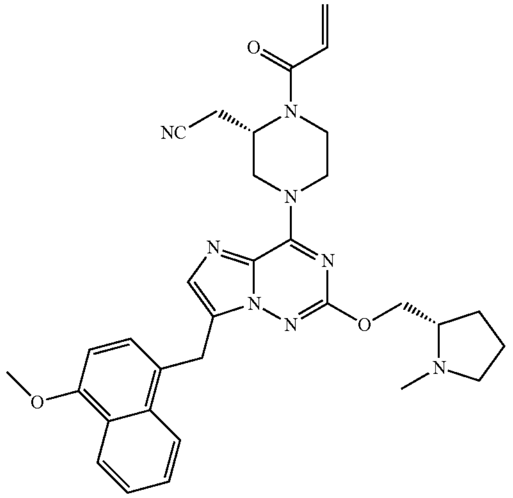
A11
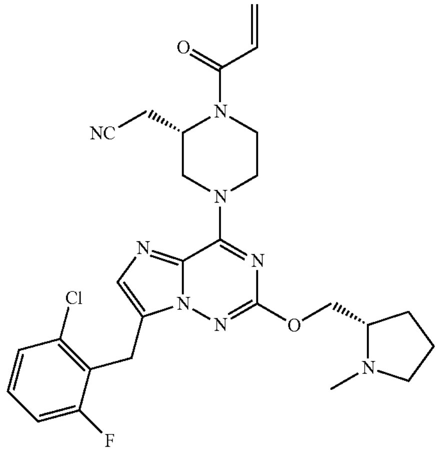
-continued
A12
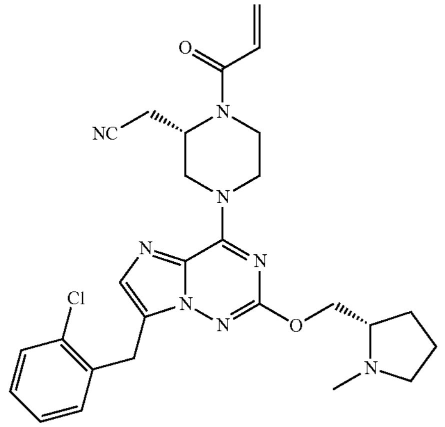
A13
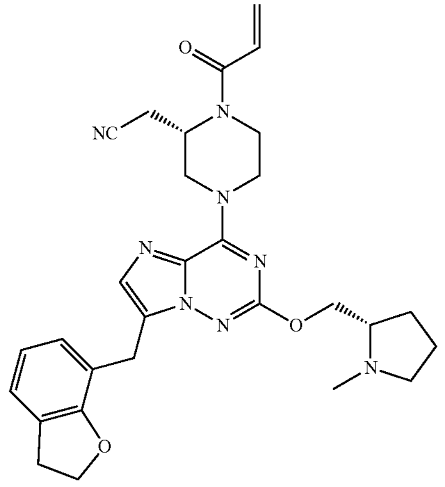
A14
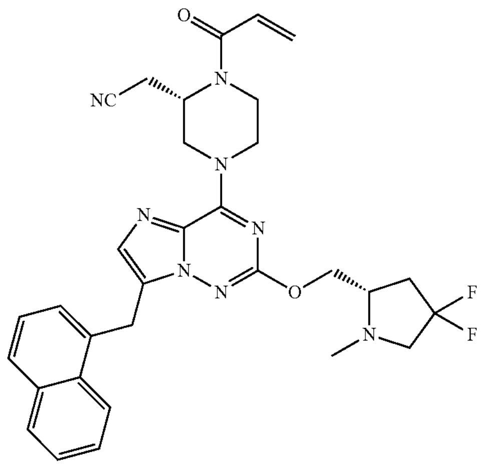

-continued
A15
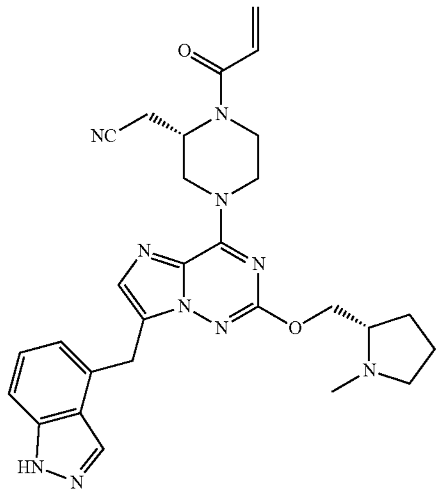
A16
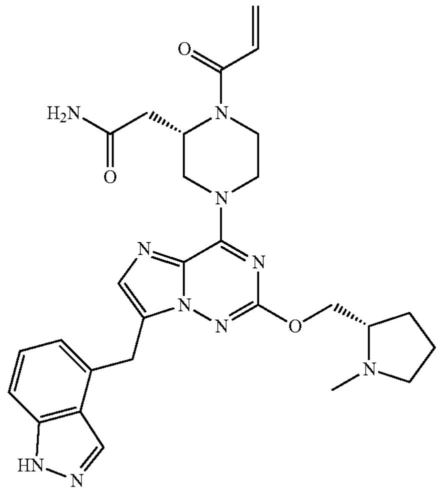
A17
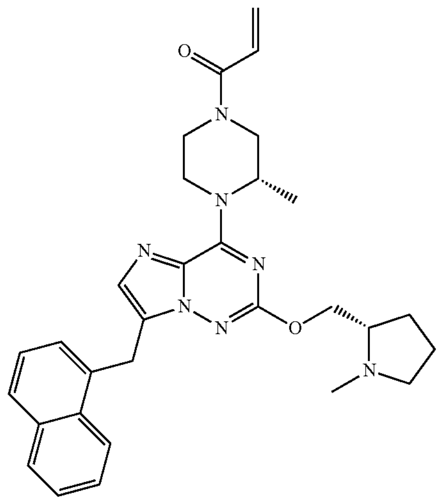
-continued
A18
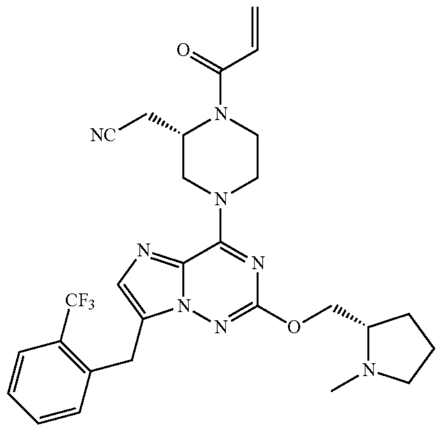
A19
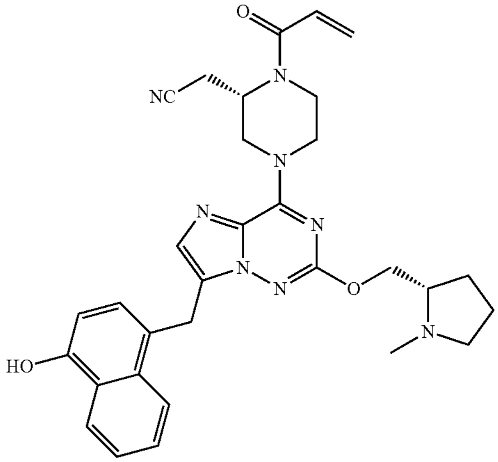
A20
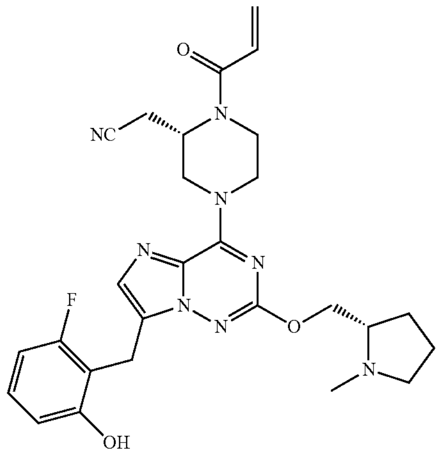

-continued
A21
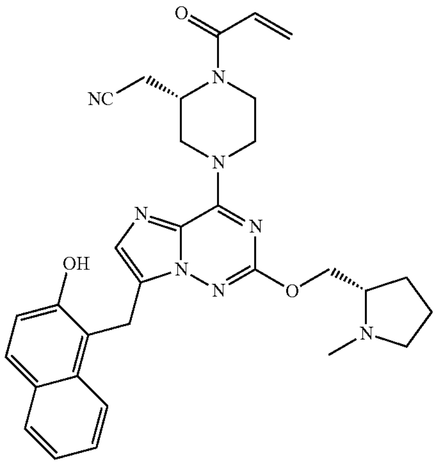
A22
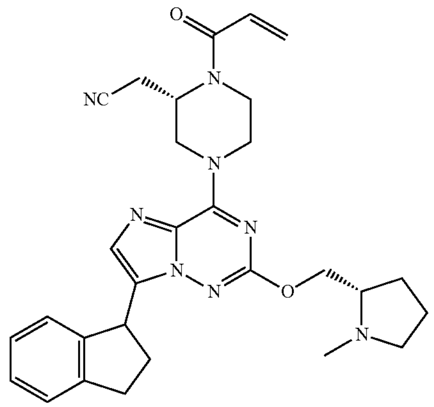
A23
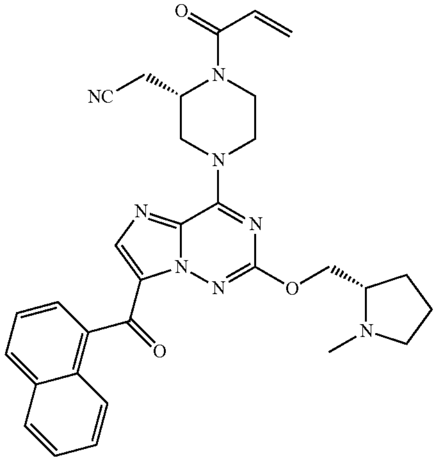
-continued
B1
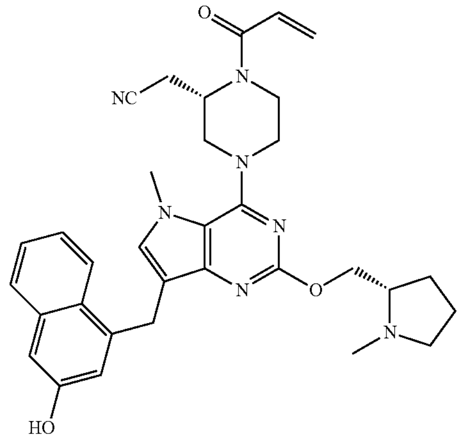
B2
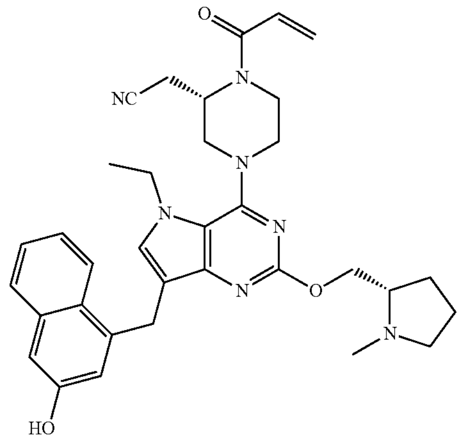
B3
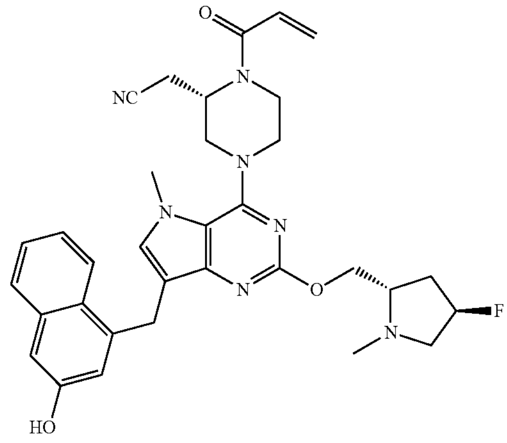

-continued

B4

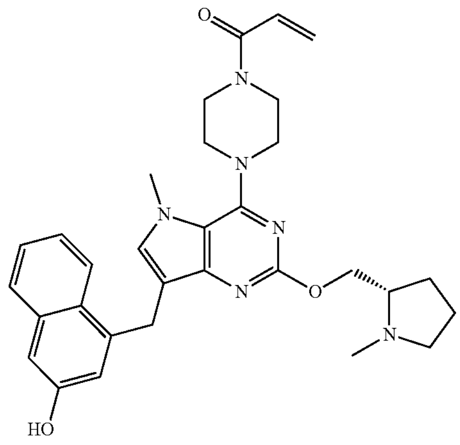

B5

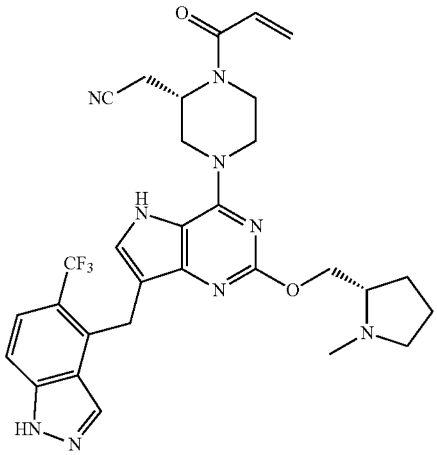

and

-continued

B6

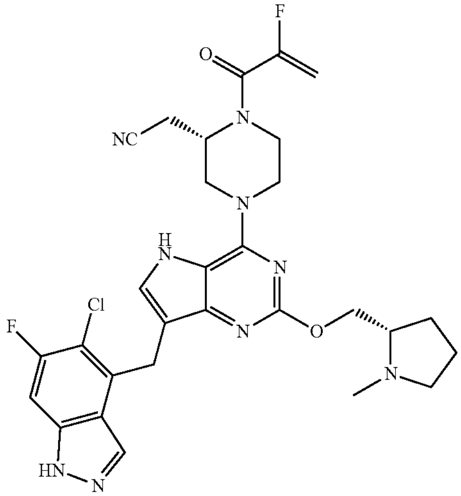

or a pharmaceutically acceptable salt thereof, or a stereoisomer thereof.

16. A pharmaceutical composition comprising the compound of claim 1 or a stereoisomer thereof, or a pharmaceutically acceptable salt thereof and a pharmaceutically acceptable excipient.

17. A method of treating cancer in a subject in need thereof, comprising administering to the subject a therapeutically effective amount of the compound of claim 1 or a stereoisomer thereof, or a pharmaceutically acceptable salt thereof.

18. A method of treating cancer in a subject in need thereof, comprising administering to the subject a therapeutically effective amount of the pharmaceutical composition of claim 16.

* * * * *